United States Patent
Cianchetta et al.

(10) Patent No.: US 12,133,853 B2
(45) Date of Patent: *Nov. 5, 2024

(54) PYRUVATE KINASE ACTIVATORS FOR USE IN TREATING BLOOD DISORDERS

(71) Applicant: Agios Pharmaceuticals, Inc., Cambridge, MA (US)

(72) Inventors: Giovanni Cianchetta, Boxford, MA (US); Tao Liu, Wellesley, MA (US); Anil Kumar Padyana, Lexington, MA (US); Zhihua Sui, Audubon, PA (US); Zhenwei Cai, Princeton, NJ (US); Dawei Cui, Shanghai (CN); Jingjing Ji, Shanghai (CN)

(73) Assignee: Agios Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/099,311

(22) Filed: Jan. 20, 2023

(65) Prior Publication Data

US 2023/0226055 A1 Jul. 20, 2023

Related U.S. Application Data

(63) Continuation of application No. 16/639,081, filed as application No. PCT/US2018/000128 on Aug. 15, 2018, now Pat. No. 11,590,132.

(60) Provisional application No. 62/673,526, filed on May 18, 2018, provisional application No. 62/673,533, filed on May 18, 2018.

(51) Int. Cl.
| | | |
|---|---|---|
| *C07D 241/36* | (2006.01) | |
| *A61K 31/5025* | (2006.01) | |
| *A61K 31/506* | (2006.01) | |
| *A61K 31/519* | (2006.01) | |
| *A61P 7/06* | (2006.01) | |
| *A61P 7/08* | (2006.01) | |
| *A61P 31/10* | (2006.01) | |
| *C07D 513/04* | (2006.01) | |
| *C07D 513/14* | (2006.01) | |
| *A61K 45/06* | (2006.01) | |

(52) U.S. Cl.
CPC ........ *A61K 31/5025* (2013.01); *A61K 31/506* (2013.01); *A61K 31/519* (2013.01); *C07D 241/36* (2013.01); *C07D 513/14* (2013.01); *A61K 45/06* (2013.01)

(58) Field of Classification Search
CPC .. C07D 241/36; C07D 513/04; C07D 513/14; A61K 31/5025; A61K 31/506; A61K 31/519; A61P 7/06; A61P 7/08; A61P 31/10; A61P 31/506; A61P 31/519
See application file for complete search history.

(56) References Cited

U.S. PATENT DOCUMENTS

| | | |
|---|---|---|
| 4,405,635 A | 9/1983 | Schnettler et al. |
| 4,883,914 A | 11/1989 | Alvarado et al. |
| 11,040,036 B2 | 6/2021 | Cianchetta et al. |
| 11,364,240 B2 | 6/2022 | Cianchetta et al. |
| 11,464,775 B2 | 10/2022 | Cianchetta et al. |
| 11,590,132 B2 | 2/2023 | Cianchetta et al. |
| 2010/0331307 A1 | 12/2010 | Salituro et al. |
| 2012/0142717 A1 | 6/2012 | Jin et al. |
| 2014/0155374 A1 | 6/2014 | Su |
| 2022/0127267 A1 | 4/2022 | Liu et al. |
| 2022/0233541 A1 | 7/2022 | Cianchetta et al. |
| 2022/0395503 A1 | 12/2022 | Cianchetta et al. |

FOREIGN PATENT DOCUMENTS

| | | |
|---|---|---|
| AR | 112690 A1 | 11/2019 |
| EA | 201590881 A1 | 8/2015 |
| EP | 3668512 A1 | 6/2020 |
| WO | 2001/009121 A2 | 2/2001 |
| WO | 2001/017956 A1 | 3/2001 |
| WO | 2010/042867 A2 | 4/2010 |
| WO | 2011/002817 A1 | 1/2011 |
| WO | 2011/137089 A1 | 11/2011 |
| WO | 2012/092442 A1 | 7/2012 |

(Continued)

OTHER PUBLICATIONS

U.S. Appl. No. 16/639,075, filed Feb. 13, 2020, U.S. Pat. No. 11,364,240, Issued.
U.S. Appl. No. 17/744,806, filed May 16, 2022, 2022-0395503, Published.
U.S. Appl. No. 17/429,073, filed Aug. 6, 2021, 2022-0127267, Published.
U.S. Appl. No. 16/639,081, filed Feb. 13, 2020, U.S. Pat. No. 11,590,132, Issued.
U.S. Appl. No. 16/952,257, filed Nov. 19, 2020, U.S. Pat. No. 11,040,036, Issued.
U.S. Appl. No. 16/639,086, filed Feb. 13, 2020, U.S. Pat. No. 11,464,775, Issued.
U.S. Appl. No. 17/586,777, filed Jan. 27, 2022, 2022-0233541, Published.

(Continued)

*Primary Examiner* — Bruck Kifle
(74) *Attorney, Agent, or Firm* — McCarter & English, LLP; Michael J. DeGrazia

(57) ABSTRACT

Described herein are compounds that activate pyruvate kinase, pharmaceutical compositions and methods of use thereof. These compounds are represented by Formula (I) wherein $R^1$, $R^2$, $R^a$, $R^b$, $R^j$, $R^k$, and Q are as defined herein.

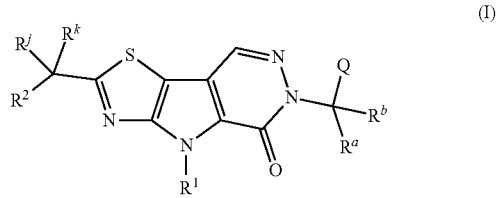

(I)

25 Claims, 5 Drawing Sheets

(56) References Cited

FOREIGN PATENT DOCUMENTS

| WO | 2012/151448 A1 | 11/2012 |
| WO | 2012/151450 A1 | 11/2012 |
| WO | 2012/151451 A1 | 11/2012 |
| WO | 2012/151452 A1 | 11/2012 |
| WO | 2014/074848 A1 | 5/2014 |
| WO | 2014/139144 A1 | 9/2014 |
| WO | 2014/139325 A1 | 9/2014 |
| WO | 2019/008025 A1 | 1/2019 |
| WO | 2019/034690 A1 | 2/2019 |
| WO | 2019/035865 A1 | 2/2019 |
| WO | 2019/035911 A1 | 2/2019 |

OTHER PUBLICATIONS

Adem et al., Pyruvate kinase activators as a therapy target: a patent review 2011-2017. Expert Opin Ther Pat. Jan. 2018;28(1):61-68.

Belikov, Pharmaceutical Chemistry. MEDpress-inform. pp. 27-29, (2007).

Dyson et al., Chemistry of Synthetic Drugs. pp. 12-19, (1964).

Gupta et al., Human pyruvate kinase M2: a multifunctional protein. Protein Sci. Nov. 2010;19(11):2031-44.

Gura, Systems for identifying new drugs are often faulty. Science. Nov. 7, 1997;278(5340):1041-2.

Jiang et al., Evaluation of thieno[3,2-b]pyrrole[3,2-d]pyridazinones as activators of the tumor cell specific M2 isoform of pyruvate kinase. Bioorg Med Chem Lett. Jun. 1, 2010;20(11):3387-93.

Johnson et al., Relationships between drug activity in NCI preclinical in vitro and in vivo models and early clinical trials. Br J Cancer. May 18, 2001;84(10):1424-31.

Linghu et al., Development of a Practical Synthesis of ERK Inhibitor GDC-0994. Org Process Res Dev. 2017;21:387-98.

Marelli et al., Tumor Targeting via Integrin Ligands. Front Oncol. Aug. 30, 2013;3:222.

Merck Manual, Acute Leukemia. Retrieved online at: https://www.merckmanuals.com/professional/hematology-and-oncology/leukemias/overview-of-leukemia. 6 pages, (2013).

Palsson-McDermott et al., Pyruvate kinase M2 regulates Hif-1a activity and IL-1beta induction and is a critical determinant of the warburg effect in LPS-activated macrophages. Cell Metab. Jan. 6, 2015;21(1):65-80.

Pearce et al., Failure modes in anticancer drug discovery and development. Cancer Drug Design and Discovery. Elsevier Inc., Stephen Neidle (Ed.). Chapter 18, pp. 424-435, (2008).

Simone, Introduction. Cecil Textbook of Medicine, 20th Edition, vol. 1. W.B. Saunders Company, Philadelphia. J. Claude Bennett, (Ed.). Part XIV, Oncology, pp. 1004-1010, (1997).

Sofan et al., Antimicrobial Activity of Newly Synthesized Thiadiazoles, 5-benzyl-2H-tetrazole and Their Nucleosides. Der Pharma Chemica. 2012;4(3):1064-73.

Su et al., The role of pyruvate kinase M2 in anticancer therapeutic treatments. Oncol Lett. Dec. 2019;18(6):5663-5672.

Tamada et al., Pyruvate kinase M2: multiple faces for conferring benefits on cancer cells. Clin Cancer Res. Oct. 15, 2012;18(20):5554-61.

Wang et al., Mathematical modeling in cancer drug discovery. Drug Discov Today. Feb. 2014;19(2):145-50.

International Search Report and Written Opinion for Application No. PCT/US2018/000128, dated Nov. 29, 2018, 10 pages.

International Search Report and Written Opinion for Application No. PCT/US2018/000129, dated Nov. 29, 2018, 10 pages.

International Search Report for Application No. PCT/US2018/000127, dated Nov. 30, 2018, 11 pages.

Russian Office Action for Application No. 2020110573 dated Dec. 24, 2021, 14 pages.

Figure 2. Table of intermediates used in Examples 1-10

| Cpds in Examples | Synthesis of the intermediates |
|---|---|
| E7-7 | $H_2N-O-S(O)(O)-OH$ + $H_2N-C(S)-C(O)-O-Et$ → 1) DMF-DMA, DCM, rt; Py, EtOH, rt; 2) NaBH$_4$; 3) CBr$_4$, PPh$_3$, DCM → (1,2,4-thiadiazol-5-yl)methyl bromide |
| E7-8 | 2-amino-thiazole-4-carboxylic acid ethyl ester + 2,5-hexanedione → 1) TsOH, toluene, MW, 150°C, 1h; 2) LiAlH$_4$, THF; 3) NCS, PPh$_3$ → 2-(2,5-dimethylpyrrol-1-yl)-5-(chloromethyl)thiazole |
| E7-9 | 1-Trt-4-(hydroxymethyl)imidazole → SOCl$_2$, CHCl$_3$ → 1-Trt-4-(chloromethyl)imidazole |
| E7-10 | ethyl 1H-pyrazole-4-carboxylate → 1) TrtCl, NaH, THF; 2) LiAlH4, THF; 3) CBr$_4$, PPh$_3$, DCM → 1-Trt-4-(bromomethyl)pyrazole |
| E7-12 | methyl 4-methylthiazole-2-carboxylate → 1) NBS, AIBN, BPO, CCl$_4$, reflux overnight; 2) DIBAL-H, THF; 3) DHP, PTSA, DCM → THPO-CH$_2$-(4-(bromomethyl)thiazol-2-yl) |
| E7-15 | 6-methyl-2-aminopyridine → 1) (Boc)$_2$O, DMAP, THF, rt, 12h; 2) NBS, AIBN, CCl$_4$, 80°C, 14h → N,N-di-Boc-6-(bromomethyl)pyridin-2-amine |
| E7-17 | ethyl 5-bromothiazole-4-carboxylate → 1) NaBH$_4$, CaCl$_2$, THF/H$_2$O; 2) NCS, PPh$_3$, DCM → 5-bromo-4-(chloromethyl)thiazole |
| E7-19 | 4-methylthiazole-5-carbaldehyde → 1) NH$_2$OH·HCl, DMSO, 90°C, 1.5 h; 2) NBS, AIBN, CCl$_4$, 80°C, 16hr → 4-(bromomethyl)thiazole-5-carbonitrile |
| E7-21 | methyl 4-methylthiazole-5-carboxylate → 1) LAH, THF, 0°C; 2) Ph$_3$PBr$_2$, DCM → 5-(bromomethyl)-4-methylthiazole |

Figure 2 - Continued

| | | | |
|---|---|---|---|
| E7-22 | HOCH2-pyridine-Cl | 1) dimethylamine in THF, t-BuONa, Xantphos, Pd(oAc)₂<br>2) SOCl₂, DCM | ClCH2-pyridine-N(Me)₂ |
| E7-23 | ethyl 2-aminothiazole-4-carboxylate | 1) NIS, DCM r.t, 24 h<br>2) t-BuNO₂, THF, 50 °C-r.t, 2h<br>3) Methyl 2,2-difluoro-2-(fluorosulfonyl)acetate, CuI, DMF, 85 °C, sealed tube<br>4) LiAlH₄, THF, 0 °C-r.t, 1h<br>5) Dibromo triphenyl phosphine DCM, 0 °C-r.t | 4-(bromomethyl)-5-CF₃-thiazole |
| E7-24 | 4-methylthiazole | 1) NCS, CCl₄, reflux, 1h<br>2) NBS, BPO, CCl₄, reflux, 3h | 5-chloro-4-(bromomethyl)thiazole |
| E7-25 | ethyl 5-bromothiazole-4-carboxylate | 1) CH₃ONa, MeOH, 50 °C, 3 h<br>2) LiAlH₄, THF | 5-methoxy-4-(hydroxymethyl)thiazole |
| E7-27 | 6-methyl-3-nitro-pyridin-2-ol (structure with OH, NO₂) | 1) MeI, K₂CO₃, DMF, rt<br>2) NBS, BPO | 6-(bromomethyl)-3-methoxy-2-nitropyridine |
| E7-28 | 2,6-dibromo-4-nitropyridine | (DMB)₂NH coupling reagent shown<br>1) Cs₂CO₃, Pd(OAc)₂, BINAP toluene, reflux<br>2) TBAF, DMF, 65 °C<br>3) CO, Pd(dppf)Cl₂, TEA, MeOH<br>4) LiAlH₄, THF<br>5) NBS, PPh₃, DCM | (DMB)₂N-pyridine(F)-CH₂Br |
| E7-29 | methyl 5-methylpyridine-2-carboxylate (N-oxide form) | 1) m-CPBA, DCM, r.t,<br>2) POCl₃, toluene, reflux<br>3) LiAlH₄, THF, 0 °C | HOCH2-pyridine(Cl)(Me) |
| E7-30 | methyl 4-fluoro-1H-pyrazole-3-carboxylate | 1) TrtCl, TEA, DCM<br>2) LiAlH₄, THF, rt<br>3) MsCl, DIPEA, DCM | Trt-N-pyrazole(F)-CH₂Cl |

Figure 2 - Continued

| | | |
|---|---|---|
| E7-41 | BnO-CH₂-CHO + 1) ≡-MgBr; 2) 2-Iodoxybenzoic acid; 3) HOSO₂ONH₂; 4) BBr₃ DCM | isothiazole-3-CH₂OH |
| E7-43 | methyl propiolate, 1) NaN₃ CH₃I CuSO₄ sodium ascorbate; 2) LAH THF | 1-methyl-1,2,3-triazole-4-CH₂OH |
| E7-46 | dimethyl 1H-pyrazole-3,5-dicarboxylate, 1) SEMCl, DIPEA; 2) NaBH₄, MeOH | SEM-protected pyrazole CH₂OH/CO₂Me regioisomers |
| E7-55 | Trt-1,2,4-triazole-3-CO₂Me, 1) LAH, THF, 0°C, 1 h; 2) MsCl, TEA, DCM, r.t. 15 h; 3) LiCl, DMSO, r.t. 2h | Trt-1,2,4-triazole-3-CH₂Cl |
| E7-56 | ClCOCH₂OBn, 1) H₂N-NH-CHO, DCM, 0 °C, 2 hr; 2) P₂S₅, dioxane 45 °C, 2 hr → 1,3,4-thiadiazole-2-CH₂OBn; 3) BBr₃; 4) PBr₃, DCM → 1,3,4-thiadiazole-2-CH₂Br | |
| E8-4 | 2-amino-6-methylpyridine, 1) (Boc)₂O; 2) (Boc)₂O, DMAP, THF; 3) NBS, AIBN, DCE; 4) (EtO)₂P(O)H, DIPEA, CH₃CN | 6-(N,N-diBoc-amino)-2-(bromomethyl)pyridine |
| E8-11 | thiazole-2-carbaldehyde, 1) NaBH4, MeOH; 2) SOCl₂, DCM | 2-(chloromethyl)thiazole |
| E8-18 | methyl 4-methylthiazole-2-carboxylate, 1) NBS, AIBN, BPO, CCl₄, reflux overnight; 2) DIBAL-H, THF; 3) DHP, PTSA, DCM; 4) PhSO₂Na, DMSO | THPO-CH₂-thiazole-CH₂SO₂Ph |
| E8-23 | methyl 1H-1,2,3-triazole-4-carboxylate, 1) SEM-Cl, NaH; 2) LAH, THF; 3) SOCl₂, DCM; 4) PhSO2Na, DMSO | SEM-1,2,3-triazole-4-CH₂SO₂Ph |

Figure 2 - Continued

| | | |
|---|---|---|
| E8-27, E8-28, E8-37, E8-38 | H₂N—(thiazole, 4-methyl, 5-Br) | 1). (Boc)₂O DCM, TEA, DMAP, r.t<br>2). N-fluorobenzenesulfonimide n-BuLi, THF<br>3). NCS, BPO, 80 °C, 2 h<br>→ BocHN—(thiazole, 4-CH₂Cl, 5-F) |
| E8-27, E8-28, E8-32, E8-40 | HN—(triazole)—CO₂Me | 1) SEM-Cl, NaH, THF, 0°C, 2hr<br>2) LAH, THF, 0°C, 1hr<br>3) SOCl₂, DCM, 0°C, 1hr<br>→ SEM-N—(triazole)—CH₂Cl |
| E8-30 | MeO₂C—(pyrazole)—N-Me | 1) LAH, THF<br>2) SOCl₂, DCM, rt, 1 hr<br>→ ClCH₂—(pyrazole)—N-Me |
| E8-31 | H₂N—(thiazole)—CO₂CH₂- | 1) TsOH, toluene MW, 150°C, 1h (with acetonylacetone)<br>2) LiAlH₄, THF<br>3) Dibromo triphenyl phosphine THF, rt, 1h<br>→ (2,5-dimethylpyrrol-1-yl)-thiazole-CH₂Br |
| E8-32<br>E8-33 | (4-methylthiazole) | 1) NCS, CCl₄, reflux, 1h<br>2) NBS, BPO, CCl₄, reflux, 3h<br>→ (5-Cl-4-CH₂Br-thiazole) |
| E8-36 | MeO—(pyridine)—CHO | NaBH₄, MeOH, r.t<br>→ MeO—(pyridine)—CH₂OH |
| E8-52 | H₂N—(5-F, 6-Me pyridine) | 1) (Boc)₂O, 60 °C<br>2) MeI, NaH, DMF<br>3) NBS, AIBN, CCl₄<br>4) DMSO, PhSO₂Na<br>→ Boc(Me)N—(5-F pyridine)—CH₂SO₂Ph |
| E8-53 | H₂N—(5-F, 6-Me pyridine) | 1) (Boc)₂O<br>2) NBS, AIBN<br>→ Boc₂N—(5-F pyridine)—CH₂Br |

PYRUVATE KINASE ACTIVATORS FOR USE IN TREATING BLOOD DISORDERS

CROSS REFERENCE TO RELATED APPLICATIONS

This application is a continuation of U.S. patent application Ser. No. 16/639,081, filed Feb. 13, 2020 which, in turn, is a 35 U.S.C. § 371 national stage filing of International Application No. PCT/US2018/000128, filed on Aug. 15, 2018 which in turn claims the benefit of priority of U.S. Provisional Patent Application Nos. 62/673,526 and 62/673,533, both filed May 18, 2018. This application also claims the benefit of priority of International Patent Application No. PCT/CN2017/097496, filed Aug. 15, 2017. The entire contents of each of the aforementioned priority applications are hereby incorporated by reference.

BACKGROUND

Pyruvate kinase deficiency (PKD) is a disease of the red blood cells caused by a deficiency of the pyruvate kinase R (PKR) enzyme due to recessive mutations of PKLR gene (Wijk et al. *Human Mutation*, 2008, 30 (3) 446-453). PKR activators can be beneficial to treat PKD, thalassemia (e.g., beta-thalessemia), hereditary elliptocytosis, abetalipoproteinemia or Bassen-Kornzweig syndrome, sickle cell disease, paroxysmal nocturnal hemoglobinuria, anemia (e.g., congenital anemias (e.g., enzymopathies), hemolytic anemia (e.g. hereditary and/or congenital hemolytic anemia, acquired hemolytic anemia, chronic hemolytic anemia caused by phosphoglycerate kinase deficiency, anemia of chronic diseases, non-spherocytic hemolytic anemia or hereditary spherocytosis).

SUMMARY

Described herein are compounds of Formulas (I), (II), (III), (IV), and (V) (collectively referred to herein as "Formulas (I)—(V)"), that activate pyruvate kinase R (PKR), wild type and/or mutant enzymes (such as those described herein), and pharmaceutically acceptable salts thereof.

In one embodiment, the invention provides a compound of Formula (I) or a pharmaceutically acceptable salt thereof:

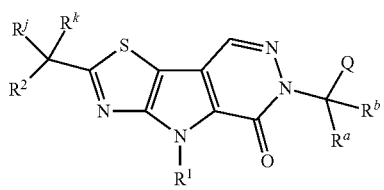

(I)

wherein $R^1$, $R^2$, $R^a$, $R^j$, $R^k$, and Q are as defined herein.

In one embodiment, the compound or pharmaceutically acceptable salt thereof is selected from the compounds of Table 1 or FIG. 1.

Also provided are pharmaceutical compositions comprising a compound of Formulas (I)—(V), or a pharmaceutically acceptable salt thereof, and a pharmaceutically acceptable carrier.

The present disclosure further provides a method of treating anemia in a subject comprising administering to the subject an effective amount of (1) a compound described herein or a pharmaceutically acceptable salt thereof; (2) a pharmaceutically acceptable composition comprising a compound described herein or a pharmaceutically acceptable salt thereof, and a pharmaceutically acceptable carrier. In certain embodiments, the anemia is a dyserythropoietic anemia such as congenital dyserythropoietic anemia type I, II, III, or IV.

The present disclosure further provides a method for treating sickle cell disease in a subject comprising administering to the subject an effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present disclosure further provides a method for treating hemolytic anemia (e.g., chronic hemolytic anemia caused by phosphoglycerate kinase deficiency, Blood Cells Mol Dis, 2011; 46(3):206) in a subject comprising administering to the subject an effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier. In certain embodiments, the hemolytic anemia is hereditary and/or congenital hemolytic anemia, acquired hemolytic anemia, or anemia as part of a multi-system disease. In certain embodiments, the hemolytic anemia is congenital anemia. In certain embodiments, the hemolytic anemia is hereditary (e.g. non-spherocytic hemolytic anemia or hereditary spherocytosis).

The present disclosure further provides a method for treating thalassemia (e.g., beta-thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), sickle cell disease, or anemia of chronic diseases in a subject comprising administering to the subject an effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier. In one embodiment, the acquired hemolytic anemia comprises congenital anemias. In certain embodiments, the provided method is to treat thalassemia. In certain embodiments, the thalassemia is beta-thalassemia.

The present disclosure further provides a method for treating pyruvate kinase deficiency (PKD) in a subject, the method comprising administering to the subject an effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier. In certain embodiments, the PKD is a deficiency of PKR. In certain embodiments, the deficiency of PKR is associated with a pyruvate kinase R mutation.

Compounds and pharmaceutical compositions described herein are activators of PKR having lower activities compared to the wild type, thus are useful for methods of the present disclosure. In certain embodiments, the PKR is a wild type. In certain embodiments, the PKR is a mutant. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, R479H, R479K, R486W, R532W, K410E, R510Q, and R490W. Without being bound by theory, in certain embodiments, the compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in the Examples. In certain embodiments, the compounds described herein are also activators of wild type PKR.

In an embodiment, the disclosure provides a method for activating PKR in red blood cells in a subject in need thereof comprising administering to the subject an effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier. In certain embodiments, the PKR is a wild type. In certain embodiments, the PKR is a mutant.

In an embodiment, the mutant PKR is selected from G332S, G364D, T384M, K410E, R479H, R479K, R486W, R532W, R510Q, and R490W. In certain embodiments, the mutant PKR is selected from A468V, A495V, I90N, T408I, and Q421K, and R498H. In certain embodiments, the mutant PKR is R532W, K410E, or R510Q.

BRIEF DESCRIPTION OF THE FIGURES

FIG. 2 shows synthesis of exemplary intermediates used in Examples 1-10.

DETAILED DESCRIPTION OF THE INVENTION

Figure 1:
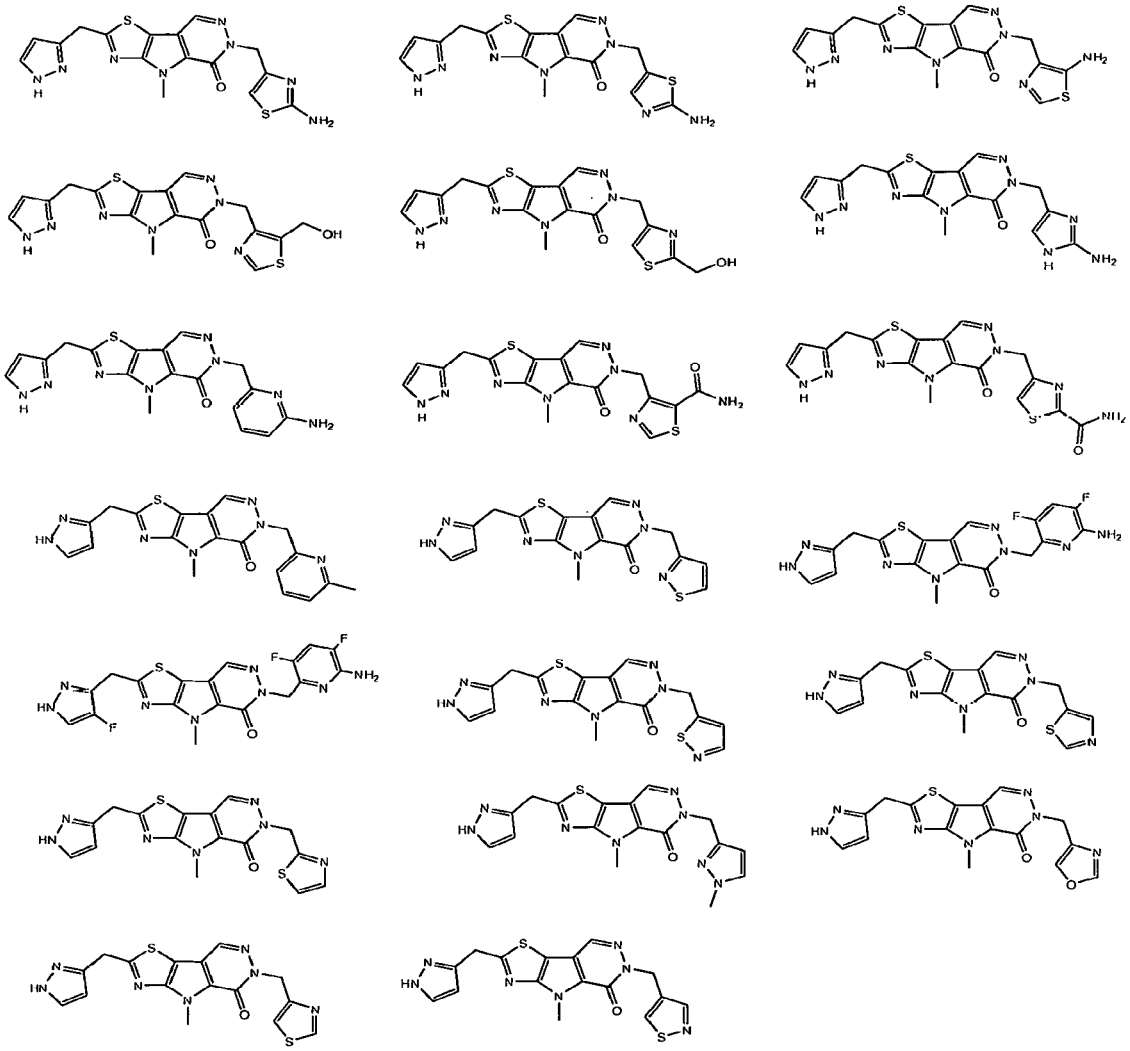
FIG. 1 is a listing of the structures of exemplary compounds of the invention.

The details of construction and the arrangement of components set forth in the following description or illustrated in the drawings are not meant to be limiting. Embodiments can be practiced or carried out in various ways. The phraseology and terminology used herein is for purpose of description and shouldn't be regarded as limiting.

Definitions

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, N Y, 1962); and Wilen, S. H. Tables of Resolving Agents and Optical Resolutions p. 268 (E. L. Eliel, Ed., Univ. of Notre Dame Press, Notre Dame, IN 1972).

The compounds described herein may also be represented in multiple tautomeric forms, in such instances, expressly includes all tautomeric forms of the compounds described herein, even though only a single tautomeric form may be represented (e.g., alkylation of a ring system may result in alkylation at multiple sites; all such reaction products are expressly included). All such isomeric forms of such compounds are expressly included. If a tautomer of a compound is aromatic, this compound is aromatic. Similarly, if a tautomer of a substitutent is a heteroaryl, this substituent is heteroaryl.

The term "alkyl" refers to a radical of a straight-chain or branched saturated hydrocarbon group having from 1 to 10 carbon atoms ("$C_{1-10}$ alkyl"). Examples of $C_{3-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is unsubstituted —$C_{1-10}$ alkyl. In certain embodiments, the alkyl group is substituted —$C_{1-10}$ alkyl.

The term "haloalkyl" refers to a substituted alkyl group, wherein one or more of the hydrogen atoms are independently replaced by a halogen, e.g., fluoro, bromo, chloro, or iodo and includes alkyl moieties in which all hydrogens have been replaced by halo (e.g., perfluoroalkyl). In some embodiments, the haloalkyl moiety has 1 to 8 carbon atoms ("$C_{1-8}$ haloalkyl").

The term "alkoxy" or "alkoxyl" refers to an —O-alkyl radical. E.g., with between 1 and 6 carbon atoms.

The term "aryloxy" refers to an —O-aryl radical. In some embodiments the aryloxy group is phenoxy.

The term "alkenyl" refers to a radical of a straight-chain or branched hydrocarbon group having from 2 to 10 carbon atoms and one or more carbon-carbon double bonds (e.g., 1, 2, 3, or 4 double bonds). The one or more carbon-carbon double bonds can be internal (such as in 2-butenyl) or terminal (such as in 1-butenyl). Examples of —$C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), pentenyl ($C_5$), pentadienyl ($C_5$), hexenyl ($C_6$), heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted —$C_{2-10}$ alkenyl. In certain embodiments, the alkenyl group is a substituted —$C_{2-10}$ alkenyl. In an alkenyl group, a C=C double bond may be an (E)- or (Z)-double bond.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). Examples of alkynyl groups include ethynyl ($C_2$), 1-propynyl ($C_3$), 2-propynyl ($C_3$), 1-butynyl ($C_4$), 2-butynyl ($C_4$), pentynyl ($C_5$), hexynyl ($C_6$) heptynyl ($C_7$), octynyl ($C_3$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted —$C_{2-10}$ alkynyl. In certain embodiments, the alkynyl group is a substituted —$C_{2-10}$ alkynyl.

The term "carbocyclyl" or "carbocyclic" refers to a radical of a non-aromatic monocyclic, bicyclic, or tricyclic or polycyclic hydrocarbon ring system having from 3 to 14 ring carbon atoms ("$C_{3-14}$ carbocyclyl") and zero heteroatoms in the non-aromatic ring system. Carbocyclyl groups include fully saturated ring systems (e.g., cycloalkyls), and partially saturated ring systems. In some embodiments, a carbocyclyl group has 3 to 10 ring carbon atoms ("$C_{3-10}$ carbocyclyl").

The term "cycloalkyl" as employed herein includes saturated cyclic, bicyclic, tricyclic, or polycyclic hydrocarbon groups having 3 to 14 carbons containing the indicated number of rings and carbon atoms (for example a $C_3$-$C_{14}$ monocyclic, $C_4$-$C_{14}$ bicyclic, $C_5$-$C_{14}$ tricyclic, or $C_6$-$C_{14}$ polycyclic cycloalkyl). In some embodiments "cycloalkyl" is a monocyclic cycloalkyl. Examples of monocyclic cycloalkyl groups include cyclopentyl ($C_5$), cyclohexyl ($C_5$). cyclopropyl ($C_3$) cyclobutyl ($C_4$), cycloheptyl ($C_7$) and cyclooctyl ($C_8$). In some embodiments "cycloalkyl" is a bicyclic cycloalkyl. Examples of bicyclic cycloalkyls include bicyclo[1.1.0]butane ($C_4$), bicyclo[1.1.1] pentane ($C_5$), spiro[2.2] pentane ($C_5$), bicyclo[2.1.0]pentane ($C_5$), bicyclo[2.1.1]hexane ($C_6$), bicyclo[3.3.3]undecane ($C_{11}$), decahydronaphthalene ($C_{10}$), bicyclo[4.3.2]undecane ($C_{11}$), spiro[5.5]undecane ($C_{11}$) and bicyclo[4.3.3]dodecane ($C_{12}$). In some embodiments "cycloalkyl" is a tricyclic cycloalkyl. Examples of tricyclic cycloalkyls include adamantane ($C_{12}$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or Spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). Exemplary heterocyclyl groups include aziridinyl, oxiranyl, thiiranyl, azetidinyl, oxetanyl, thietanyl, tetrahydrofuranyl, dihydrofuranyl, tetrahydrothiophenyl, dihydrothiophenyl, pyrrolidinyl, dihydropyrrolyl, pyrrolyl-2,5-dine, dioxolanyl, oxathiolanyl, dithiolanyl, triazolinyl, oxadiazolinyl, thiadiazolinyl, piperidinyl, tetrahydropyranyl, dihydropyridinyl, thianyl, piperazinyl, morpholinyl, dithianyl, dioxanyl, triazinanyl, azepanyl, oxepanyl, thiepanyl, azocanyl, oxecanyl, thiocanyl, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In some embodiments, the heteroaryl can be a 5- or 6-membered monocyclic heteroaryl containing 1-4 heteroatoms. In some embodiments the heteroaryl can be an 8-12 membered bicyclic heteroaryl having 1-6 heteroatoms. A "5- or 6-membered monocyclic heteroaryl" or "5-membered or 6-membered monocyclic heteroaryl" refers to a 5- or 6-membered monocyclic and unfused 4n+2 aromatic ring system having ring carbon atoms and 1-4 ring heteroatoms. Exemplary monocyclic 5- or 6-membered heteroaryl groups include pyrrolyl, furanyl, thiophenyl, imidazolyl, pyrazolyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, triazinyl, and tetrazinyl. As used herein, if a tautomer of a radical is heteroaryl, this radical is heteroaryl. The term "tautomers" or "tautomeric" refers to two or more interconvertible compounds/substituents resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

The term "saturated" refers to a moiety that does not contain a double or triple bond, i.e., the moiety only contains single bonds.

The term "optionally substituted" refers to being substituted or unsubstituted. In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent (e.g. $C_{1-6}$ alkyl, halogen, nitro, cyano, hydroxyl, $C_{1-6}$ haloalkyl, $C_{1-6}$ haloalkoxy, $C_{1-6}$ acyl, $C_{3-6}$ cycloalkyl, $C_{6-10}$ aryl, monocyclic or bicyclic heteroaryl, and monocyclic or bicyclic heterocyclyl), at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valences of the heteroatoms and results in the formation of a stable moiety. The invention is not intended to be limited in any manner by the exemplary substituents described herein.

A "substitutable ring carbon atom" refers to a carbon atom on an aryl/heteroaryl/carbocyclyl/heterocyclyl ring with at least one hydrogen present on the carbon atom that is replaced with a permissible substituent as defined above. A "substitutable ring nitrogen atom" refers to a nitrogen atom on an heteroaryl-heterocyclyl ring with at least one hydrogen present on the nitrogen atom that is replaced with a permissible substituent.

Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valences of the heteroatoms and results in the formation of a stable moiety. The invention is not intended to be limited in any manner by the exemplary substituents described herein.

The term "halo" or "halogen" refers to fluorine, chlorine, bromine, or iodine.

The term "acyl" refers to a group having the general formula $—C(=O)R^{X1}$, $—C(=O)OR^{X1}$, $—C(=O)—O—C(=O)R^{X1}$, $—C(=O)SR^{X1}$, $—C(=O)N(R^{X1})_2$, $—C(=S)R^{X1}$, $—C(=S)N(R^{X1})_2$, and $—C(=S)S(R^{X1})$, $—C(=NR^{X1})R^{X1}$, $—C(=NR^{X1})OR^{X1}$, $—C(=NR^{X1})SR^{X1}$, and $—C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched $C_{1-10}$ alkyl; cyclic or acyclic, substituted or unsubstituted, branched or unbranched $C_{2-10}$ alkenyl; substituted or unsubstituted $C_{2-10}$ alkynyl; substituted or unsubstituted $C_{6-12}$ aryl, substituted or unsubstituted heteroaryl, when valency permits. Exemplary acyl groups include aldehydes (—CHO), carboxylic acids (—$CO_2H$), ketones, acyl halides, esters, amides, imines, carbonates, carbamates, and ureas.

In certain embodiments, the substituent present on a nitrogen atom, on an oxygen atom or on a sulfur atom is a nitrogen protecting group, an oxygen protecting group or a sulfur protecting group, respectively. Nitrogen, oxygen and sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference. For example, nitrogen protecting groups include, but are not limited to, formamide, acetamide, chloroacetamide, trichloroacetamide, trifluoroacetamide, phenylacetamide, methyl carbamate, ethyl carbamate, 9-fluorenylmethyl carbamate (Fmoc), t-butyl carbamate (BOC or Boc), 1-adamantyl carbamate (Adoc), vinyl carbamate (Voc), allyl carbamate (Alloc), 2-(trimethylsilyl) ethoxy]methyl (SEM), p-toluenesulfonamide (Ts), benzenesulfonamide, 2,3,6-trimethyl-4-methoxybenzenesulfonamide (Mtr), 2,4,6-trimethoxybenzenesulfonamide (Mtb), phenothiazinyl-(10)-acyl derivative, N'-p-toluenesulfonylaminoacyl derivative, etc. Exemplary oxygen protecting groups include, but are not limited to, methyl, methoxymethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), tetrahydropyranyl (THP), methanesulfonate (mesylate), benzylsulfonate, and tosylate (Ts).

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), ortrifluoromethanesulfonate (triflate, —OTf).

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+ (C_{1-4} alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomologus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. In certain embodiments, the subject is a patient. The term "patient" refers to a human subject in need of treatment of a disease. In certain embodiments, the term "patient" is a human adult over 18 years old in need of treatment of a disease. In certain embodiments, the term "patient" is a human child no more than 18 years old in need of treatment of a disease. In certain embodiments, the patient is not under regular transfusion (e.g. having had no more than 4 transfusion episodes in the 12-month period). In certain embodiments, the patient is under regular transfusion (e.g. having had at least 4 transfusion episodes in the 12-month period). In certain embodiments, the subject has undergone splenectomy. In certain embodiments, the subject has undergone splenectomy and is under regular transfusion. In certain embodiments, the subject has undergone splenectomy and is not under regular transfusion.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed (i.e., therapeutic treatment). In other embodiments, treatment may be administered in the absence of signs or symptoms of the disease. For example, treatment may be administered to a susceptible subject prior to the onset of symptoms (i.e., prophylactic treatment) (e.g., in light of a history of symptoms and/or in light of exposure to a pathogen). Treatment may also be continued after symptoms have resolved, for example, to delay or prevent recurrence. In certain embodiments, treatment includes delaying onset of at least one symptom of the disorder for a period of time.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, the effective amount is to generate a subject's hemoglobin response of ≥1.5 g/dL increase in Hb concentration from baseline. The subject's baseline Hb concentration is the average of all available Hb concentrations before the treatment with the compound. In certain embodiments, the effective amount is to generate a subject's hemoglobin response of ≥1.0 g/dL increase in Hb concentration from baseline. In certain embodiments, the effective amount is to generate a subject's hemoglobin response of ≥2.0 g/dL increase in Hb concentration from baseline. In certain embodiments, an effective amount is the amount of a compound described herein in a single dose. In certain embodiments, an effective amount is the combined amounts of a compound described herein in multiple doses. In certain embodiments, the effective amount is therapeutically effective amount.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for eliciting measurable activation of wild-type or mutant PKR. In certain embodiments, a therapeutically effective amount is an amount sufficient for regulating 2,3-diphosphoglycerate and/or ATP levels in blood in need thereof or for treating pyruvate kinase deficiency (PKD), hemolytic anemia (e.g., chronic hemolytic anemia, hereditary non-spherocytic anemia), sickle cell disease, thalassemia (e.g., beta-thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), anemia of chronic diseases or treating diseases or conditions that are associated with increased 2,3-diphosphoglycerate levels (e.g.; liver diseases). In certain embodiments, a therapeutically effective amount is an amount sufficient for eliciting measurable activation of wild-type or mutant PKR and for regulating 2,3-diphosphoglycerate levels in blood in need thereof or for treating pyruvate kinase deficiency (PKD), hemolytic anemia (e.g., chronic hemolytic anemia, hereditary non-spherocytic anemia), sickle cell disease, thalassemia (e.g., beta-thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), anemia of chronic diseases or treating diseases or conditions that are associated with increased 2,3-diphosphoglycerate levels (e.g., liver diseases). In one aspect, the therapeutically effective amount is the amount required to generate a subject's hemoglobin response of ≥1.0 g/dL (such as ≥1.5 g/dL or ≥2.0 g/dL) increase in Hb concentration from baseline. The subject's baseline Hb concentration is the average of all available Hb concentrations within at least two weeks (e.g. 3 weeks, 4 weeks, 5 weeks, or 6 weeks) before treatment with a compound described herein. In certain aspects, the therapeutically effective amount is the amount required to reduce the patient's transfusion burden. In one aspect, the therapeutically effective amount is between 0.01-100 mg/kg body weight/day of the provided compound, such as e.g., 0.1-100 mg/kg body weight/day. In certain embodiments, the therapeutically effective amount is to reduce the patient's transfusion burden.

As used herein, reduction in transfusion burden means at least 20% reduction in the number of RBC units transfused within at least 5 weeks of treatment. In certain embodiments, the reduction in transfusion burden is ≥33% reduction in the number of RBC units transfused within at least 5 weeks of treatment. In certain embodiments, reduction of transfusion burden is observed in at least 10 weeks (e.g., at least 20 weeks or at least 24 weeks) of treatment.

As used herein, sickle cell disease (SCD), Hemoglobin SS disease, and sickle cell anemia are used interchangeably. Sickle cell disease (SCD) describes a group of inherited red blood cell disorders. In certain embodiments, subjects with SCD have abnormal hemoglobin, called hemoglobin S or sickle hemoglobin, in their red blood cells. In certain embodiments, people having SCD have at least one abnormal genes causing the body to make hemoglobin S. In certain embodiments, people having SCD have two hemoglobin S genes, Hemoglobin SS.

Thalassemia is an inherited blood disorder in which the body makes an abnormal form of hemoglobin. In certain embodiments, the abnormal form of hemoglobin results in deficiency of either alpha or beta globin. In certain embodiments, the disorder results in large numbers of red blood cells being destroyed, which leads to anemia. In certain embodiments, the thalassemia is alpha thalassemia. In certain embodiments, the thalassemia is beta thalassemia.

The term "activator" as used herein means an agent that (measurably) increases the activity of wild type pyruvate kinase R (wt PKR) or causes wild type pyruvate kinase R (wt PKR) activity to increase to a level that is greater than wt PKR's basal levels of activity or an agent that (measurably) increases the activity of a mutant pyruvate kinase R (mPKR) or causes mutant pyruvate kinase R (mPKR) activity to increase to a level that is greater than that mutant PKR's basal levels of activity, for examples, to a level that is 20%, 40%, 50%, 60%, 70%, 80%, 90% or 100% of the activity of wild type PKR.

The term "packed red blood cells" or PRBCs as used herein refer to red blood cells made from a unit of whole blood by centrifugation and removal of most of the plasma. In certain embodiments, a PRBC unit has a hematocrit of at least about 95%. In certain embodiments, a PRBC unit has a hematocrit of at least about 90%, 80%, 70%, 60%, 50%, 40%, 30%, 20%, or 10%.

The term "ex vivo" referring to a method as used herein means that the method takes place outside an organism. For example, a cell (e.g., red blood cells), a tissue or blood (containing at least red blood cells, plasma and hemoglobin) may be extracted from the organism to be contacted with one or more compounds provided herein or a pharmaceutically acceptable salt thereof or a pharmaceutical composition thereof, optionally under artificially controlled conditions (e.g., temperature).

The term "in vitro" referring to a method as used herein means that the method takes place outside an organism and is contained within an artificial environment. For example, a cell (e.g., red blood cells), a tissue or blood (containing at least red blood cells, plasma and hemoglobin) may be extracted from the organism to be contacted with one or more compounds provided herein or a pharmaceutically acceptable salt thereof or a pharmaceutical composition thereof, in a contained, artificial environment (e.g., a culture system), such as in a test tube, in a culture, in flask, in a microtiter plate, on a Petri dish, and the like.

Compounds

Described herein are compounds and compositions that activate wild type PKR and/or mutant PKRs such as those described herein. In one embodiment, provided is a compound of Formulas (I)—(V), or a pharmaceutically acceptable salt thereof, or a pharmaceutical composition comprising a compound of Formulas (I)—(V), or a pharmaceutically acceptable salt thereof.

In a first embodiment of the invention, provided is a compound represented by Formula (I):

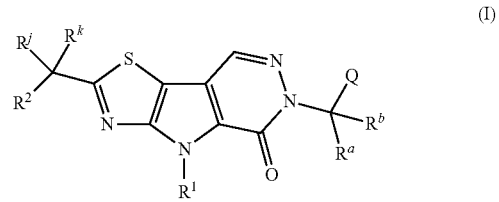

or a pharmaceutically acceptable salt thereof, wherein:
$R^1$ is hydrogen, an optionally substituted alkyl, an optionally substituted haloalkyl, an optionally substituted alkenyl, an optionally substituted alkynyl, an optionally substituted cycloalkyl, an optionally substituted heterocyclyl, an optionally substituted aryl, —$OR^{o1}$, —$C(=O)R^{c1}$, or a nitrogen protecting group; wherein:
$R^{o1}$ is hydrogen, optionally substituted alkyl, or an oxygen protecting group;
$R^{c1}$ is optionally substituted alkyl or —$N(R^{cn})_2$, wherein each instance of
$R^{cn}$ is independently hydrogen, —$C_{1-6}$ alkyl, or a nitrogen protecting group;
$R^2$ and Q are each independently an optionally substituted 5- or 6-membered monocyclic heteroaryl;
$R^a$ and $R^b$ are each independently hydrogen, a halogen, —CN, —$NO_2$, —$N_3$, an optionally substituted alkyl, —$OR^{o3}$, —$N(R^{n1})_2$, —$C(=O)N(R^{n1})_2$, or —$C(=O)R^{c2}$; or alternatively $R^a$ and $R^b$ can be taken together with the carbon atom to which they are attached to form an optionally substituted cycloalkyl or an optionally substituted heterocyclyl; wherein:

each instance of $R^{n1}$ is independently hydrogen, an optionally substituted —$C_1$-$C_6$ alkyl, or a nitrogen protecting group;

$R^{o3}$ is hydrogen, an optionally substituted —$C_1$-$C_6$ alkyl, or an oxygen protecting group; and $R^{c2}$ is an optionally substituted —$C_1$-$C_6$ alkyl; and $R^j$ and $R^k$ are each independently hydrogen, a halogen, —CN, —N($R^{n5}$)$_2$, —N($R^{n5}$)C(=O) $R^{c5}$, —C(=O)N ($R^{n5}$)$_2$, —C(=O)O$R^{c5}$, —C(=O)O$R^{o7}$, —S(=O)$_2R^{js}$, —S(=O)$R^{js}$, or an optionally substituted —$C_1$-$C_6$ alkyl; or alternatively $R^j$ and $R^k$ can be taken together with the carbon atom to which they are attached to form C=O, an optionally substituted $C_1$-$C_6$ monocyclic cycloalkyl ring, or an optionally substituted $C_3$-$C_6$ monocyclic heterocyclyl ring; wherein:

each instance of $R^{n5}$ is independently hydrogen, an optionally substituted —$C_1$-$C_6$ alkyl, —O$R^{o8}$, or a nitrogen protecting group, wherein $R^{o8}$ is hydrogen, an optionally substituted —$C_1$-$C_6$ alkyl, or an oxygen protecting group;

each instance of $R^{o7}$ is independently hydrogen, an optionally substituted —$C_1$-$C_6$ alkyl, or an oxygen protecting group;

each instance of $R^{c5}$ is independently an optionally substituted —$C_1$-$C_6$ alkyl; and each instance of $R^{js}$ is independently an optionally substituted —$C_1$-$C_6$ alkyl, an optionally substituted $C_{6-12}$ aryl, an optionally substituted heteroaryl, or a sulfur protecting group.

In a second embodiment of the invention, provided is a compound represented by Formula (I) or a pharmaceutically acceptable salt thereof, wherein the 5- or 6-membered monocyclic heteroaryl represented by $R^2$ is optionally substituted at each substitutable ring carbon atom by $R^p$ and optionally substituted at each substitutable ring nitrogen atom by $R^{n6}$; wherein:

each instance of $R^p$ is independently hydrogen, a halogen, —CN, —NO$_2$, —N$_3$, an optionally substituted alkyl, an optionally substituted alkenyl, an optionally substituted alkynyl, an optionally substituted cycloalkyl, an optionally substituted aryl, an optionally substituted heterocyclyl, an optionally substituted heteroaryl, —O$R^{o6}$, —S$R^{s2}$, —N($R^{n3}$)$_2$, —C(=O)N($R^{n3}$)$_2$, —N($R^{n3}$)C(=O)$R^{c4}$, —C(=O)$R^{c4}$, —C(=O)O$R^{o6}$, —OC(=O)$R^{c4}$, —S(=O)$R^{s2}$, —S(=O)$_2R^{s2}$, —S(=O)O$R^{o6}$, —OS(=O)$R^{c4}$, —S(=O)$_2$O$R^{c6}$, —OS(=O)$_2R^{c4}$, —S(=O)N($R^{n3}$)$_2$, —S(=O)$_2$N($R^{n3}$)$_2$, —N($R^{n3}$)S(=O)$R^{s2}$, —N($R^{n3}$)S(=O)$_2R^{s2}$, —N($R^{n3}$)C(=O)O$R^{o6}$, —OC(=O)N($R^{n3}$)$_2$, —N($R^{n3}$)C(=O)N($R^{n3}$)$_2$, —N($R^{n3}$)S(=O)N($R^{n3}$)$_2$, —N($R^{n3}$)S(=O)$_2$N($R^{n3}$)$_2$, —N($R^{n3}$)S(=O) O$R^{o6}$, —N($R^{n3}$)S(=O)$_2$O$R^{o6}$, —OS(=O)N($R^{n3}$)$_2$, or —OS(=O)$_2$N($R^{n3}$)$_2$, or alternatively two instances of $R^p$ attached to the same or adjacent carbon atoms, can be taken together with the carbon atom(s) to which they are attached to form an optionally substituted cycloalkyl or a heterocycloalkyl; wherein:

each instance of $R^{n3}$ is independently hydrogen, an optionally substituted —$C_1$-$C_6$ alkyl, or a nitrogen protecting group;

each instance of $R^{o6}$ is independently hydrogen, an optionally substituted —$C_1$-$C_6$ alkyl, or an oxygen protecting group; and each instance of $R^{c4}$ is an optionally substituted —$C_1$-$C_6$ alkyl;

each instance of $R^{s2}$ is independently an optionally substituted —$C_1$-$C_6$ alkyl or a sulfur protecting group; and $R^{n6}$ is hydrogen, an optionally substituted —$C_1$-$C_6$ alkyl, or a nitrogen protecting group;

wherein the remaining variables are as defined in the first embodiment.

In a third embodiment of the invention, provided is a compound represented by Formula (I) or a pharmaceutically acceptable salt thereof, wherein the 5- or 6-membered monocyclic heteroaryl represented by $R^2$ is selected from one of the following:

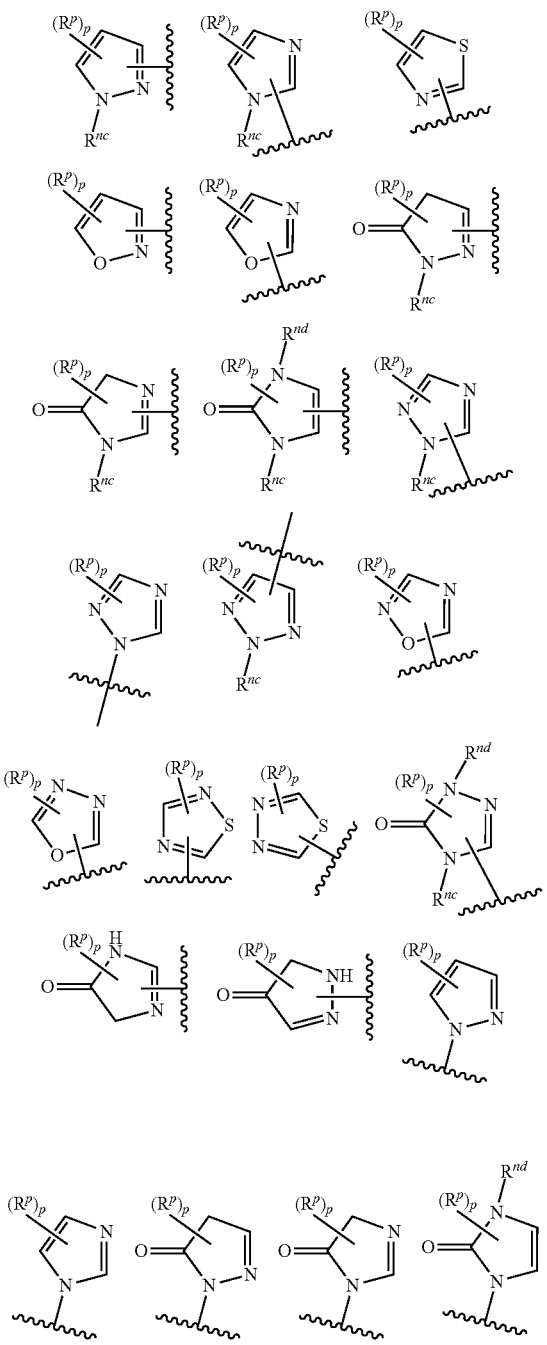

-continued

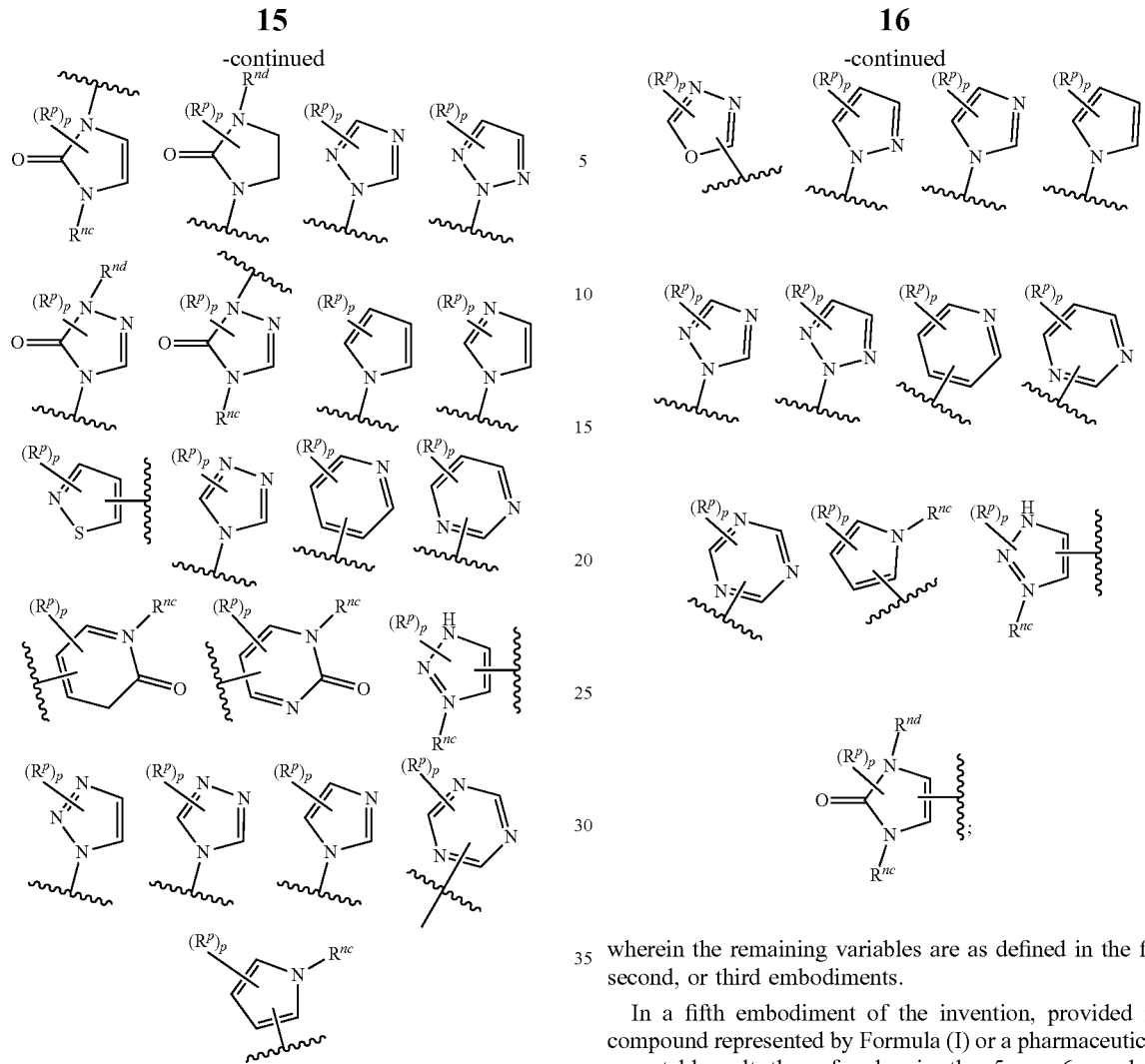

wherein:
each instance of $R^{nc}$ and $R^{nd}$ is independently hydrogen, optionally substituted —$C_1$-$C_6$ alkyl, or a nitrogen protecting group;
p is 0, 1, 2, 3, or 4, as valency permits;
wherein the remaining variables are as defined in the first or second embodiments.

In a fourth embodiment of the invention, provided is a compound represented by Formula (I) or a pharmaceutically acceptable salt thereof, wherein the 5- or 6-membered monocyclic heteroaryl represented by $R^2$ is selected from one of the following:

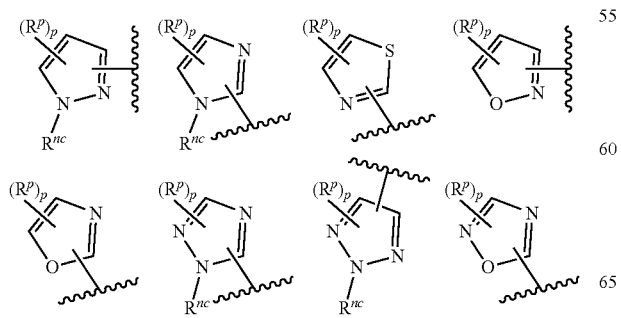

wherein the remaining variables are as defined in the first, second, or third embodiments.

In a fifth embodiment of the invention, provided is a compound represented by Formula (I) or a pharmaceutically acceptable salt thereof, wherein the 5- or 6-membered monocyclic heteroaryl represented by $R^2$ is selected from one of the following:

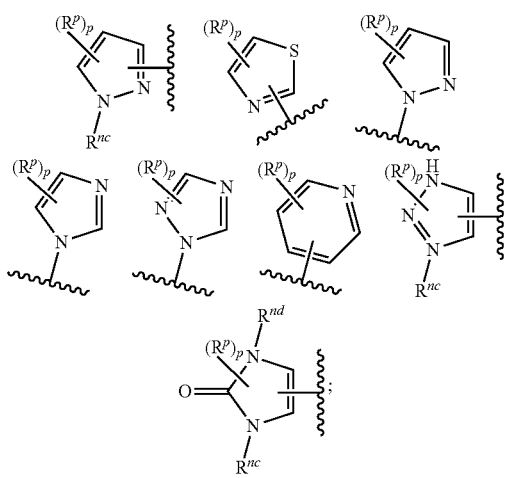

Wherein the remaining variables are as defined in the first, second, third, or fourth embodiments.

In a sixth embodiment of the invention, provided is a compound represented by Formula (II):

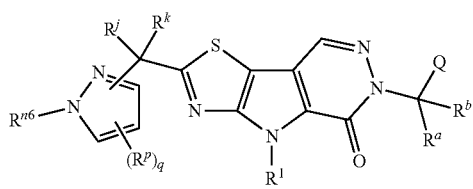
(II)

or a pharmaceutically acceptable salt thereof, wherein q is 0, 1, 2, or 3; wherein the remaining variables are as defined in the first, second, third, fourth, or fifth embodiments. In certain embodiments, provided is a compound represented by one of the following formulae:

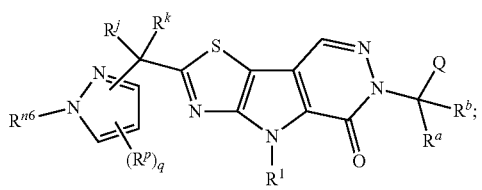
(II-a)

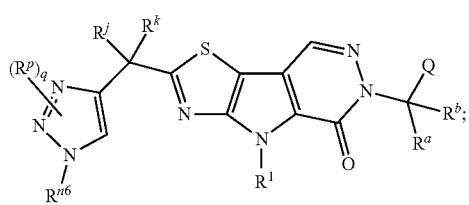
(II-b)

a pharmaceutically acceptable salt thereof.

In a seventh embodiment of the invention, provided is a compound represented by Formula (III):

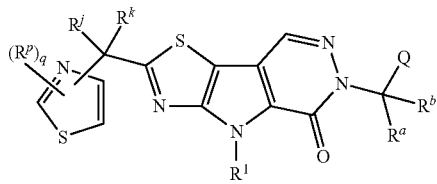
(III)

or a pharmaceutically acceptable salt thereof, wherein q is 0, 1, 2, or 3; wherein the remaining variables are as defined in the first, second, third, fourth, fifth, or sixth embodiments:

In an eighth embodiment of the invention, provided is a compound represented by Formula (IV):

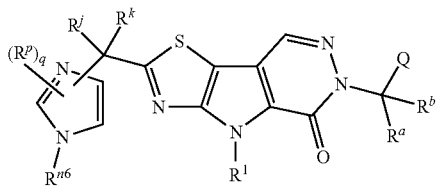
(IV)

or a pharmaceutically acceptable salt thereof, wherein q is 0, 1, 2, or 3; wherein the remaining variables are as defined in the first, second, third, fourth, fifth, sixth, or seventh embodiments.

In a ninth embodiment of the invention, provided is a compound represented by Formula (V):

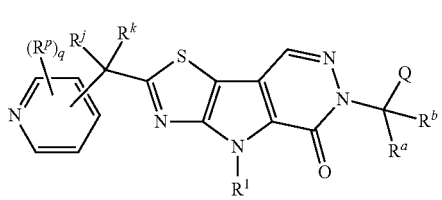
(V)

or a pharmaceutically acceptable salt thereof, wherein q is 0, 1, 2, or 3; wherein the remaining variables are as defined in the first, second, third, fourth, fifth, sixth, seventh, or eighth embodiments.

In a tenth embodiment of the invention, provided is a compound represented by Formula (II), (III), (IV), or (V) or a pharmaceutically acceptable salt thereof, wherein $R^{n6}$ is hydrogen or a —$C_{1-4}$ alkyl; wherein the remaining variables are as defined in the second, third, fourth, fifth, sixth, seventh, eighth, or ninth embodiments.

In an eleventh embodiment of the invention, provided is a compound represented by Formula (II), (III), (IV), or (V) or a pharmaceutically acceptable salt thereof, wherein each instance of $R^p$ is independently hydrogen, halogen, optionally substituted $C_{1-4}$ alkyl, —CN, —$NO_2$, —$N_3$, —$OR^{o4}$, —$N(R^{n2})_2$, —C(=O)N($R^{n2}$)$_2$, —C(=O)$R^{c3}$, or —C(=O)$OR^{o4}$; wherein the remaining variables are as defined in the second, third, fourth, fifth, sixth, seventh, eighth, ninth, or tenth embodiments.

In a twelfth embodiment of the invention, provided is a compound represented by Formula (I), (II), (III), (IV), or (V) or a pharmaceutically acceptable salt thereof, wherein the 5- or 6-membered monocyclic heteroaryl represented by Q is selected from the following:

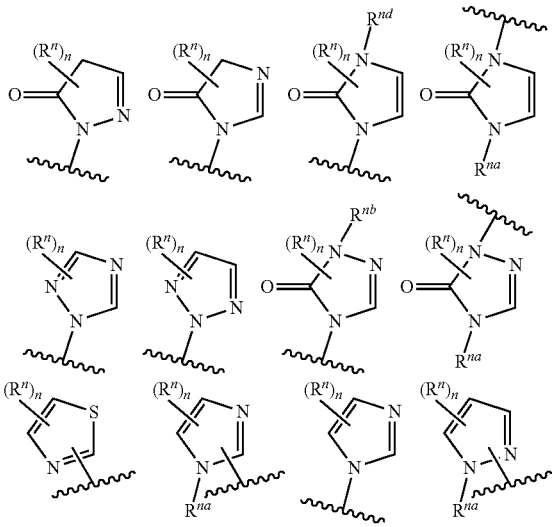

-continued

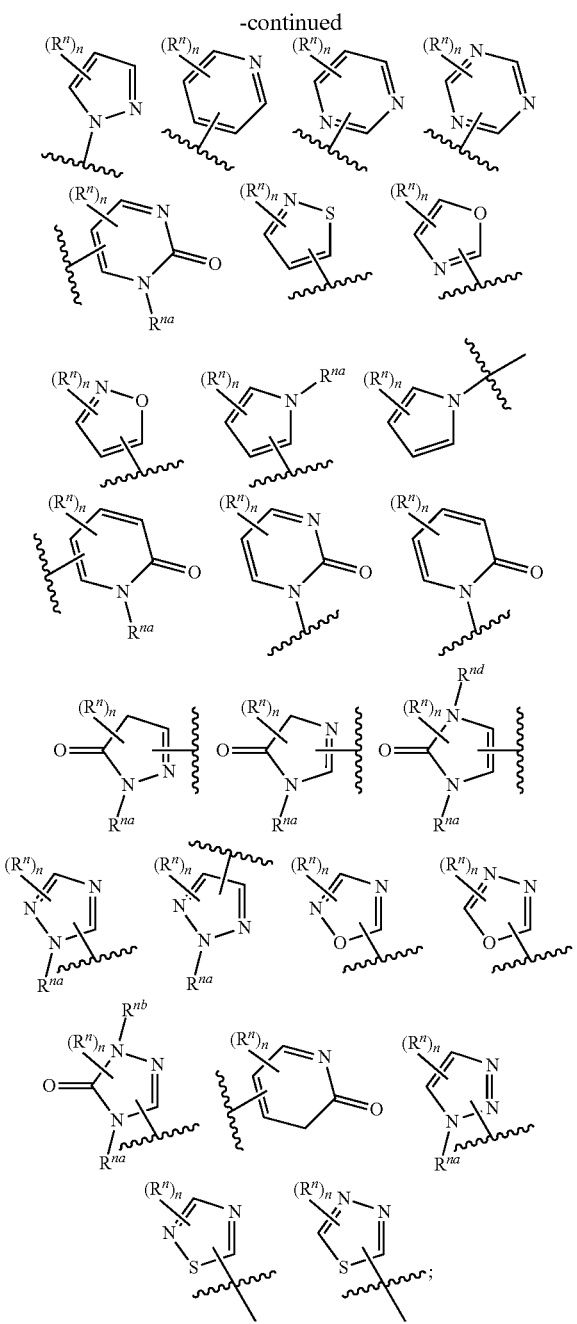

wherein:
each instance of R" is independently hydrogen, a halogen, —CN, —NO$_2$, —N$_3$, an optionally substituted alkyl, an optionally substituted alkenyl, an optionally substituted alkynyl, an optionally substituted cycloalkyl, an optionally substituted aryl, an optionally substituted heterocyclyl, an optionally substituted heteroaryl, —OR$^{o4}$, —SR$^{s1}$, —N(R$^{n2}$)$_2$, —C(=O)N(R$^{n2}$)$_2$, —N(R$^{n2}$)C(=O)R$^{n3}$, —C(=O)R$^{c3}$, —C(=O)OR$^{o4}$, —OC(=O)R$^{c3}$, —S(=O)R$^{s1}$, —S(=O)$_2$R$^{s1}$, —S(=O)OR$^{o4}$, —OS(=O)R$^{n3}$, —S(=O)$_2$OR$^{o4}$, —OS(=O)$_2$R$^{n3}$, —S(=O)N(R$^{n2}$)$_2$, —S(=O)$_2$N(R$^{n2}$)$_2$, —N(R$^{n2}$)S(=O)R$^{s1}$, —N(R$^{n2}$)S(=O)$_2$R$^{s1}$, —N(R$^{n2}$)C(=O)OR$^{o4}$, —OC(=O)N(R$^{n2}$)$_2$, —N(R$^{n2}$)C(=O)N(R$^{n2}$)$_2$, —N(R$^{n2}$)S(=O)N(R$^{n2}$)$_2$, —N(R$^{n2}$)S(=O)$_2$N(R$^{n2}$)$_2$, —N(R$^{n2}$)S(=O)OR$^{o4}$, —N(R$^{n2}$)S(=O)$_2$OR$^{o4}$, —OS(=O)N(R$^{n2}$)$_2$, or —OS(=O)$_2$N(R$^{n2}$)$_2$; or two instances of R" attached to the same or adjacent carbon atoms, taken together with the carbon atoms to which they are attached to form an optionally substituted cycloalkyl or a heterocycloalkyl; wherein:
  each instance of R$^{n2}$ is independently hydrogen, an optionally substituted —C$_1$-C$_6$ alkyl, or a nitrogen protecting group;
  each instance of R$^{o4}$ is independently hydrogen, an optionally substituted —C$_1$-C$_6$ alkyl, or an oxygen protecting group;
  each instance of R$^{c3}$ is independently an optionally substituted —C$_1$-C$_6$ alkyl;
  each instance of R$^{s1}$ is independently an optionally substituted —C$_1$-C$_6$ alkyl or a sulfur protecting group;
  n is 0, 1, 2, or 3, as valency permits; and
  each of R$^{na}$, R$^{nb}$, and R$^{nd}$ is independently hydrogen, an optionally substituted —C$_1$-C$_6$ alkyl, or a nitrogen protecting group.
wherein the remaining variables are as defined in the first, second, third, fourth, fifth, sixth, seventh, eighth, ninth, tenth, or eleventh embodiments.

In a thirteenth embodiment of the invention, provided is a compound represented by Formula (I), (II), (III), (IV), or (V) or a pharmaceutically acceptable salt thereof, wherein the 5- or 6-membered monocyclic heteroaryl represented by Q is selected from the following:

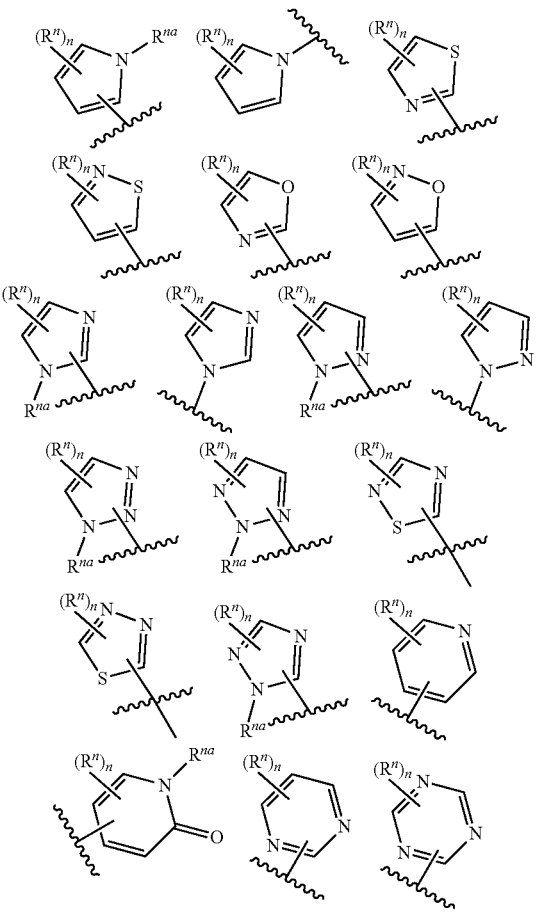

-continued

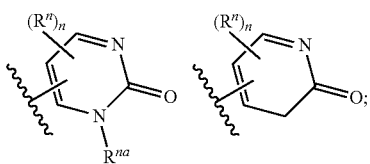

wherein the remaining variables are as defined in the first, second, third, fourth, fifth, sixth, seventh, eighth, ninth, tenth, eleventh, or twelfth embodiments.

In a fourteenth embodiment of the invention, provided is a compound represented by Formula (I), (II), (III), (IV), or (V) or a pharmaceutically acceptable salt thereof, wherein the 5- or 6-membered monocyclic heteroaryl represented by Q is selected from the following:

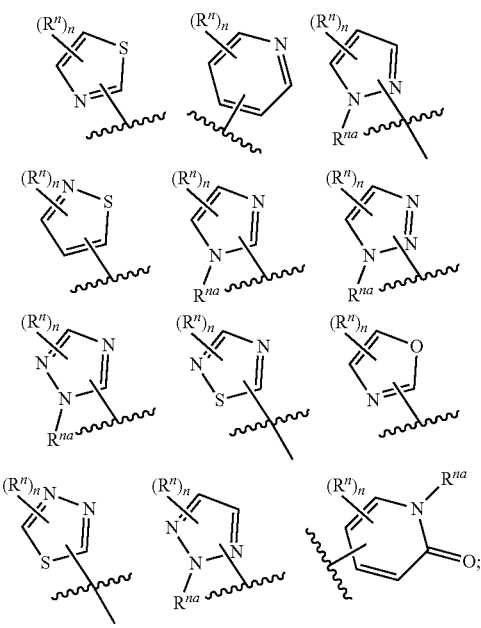

wherein the remaining variables are as defined in the first, second, third, fourth, fifth, sixth, seventh, eighth, ninth, tenth, eleventh, twelfth, or thirteenth embodiments.

In a fifteenth embodiment of the invention, provided is a compound represented by Formula (I), (II), (III), (IV), or (V) or a pharmaceutically acceptable salt thereof, wherein Q is

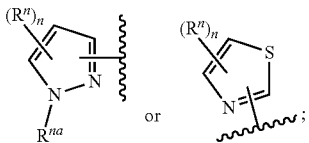

wherein the remaining variables are as defined in the first, second, third, fourth, fifth, sixth, seventh, eighth, ninth, tenth, eleventh, twelfth, thirteenth, or fourteenth embodiments. In further embodiments, provided is a compound represented by Formula (I), (II), (III), (IV), or (V) or a pharmaceutically acceptable salt thereof, wherein Q is

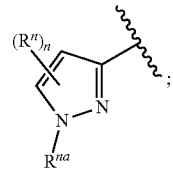

wherein the remaining variables are as defined in the first, second, third, fourth, fifth, sixth, seventh, eighth, ninth, tenth, eleventh, twelfth, thirteenth, or fourteenth embodiments.

In a sixteenth embodiment of the invention, provided is a compound represented by Formula (I), (II), (III), (IV), or (V) or a pharmaceutically acceptable salt thereof, wherein Q is

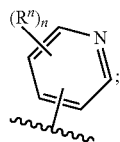

wherein the remaining variables are as defined in the first, second, third, fourth, fifth, sixth, seventh, eighth, ninth, tenth, eleventh, twelfth, thirteenth, or fourteenth embodiments. In further embodiments, provided is a compound represented by Formula (I), (II), (III), (IV), or (V) or a pharmaceutically acceptable salt thereof, wherein Q is

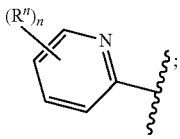

wherein the remaining variables are as defined in the first, second, third, fourth, fifth, sixth, seventh, eighth, ninth, tenth, eleventh, twelfth, thirteenth, or fourteenth embodiments. In certain embodiments, $R^2$ and Q are the same. In certain embodiments, $R^2$ and Q are different.

In a seventeenth embodiment of the invention, provided is a compound represented by Formula (I), (II), (III), (IV), or (V) or a pharmaceutically acceptable salt thereof, wherein $R^{na}$ is hydrogen or —$C_{1-4}$ alkyl; wherein the remaining variables are as twelfth, thirteenth, fourteenth, or fifteenth embodiments.

In a seventeenth embodiment of the invention, provided is a compound represented by Formula (I), (II), (III), (IV), or (V) or a pharmaceutically acceptable salt thereof, wherein $R^{nb}$ is hydrogen or —$C_{1-4}$ alkyl; wherein the remaining variables are as twelfth, thirteenth, fourteenth, or fifteenth embodiments.

In a seventeenth embodiment of the invention, provided is a compound represented by Formula (I), (II), (III), (IV), or (V) or a pharmaceutically acceptable salt thereof, wherein $R^{nd}$ is hydrogen or —$C_{1-4}$ alkyl; wherein the remaining variables are as twelfth, thirteenth, fourteenth, or fifteenth embodiments.

In an eighteenth embodiment of the invention, provided is a compound represented by Formula (I), (II), (III), (IV), or (V) or a pharmaceutically acceptable salt thereof, wherein each instance of $R^n$ is independently hydrogen, halogen, optionally substituted $C_{1-4}$ alkyl, —CN, —$NO_2$, —$N_3$, —OR$^{o4}$, —N(R$^{n2}$)$_2$, —C(=O)N(R$^{n2}$)$_2$, C(=O)R$^{c3}$, or —C(=O)OR$^{o4}$; wherein the remaining variables are as defined in the twelfth, thirteenth, fourteenth, fifteenth, sixteenth, or seventeenth embodiments.

In a nineteenth embodiment of the invention, provided is a compound represented by Formula (I), (II), (III), (IV), or (V) or a pharmaceutically acceptable salt thereof, wherein R' is hydrogen or a —C$_1$-C$_4$ alkyl; wherein the remaining variables are as defined in the first, second, third, fourth, fifth, sixth, seventh, eighth, ninth, tenth, eleventh, twelfth, thirteenth, fourteenth, fifteenth, sixteenth, seventeenth, or eighteenth embodiments.

In a twentieth embodiment of the invention, provided is a compound represented by Formula (I), (II), (III), (IV), or (V) or a pharmaceutically acceptable salt thereof, wherein R$^1$ is methyl; wherein the remaining variables are as defined in the first, second, third, fourth, fifth, sixth, seventh, eighth, ninth, tenth, eleventh, twelfth, thirteenth, fourteenth, fifteenth, sixteenth, seventeenth, or eighteenth embodiments.

In a twenty-first embodiment of the invention, provided is a compound represented by Formula (I), (II), (III), (IV), or (V) or a pharmaceutically acceptable salt thereof, wherein R$^j$ and R$^k$ are each independently hydrogen, a halogen, —OR$^{o7}$, or a —C$_1$-C$_4$ alkyl; or alternatively R$^j$ and R$^k$ are joined together to form =O wherein the remaining variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, or twentieth embodiments.

In a twenty-second embodiment of the invention, provided is a compound represented by Formula (I), (II), (III), (IV), or (V) or a pharmaceutically acceptable salt thereof, wherein R$^j$ and R$^k$ are each hydrogen; wherein the remaining variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, or twenty-first embodiments.

In a twenty-third embodiment of the invention, provided is a compound represented by Formula (I), (II), (III), (IV), or (V) or a pharmaceutically acceptable salt thereof, wherein R$^a$ and R$^b$ are each hydrogen; wherein the remaining variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, or twenty-second embodiments.

In a twenty-fourth embodiment of the invention, provided is a compound represented by Formula (I), (II), (III), (IV), or (V) or a pharmaceutically acceptable salt thereof, wherein q is 0 or 1; wherein the remaining variables are as defined in the fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, or twenty-third embodiments.

In a twenty-fifth embodiment of the invention, provided is a compound represented by Formula (I), (II), (III), (IV), or (V) or a pharmaceutically acceptable salt thereof, wherein n is 0 or 1; wherein the remaining variables are as defined in the twelfth, thirteenth, fourteenth, fifteenth, sixteenth, seventeenth, eighteenth, nineteenth, twentieth, twenty-first, twenty-second, twenty-third, or twenty-fourth embodiments.

In one embodiment, the compound of pharmaceutically acceptable salt thereof is selected from the compounds of Formulas (I)—(V), in the Examples, and in Table 1 and FIG. 1.

Compounds described herein are useful as activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, R479H, R479K, R486W, R532W, K410E, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Examples 11-17. Compounds described herein are also useful as activators of wild type PKR.

In an embodiment, to increase the lifetime of the red blood cells, a compound, composition or pharmaceutical composition described herein is added directly to whole blood or packed red blood cells extracorporeally or be provided to the patient directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the level of 2,3-DPG and/or ATP from the blood. A decrease in the level of 2, 3-DPG concentration induces a leftward shift of the oxygen-hemoglobin dissociation curve and shifts the allosteric equilibrium to the R, or oxygenated state, thus producing a therapeutic inhibition of the intracellular polymerization that underlies sickling by increasing oxygen affinity due to the 2,3-DPG depletion, thereby stabilizing the more soluble oxy-hemoglobin. Accordingly, in one embodiment, compounds and pharmaceutical compositions described herein are useful as antisickling agents. In another embodiment, to regulate 2,3-diphosphoglycerate, a compound, composition or pharmaceutical composition described herein is added directly to whole blood or packed red blood cells extracorporeally or be provided to the patient directly (e.g., by i.p., i.v., i.m., oral, inhalation (aerosolized delivery), transdermal, sublingual and other delivery routes). In another embodiment, a compound, composition or pharmaceutical composition described herein can increase the level of ATP and help to protect the cells from reactive oxygen species (Mol Cell. 2012 Oct. 26; 48(2): 158-167).

In Table 1, a compound described herein may have an AC$_{50}$ of wild type PKR, PKR K410E or PKR 510Q. "A" refers to an AC$_{50}$ less than 0.300 µM; "B" refers to an AC$_{50}$ from 0.301 µM to 0.800 µM; and "C" refers to an AC$_{50}$ greater than 0.800 µM. The AC$_{50}$ of wild type PKR for certain compounds was additionally determined in a cell-based ATP assay. "AA" refers to an AC$_{50}$ less than or equal to 1 µM and "BB" refers to an AC$_{50}$ more than 1 µM.

TABLE 1

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| | A | A | A | AA |
| | A | A | A | AA |
| | A | A | A | AA |
| | A | A | A | AA |
| | A | A | A | AA |
| | A | A | A | AA |
| | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| | A | A | A | AA |
| | A | A | A | AA |
| | A | A | A | AA |
| | A | A | A | AA |
| | A | A | A | AA |
| | A | A | A | AA |
| | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| (structure) | A | A | A | AA |
| (structure) | A | A | A | AA |
| (structure) | A | A | A | AA |
| (structure) | A | A | A | AA |
| (structure) | A | A | A | AA |
| (structure) | A | A | A | AA |
| (structure) | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| [structure] | A | A | A | AA |
| [structure] | A | A | A | AA |
| [structure] | A | A | A | AA |
| [structure] | A | A | A | AA |
| [structure] | A | A | A | AA |
| [structure] | A | A | A | AA |
| [structure] | A | A | A | AA |
| [structure] | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| | A | A | A | AA |
| | C | C | C | BB |
| | A | A | A | AA |
| | A | A | A | AA |
| | A | A | A | AA |
| | A | A | A | AA |
| | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| (structure) | B | A | A | AA |
| (structure) | A | A | A | AA |
| (structure) | A | A | A | AA |
| (structure) | A | A | A | AA |
| (structure) | A | A | A | AA |
| (structure) | A | A | A | AA |
| (structure) | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| (structure) | A | A | A | AA |
| (structure) | A | A | A | AA |
| (structure) | A | A | A | AA |
| (structure) | A | A | A | AA |
| (structure) | A | A | A | AA |
| (structure) | A | A | A | AA |
| (structure) | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| (structure) | A | A | A | AA |
| (structure) | A | A | A | AA |
| (structure) | A | A | A | AA |
| (structure) | A | A | A | AA |
| (structure) | A | A | A | AA |
| (structure) | A | A | A | AA |
| (structure) | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| | A | A | A | AA |
| | A | A | A | AA |
| | A | A | A | AA |
| | A | A | A | AA |
| | A | A | A | AA |
| | A | A | A | AA |
| | C | C | C | BB |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| (structure) | A | A | A | AA |
| (structure) | A | A | A | AA |
| (structure) | A | A | A | AA |
| (structure) | A | A | A | AA |
| (structure) | A | A | A | AA |
| (structure) | A | A | A | AA |
| (structure) | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| (structure) | A | A | A | AA |
| (structure) | A | A | A | AA |
| (structure) | A | A | A | AA |
| (structure) | A | A | A | AA |
| (structure) | A | A | A | AA |
| (structure) | C | C | C | BB |
| (structure) | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| (structure) | A | A | A | AA |
| (structure) | A | A | A | AA |
| (structure) | A | A | A | AA |
| (structure) | A | A | A | AA |
| (structure) | A | A | A | AA |
| (structure) | A | A | A | AA |
| (structure) | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| (structure) | A | A | A | AA |
| (structure) | A | A | A | AA |
| (structure) | A | A | A | AA |
| (structure) | A | A | A | AA |
| (structure) | A | A | A | AA |
| (structure) | B | B | C | BB |
| (structure) | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| (structure) | A | A | A | AA |
| (structure) | A | A | A | AA |
| (structure) | A | A | A | AA |
| (structure) | A | A | A | AA |
| (structure) | A | A | A | AA |
| (structure) | C | C | C | BB |
| (structure) | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| (structure) | A | A | A | AA |
| (structure) | A | A | A | AA |
| (structure) | A | A | A | AA |
| (structure) | A | A | B | AA |
| (structure) | A | A | A | AA |
| (structure) | A | A | A | AA |
| (structure) | A | A | A | AA |

TABLE 1-continued

Activation of wild type and mutant PKR by exemplary compounds

| Compound | PKR WT AC$_{50}$ | PKR K410E AC$_{50}$ | PKR R510Q AC$_{50}$ | Cell based ATP assay AC$_{50}$ |
|---|---|---|---|---|
| *(structure)* | A | A | A | AA |
| *(structure)* | A | A | A | AA |
| *(structure)* | C | C | A | BB |
| *(structure)* | A | A | A | AA |
| *(structure)* | A | A | A | AA |
| *(structure)* | A | A | A | AA |
| *(structure)* | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| (structure) | A | A | A | AA |
| (structure) | A | A | A | AA |
| (structure) | A | A | A | AA |
| (structure) | A | A | A | AA |
| (structure) | A | A | A | AA |
| (structure) | A | A | B | AA |
| (structure) | A | A | B | BB |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| (structure) | A | A | A | AA |
| (structure) | A | A | A | AA |
| (structure) | A | A | A | AA |
| (structure) | A | A | A | AA |
| (structure) | A | A | A | AA |
| (structure) | A | A | A | AA |
| (structure) | A | A | A | AA |

TABLE 1-continued
Activation of wild type and mutant PKR by exemplary compounds
| Compound | PKR WT AC$_{50}$ | PKR K410E AC$_{50}$ | PK R510Q AC$_{50}$ | Cell based ATP assay AC$_{50}$ |
|---|---|---|---|---|
| 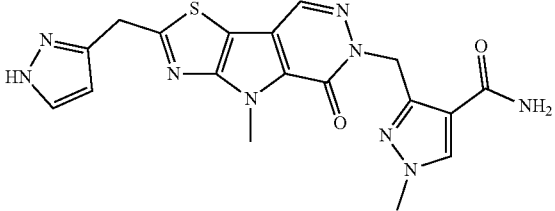 [SMILES: Cn1cc(C(N)=O)c(Cn2ncc3c4sc(Cc5cc[nH]n5)nc4n(C)c3c2=O)n1] | C | B | C | BB |
| 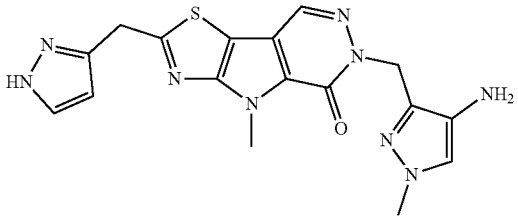 [SMILES: Cn1cc(N)c(Cn2ncc3c4sc(Cc5cc[nH]n5)nc4n(C)c3c2=O)n1] | A | A | A | AA |
| 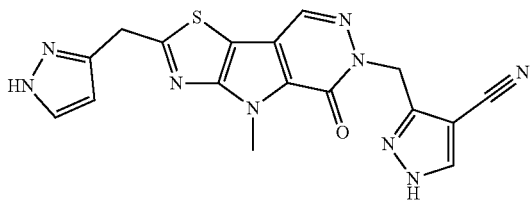 [SMILES: Cn1c2nc(Cc3cc[nH]n3)sc2c2cnn(Cc3n[nH]cc3C#N)c(=O)c21] | A | A | A | AA |
| 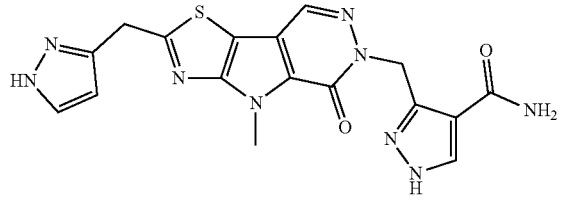 [SMILES: Cn1c2nc(Cc3cc[nH]n3)sc2c2cnn(Cc3n[nH]cc3C(N)=O)c(=O)c21] | A | A | A | AA |
| 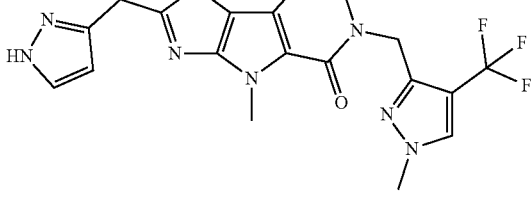 | A | A | A | AA |
| 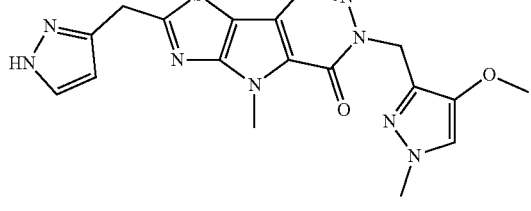 | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| | A | A | A | AA |
| | A | A | A | AA |
| | A | A | A | AA |
| | A | A | A | AA |
| | A | A | A | AA |
| | A | A | A | AA |
| | B | A | A | AA |

TABLE 1-continued
Activation of wild type and mutant PKR by exemplary compounds
| Compound | PKR WT AC$_{50}$ | PKR K410E AC$_{50}$ | PK R510Q AC$_{50}$ | Cell based ATP assay AC$_{50}$ |
|---|---|---|---|---|
| 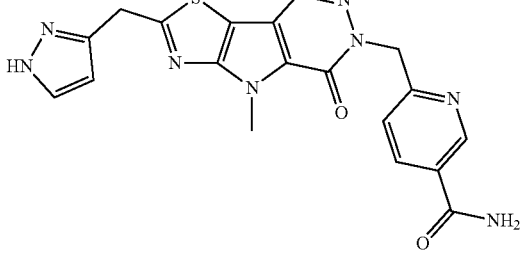 | B | A | C | AA |
| 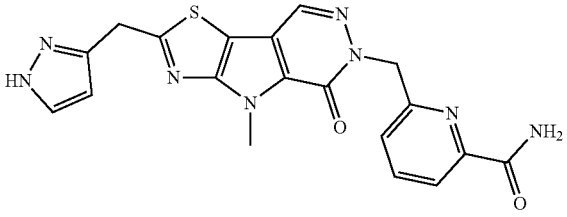 [SMILES: Cn1c2nc(Cc3cc[nH]n3)sc2c2cnn(Cc3cccc(C(N)=O)n3)c(=O)c21] | A | A | A | AA |
| 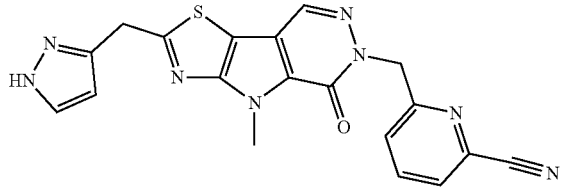 [SMILES: Cn1c2nc(Cc3cc[nH]n3)sc2c2cnn(Cc3cccc(C#N)n3)c(=O)c21] | A | A | A | AA |
| 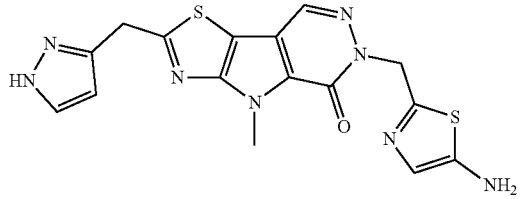 [SMILES: Cn1c2nc(Cc3cc[nH]n3)sc2c2cnn(Cc3ncc(N)s3)c(=O)c21] | A | A | A | AA |
| 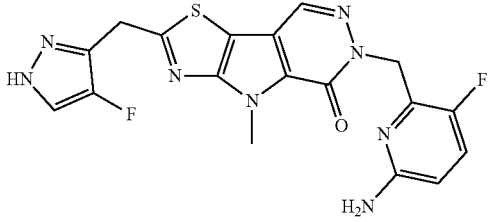 | A | A | A | AA |
| 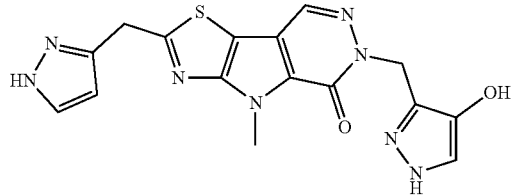 [SMILES: Cn1c2nc(Cc3cc[nH]n3)sc2c2cnn(Cc3n[nH]cc3O)c(=O)c21] | A | A | A | AA |

TABLE 1-continued
Activation of wild type and mutant PKR by exemplary compounds
| Compound | PKR WT AC$_{50}$ | PKR K410E AC$_{50}$ | PK R510Q AC$_{50}$ | Cell based ATP assay AC$_{50}$ |
|---|---|---|---|---|
| 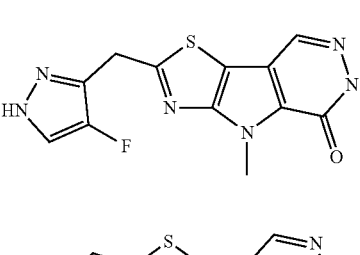 | A | A | A | AA |
| 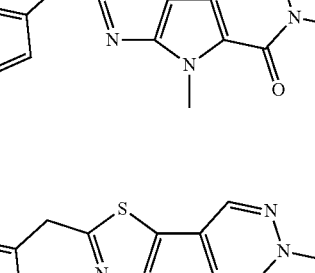 | A | A | A | AA |
| 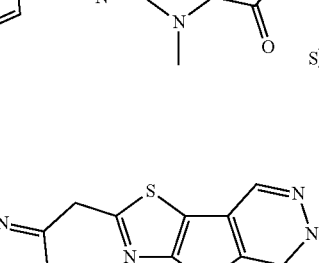 | A | A | A | AA |
| 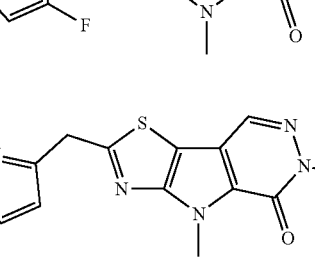 | A | A | A | AA |
| 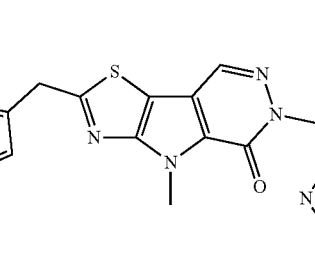 | A | A | A | AA |
|  | A | A | B | AA |
|  | A | A | A | AA |

TABLE 1-continued
Activation of wild type and mutant PKR by exemplary compounds
| Compound | PKR WT AC$_{50}$ | PKR K410E AC$_{50}$ | PK R510Q AC$_{50}$ | Cell based ATP assay AC$_{50}$ |
|---|---|---|---|---|
| 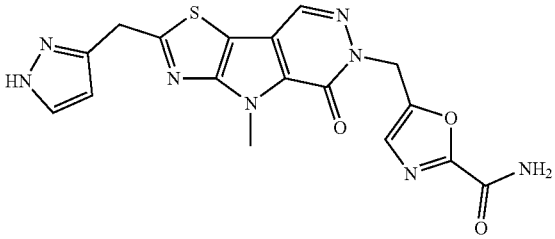 [SMILES: Cn1c2nc(Cc3cc[nH]n3)sc2c2cnn(Cc3cnc(C(N)=O)o3)c(=O)c21] | B | B | B | BB |
| 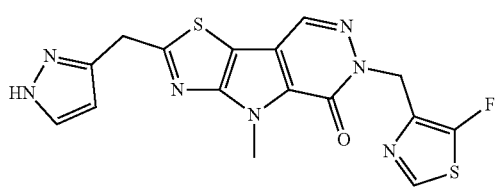 [SMILES: Cn1c2nc(Cc3cc[nH]n3)sc2c2cnn(Cc3ncsc3F)c(=O)c21] | A | A | A | AA |
| 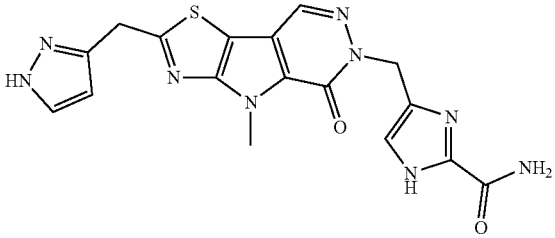 [SMILES: Cn1c2nc(Cc3cc[nH]n3)sc2c2cnn(Cc3c[nH]c(C(N)=O)n3)c(=O)c21] | A | A | A | AA |
| 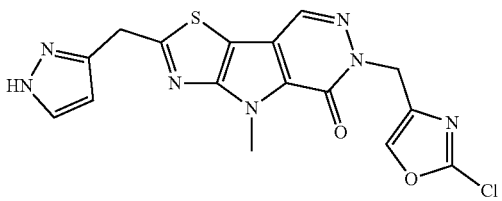 [SMILES: Cn1c2nc(Cc3cc[nH]n3)sc2c2cnn(Cc3coc(Cl)n3)c(=O)c21] | A | A | A | AA |
| 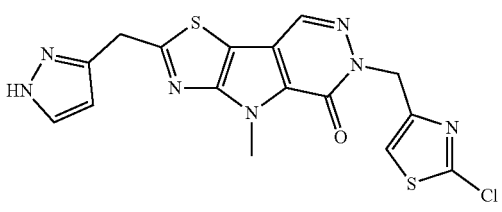 | A | A | A | AA |
| 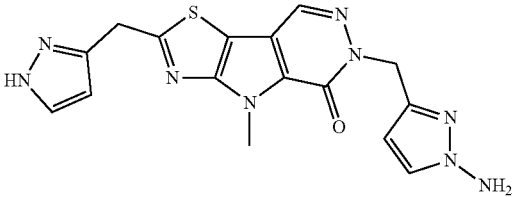 | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| | C | C | C | BB |
| | A | A | A | AA |
| | B | B | B | BB |
| | A | A | A | AA |
| | C | C | A | BB |
| | C | C | C | BB |
| | B | B | C | BB |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| (structure) | A | A | A | AA |
| (structure) | A | A | A | AA |
| (structure) | C | C | C | BB |
| (structure) | C* | C* | C* | AA |
| (structure) | B | B | A | BB |
| (structure) | B | B | B | BB |
| (structure) | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| (structure) | A | B | A | AA |
| (structure) | A | A | A | AA |
| (structure) | A | A | A | AA |
| (structure) | C | C | C | BB |
| (structure) | A | A | A | AA |
| (structure) | A | A | A | AA |
| (structure) | A | A | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| (structure) | A | A | A | AA |
| (structure) | A | A | A | AA |
| (structure) | C | C | C | BB |
| (structure) | C* | C* | C* | AA |
| (structure) | B* | A* | A* | AA |
| (structure) | C | C | C | BB |
| (structure) | B | B | A | AA |

TABLE 1-continued

Activation of wild type and mutant PKR by exemplary compounds

| Compound | PKR WT AC$_{50}$ | PKR K410E AC$_{50}$ | PK R510Q AC$_{50}$ | Cell based ATP assay AC$_{50}$ |
|---|---|---|---|---|
| | C | C | C | No Fit |
| | C | C | C | No Fit |
| | No Fit | No Fit | No Fit | No Fit |
| | A | A | A | AA |
| | A | A | A | AA |
| | B | C | B | AA |

\* indicates the value is based on the average of multiple tested results.

The compounds described herein can be made using a variety of synthetic techniques as set forth in the Examples. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Certain activator compounds useful as PKR wild type and/or mutant activators are those that demonstrate specificity and activation of PKR enzyme (wild type and/or a mutant enzyme) in the absence of FBP to a level greater than that of 10, 15, 20, 25, 30, 35, 40, 45, 50, 55, 60, 65, 70, 75, 80, 85, 90, 95, 99, or 100% in the presence of FBP.

Synthesis of the Compounds of the Invention

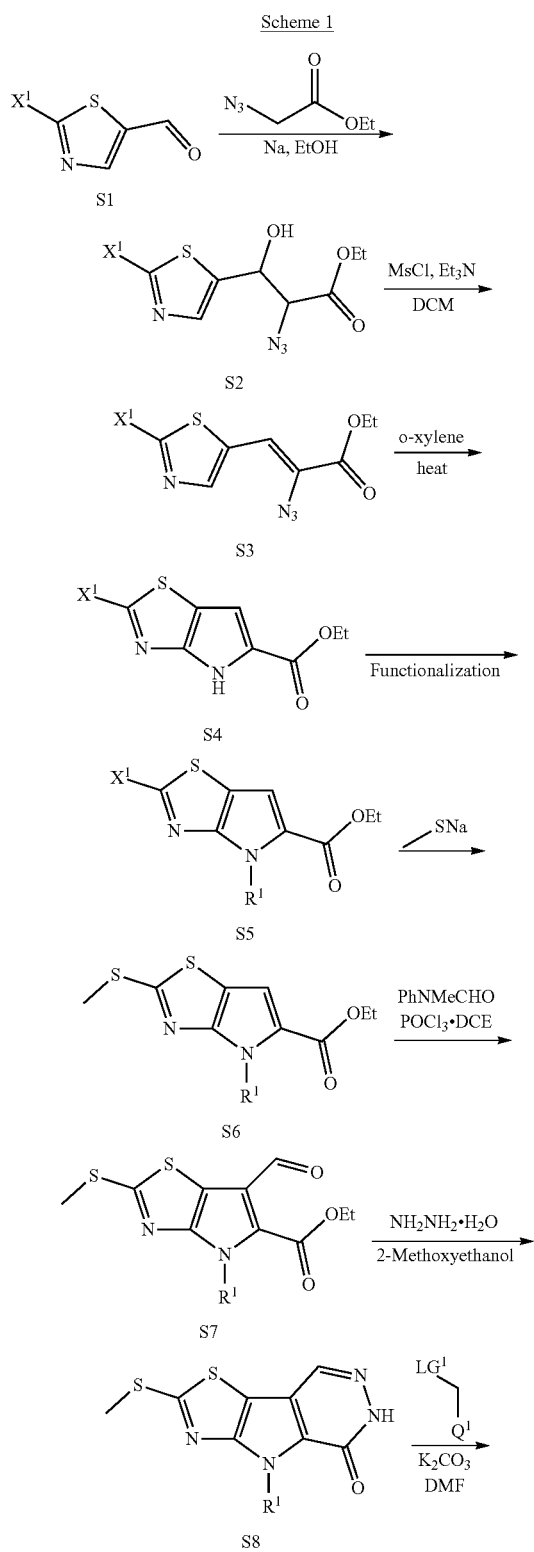

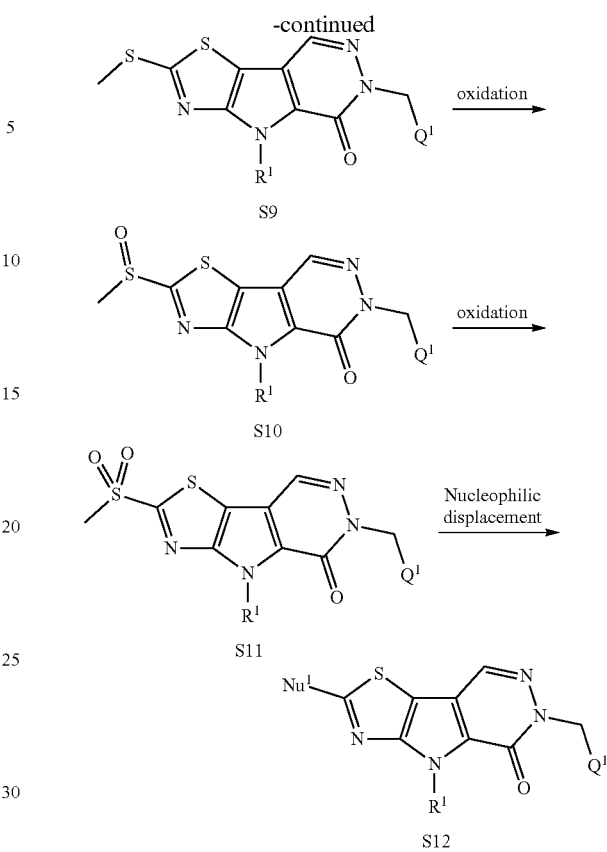

In some embodiments, compounds of Formula (I) can be prepared using methods illustrated in Scheme 1. Thiazolyl aldehyde of formula S1 reacts with ethyl azidoacetate under nucleophilic addition conditions (e.g. a base) in an appropriate solvent (e.g. ethanol) to give intermediates of formula S2. The hydroxyl group of formula S2 can be converted to a leaving group and subject to elimination to give formula S3. Cyclization and subsequent functionalization of the amino group provides bicyclic compound of formula S5, which undergoes nucleophilic displacement with sodium methanethiolate, followed by oxidation to give formula S7. Further cyclization of formula S7 in the presence of hydrazine, followed by nucleophilic displacement with $LG^1$-$CH_2$-$Q^1$ in the presence of a base provides intermediates of formula S9. The sulfur group in formula S9 can be oxidized to sulfinyl or sulfonyl to provide formula S10 or S11, which is a substrate for further nucleophilic displacement to generate a general formula S12. As used herein, $X^1$ is a leaving group as defined herein. In certain embodiments, $X^1$ is halogen, alkanesulfonyloxy, arenesulfonyloxy, diazonium, alkyl diazenes, aryl diazenes, alkyl triazenes, aryl triazenes, nitro, alkyl nitrate, aryl nitrate, alkyl phosphate, aryl phosphate, alkyl carbonyl oxy, aryl carbonyl oxy, alkoxcarbonyl oxy, aryoxcarbonyl oxy ammonia, alkyl amines, aryl amines, hydroxyl group, alkyloxy group, aryloxy group; $LG^1$ is a leaving group as defined herein; $Q^1$ is optionally substituted cycloalkyl, optionally substituted heterocyclyl, optionally substituted aryl, or optionally substituted heteroaryl (e.g. optionally substituted 5- or 6-membered monocyclic heteroaryl); and $Nu^1$ is a nucleophile as defined herein (e.g. optionally substituted 5- or 6-membered monocyclic heteroaryl alkylene). $Nu^1$ of compound of formula S12 can be further converted to other functionalities with standard Scheme 2

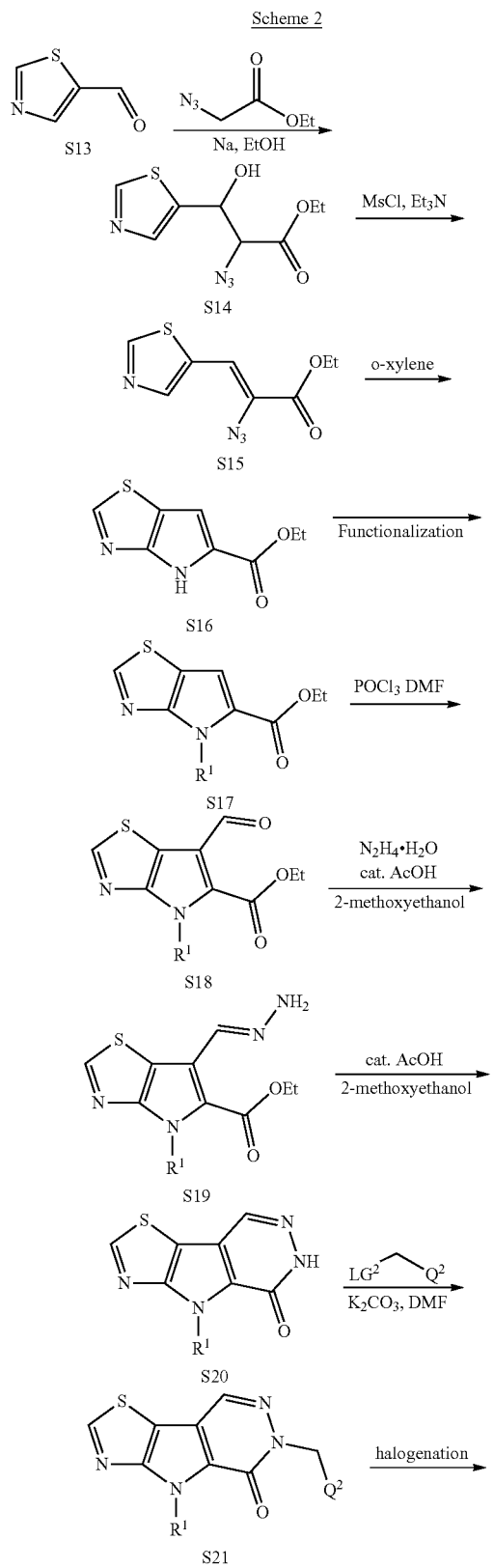

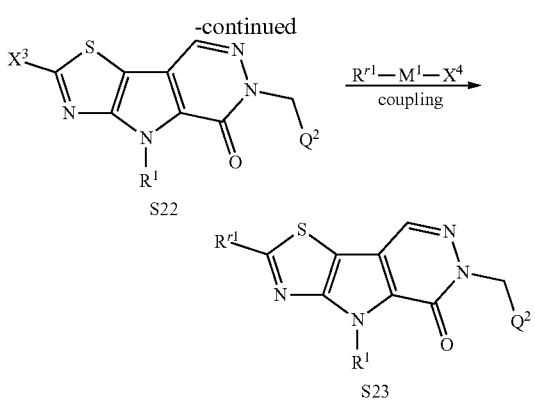

In some embodiments, compounds of Formula (I) can be prepared using methods shown in Scheme 2. Similar to Scheme 1, formula S21 can be prepared from thiazole aldehyde of formula S13. Halogenation of formula S21 gives formula S22, which can undergo an organo coupling reaction with an alkyl metal, alkenyl metal, alkynyl metal, aryl metal, heteroaryl metal, heterocyclyl metal, or cycloalkyl metal to give a compound of formula S23. As used herein, $X^3$ is a halogen; $R^1$ is as defined in the first embodiment of the invention; $LG^2$ is a leaving group as defined herein; $Q^2$ is optionally substituted cycloalkyl, optionally substituted heterocyclyl, optionally substituted aryl, or optionally substituted heteroaryl (e.g. optionally substituted 5- or 6-membered monocyclic heteroaryl); $M^1$ is a metal (e.g. Li, Na, K, Mg, Zn, Sn, B, Pd, Si, Cu etc.), $X^4$ is halogen or alkyl sulfonic acid ester or an aryl sulfonic acid ester; $R^{r1}$ is optionally substituted alkyl, optionally substituted alkenyl, optionally substituted alkynyl, optionally substituted cycloalkyl, optionally substituted heterocyclyl, optionally substituted aryl, or optionally substituted heteroaryl. In certain embodiments, the organo coupling reaction is Negishi reaction; $X^3$ is I; and $M^1$ is Zn.

Compounds of formula S22 and S23 are useful intermediates to introduce more functionalities at $X^3$ and/or $R^{r1}$ position (Scheme 3). In certain embodiments, the compound of formula 23-i can be further oxidized to form formula S24. Nucleophilic addition of S24 with an appropriate nucleophile generates a compound of S25. In another embodiment, compounds of formula S22 can be coupled with vinyl metal to introduce the vinyl group to the thiazole ring. Oxidation of the vinyl group followed by nucleophilic addition provides a compound of formula S28. As used herein, $Nu^t$ is a nucleophile. In certain embodiments, $R^{r1}$ is optionally substituted 5- or 6-membered monocyclic heteroarylalkylene and $Q^2$ is optionally substituted 5- or 6-membered monocyclic heteroaryl.

Scheme 3

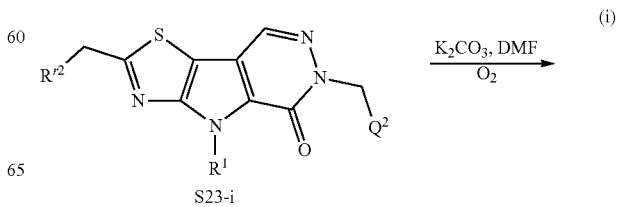

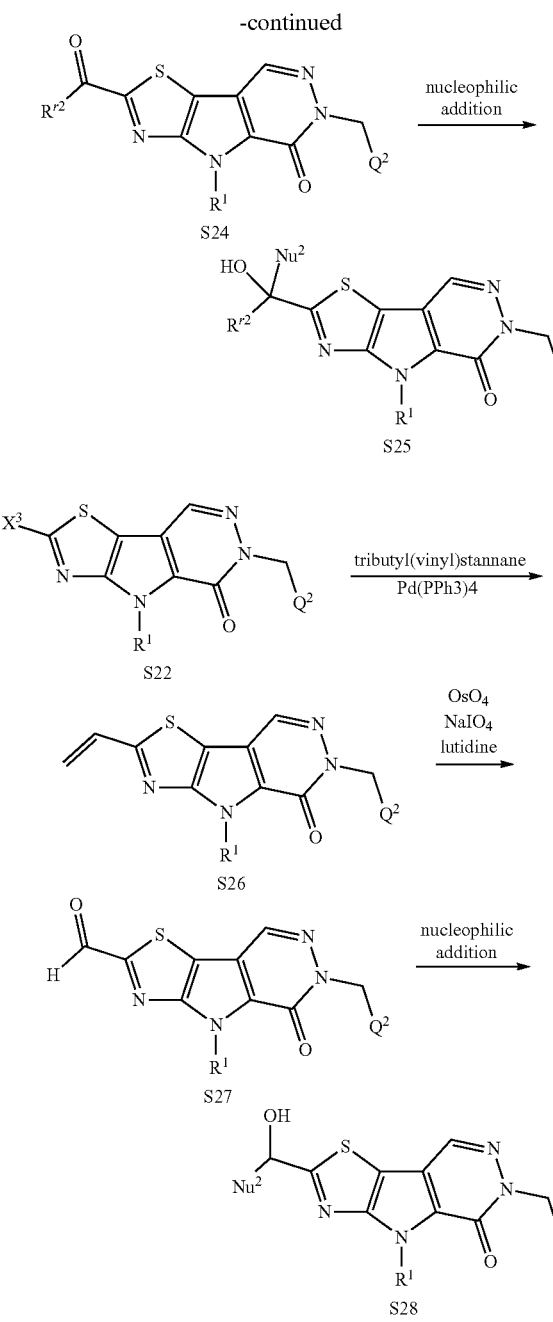

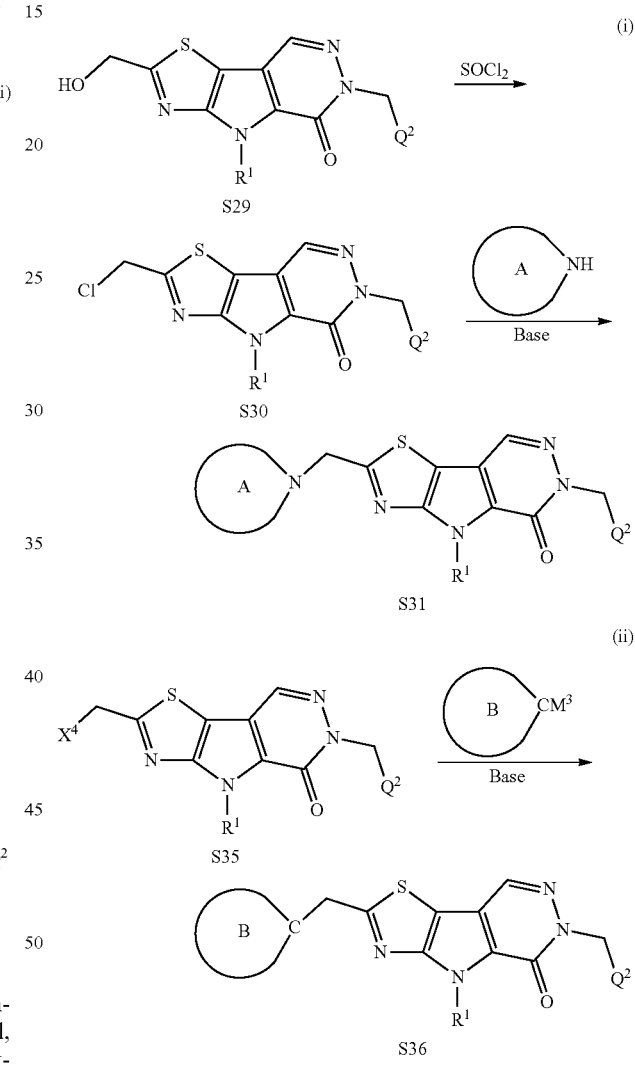

group, a primary amine group, a secondary amine group, a halide, cyanide, azide, alcoxide, organic metal, or inorganic base.

In some embodiments, compounds as described herein can be prepared using methods shown in Scheme 4. Nucleophilic displacement of formulae S30 and S33 with a secondary cyclic amine provides formulae S31 and S34 respectively. Organo-coupling reactions (e.g. Suzuki coupling, Stillecoupling etc.) of compound S35 provide a compound of formulae S36(i)-(ii).

As used herein, $R^{r2}$ is optionally substituted alkyl, optionally substituted alkenyl, optionally substituted alkynyl, optionally substituted cycloalkyl, optionally substituted heterocyclyl, optionally substituted aryl, or optionally substituted heteroaryl; and $Q^2$ is as defined in Scheme 2. In certain embodiments, $R^{r2}$ and $Q^2$ are each independently optionally substituted 5- or 6-membered monocyclic heteroaryl.

As used herein, a nucleophile is a chemical species that donates an electron pair to an electrophile to form a chemical bond in relation to a reaction. All molecules or ions with a free pair of electrons or at least one pi bond can act as nucleophiles. Exemplary nucleophiles comprise at least one group possessing nucleophilic functionality, for example, an alpha carbon (e.g. the carbon adjacent to carbonyl, sulfonyl, sulfinyl, aryl group, or heteroaryl), a thiol group, a hydroxyl As used herein,

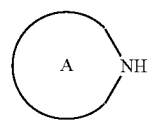

represents a 5- or 6-membered monocyclic heteroaryl ring A with a nitrogen as a ring atom. As used herein

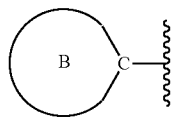

represents a 5- or 6-membered monocyclic heteroaryl ring B with the point of attachment on the carbon ring atom.

$R^1$ is as defined in the first embodiment. $X^4$ is halogen or —OTf. $M^4$ is an organic metal with appropriate ligands if needed (organic or inorganic) as valency permits. Exemplified $M^4$ includes, but is not limited to organic Li, Sn, B (e.g. boronic acids and boronic esters), Zn, Mg, Si, Pd, and Cu.

Methods of Treatment

In one embodiment, provided is a method for treating a disease, condition or disorder as described herein (e.g., treating) comprising administering a compound, a pharmaceutically acceptable salt of a compound or pharmaceutical composition comprising a compound described herein (e.g., a compound of Formulas (I)—(V), in the Examples, and in Table 1 and FIG. 1.

The compounds and compositions described herein can be administered to cells in culture, e.g. in vitro or ex vivo, or to a subject, e.g., in vivo, to treat, and/or diagnose a variety of disorders, including those described herein below.

In one embodiment of the invention provided is a method for increasing the lifetime of red blood cells (RBCs) in need thereof comprising contacting blood with an effective amount of (1) a compound described herein (e.g., Formulas (I)—(V), in the Examples, and in Table 1 and FIG. 1, or a pharmaceutically acceptable salt thereof; (2) a pharmaceutically acceptable composition comprising a compound described herein or a pharmaceutically acceptable salt thereof, and a pharmaceutically acceptable carrier.

In a further embodiment the compound or pharmaceutical composition is added directly to whole blood or packed red blood cells (e.g. extracorporeally). In another embodiment, the compound or pharmaceutical composition is administered to a subject in need thereof.

In one embodiment of the invention provided is a method for regulating 2,3-diphosphoglycerate levels in blood in need thereof contacting blood with an effective amount of (1) a compound described herein (e.g., a compound of Formulas (I)—(V), in the Examples, and in Table 1 and FIG. 1, or a pharmaceutically acceptable salt thereof; (2) a pharmaceutically acceptable composition comprising a compound described herein or a pharmaceutically acceptable salt thereof, and a pharmaceutically acceptable carrier.

In one embodiment of the invention provided is a method for treating sickle cell disease comprising administering to a subject in need thereof with an effective amount of (1) a compound described herein (e.g., a compound of Formulas (I)—(V), in the Examples, and in Table 1 and FIG. 1, or a pharmaceutically acceptable salt thereof; (2) a pharmaceutically acceptable composition comprising a compound described herein or a pharmaceutically acceptable salt thereof, and a pharmaceutically acceptable carrier.

As used here, sickle cell disease (SCD), Hemoglobin SS disease, and sickle cell anemia are used interchangeably. Sickle cell disease (SCD) describes a group of inherited red blood cell disorders. In certain embodiments, subjects with SCD have abnormal hemoglobin, called hemoglobin S or sickle hemoglobin, in their red blood cells. In certain embodiments, a subject having SCD has at least one abnormal genes causing the body to make hemoglobin S. In certain embodiments, a subject having SCD has two hemoglobin S genes, Hemoglobin SS.

In one embodiment of the invention provided is a method of treating pyruvate kinase deficiency (PKD) in a subject comprising administering to the subject an effective amount of (1) a compound described herein (e.g., a compound of Formulas (I)—(V), in the Examples, and in Table 1 and FIG. 1, or a pharmaceutically acceptable salt thereof; (2) a pharmaceutically acceptable composition comprising a compound described herein or a pharmaceutically acceptable salt thereof, and a pharmaceutically acceptable carrier.

As described herein, PKD is a deficiency of PKR. In certain embodiments, the deficiency of PKR is associated with a PKR mutation. In certain embodiments, PKD refers to presence of at least 2 mutant alleles in the PKLR gene. In certain embodiments, at least 1 of the at least 2 mutant alleles in the PKLR gene is a missense mutation. In certain embodiments, a PKD patient has an Hb concentration less than or equal to 10.0 g/dL. In certain embodiments, the patient is not under regularly transfusion (e.g. having had no more than 4 transfusion episodes in the 12-month period). In certain embodiments, the patient is under regularly transfusion (e.g. having had at least 4 transfusion episodes in the 12-month period). In certain embodiments, the patient is under a regularly transfusion having at least 6 transfusion episodes in the 12-month period In certain embodiments, the patient under regular transfusion has hemoglobin (Hb)≤12.0 g/dL (if male) or ≤11.0 g/dL (if female). example 15 In certain embodiments, the patient has undergone splenectomy.

In an embodiment, the PKR mutation is selected from the group consisting of A31V, A36G, G37Q, R40W, R40Q, L73P, S80P, P82H, R86P, I90N, T93I, G95R, M107T, G111R, A115P, S120F, H121Q, S130P, S130Y, V134D, R135D, A137T, G143S, I153T, A154T, L155P, G159V, R163C, R163L, T164N, G165V, L167M, G169G, E172Q, W201R, I219T, A221Y, D221N, G222A, I224T, G232C, N253D, G263R, G263W, E266K, V269F, L272V, L272P, G275R, G275R, E277K, V280G, D281N, F287V, F287L, V288L, D293N, D293V, A295I, A295V, I310N, I314T, E315K, N316K, V320L, V320M, S330R, D331N, D331G, D331E, G332S, V335M, A336S, R337W, R337P, R337Q, D339N, D339Q, G341A, G341D, I342F, K348N, A352D, I357T, G358R, G358E, R359C, R359H, C360Y, N361D, G364D, K365M, V368F, T371I, L374P, S376I, T384M, R385W, R385K, E387G, D390N, A392T, N393D, N393S, N393K, A394S, A394D, A394V, V395L, D397V, G398A, M403I, G406R, E407K, E407G, T408P, T408A, T408I, K410E, G411S, G411A, Q421K, A423A, A423A, R426W, R426Q, E427A, E427N, A431T, R449C, I457V, G458D, A459V, V460M, A468V, A468G, A470D, T477A, R479C, R479H, S485F, R486W, R486L, R488Q, R490W, I494T, A495T, A495V, R498C, R498H, A503V, R504L, Q505E, V506I, R510Q, G511R, G511E, R518S, R531C, R532W, R532Q, E538D, G540R, D550V, V552M, G557A, R559G, R559P, N566K, M568V, R569Q, R569L, Q58X, E174X, W201X, E241X, R270X, E440X, R486X, Q501X, L508X, R510X, E538X, R559X. These mutations are described in Canu Blood Cells, Molecules and Diseases 2016, 57, pp. 100-109. In an embodiment, the mutant PKR is selected from G332S, G364D, T384M, K410E, R479H, R479K, R486W, R532W, R510Q, and R490W. In certain embodiments, the mutant PKR is selected from A468V, A495V, I90N, T408I, and Q421K, and R498H. In certain embodiments, the mutant PKR is R532W, K410E, or R510Q.

In one embodiment of the invention provided is a method of treating anemia in a subject comprising administering to the subject an effective amount of (1) a compound described herein (e.g., a compound of Formulas (I)—(V), in the Examples, and in Table 1 and FIG. 1, or a pharmaceutically acceptable salt thereof; (2) a pharmaceutically acceptable composition comprising a compound described herein or a pharmaceutically acceptable salt thereof, and a pharmaceutically acceptable carrier. In certain embodiments, the anemia is a dyserythropoietic anemia such as congenital dyserythropoietic anemia type I, II, III, or IV. In certain embodiments, the anemia is hemolytic anemia. In certain embodiments, the hemolytic anemia is a congenital and/or hereditary form of hemolytic anemia such as PKD, sickle cell disease, thalassemias (e.g. alpha or beta), hereditary spherocytosis, hereditary elliptocytosis), paroxysmal nocturnal hemoglobinuria, abeta-liproteinemia (Bassen-Kornzweig syndrome). In certain embodiments, the hemolytic anemia is acquired hemolytic anemia such as autoimmune hemolytic anemia, drug-induced hemolytic anemia. In certain embodiments, the hemolytic anemia is anemia as part of a multi-system disease, such as the anemia of Congenital Erythropoietic Purpura, Fanconi, Diamond-Blackfan.

As used herein, the term "anemia" refers to a deficiency of red blood cells (RBCs) and/or hemoglobin. As used herein, anemia includes all types of clinical anemia, for example (but not limited to): microcytic anemia, iron deficiency anemia, hemoglobinopathies, heme synthesis defect, globin synthesis defect, sideroblastic defect, normocytic anemia, anemia of chronic disease, aplastic anemia, hemolytic anemia, macrocytic anemia, megaloblastic anemia, pernicious anemia, dimorphic anemia, anemia of prematurity, Fanconi anemia, hereditary spherocytosis, sickle cell disease, warm autoimmune hemolytic anemia, cold agglutinin hemolytic anemia, osteopetrosis, thalassemia, and myelodysplastic syndrome.

In certain embodiments, anemia can be diagnosed on a complete blood count. In certain embodiments, anemia can be diagnosed based on the measurement of one or more markers of hemolysis (e.g. RBC count, hemoglobin, reticulocytes, schistocytes, lactate Dehydrogenase (LDH), haptoglobin, bilirubin, and ferritin) and/or hemosiderinuria mean corpuscular volume (MCV) and/or red cell distribution width (RDW). In the context of the present invention, anemia is present if an individual has a hemoglobin (Hb) less than the desired level, for example, the Hb concentration of less than 14 g/dL, more preferably of less than 13 g/dL, more preferably of less than 12 g/dL, more preferably of less than 11 g/dL, or most preferably of less than 10 g/dL.

In certain embodiments, provided herein is a method of increasing amount of hemoglobin in a subject in thereof by administering an effective amount of a compound as described herein, or a pharmaceutically acceptable salt thereof, or a pharmaceutically acceptable composition thereof. In certain embodiments, the provided method increases hemoglobin concentration in the subject. In certain embodiments, the provided method increases Hb concentration to a desired level, for example, above 10 g/dL, more preferably above 11 g/dL, more preferably above 12 g/dL, more preferably above 13 g/dL, or most preferably above 14 g/dL. In certain embodiments, the provided method increases Hb concentration by at least about 0.5 g/dL. In certain embodiments, the provided method increases Hb concentration by at least about 1.0 g/dL. In certain embodiments, the provided method increases Hb concentration by at least about 1.5 g/dL. In certain embodiments, the provided method increases Hb concentration by at least about 2.0 g/dL. In certain embodiments, the provided method increases Hb concentration by at least about 2.5 g/dL. In certain embodiments, the provided method increases Hb concentration by at least about 3.0 g/dL. In certain embodiments, the provided method increases Hb concentration by at least about 3.5 g/dL. In certain embodiments, the provided method increases Hb concentration by at least about 4.0 g/dL. In certain embodiments, the provided method increases Hb concentration by at least about 4.5 g/dL. In certain embodiments, the provided method increases Hb concentration by at least about 5.0 g/dL. In certain embodiments, the provided method increases Hb concentration by at least about 5.5 g/dL. In certain embodiments, the provided method increases Hb concentration by at least about 6.0 g/dL.

In one embodiment of the invention provided is a method for treating hemolytic anemia comprising administering to a subject an effective amount of (1) a compound described herein (e.g., a compound of Formulas (I)—(V), in the Examples, and in Table 1 and FIG. 1, or a pharmaceutically acceptable salt thereof; (2) a pharmaceutically acceptable composition comprising a compound described herein or a pharmaceutically acceptable salt thereof, and a pharmaceutically acceptable carrier.

In a further embodiment, the hemolytic anemia is hereditary and/or congenital hemolytic anemia, acquired hemolytic anemia, or anemia as part of a multisystem disease. In certain embodiments, the hemolytic anemia is congenital anemia. In certain embodiments, the hemolytic anemia is hereditary (e.g. non-spherocytic hemolytic anemia or hereditary spherocytosis).

In one embodiment of the invention provided is a method of treating thalassemia;
hereditary spherocytosis; hereditary elliptocytosis; abeta-lipoproteinemia or Bassen-Kornzweig syndrome; paroxysmal nocturnal hemoglobinuria; acquired hemolytic anemia (e.g., congenital anemias (e.g., enzymopathies)); sickle cell disease; or anemia of chronic diseases comprising administering to a subject an effective amount of (1) a compound described herein (e.g., a compound of Formulas (I)—(V), in the Examples, and in Table 1 and FIG. 1, or a pharmaceutically acceptable salt thereof; (2) a pharmaceutically acceptable composition comprising a compound described herein or a pharmaceutically acceptable salt thereof, and a pharmaceutically acceptable carrier. In one embodiment, the acquired hemolytic anemia comprises congenital anemias. In certain embodiments, the provided method is to treat thalassemia. In certain embodiments, the thalassemia is beta-thalassemia.

As used herein, thalassemia is an inherited blood disorder in which the body makes an abnormal form of hemoglobin. In certain embodiments, the disorder results in large numbers of red blood cells being destroyed, which leads to anemia. In certain embodiments, the thalassemia is alpha thalassemia. In certain embodiments, the thalassemia is beta thalassemia.

In one embodiment of the invention provided is a method for activating mutant PKR in red blood cells comprising administering to a subject in need thereof an effective amount of (1) a compound described herein (e.g., a compound of Formulas (I)—(V), in the Examples, and in Table 1 and FIG. 1, or a pharmaceutically acceptable salt thereof; (2) a pharmaceutically acceptable composition comprising a compound described herein or a pharmaceutically acceptable salt thereof, and a pharmaceutically acceptable carrier. In one embodiment, the method is an ex vivo method. In another embodiment, the method is an in vitro method. In some embodiments, the blood or the red blood cells are derived or obtained from a subject suffering from or susceptible to a disease or disorder selected from the group consisting of pyruvate kinase deficiency (PKD), thalassemia (e.g., beta thalassemia), hereditary spherocytosis, hereditary elliptocytosis, abetalipoproteinemia or Bassen-Kornzweig syndrome, sickle cell disease, paroxysmal nocturnal hemoglobinuria, anemia (e.g., dyserythropoetic anemia), hemolytic anemia, and anemia of chronic diseases. In some embodiments, the hemolytic anemia is hereditary and/or congenital hemolytic anemia, acquired hemolytic anemia, or anemia as part of a multi-system disease.

In one embodiment of the invention provided is a method for activating wild-type PKR in red blood cells comprising administering to a subject in need thereof an effective amount of (1) a compound described herein (e.g., a compound of Formulas (I)—(V), in the Examples, and in Table 1 and FIG. 1, or a pharmaceutically acceptable salt thereof; (2) a pharmaceutically acceptable composition comprising a compound described herein or a pharmaceutically acceptable salt thereof, and a pharmaceutically acceptable carrier. In one embodiment, the method is an ex vivo method. In another embodiment, the method is an in vitro method. In some embodiments, the blood or the red blood cells are derived or obtained from a subject suffering from or susceptible to a disease or disorder selected from the group consisting of pyruvate kinase deficiency (PKD), thalassemia (e.g., beta thalassemia), hereditary spherocytosis, hereditary elliptocytosis, abetalipoproteinemia or Bassen-Kornzweig syndrome, sickle cell disease, paroxysmal nocturnal hemoglobinuria, anemia (e.g., dyserythropoetic anemia), hemolytic anemia, and anemia of chronic diseases. In some embodiments, the hemolytic anemia is hereditary and/or congenital hemolytic anemia, acquired hemolytic anemia, or anemia as part of a multi-system disease.

In one embodiment of the invention provided is a use of (1) a compound described herein (e.g., a compound of Formulas (I)—(V), in the Examples, and in Table 1 and FIG. 1, or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for increasing the lifetime of red blood cells (RBCs) in need thereof.

In a further embodiment the compound or pharmaceutical composition is formulated to be added directly to whole blood or packed red blood cells extracorporeally. In another embodiment, the compound or pharmaceutical composition is formulated to be administered to a subject in need thereof.

In one embodiment of the invention provided is a use of (1) a compound described herein (e.g., a compound of Formulas (I)—(V), in the Examples, and in Table 1 and FIG. 1, or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for regulating 2,3-diphosphoglycerate levels in blood in need thereof.

In one embodiment of the invention provided is a use of (1) a compound described herein (e.g., a compound of Formulas (I)—(V), in the Examples, and in Table 1 and FIG. 1, or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for treating anemia. In certain embodiments, the anemia is a dyserythropoietic anemia such as congenital dyserythropoietic anemia type I, II, III, or IV. In certain embodiments, the anemia is hemolytic anemia. In certain embodiments, the hemolytic anemia is a congenital and/or hereditary form of hemolytic anemia such as PKD, sickle cell disease, thalassemias (e.g. alpha or beta), hereditary spherocytosis, hereditary elliptocytosis), paroxysmal nocturnal hemoglobinuria, abeta-liproteinemia (Bassen-Kornzweig syndrome). In certain embodiments, the hemolytic anemia is acquired hemolytic anemia such as autoimmune hemolytic anemia, drug-induced hemolytic anemia. In certain embodiments, the hemolytic anemia is anemia as part of a multi-system disease, such as the anemia of Congenital Erythropoietic Purpura, Fanconi, Diamond-Blackfan.

In one embodiment of the invention provided is a use of (1) a compound described herein (e.g., a compound of Formulas (I)—(V), in the Examples, and in Table 1 and FIG. 1, or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for treating hemolytic anemia.

In one embodiment of the invention provided is a use of (1) a compound described herein (e.g., a compound of Formulas (I)—(V), in the Examples, and in Table 1 and FIG. 1, or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for treating sickle cell disease.

In one embodiment of the invention provided is a use of (1) a compound described herein (e.g., a compound of Formulas (I)—(V), in the Examples, and in Table 1 and FIG. 1, or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for treating pyruvate kinase deficiency (PKD) in a subject.

As described herein, PKD is a deficiency of PKR. In certain embodiments, the deficiency of PKR is associated with a PKR mutation.

In one embodiment of the invention provided is a use of (1) a compound described herein (e.g., a compound of Formulas (I)—(V), in the Examples, and in Table 1 and FIG. 1, or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for treating thalassemia; hereditary spherocytosis; hereditary elliptocytosis; abetalipoproteinemia or Bassen-Kornzweig syndrome; paroxysmal nocturnal hemoglobinuria; acquired hemolytic anemia; or anemia of chronic diseases.

In one embodiment of the invention provided is a use of (1) a compound described herein (e.g., a compound of Formulas (I)—(V), in the Examples, and in Table 1 and FIG. 1, or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for activating mutant PKR in red blood cells.

In one embodiment of the invention provided is a use of (1) a compound described herein (e.g., a compound of Formulas (I)—(V), in the Examples, and in Table 1 and FIG. 1), or a pharmaceutically acceptable salt thereof; (2) a pharmaceutically acceptable composition comprising a compound described herein or a pharmaceutically acceptable salt thereof, and a pharmaceutically acceptable carrier for the preparation of a medicament for activating wild-type PKR in red blood cells.

In one embodiment of the invention, provided is a method of activating pyruvate kinase R (PKR), comprising contacting the PKR with an effective amount of (1) a compound described herein (e.g., a compound of Formulas (I)—(V), in the Examples, and in Table 1 and FIG. 1), or a pharmaceutically acceptable salt thereof; or (2) a pharmaceutically acceptable composition comprising a compound described herein or a pharmaceutically acceptable salt thereof, and a pharmaceutically acceptable carrier. In one embodiment, the PKR is a wild-type PKR. In another embodiment, the PKR is a mutant PKR. In some embodiments, the PKR is expressed in red blood cells. In one embodiment, the method is an ex vivo method. In another embodiment, the method is an in vitro method. In some embodiments, the blood or the red blood cells are derived or obtained from a subject suffering from or susceptible to a disease or disorder selected from the group consisting of pyruvate kinase deficiency (PKD), thalassemia (e.g., beta thalassemia), hereditary spherocytosis, hereditary elliptocytosis, abetalipoproteinemia or Bassen-Kornzweig syndrome, sickle cell disease, paroxysmal nocturnal hemoglobinuria, anemia (e.g., dyserythropoetic anemia), hemolytic anemia, and anemia of chronic diseases. In some embodiments, the hemolytic anemia is hereditary and/or congenital hemolytic anemia, acquired hemolytic anemia, or anemia as part of a multisystem disease.

Since the compounds and compositions described herein act on the same biological pathway and have the similar mode of action as the compounds described in WO2012/151451, the compounds and compositions presented herein can activate the PKR mutants as described in WO2012/151451.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound provided herewith, and which does not destroy the pharmacological activity thereof and is nontoxic when administered in doses sufficient to deliver an effective amount of the compound.

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions provided herewith may be administered orally, parenterally, by inhalation spray, topically, rectally, nasally, buccally, vaginally or via an implanted reservoir, preferably by oral administration or administration by injection. The pharmaceutical compositions provided herewith may contain any conventional non-toxic pharmaceutically-acceptable carriers, adjuvants or vehicles.

The pharmaceutical compositions provided herewith may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents.

When the compositions provided herewith comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with the compounds provided herewith in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

EXPERIMENTAL

| Abbreviations list: | |
|---|---|
| abbrv. | Full Name |
| anhy. | anhydrous |
| min | minute(s) |
| mL | milliliter |
| mmol | millimole(s) |
| MS | mass spectrometry |
| TLC | thin layer chromatography |
| LCMS | Liquid chromatography-mass spectrometry |

95
-continued

Abbreviations list:

| abbrv. | Full Name |
|---|---|
| DAST | Diethylaminosulfurtrifluoride |
| DCM | dichloromethane |
| Et2O | diethyl ether |
| EtOAc | ethyl acetate |
| MeCN | acetonitrile |
| THF | tetrahydrofuran |
| AcOH | acetic acid |
| $H_2SO_4$ | sulfuric acid |
| KOH | potassium hydroxide |
| $K_2CO_3$ | potassium carbonate |
| TFA | trifluoroacetic acid |
| $NaBH_4$ | sodium borohydride |
| LiHMDS | lithium hexamethyldisilylamide |
| $Et_3N$ or TEA | Triethylamine |
| DMAP | 4-(dimethylamino)pyridine |
| BINAP | 2,2'bis(diphenylphosphanyl)-1,1'-binaphthyl |
| PEP | Phospho(enol)pyruvic acid |
| DTT | DL-Dithiothreitol |
| NADH | β-Nicotinamide adenine dinucleotide, reduced |
| p-TsOH | p-Toluenesulfonic acid |
| aq. | aqueous |
| satd. | saturated |
| hrs | hours |
| mol | mole(s) |
| NMR | nuclear magnetic resonance |
| HPLC | high-performance liquid chromatography |
| MTBE | Methyl tert-butyl ether |
| $CHCl_3$ | chloroform |
| DMF | dimethylformamide |
| EtOH | ethyl alcohol |
| MeOH | methyl alcohol |
| PE | petroleum ether |
| DMSO | dimethyl sulfoxide |
| HCl | hydrochloric acid |
| $NH_4Cl$ | ammonium chloride |
| NaOH | sodium hydroxide |
| $Na_2CO_3$ | sodium carbonate |
| $Na_2SO_4$ | sodium sulfate |
| $NaHCO_3$ | sodium bicarbonate |
| $NaBH_4$ | sodium borohydride |
| Py or Pyr | pyridine |
| DIPEA | N,N-diisopropylethylamine |
| dppf | 1,1'-bis(diphenylphosphino)ferrocene |
| LDH | Lactate Dehydrogenase |
| BSA | Bovine serum Albumin |
| SEM | 2-(Trimethylsilyl)ethoxymethyl |
| DCE | 1,2-dichloroethane |

General Experimental

In the following examples, the chemical reagents were purchased from commercial sources (such as Alfa, Acros, Sigma Aldrich, TCI and Shanghai Chemical Reagent Company), and used without further purification. Flash chromatography was performed on an Ez Purifier III via column with silica gel particles of 200-300 esh. Analytical and preparative thin layer chromatography plates (TLC) were HSGF 254 (0.15-0.2 mm thickness, Shanghai Anbang Company, China). Nuclear magnetic resonance (NMR) spectra were recorded using Brucker AMX-300 or AMX-400 NMR (Brucker, Switzerland). Chemical shifts were reported in parts per million (ppm, δ) etero (ESI) from a Waters LCT TOF Mass Spectrometer (Waters, USA). HPLC chromatographs were recorded on Agilent 1200 Liquid Chromatography (Agilent, USA, column: Ultimate 4.6 m×50 mm, 5 M, mobile phase A: 0.1% formic acid in water; mobile phase B: acetonitrile). Microwave reactions were run on an Initiator 2.5 Microwave Synthesizer (Biotage, Sweden).

HPLC conditions used in the experiments described herein are as follows:

Method 1:
Instrument: Shimadzu LC-2010AHT
Column: YMC-Triart C18, 50×4.6 mm, 5 μm
Mobilephase: Solvent A: $H_2O/CH_3OH/TFA=90/10/0.1$, Solvent B: $H_2O/CH_3OH/TFA=90/10/0.1$
Flow rate: 2.5 mL/min; Column temperature: 35° C.; Wavelength: 220 nm/254 nm Method 2:
Instrument: Shimadzu LC-2010AHT
Column: YMC-Triart C18, 50×4.6 mm, 5 μm
Mobilephase: Solvent A: $H_2O/CH_3OH/TFA=90/10/0.1$, Solvent B: $H_2O/CH_3OH/TFA=90/10/0.1$
Flow rate: 2.5 mL/min; Column temperature: 35° C.; Wavelength: 220 nm/254 nm Prep-HPLC conditions used in the experiments described herein are as follows:
Instrument: Waters 2545B/2767
Column: YMC-Triart C18, 50×4.6 mm, 5 μm
Mobilephase: Solvent A: $H_2O$ (01.% FA), Solvent B: $CH_3OH$ or $CH_3CN$
Flow rate: 20 mL/min; Column temperature: 35° C.; Wavelength: 220 nm/254 nm

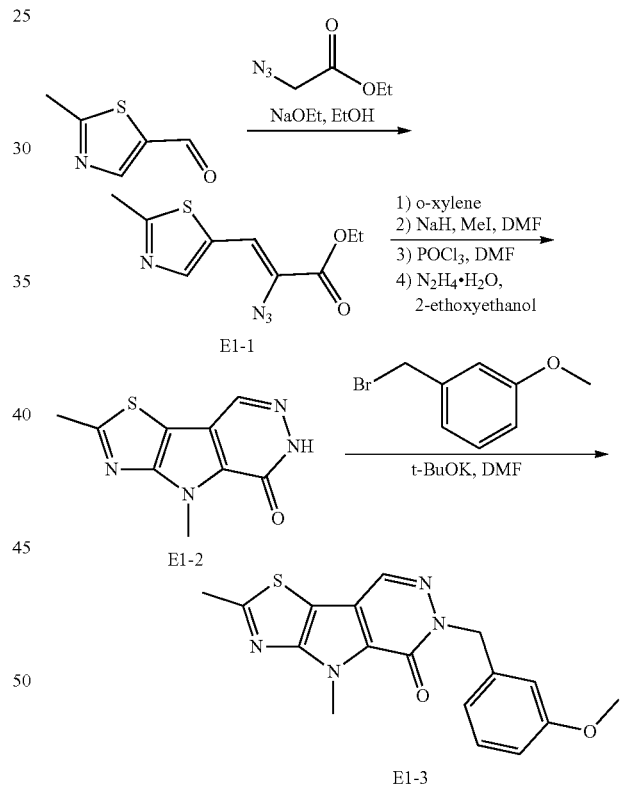

Step A. Ethyl (Z)-2-azido-3-(2-methylthiazol-5-yl) acrylate

To a solution of NaOEt (803 mg, 11.79 mmol) in EtOH (10 mL) between about −10° C. and about −5° C. was added drop wise a solution of 2-methylthiazole-5-carbaldehyde (500 mg, 3.93 mmol) and ethyl 2-azidoacetate (1.53 g, 11.79 mmol) in anhydrous EtOH (3 mL). The reaction mixture was stirred for about 1 hr. while the temperature maintained below 0° C., then warmed to r.t. and stirred for another 2 hr. The resulting mixture was poured into saturated aqueous NH$_4$Cl (50 mL) at 0° C. and extracted with EtOAc. The combined organic layers were washed with brine, dried over anhydrous Na$_2$SO$_4$ and concentrated under reduced pressure to give the desired product (500 mg) which was directly used in the next step without any purification. LCMS: m/z 239 (M+H)$^+$.

Step B. Ethyl 2-methyl-4H-pyrrolo[2,3-d]thiazole-5-carboxylate

A mixture of ethyl (Z)-2-azido-3-(2-methylthiazol-5-yl)acrylate (500 mg, 2.1 mmol) in o-xylene (5 mL) was stirred at 140° C. for 2 hr. then cooled down to r.t. and then directly purified by column chromatography on silica gel (eluent: pentane/EtOAc=6/1 to give the desired product (220 mg, 49.8% yield). LCMS: m/z 211 (M+H)$^+$.

Step C. Ethyl 2,4-dimethyl-4H-pyrrolo[2,3-d]thiazole-5-carboxylate

To a solution of ethyl 2-methyl-4H-pyrrolo[2,3-d]thiazole-5-carboxylate (160 mg, 0.76 mmol) in DMF (3 mL) at 0° C. was added NaH (36.5 mg, 1.52 mmol). The reaction mixture was stirred at r.t. for 0.5 hr., followed by addition of CH$_3$I (47 µL, 0.76 mmol). The resulting mixture was stirred at r.t for 0.5 hr. then poured into saturated aqueous NH$_4$Cl at 0° C. and extracted with EtOAc. The combined organic layers were washed with brine, dried over anhydrous Na$_2$SO$_4$ and concentrated under reduced pressure. The residue was purified by column chromatography on silica gel (eluent: pentane/ethyl acetate=6/1) to give the desired product (124 mg, 72.6% yield). LCMS: in/z 225 (M+H)$^+$.

Step D. Ethyl 6-formyl-2,4-dimethyl-4H-pyrrolo[2,3-d]thiazole-5-carboxylate

To a mixture of ethyl 2,4-dimethyl-4H-pyrrolo[2,3-d] thiazole-5-carboxylate (100 mg, 0.446 mmol) in DMF (1 mL)) at 0° C. was added POCl$_3$ (122.5 µL, 1.338 mmol). The reaction mixture was stirred at 100° C. for 2 hr. then poured into saturated aqueous NaHCO$_3$ at 0° C. and extracted with EtOAc. The combined organic layers were washed with brine, dried over anhydrous Na$_2$SO$_4$ and concentrated under reduced pressure. The residue was purified by column chromatography on silica gel (eluent: pentane/ethyl acetate=5/1) to give the desired product (57 mg, 50.7% yield). LCMS: m/z 253 (M+H)$^+$.

Step E. 2,4-Dimethyl-4,6-dihydro-5H-thiazolo[5',4':4,5]pyrrolo[2,3-d] pyridazin-5-one To a mixture of ethyl 6-formyl-2,4-dimethyl-4H-pyrrolo[2,3-d] thiazole-5-carboxylate (57 mg, 0.226 mmol) in 2-ethoxyethanol (2 mL) was added N$_2$H$_4$·H$_2$O (53.7 µL, 1.130 mmol). The reaction mixture was stirred at 100° C. for 1 hr. then poured into H$_2$O and extracted with EtOAc. The combined organic layers were washed with brine; dried over anhydrous Na$_2$SO$_4$ and concentrated under reduced pressure. The residue was purified by column chromatography on silica gel (eluent: pentane/ethyl acetate=5/1) to give the desired product (49 mg, 98.4% yield). LCMS: m/z 221 (M+H)$^+$.

Step F. 6-(3-Methoxybenzyl)-2,4-dimethyl-4,6-dihydro-5H-thiazolo[5',4':4,5] pyrrolo[2,3-d] pyridazin-5-one To a mixture of 2,4-dimethyl-4,6-dihydro-5H-thiazolo[5',4':4,5]pyrrolo[2,3-d]pyridazin-5-one (49 mg, 0.223 mmol) in DMF (1 mL) at 0° C. was added t-BuOK (50.8 mg, 0.454 mmol). The reaction mixture was stirred at r.t. for 0.5 hr., followed by addition of 1-(chloromethyl)-3-methoxybenzene (34.9 mg, 0.223 mmol). The resulting mixture was stirred at r.t. for 1 hr. then poured into saturated aqueous NH$_4$Cl solution at 0° C. and extracted with EtOAc. The combined organic layers were washed with brine, dried over anhydrous Na$_2$SO$_4$ and concentrated under reduced pressure. The residue was purified by column chromatography on silica gel (eluent: pentane/ethyl acetate=3/1) to give the desired product. LCMS: m/z 341 (M+H)$^+$. $^1$H NMR (400 MHz, DMSO-d$_6$) δ 8.56 (s, 1H), 7.23 (t, 1H), 6.92-6.72 (m, 3H), 5.32 (s, 2H), 4.26 (s, 3H), 3.72 (s, 3H), 2.85 (s, 3H).

Example 1 provides exemplified synthesis of compound E1-3. It is understood that different compounds can be synthesized with appropriate heteroaryl-CH$_2$-halide.

Examples 2. Preparation of Compounds of Formula E2-vii with Scheme E2

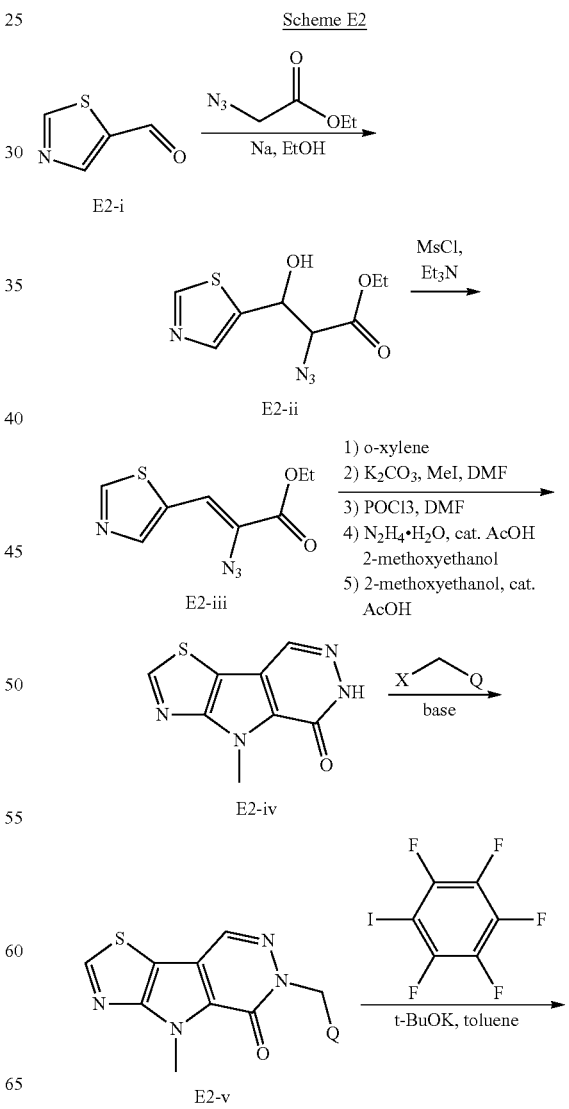

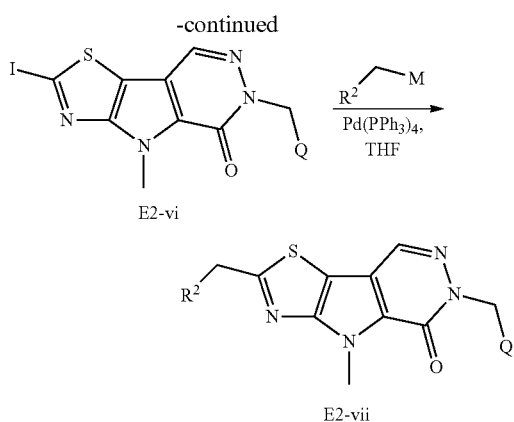

Wherein X is a leaving group (e.g. C, Br or I, OMs, or OTs); M is an organic metal complex (e.g. organoboron complex such as boronic acid or pinaco boron complex, organotin complex such as —Sn(Bu$^t$)$_3$; organozinc complex such as —Zn(halogen)); Q and R$^2$ are each independently optionally substituted 5-membered or 6-membered heteroaryl. Similar to the synthesis of compounds of Formula E1-v in Example 1, compound E2-iv can be synthesized from thiazole aldehyde E2-i with a few modifications (e.g. reaction of compound E2-ii with MsCl followed by elimination to give compound E2-iii; the tricyclic system can be formed with cat. AcOH in 2-methoxyethanol). Substitution and iodination of compound E2-iv provides compound E2-vi. Coupling of compound E2-vi with organometal in presence of a catalyst gives compound E2-vii.

Example 2A. Synthesis of 4-methyl-4,6-dihydro-5H-thiazolo[5',4':4,5]pyrrolo-[2,3-d]pyridazin-5-one

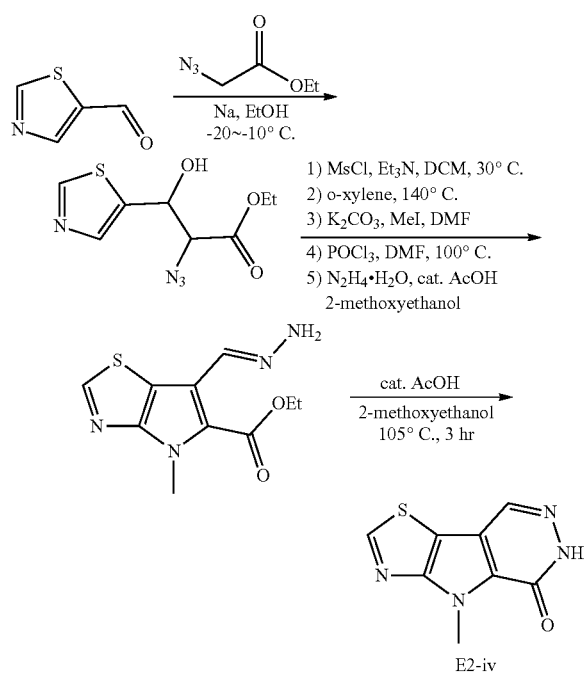

Step A. Ethyl 2-azido-3-hydroxy-3-(thiazol-5-yl)propanoate

Sodium (12.2 g, 0.531 mol) was slowly added at r.t. to a stirred solution of dry EtOH (300 mL). The reaction mixture was then cooled to −20° C., followed by drop wise addition of a solution of ethyl 2-azidoacetate (68.5 g, 0.531 mol) and thiazole-5-carbaldehyde (20.0 g, 0.177 mol) in anhydrous EtOH (100 mL) while keeping the temperature between −20° C. to −15° C. After the addition, the reaction mixture was stirred at −20° C. for additional 1 hr. and then poured into saturated aqueous NH$_4$Cl (1 L). The resulting mixture was saturated with NaCl and extracted with EtOAc. The combined organic phase was washed with brine, dried over anhydrous Na$_2$SO$_4$ and concentrated under reduced pressure. The residue was purified by column chromatography on silica gel using (eluent: PE/EtOAc=6/1 to 5/1 to 1/1) to afford desired product (34 g) as pale. LCMS: m/z=243 (M+H)$^+$.

Step B. Ethyl (Z)-2-azido-3-(thiazol-5-yl)acrylate

To a stirred mixture of ethyl 2-azido-3-hydroxy-3-(thiazol-5-yl)propanoate (103 g, 0.426 mol) in dry DCM (1.5 L) at −35° C. was added MsCl (146 g, 1.28 mol), followed by drop wise addition of TEA (301 g, 2.98 mol) while keeping the temperature between −35° C. to −30° C. After the addition, the reaction mixture was stirred at −30° C. for another 15 min then poured into saturated aqueous NH$_4$Cl (1.5 L). The resulting mixture was saturated with NaCl and extracted with DCM twice. The combined organic layers were washed in sequence with aqueous HCl (1 M) and brine, dried over anhydrous Na$_2$SO$_4$ and concentrated under reduced pressure. The residue was purified by column chromatography on silica gel using (eluent: PE/EtOAc=5/1) to afford the desired product (82.0 g, 86.3% yield). LCMS: m/z=225 (M+H)$^+$.

Steps C-E

To synthesize ethyl 4H-pyrrolo[2,3-d]thiazole-5-carboxylate, ethyl 4-methyl-4H-pyrrolo[2,3-d]thiazole-5-carboxylate, and ethyl 6-formyl-4-methyl-4H-pyrrolo[2,3-d]thiazole-5-carboxylate were similar to the procedures in Example 1.

Step F. Ethyl (E)-6-(hydrazonomethyl)-4-methyl-4H-pyrrolo[2,3-d]thiazole-5-carboxylate To a stirred mixture of N$_2$H$_4$·H$_2$O (2.0 g, 98%, 40 mmol) in 2-methoxyethanol (50 mL) at r.t. was added ethyl 6-formyl-4-methyl-4H-pyrrolo[2,3-d] thiazole-5-carboxylate (4.8 g, 20 mmol), followed by addition of 20 drops of AcOH. The reaction mixture was stirred at r.t. for about 30 min till the mixture turned clear. The resulting mixture was poured into water (100 mL) with stirring and extracted with DCM. The combined organic layers were dried over anhydrous Na$_2$SO$_4$ and concentrated under reduced pressure to afford the desired product which was used in the next step without further purification. LCMS: m/z=253 (M+H)$^+$.

Step G. 4-Methyl-4,6-dihydro-5H-thiazolo[5',4':4,5]pyrrolo[2,3-d]pyridazin-5-one To a stirred suspension of ethyl (E)-6-(hydrazonomethyl)-4-methyl-4H-pyrrolo[2,3-d]thiazole-5-carboxylate (4.8 g, 0.19 mol) in 2-methoxyethanol (50 mL) at r.t. was added AcOH (20 drops). The reaction suspension was stirred at 105° C. for 3 hr. and then filtered. The filter cake was washed with water and dried under high vacuum to get the first batch of the desired product. The filtrate was diluted with water and extracted with DCM twice. The organic layers were washed with brine, dried over anhydrous $Na_2SO_4$ and concentrated under reduced pressure to afford the second batch of the desired product. The combined two batches of the desired product (2.5 g) was directly used in the next step without further purification. LCMS: m/z=207 (M+H)$^+$. 1H NMR (400 MHz, DMSO) δ 12.68 (s, 1H), 9.35 (s, 1H), 8.55 (s, 1H), 4.30 (s, 3H Example 3. Synthesis of Compounds E3-vii and E3-viii Example 3A. Synthesis of 4-methyl-2-(methylthio)-4,6-dihydro-5H-thiazolo[5',4':4,5]pyrrolo[2,3-d]pyridazin-5-one

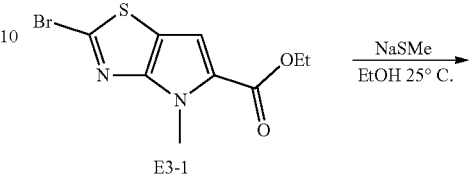

Scheme E3

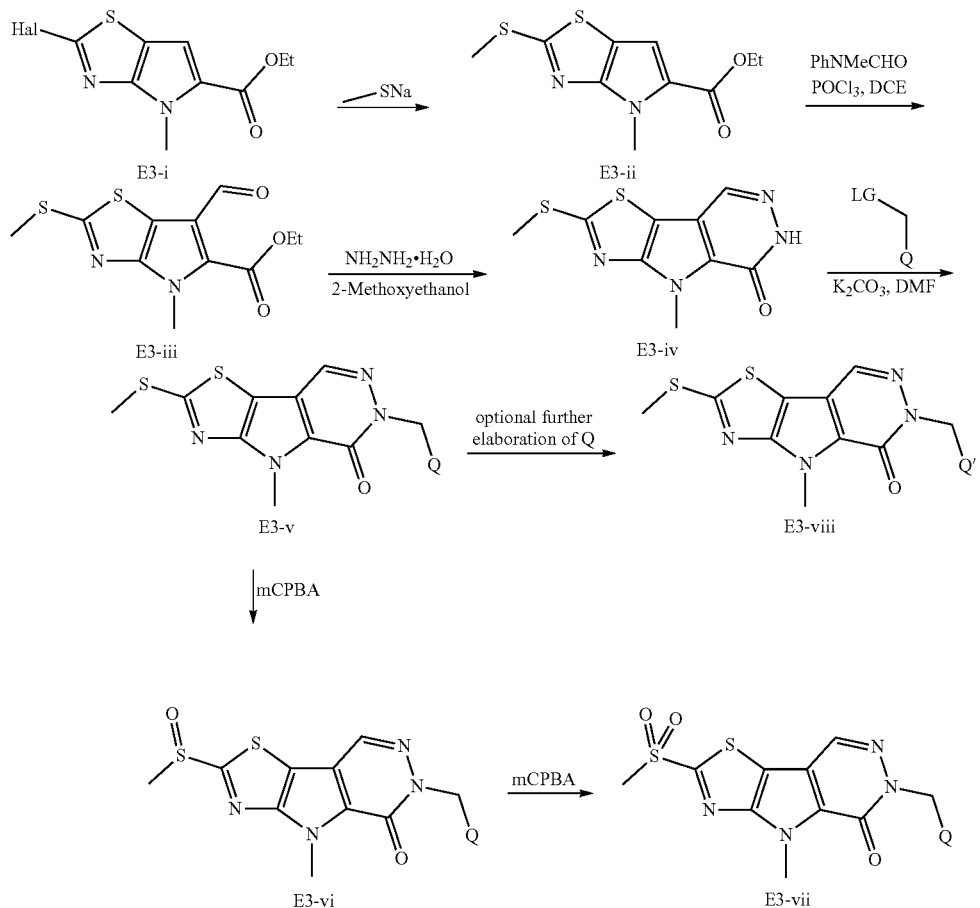

wherein Hal is halogen (e.g. Cl, Br or I); LG is a leaving group (e.g. Cl, Br, I, OMs, or OTs); Q is optionally substituted 5-membered or 6-membered heteroaryl; and Q' is further functionalized 5-membered or 6-membered heteroaryl. Aromatic substitution reaction of compound E3-i with sodium methanethiolate provides compound E3-ii, which can be converted to compound E3-v using the synthesis of compound E1-iii to E1-vi. Oxidation of compound E3-v with mCPBA gives compound E3-vi and E3-vii respectively.

-continued

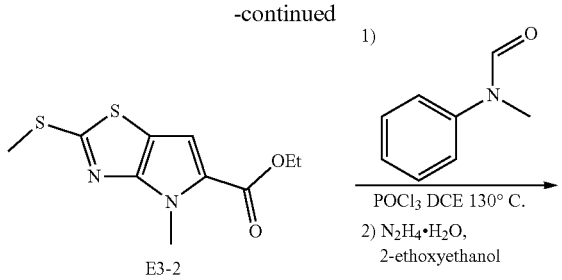

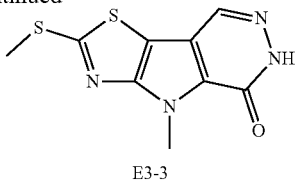

E3-3

Step A: Ethyl 4-methyl-2-(methylthio)-4H-pyrrolo[2,3-d]thiazole-5-carboxylate To a mixture of ethyl 2-bromo-4-methyl-4H-pyrrolo[2,3-d]thiazole-5-carboxylate (500.0 mg, 1.73 mmol) in EtOH (10.0 mL) was added NaSMe (240.0 mg, 3.5 mmol). The reaction mixture was stirred at 25° C. for 3 hr then quenched with ice water and extracted with DCM. The combined organic layers were washed with brine, dried over anhydrous $Na_2SO_4$ and concentrated under reduced pressure to afford desired product (460 mg) which was directly used in the next step without any purification. LC-MS: m/z 257 (M+H)$^+$.

Step B: Ethyl 6-formyl-4-methyl-2-(methylthio)-4H-pyrrolo[2,3-d]thiazole carboxylate To a solution of ethyl 4-methyl-2-(methylthio)-4H-pyrrolo[2,3-d]thiazole carboxylate (460.0 mg, 1.8 mmol) and N-methyl-N-phenylformamide (490 mg, 3.6 mmol) in DCE (10 mL) was added $POCl_3$ (550.0 mg, 3.6 mmol). The resulting mixture was stirred at 130° C. for 3 hr. then quenched with ice water and extracted with DCM. The combined organic layers were washed with brine, dried over anhydrous $Na_2SO_4$ and concentrated under reduced pressure. The residue was purified by column chromatography on silica gel (eluent: PE/EtOAc=8/1) to give the desired product (320.0 mg, 63% yield). LC-MS: m/z 285 (M+H)$^+$.

Step C: 4-Methyl-2-(methylthio)-4,6-dihydro-5H-thiazolo[5',4':4,5]pyrrolo[2,3-d]pyridazin-5-one To a solution of ethyl 6-formyl-4-methyl-2-(methylthio)-4H-pyrrolo[2,3-d]thiazole-5-carboxylate (300.0 mg, 1.06 mmol) in EtOH (5.0 mL) was added $N_2H_4 \cdot H_2O$ (2 mL, 98% wt). The reaction mixture was stirred at r.t. for 1 hr. then heated to 60° C. for overnight then cooled down. The solid was collected by filtration and dried under high vacuum to afford the desired product (180.0 mg, 67% yield). LC-MS: m/z 253 (M+H)$^+$. $^1$H NMR (400 MHz, DMSO-$d_6$) δ 12.61 (s, 1H), 8.48 (s, 1H), 4.22 (s, 3H), 2.81 (s, 3H).

Example 3B. Synthesis of 6-((2-aminopyridin-4-yl)methyl)-4-methyl-2-(methylsulfinyl)-4H-thiazolo[5',4':4,5]pyrrolo[2,3-d]pyridazin-5(6H)-one

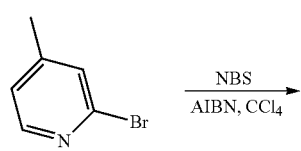

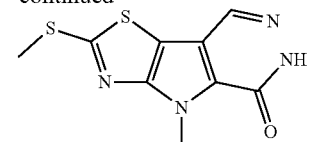

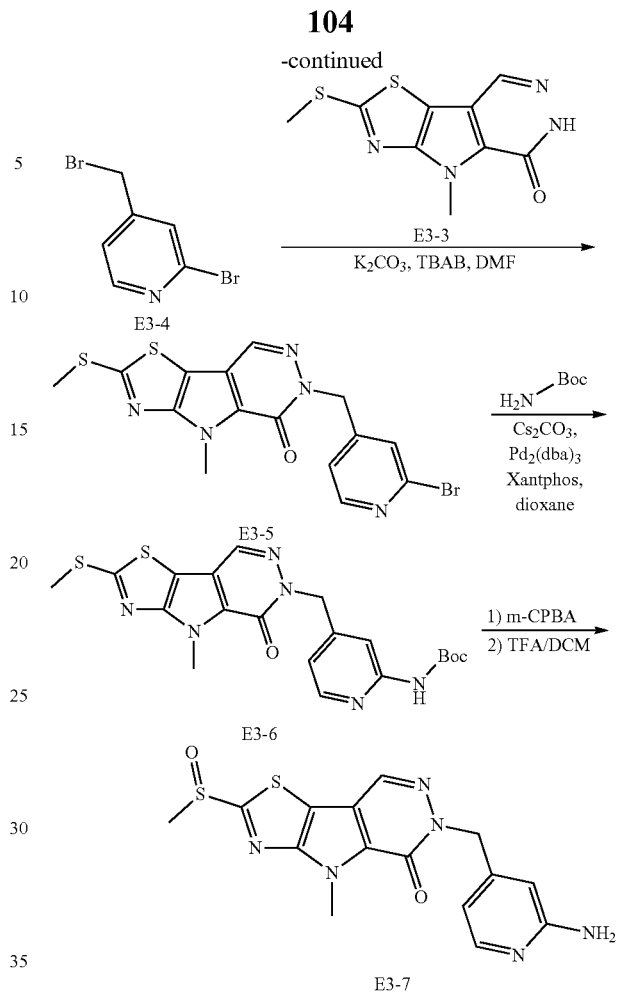

Step A. 2-Bromo-4-(bromomethyl)pyridine

A mixture of 2-bromo-4-methylpyridine (1 g, 5.81 mmol), NBS (1.1 g, 6.39 mmol) and a catalytic amount of AIBN (100 mg) in $CCl_4$ (10 mL) was stirred at 80° C. overnight. The resulting mixture was concentrated under reduced pressure and the residue was purified by column chromatography on silica gel (eluent: PE/EtOAc=200/1) to give the desired product E3-4 (500 mg, 34.28% yield).

Step B. 6-((2-Bromopyridin-4-yl)methyl)-4-methyl-2-(methylthio)-4H-thiazolo[5',4':4,5]pyrrolo[2,3-d]pyridazin-5(6H)-one A mixture of 4-methyl-2-(methylthio)-4H-thiazolo[5',4':4,5]pyrrolo[2,3-d]pyridazin-5(6H)-one (100 mg, 0.40 mmol), and $K_2CO_3$ (164 mg, 1.19 mmol) in DMF (8 mL) was stirred at 60° C. for 2 hr., followed by addition of a solution of 2-bromo-4-(bromomethyl)pyridine (199 mg, 0.80 mmol) in DMF (2 mL) and a catalytic amount of TBAB (13 mg). The mixture was stirred at 60° C. overnight then quenched with water (20 mL) and extracted with EtOAc. The combined organic layers were washed with saturated aqueous $NH_4Cl$, dried over anhydrous $Na_2SO_4$ and concentrated under reduced pressure. The residue was purified by column chromatography on silica gel (eluent: PE/EtOAc=10/1) to give the desired product (150 mg, 89.62% yield). LCMS: m/z 423 (M+H)$^+$.

Step C. Tert-butyl (4-((4-methyl-2-(methylthio)-5-oxo-4H-thiazolo[5',4':4,5]pyrrolo[2,3-d] pyridazin-6 (5H)-yl)methyl)pyridin-2-yl)carbamate A mixture of 6-((2-bromopyridin-4-yl)methyl)-4-methyl-2-(methylthio)-4H-thiazolo[5',4':4,5]pyrrolo[2,3-d]pyridazin-5(6H)-one (100 mg, 0.24 mmol), tert-butyl carbamate (83 mg, 0.71 mmol), $K_3PO_4$ (201 mg, 0.95 mmol), $Pd_2(dba)_3$ (18 mg, 0.02 mmol) and Xantphos (11 mg, 0.02 mmol) in dioxane (10 mL) was stirred at 100° C. under nitrogen overnight. The resulting mixture was quenched with water and extracted with EtOAc. The combined organic layers were washed with brine, dried over anhydrous $Na_2SO_4$ and concentrated under reduced pressure. The residue was purified by column chromatography on silica gel (eluent: PE/EtOAc=3/1) to give the desired product (100 mg, 92.10% yield). LCMS: m/z 459 (M+H)$^+$.

Step D. Tert-butyl (4-((4-methyl-2-(methylsulfinyl)-5-oxo-4H-thiazolo[5',4':4,5] pyrrolo[2,3-d] pyridazin-6(5H)-yl)methyl)pyridin-2-yl)carbamate To a mixture of tert-butyl(4-((4-methyl-2-(methylthio)-5-oxo-4H-thiazolo[5',4':4,5]pyrrolo[2,3-d]pyridazin-6(5H)-yl)methyl)pyridin-2-yl)carbamate (100 mg, 0.22 mmol) in DCM (5 mL) at 0° C. was added 3-chloroperoxybenzoic acid (38 mg, 0.22 mmol). The reaction mixture was stirred at 0° C. for 1 hr. then quenched with water and extracted with DCM. The combined organic layers were washed with saturated aqueous $NaHCO_3$, dried over anhydrous $Na_2SO_4$ and concentrated under reduced pressure to give the desired product (100 mg, 96.63% yield) which was directly used in the next step without any purification. LCMS: m/z 475 (M+H)$^+$.

Step E. 6-((2-Aminopyridin-4-yl)methyl)-4-methyl-2-(methylsulfinyl)-4H-thiazolo [5',4':4,5]pyrrolo[2,3-d]pyridazin-5(6H)-one A mixture of tert-butyl (4-((4-methyl-2-(methylsulfinyl)-5-oxo-4H-thiazolo[5',4':4,5]pyrrolo[2,3-d]pyridazin-6(5H)-yl)methyl)pyridin-2-yl)carbamate (100 mg, 0.21 mmol) in TFA (1 mL) and DCM (3 mL) was stirred at r.t. for 1 h then concentrated under reduced pressure. The residue was purified by prep-HPLC to give the desired product (20 mg, 25.35% yield). LCMS: m/z 375 (M+H)$^+$. $^1$H NMR (400 MHz, DMSO-$d_6$) δ 8.67 (s, 1H), 7.73 (d, 1H), 6.30 (d, 1H), 6.12 (s, 1H), 5.89 (s, 2H), 5.24-5.03 (m, 2H), 4.29 (s, 3H), 3.03 (s, 3H).

The procedure set forth above was used to produce following compounds using appropriate starting materials. Standard protection and deprotection can be used when necessary.

| Cpd No. | Structure and chemical name | Charaterization |
|---|---|---|
| E3-8 | 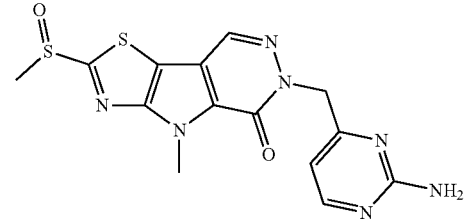 [SMILES: Cn1c2nc(S(C)=O)sc2c2cnn(Cc3ccnc(N)n3)c(=O)c21]<br>6-((2-aminopyrimidin-4-yl)methyl)-4-methyl-2-(methylsulfinyl)-4H-thiazolo[5',4':4,5]pyrrolo[2,3-d]pyridazin-5(6H)-one | LC-MS: m/z 376 (M + H)$^+$.<br>$^1$H NMR (400 MHz, DMSO-$d_6$) δ 8.76 (s, 1H), 8.12 (d, 1H), 6.60 (s, 2H), 6.22 (d, 1H), 5.20 (t, 2H), 4.28 (s, 3H), 3.12 (s, 3H). |
| E3-9 | 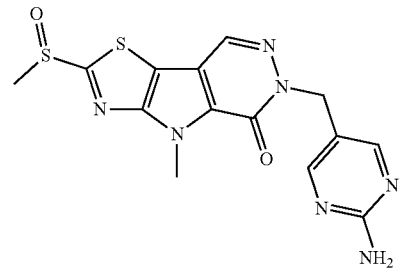 [SMILES: Cn1c2nc(S(C)=O)sc2c2cnn(Cc3cnc(N)nc3)c(=O)c21]<br>6-((2-Aminopyrimidin-5-yl)methyl)-4-methyl-2-(methylsulfinyl)-4,6-dihydro-5H-thiazolo[5',4':4,5]pyrrolo[2,3-d]pyridazin-5-one | LC-MS: 376 (M + H)$^+$.<br>$^1$H NMR (400 MHz, DMSO-$d_6$) δ 8.70 (s, 1H), 8.29 (s, 2H), 6.66 (s, 2H), 5.16 (s, 2H), 4.28 (s, 3H), 3.10 (s, 3H). |

Example 3C. Synthesis of 6-((2-aminothiazol-5-yl)methyl)-4-methyl-2-(methyl sulfinyl)-4H-thiazolo[5',4':4,5]pyrrolo[2,3-d]pyridazin-5(6H)-one

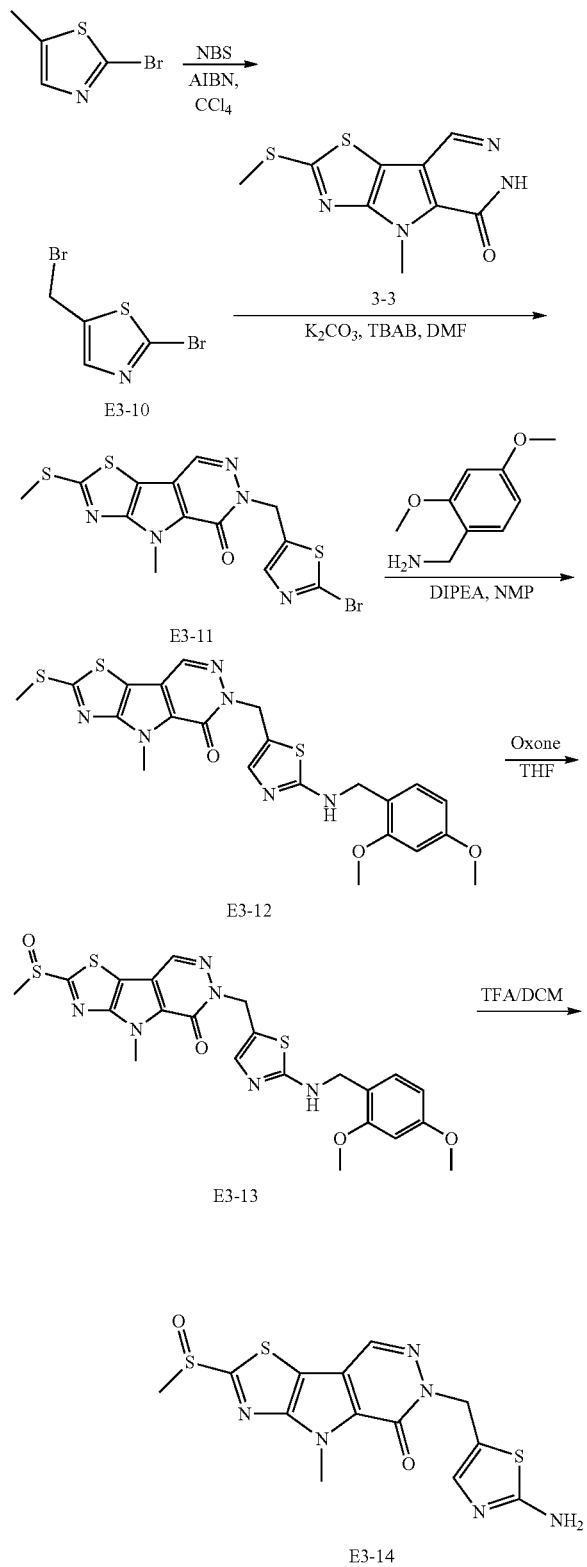

Step A-B

2-Bromo-5-(bromomethyl)thiazole and 6-((2-Bromothiazol-5-yl)methyl)-4-methyl-2-(methylthio)-4H-thiazolo[5',4':4,5]pyrrolo[2,3-d]pyridazin-5(6H)-one were synthesized similar to Example 3B.

Step C. 6-((2-((2,4-dimethoxybenzyl)amino)thiazol-5-yl)methyl)-4-methyl-2-(methylthio)-4H-thiazolo[5',4':4,5]pyrrolo[2,3-d]pyridazin-5(6H)-one A mixture of 6-((2-bromothiazol-5-yl)methyl)-4-methyl-2-(methylthio)-4H-thiazolo[5',4':4,5]pyrrolo[2,3-d]pyridazin-5(6H)-one (130 mg, 0.30 mmol) and DIPEA (0.1 mL) in NMP (0.1 mL) and (2,4-dimethoxyphenyl)methanamine (0.1 mL) was stirred at 150° C. for 4 hr. Then the traction mixture was quenched with water (10 mL), extracted with EtOAc. The combined organic layers were washed with brine, dried over anhydrous $Na_2SO_4$ and concentrated under reduced pressure. The residue was purified by column chromatography on silica gel (eluted with PE/EtOAc=5/1) to give the desired product (60 mg, 38.4% yield). LC-MS: m/z 515 (M+H)$^+$.

Step D. 6-((2-((2,4-dimethoxybenzyl)amino)thiazol-5-yl)methyl)-4-methyl-2-(methylsulfinyl)-4H-thiazolo[5',4':4,5]pyrrolo[2,3-d]pyridazin-5(6H)-one To a mixture of 6-((2-((2,4-dimethoxybenzyl)amino)thiazol-5-yl)methyl)-4-methyl-2-(methylthio)-4H-thiazolo[5',4':4,5]pyrrolo[2,3-d]pyridazin-5(6H)-one (50 mg, 0.10 mmol) in THF (3 mL) at 0° C. was added oxone (61 mg, 0.10 mmol). The mixture was stirred at 0° C. for 1 hr, then quenched with saturated aqueous $Na_2S_2O_3$ solution (5 mL) and extracted with DCM. The combined organic layers were washed with brine, dried over anhydrous $Na_2SO_4$ and concentrated under reduced pressure to give the desired product (30 mg, 50.1% yield) which was used directly in the next step without further purification. LC-MS: m/z 531 (M+H)$^+$.

Step E 6-((2-Aminothiazol-5-yl)methyl)-4-methyl-2-(methylsulfinyl)-4H-thiazolo[5',4':4,5]pyrrolo[2,3-d]pyridazin-5(6H)-one was synthesized similar to Example 3B. LC-MS: m/z 381 (M+H)$^+$. $^1$H NMR (400 MHz, DMSO-d$_6$) δ 8.70 (s, 1H), 6.97 (s, 1H), 6.87 (s, 2H), 5.28 (s, 2H), 4.29 (s, 3H), 3.11 (s, 3H).

The procedure set forth above was used to produce following compounds using appropriate starting materials. Standard protection and deprotection can be used when necessary.

| Cpd No. | Structure and chemical name | Characterization |
|---|---|---|
| E3-15 | 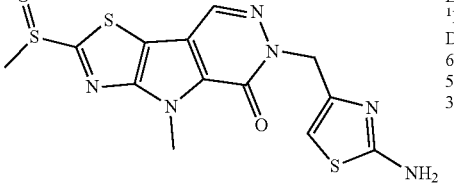<br>6-((2-aminothiazol-4-yl)methyl)-4-methyl-2-(methylsulfinyl)-4,6-dihydro-5H-thiazolo[5',4':4,5]pyrrolo[2,3-d]pyridazin-5-one | LCMS: m/z 381 (M + H)⁺.<br>$^1$H NMR (400 MHz, DMSO-$d_6$) δ 8.69 (s, 1H), 6.92 (s, 2H), 6.21 (s, 1H), 5.26-5.05 (m, 2H), 4.30 (s, 3H), 3.11 (s, 3H). |

Examples 4. Synthesis of 6-((1H-pyrazol-3-yl)methyl)-2-((1H-pyrazol-5-yl)methyl)-4-methyl-4H-thiazolo[5',4':4,5]pyrrolo[2,3-d]pyridazin-5(6H)-one Example 4A. Synthesis of 3-((phenylsulfonyl)methyl)-1-((2-(trimethylsilyl) ethoxy)methyl)-1H-pyrazole

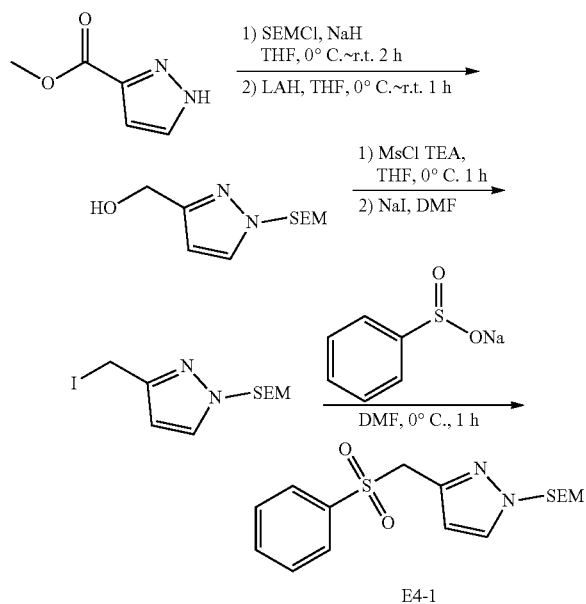

E4-1

Step A. Methyl 1-((2-(trimethylsilyl)ethoxy)methyl)-1H-pyrazole-3-carboxylate

At 0° C. under N₂ atmosphere, to a stirred solution of methyl 1H-pyrazole-3-carboxylate (90 g, 0.72 mol) in THF (1 L) was added NaH (20.7 g, 0.864 mol, 60%). The resulting mixture was slowly warmed up to r.t and stirred for 1 h. The reaction mixture was then cooled back to 0° C. and SEMCl (151.5 mL, 0.842 mol) was added drop wise. The stirring was continued for another 2 hr before quenched with sat. NH₄Cl and extracted with ethyl acetate (3×). The combined organic layers were washed with brine and dried over Na₂SO₄. Solvents were removed under vacuum to provide crude product 210 g which was used in the next step without purification.

Step B. (1-((2-(trimethylsilyl)ethoxy)methyl)-1H-pyrazol-3-yl)methanol

At 0° C. under N₂ atmosphere, to the suspension of LAH (16.9 g, 0.44 mol) in THF (760 mL) was added the crude methyl 1-((2-(trimethylsilyl)ethoxy)methyl)-1H-pyrazole-3-carboxylate (76 g). The resulting mixture was slowly warmed up to r.t. and stirred for 1 hr. The reaction mixture was cooled back to 0° C. and H₂O (15.6 mL), 10% NaOH (15.6 mL), H₂O (15.6 mL) was added successively. The resulting mixture was filtered through a pad of celite and washed with MTBE (4×). The combined organic fractions were dried over Na₂SO₄. Solvents were removed under reduced pressure to provide crude product 69.4 g which was used in the next step without purification. LC-MS: m/z 229 (M+H)⁺.

Step C. 3-(iodomethyl)-1-((2-(trimethylsilyl)ethoxy)methyl)-1H-pyrazole

At 0° C. under N₂ atmosphere, to a stirred solution of (1-((2-(trimethylsilyl)ethoxy)methyl)-1H-pyrazol-3-yl)methanol (61.5 g, theoretically 0.262 mol) in THF (310 mL) was added TEA (55.42 mL, 0.393 mol) followed by MsCl (24 mL, 0.314 mol). The reaction was warmed up to r.t and stirred for 1 hr before the introduction of NaI (196.5 g, 1.31 mol, in 310 mL DMF). The resulting mixture was stirred for another 1 hr and quenched with ice-water, extracted with MTBE (3×). The combined organic layers were washed with sat. Na₂S₂O₃ and brine, dried over Na₂SO₄ and concentrated to provide 77.5 g crude product used in the next step without purification. LC-MS: m/z 339 (M+H)⁺.

Step D. 3-((phenylsulfonyl)methyl)-1-((2-(trimethylsilyl)ethoxy)methyl)-1H-pyrazole At 0° C. under N₂ atmosphere, to a stirred solution of (1-((2-(trimethylsilyl)ethoxy)methyl)-1H-pyrazol-3-yl)methanol (77.5 g, theoretically 0.229 mol) in DMF (600 mL) was added sodium benzenesulfinate (53.5 g, 0.32 mol) and stirred for 1 hr at 0° C. After warmed up to r.t., the reaction mixture was quenched with ice-water and sat. Na₂S₂O₃, extracted with ethyl acetate (3×). The combined organic layers were washed with sat. NaHCO₃ and brined successively, dried over Na₂SO₄. Solvents were removed under vacuum and the residue was purified by flash chromatography (silica gel, 20%~70% ethyl acetate in petroleum ether) to provide 56.7 g as a light yellow oil. LCMS: [M+H]⁺ 353. 1H NMR (400 MHz, DMSO) δ 7.85-7.77 (m, 4H), 7.62 (dd, 2H), 6.19 (d, 1H), 5.35 (d, 2H), 4.70 (d, 2H), 3.44-3.38 (m, 2H), 0.88-0.77 (m, 2H), −0.01 (s, 9H).

Example 4B. Synthesis of 6-((1H-pyrazol-3-yl) methyl)-2-((1H-pyrazol-5-yl)methyl)-4-methyl-4H-thiazolo[5',4':4,5]pyrrolo[2,3-d]pyridazin-5(6H)-one

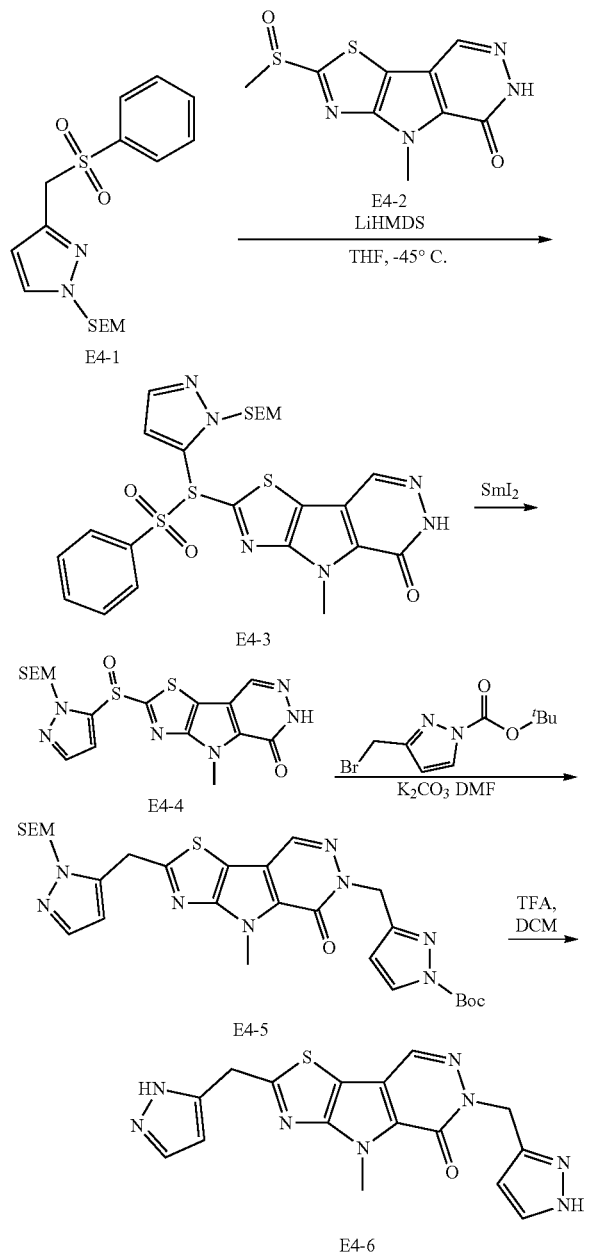

Step A. 4-methyl-2-((phenylsulfonyl)(1-((2-(trimethylsilyl)ethoxy)methyl)-1H-pyrazol-5-yl)methyl)-4H-thiazolo[5',4':4,5]pyrrolo[2,3-d]pyridazin-5(6H)-one To a solution of 3-((phenylsulfonyl)methyl)-1-((2-(trimethylsilyl)ethoxy)methyl)-1H-pyrazole (1.8 g, 5.1 mmol) in dry THF (30 mL) at −40° C. was added LiHMDS (7.5 mL, 7.5 mmol) drop-wise. The mixture was stirred at room temperature for 30 min, followed by addition of a suspension of 4-methyl-2-(methylsulfinyl)-4H-thiazolo[5',4':4,5]pyrrolo[2,3-d]pyridazin-5(6H)-one (580 mg, 2.7 mmol) in dry THF (30 mL) at room temperature. The mixture was stirred at r.t. for another 1 hr and poured into ice-cooled saturated aqueous NH$_4$Cl (20 mL) and extracted with EtOAc (3×100 mL). The combined organic layers were washed with water (60 mL), dried over anhydrous Na$_2$SO$_4$ and concentrated under reduced pressure. The residue was purified by flash chromatography (silica gel, 0-2.5% methanol in dichloromethane) to give the desired product (800 mg, 66%). LC-MS (ESI) found: 557 (M+H)$^+$. 1H NMR (400 MHz, DMSO) δ 12.78 (s, 1H), 8.65 (s, 1H), 8.03 (d, 1H), 7.84-7.78 (m, 3H), 7.67-7.59 (m, 2H), 6.94 (s, 1H), 6.72 (d, 1H), 5.48 (d, 2H), 4.29 (s, 3H), 3.56 (dd, 2H), 0.88 (dd, 2H), 0.00 (s, 9H).

Step B. 4-methyl-2-((1-((2-(trimethylsilyl)ethoxy) methyl)-1H-pyrazol-5-yl)methyl)-4H-thiazolo[5',4': 4,5]pyrrolo[2,3-d]pyridazin-5(6H)-one To a mixture of 4-methyl-2-((phenylsulfonyl)(1-((2-(trimethylsilyl)ethoxy)methyl)-1H-pyrazol-5-yl)methyl)-4H-thiazolo[5',4':4,5]pyrrolo[2,3-d]pyridazin-5(6H)-one (0.8 g, 1.41 mmol) in THF (5 mL) and MeOH (10 mL) under N$_2$ was added dropwise SmI$_2$ (0.1M/THF, 45 mL) under ice-bath After stirred for 10 min, the reaction was quenched with saturated aqueous NH$_4$Cl (50 mL) and extracted with EAOAc (50 mL×3). The combined organic layers were washed with water (60 mL), dried over anhydrous Na$_2$SO$_4$ and concentrated under reduced pressure. The residue was purified by flash chromatography (silica gel, 0~3% methanol in dichloromethane) to give the desired product (310 mg, 51.0%). LC-MS found: 417 (M+H)$^+$. $^1$H NMR (400 MHz, CDCl$_3$) δ 8.31 (s, 1H), 7.60 (d, 1H), 6.39 (d, 1H), 5.49 (s, 2H), 4.58 (s, 2H), 4.43 (s, 3H), 3.62 (t, 2H), 0.95 (t, 2H), 0.0 (s, 9H).

Step C. tert-butyl 3-((4-methyl-5-oxo-2-((1-((2-(trimethylsilyl)ethoxy)methyl)-1H-pyrazol-5-yl) methyl)-4H-thiazolo[5',4':4,5]pyrrolo[2,3-d] pyridazin-6(5H)-yl)methyl)-1H-pyrazole-1-carboxylate To a mixture of 4-methyl-2-((1-((2-(trimethylsilyl) ethoxy)methyl)-1H-pyrazol-5-yl)methyl)-4H-thiazolo[5',4': 4,5] pyrrolo[2,3-d]pyridazin-5(6H)-one (30 mg, 0.07 mmol) and K$_2$CO$_3$ (25 mg, 0.18 mmol) in DMF (5.0 mL) was bubbled with argon and stirred at 50° C. for 1 hr. Then tert-butyl 3-(bromomethyl)-1H-pyrazole-1-carboxylate (37 mg, 0.14 mmol) was added. After stirred at 50° C. overnight under argon, the reaction mixture was cooled down to r.t. and quenched with saturated aqueous NH$_4$Cl (20 mL) and extracted with EAOAc (30 mL×3). The combined organic layers were washed with water (40 mL), dried over anhydrous Na$_2$SO$_4$ and concentrated under reduced pressure. The residue was purified by Prep-TLC (DCM:MeOH=15:1) to give desire product (15 mg, 35.0%). LC-MS (ESI) found: 597 (M+H)$^+$.

Step D. 6-((1H-pyrazol-3-yl)methyl)-2-((1H-pyrazol-5-yl)methyl)-4-methyl-4H-thiazolo[5',4':4,5] pyrrolo[2,3-d]pyridazin-5(6H)-one To a solution of tert-butyl 34(4-methyl-5-oxo-2-((1-((2-(trimethylsilyl)ethoxy)methyl)-1H-pyrazol-5-yl)methyl)-

4H-thiazolo[5',4':4,5]pyrrolo[2,3-d]pyridazin-6(5H)-yl) methyl)-1H-pyrazole-1-carboxylate (15 mg, 0.025 mmol) in DCM (5 mL) was added TFA (1 mL). The reaction mixture was stirred at room temperature overnight before concentrated and purified by Pre-TLC (DCM:MeOH=15:1) to give desire product (5 mg, 50%). LC-MS, found: 367 (M+H)$^+$. $^1$H NMR (400 MHz, DMSO) δ 12.80 (s, 1H), 12.65 (s, 1H), 8.50 (s, 1H), 7.71 (brs, 1H), 7.60 (brs, 1H), 6.26 (d, 1H), 6.11 (d, 1H), 5.32 (s, 2H), 4.49 (s, 2H), 4.27 (s, 3H).

Example 5. Synthesis of 4-methyl-2-(methylsulfinyl)-4,6-dihydro-5H-thiazolo[5',4':4,5]pyrrolo[2,3-d]pyridazin-5-one

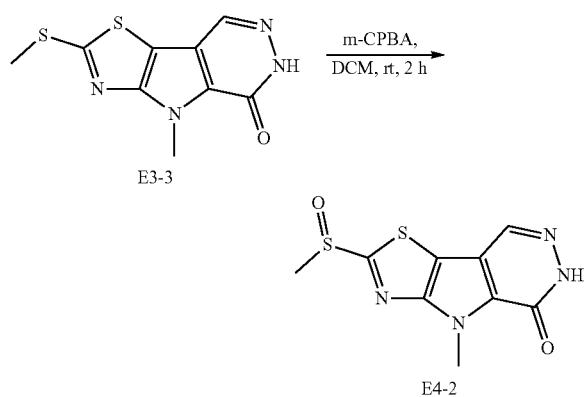

To a stirred suspension of 4-methyl-2-(methylthio)-4,6-dihydro-5H-thiazolo[5',4':4,5]pyrrolo[2,3-d]pyridazin-5-one (1.01 g, 4.0 mmol) in DCM (20 mL) was added 3-chloro-benzoperoxoic acid (0.77 g, 3.8 mmol) at r.t. The mixture stirred at r.t. for 2 hr. Then the mixture was filtered washed with EtOAc and triturated with MeOH. The solid was dried in vacuum to give 4-methyl-2-(methylsulfinyl)-4,6-dihydro-5H-thiazolo[5',4':4,5]pyrrolo[2,3-d]pyridazin-5-one (600 mg). LCMS: m/z 269 (M+H)$^+$. 1H NMR (400 MHz, DMSO) δ 12.78 (s, 1H), 8.64 (s, 1H), 4.28 (s, 3H), 3.11 (s, 3H).

Example 6. Synthesis of 4-methyl-2-(methylsulfonyl)-4,6-dihydro-5H-thiazolo[5',4':4,5]pyrrolo[2,3-d]pyridazin-5-one

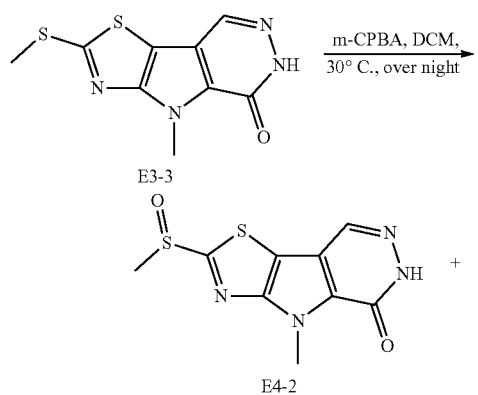

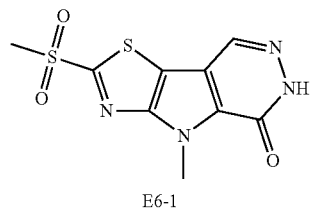

Three necked flask charged with 4-methyl-4,6-dihydro-5H-thiazolo[5',4':4,5]pyrrolo[2,3-d]pyridazin-5-one (30 g, 0.119 mol, 1.0 eq) in DCM (600 mL) m-CPBA (61.5 g, 3 eq) was added at 20° C. in three portions. The mixture was stirred at 30° C. overnight, LC-MS indicated 100% consumption of starting material, 20% of E4-2 and 80% of E6-1 were formed. The mixture was cooled to r.t., another portion of m-CPBA (1.0 eq) was added. The reaction mixture was stirred at 30° C. for 2 hr, LC-MS indicated E4-2 (LCMS: m/z 269 (M+H)$^+$.) <8%. The mixture was cooled to r.t. and filtered. The filtered cake was suspension in MeOH (500 mL) and stirred at r.t. for 1 hr. Solid was collected by filtration, washed with ethylacetate, dried in vacuum to afford 28 g of mixture of 5% of E4-2 and 95% of E6-1. The mixture (28 g) was suspended in DMSO (600 mL), heated to 120° C.~130° C. to form a clear solution. Then cooled to r.t., solid precipitated. The mixture was filtered and dried to provide 23 g of pure E6-1, LCMS: m/z 285 (M+H)$^+$. 1H NMR (400 MHz, DMSO) δ12.87 (s, 1H), 8.69 (s, 1H), 4.32 (s, 3H), 3.56 (s, 3H).

Example 7. Synthesis of Compounds E7-v and E7-viii

Scheme E7

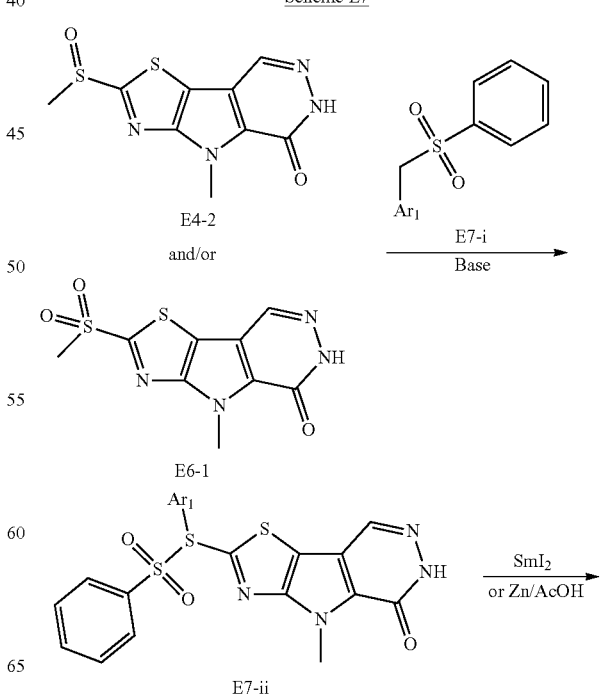

-continued

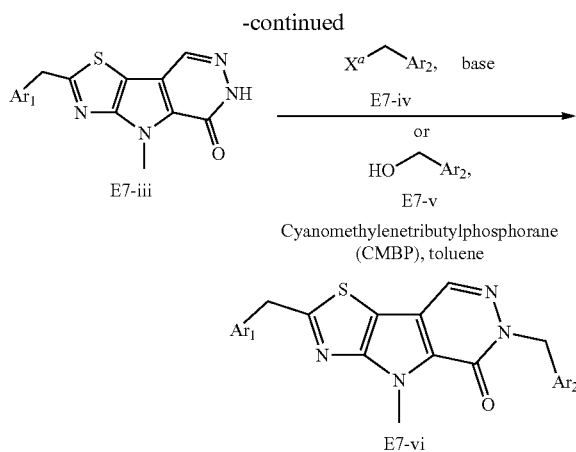

Nucleophilic aromatic substitution between compound E7-i and compound E4-2, and/or compound E6-1, gives intermediate E7-ii. Reduction of the phenylsulfonyl group of compound E7-ii affords intermediate E7-iii. Using standard alkylation reaction of E7-iv and compound E7-iii in the presence of base (e.g. $K_2CO_3$, $K_3PO_4$, t-BuOK, or $Cs_2CO_3$) gives compound E7-vi, wherein $X^a$ is a leaving group such as Cl, Br, I, OMs, OTs; $Ar_1$ and $Ar_2$ are each independently optionally substituted 5-membered or 6-membered monocyclic heteroaryl. Compound E7-vi can also be synthesized from Mitsunobu reaction of compound E7-iii with E7-v using Cyanomethylene-tributylphosphorane (CMBP) in toluene.

Example 7A. Synthesis of 4-methyl-2-((1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one

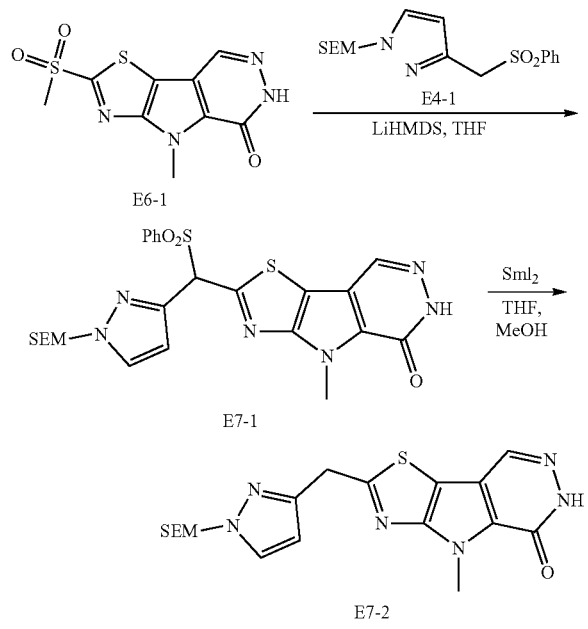

Step A. 4-methyl-2-((phenylsulfonyl)(1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one To a solution of 3-((phenylsulfonyl)methyl)-1-((2-(trimethylsilyl)ethoxy)methyl)-1H-pyrazole (26 g, 78.86 mmol, 2.1 eq) in anhydrous THF (700 mL) was added LiHMDS (81.2 mL, 81.2 mmol, 1 M in THF, 2.31 eq) at −40° C. The reaction was warmed up to room temperature and stirred for 1 hr. Then 4-methyl-2-(methylsulfonyl)-4H-thiazolo[5',4':4,5]pyrrolo[2,3-d]pyridazin-5(6H)-one (10 g, 35.17 mmol, 1 eq) was added to the mixture at room temperature. The reaction was stirred for another 0.5 hr at room temperature. The reaction was poured into saturated ammonium chloride solution (500 mL) at 0° C. and extracted with ethyl acetate twice. The combined organic layers were washed with water and brine, dried and concentrated to give a yellow residue. The residue was purified by silica gel chromatography (dichloromethane:methanol=100:1 to 30:1) to give 4-methyl-2-((phenylsulfonyl)(1-((2-(trimethylsilyl)ethoxy)methyl)-1H-pyrazol-3-yl)methyl)-4H-thiazolo[5',4':4,5]pyrrolo[2,3-d]pyridazin-5(6H)-one (13 g). LC-MS ESI M/Z=557 (M+H)⁺. 1H NMR (400 MHz, DMSO) δ 12.81 (s, 1H), 8.65 (s, 1H), 8.03 (d, 1H), 7.84-7.78 (m, 3H), 7.66 (t, 2H), 6.94 (s, 1H), 6.72 (d, 1H), 5.50 (d, 2H), 4.29 (s, 3H), 3.56 (dd, 2H), 0.91 (dd, 2H), 0.02 (s, 9H).

Step B. 4-methyl-2-((1-((2-(trimethylsilyl)ethoxy)methyl)-1H-pyrazol-3-yl)methyl)-4,6-dihydro-5H-thiazolo[5',4':4,5]pyrrolo[2,3-d]pyridazin-5-one To a solution of 4-methyl-2-((phenylsulfonyl)(1-((2-(trimethylsilyl)ethoxy)methyl)-1H-pyrazol-3-yl)methyl)-4H-thiazolo[5',4':4,5]pyrrolo[2,3-d]pyridazin-5(6H)-one (8 g, 14.37 mmol, 1 eq) in THF (500 mL) and MeOH (500 mL) was added $SmI_2$ (503 mL, 50.29 mmol, 0.1 M in THF, 3.5 eq) at room temperature. The reaction was stirred for 0.5 hr and concentrated. The residue was purified by silica gel chromatography (Petroleum ether:Ethyl acetate:Methanol=75:25:0 to 20:20:1) to give 4-methyl-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (4.3 g). LC-MS ESI M/Z=417 (M+H)⁺. ¹H NMR (400 MHz, CDCl₃) δ 8.31 (s, 1H), 7.60 (d, 1H), 7.28 (s, 1H), 6.39 (d, 1H), 5.49 (s, 2H), 4.58 (s, 2H), 4.43 (s, 3H), 3.62 (t, 2H), 0.95 (t, 2H), 0.0 (s, 9H).

Example 7B. Synthesis of 6-((1H-imidazol-2-yl)methyl)-2-((1H-pyrazol-3-yl)methyl)-4-methyl-4H-thiazolo[5',4':4,5]pyrrolo[2,3-d]pyridazin-5(6H)-one

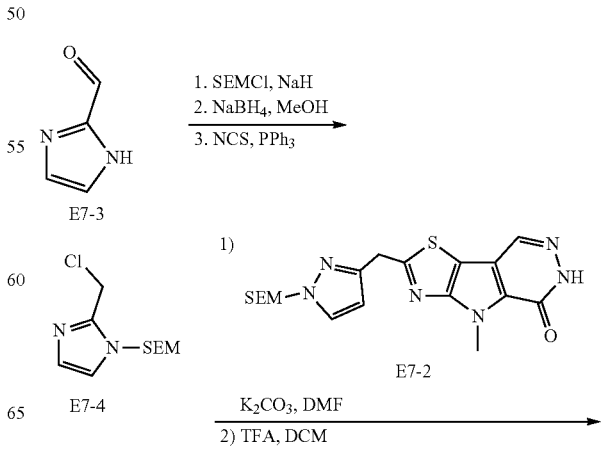

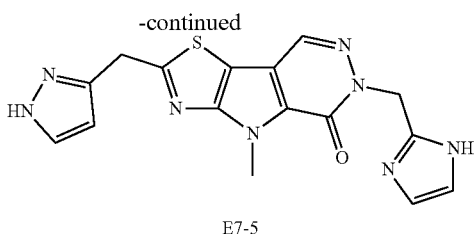

E7-5

Step A. 1-((2-(trimethylsilyl)ethoxy)methyl)-1H-imidazole-2-carbaldehyde

A sample of NaH was washed with hexane (2×10 mL) under N₂. The flask was charged dry DMF (20 mL) and 1H-imidazole-2-carbaldehyde (500 mg, 5.2 mmol) was added in small portions. After stirring at room temperature for 1.5 h, SEMCl (864 mg, 5.2 mmol) was added dropwise. The reaction mixture was stirred at r.t. for 30 min. The reaction mixture was poured into water, extracted with EtOAc. The organic layer was washed with brine, dried over Na₂SO₄, concentrated under reduced pressure to afford crude 1-((2-(trimethylsilyl)ethoxy)methyl)-1H-imidazole-2-carbaldehyde (800 mg). LCMS: 227 (M+H)⁺.

Step B. (1-((2-(trimethylsilyl)ethoxy)methyl)-1H-imidazol-2-yl)methanol

To a stirred mixture of 1-((2-(trimethylsilyl)ethoxy)methyl)-1H-imidazole-2-carbaldehyde (1.6 g, 7 mmol) in THF (20 mL) was added NaBH₄ (1.34 g, 35 mmol) at 0° C. The reaction mixture was stirred at r.t. for 30 min. The reaction mixture was poured into aq. NH₄Cl and extracted with EtOAc. The organic layer was washed with brine, dried over Na₂SO₄, concentrated under reduced pressure to afford crude (1-((2-(trimethylsilyl)ethoxy)methyl)-1H-imidazol-2-yl)methanol (1.3 g).

Step C. 2-(chloromethyl)-1-((2-(trimethylsilyl)ethoxy)methyl)-1H-imidazole

To a stirred mixture of (1-((2-(trimethylsilyl)ethoxy)methyl)-1H-imidazol-2-yl)methanol (400 mg, 1.75 mmol) in DCM (20 mL) were added NCS (466 mg, 3.5 mmol) and PPh₃ (920 mg, 3.5 mmol) at r.t. The mixture was stirred at r.t for 2 h. The reaction mixture was poured into water and extracted with DCM. The mixture was washed with water and the organic layer was concentrated under reduced pressure. The residue was purified by Pre-TLC (PE:EtOAc=1:1) to afford 2-(chloromethyl)-1-((2-(trimethylsilyl)ethoxy)methyl)-1H-imidazole. LCMS: 247 (M+H)⁺. To a stirred mixture of 4-methyl-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (50 mg, 0.12 mmol) in dry DMF (5 mL) was added K₂CO₃ (66 mg, 0.48 mmol) at 60° C. under N₂. After 20 min, compound E7-2 (60 mg, 0.24 mmol), in dry DMF (2 mL) was added at 60° C. under N₂. The mixture was stirred at 60° C. for 1.5 h under N₂. The reaction mixture was cooled to r.t and adjusted at pH=5~6 with 0.5N aq. HCl. Then the mixture was extracted with EtOAc, washed with water and brine. The organic layer was dried over Na₂SO₄, concentrated under reduced pressure and purified by Prep-TLC (PE:EtOAc=1:1.5) to afford 4-methyl-6-((1-((2-(trimethylsilyl)ethoxy)methyl)-1H-imidazol-2-yl)methyl)-2-((1-((2-pyrrolo[2,3-d]pyridazin-5(6H)-one (25 mg). LCMS: 627 (M+H)⁺. A mixture of 4-methyl-6-((1-((2-(trimethylsilyl)ethoxy)methyl)-1H-imidazol-2-yl)methyl)-2-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (25 mg, 0.04 mmol) in DCM/TFA (2 mL/2 mL) was stirred at r.t for 1 hour. The reaction mixture was concentrated. The residue was purified by prep-HPLC to afford desired product (1.3 mg). LCMS: 367 (M+H)⁺. ¹H NMR (400 MHz, DMSO-d6) δ 8.51 (s, 1H), 7.66 (d, 1H), 6.9 (s, 2H), 6.27 (d, 1H), 5.34 (s, 2H), 4.51 (s, 2H), 4.27 (s, 3H).

The following compounds were synthesized according to Scheme E7 and the procedure of Example 7A-7B using the appropriate starting material. Standard protection and deprotection methods are used when necessary.

| Cpd No. | Structure and chemical name | Charaterization |
|---|---|---|
| E7-6 | 2-((1H-pyrazol-3-yl)methyl)-4-methyl-6-(thiazol-4-ylmethyl)-4H-thiazolo[5',4':4,5]pyrrole[2,3-d]pyridazin-5(6H)-one | LCMS: 384 (M + H)⁺.. ¹H NMR (400 MHz, DMSO) δ 12.78 (s, 1H), 9.03 (d, 1H), 8.52 (s, 1H), 7.71 (s, 1H), 7.42 (d, 1H), 6.27 (d, 1H), 5.48 (s, 2H), 4.48 (s, 2H), 4.27 (s, 3H). |
| E7-7 | 6-((1,2,4-thiadiazol-5-yl)methyl)-2-((1H-pyrazol-3-yl)methyl)-4-methyl-4H-thiazolo[5',4':4,5]pyrrolo[2,3-d]pyridazin-5(6H)-one | LCMS: 385 (M + H)+. 1HNMR(400 MHz, DMSO) δ 12.79 (s, 1H), 8.84 (s, 1H), 8.64 (s, 1H), 7.72 (s, 1H), 6.27 (d, 1H), 5.84 (s, 2H), 4.51 (s, 2H), 4.28 (s, 3H) |

| Cpd No. | Structure and chemical name | Characterization |
|---|---|---|
| E7-8 | 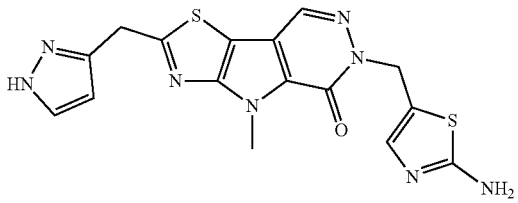<br>2-((1H-pyrazol-3-yl)methyl)-6-((2-aminothiazol-5-yl)methyl)-4-methyl-4H-thiazolo[5',4':4,5]pyrrolo[2,3-d]pyridazin-5(6H)-one | LCMS: m/z 399 (M + H)+.<br>1H NMR (400 MHz, DMSO-d6) δ 12.78 (s, 1H), 8.52 (s, 1H), 7.70 (s, 1H), 6.91 (s, 1H), 6.87 (br s, 2H), 6.27 (d, 1H), 5.26 (s, 2H), 4.49 (s, 2H), 4.27 (s, 3H). |
| E7-9 | 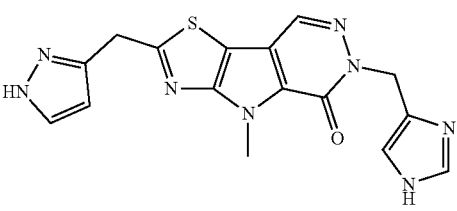 [SMILES: Cn1c2nc(Cc3cc[nH]n3)sc2c2cnn(Cc3c[nH]cn3)c(=O)c21]<br>6-((1H-imidazol-4-yl)methyl)-2-((1H-pyrazol-3-yl)methyl)-4-methyl-4H-thiazolo[5',4':4,5]pyrrolo[2,3-d]pyridazin-5(6H)-one | LCMS: m/z 367 (M + H)+.<br>1H NMR (400 MHz, DMSO-d6) δ 8.48 (s, 1H), 7.68 (s, 1H), 7.52 (s, 1H), 6.91 (s, 1H), 6.27 (d, 1H), 5.25 (s, 2H), 4.50 (s, 2H), 4.28 (s, 3H). |
| E7-10 | 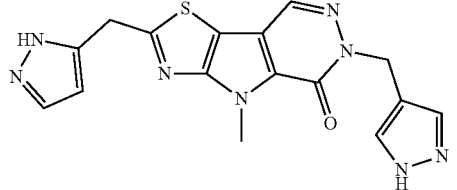 [SMILES: Cn1c2nc(Cc3ccn[nH]3)sc2c2cnn(Cc3cn[nH]c3)c(=O)c21]<br>6-((1H-pyrazol-4-yl)methyl)-2-((1H-pyrazol-5-yl)methyl)-4-methyl-4H-thiazolo[5',4':4,5]pyrrolo[2,3-d]pyridazin-5(6H)-one | LC-MS: m/z 367 (M + H)+.<br>1H NMR (400 MHz, DMSO) δ 12.77 (brs, 2H), 8.49 (s, 1H), 7.72-7.35 (m, 3H), 6.25 (s, 1H), 5.20 (s, 2H), 4.48 (s, 2H), 4.27 (s, 3H). |
| E7-11 | 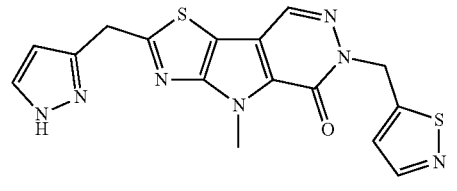 [SMILES: Cn1c2nc(Cc3cc[nH]n3)sc2c2cnn(Cc3ccns3)c(=O)c21]<br>2-((1H-pyrazol-3-yl)methyl)-6-(isothiazol-5-ylmethyl)-4-methyl-4H-thiazolo[5',4':4,5]pyrrolo[2,3-d]pyridazin-5(6H)-one | LC-MS: m/z 384 (M + 1)+.<br>1H NMR (400 MHz, DMSO) δ 12.77 (s, 1H), 8.59 (s, 1H), 8.46 (d, 1H), 7.71 (s, 1H), 7.42 (d, 1H), 6.26 (d, 1H), 5.66 (s, 2H), 4.48 (s, 2H), 4.28 (s, 3H). |

| Cpd No. | Structure and chemical name | Characterization |
|---|---|---|
| E7-12 | 2-((1H-pyrazol-3-yl)methyl)-6-((2-(hydroxymethyl)thiazol-4-yl)methyl)-4-methyl-4H-thiazolo[5',4':4,5]pyrrolo[2,3-d]pyridazin-5(6H)-one | LCMS: m/z 414 (M + H)+.<br>1H NMR (400 MHz, DMSO) δ 12.78 (s, 1H), 8.48 (s, 1H), 7.70 (s, 1H), 7.28 (s, 1H), 6.26 (d, 1H), 6.15 (t, 1H), 5.39 (s, 2H), 4.66 (d, 2H), 4.49 (s, 2H), 4.25 (s, 3H). |
| E7-13 | 4-((2-((1H-pyrazol-3-yl)methyl)-4-methyl-5-oxo-4H-thiazolo[5',4':4,5]pyrrolo[2,3-d]pyridazin-6(5H)-yl)methyl)thiazole-2-carboxamide | LCMS: m/z 427 (M + H)+.<br>1H NMR (400 MHz, DMSO) δ 12.78 (s, 1H), 8.51 (s, 1H), 8.11 (s, 1H), 7.78 (s, 1H), 7.70-7.60 (m, 2H), 6.27 (d, 1H), 5.50 (s, 2H), 4.48 (s, 2H), 4.26 (s, 3H). |
| E7-14 | 6-((1H-1,2,3-triazol-4-yl)methyl)-2-((1H-pyrazol-3-yl)methyl)-4-methyl-4H-thiazolo[5',4':4,5]pyrrolo[2,3-d]pyridazin-5(6H)-one | LCMS: m/z 368 (M + H)+.<br>1H NMR (400. MHz, DMSO-d6) δ 14.89 (s, 1H), 12.78 (s, 1H), 8.51 (s, 1H), 7.95-7.54 (m, 2H), 6.26 (d, 1H), 5.42 (s, 2H), 4.49 (s, 2H), 4.27 (s, 3H). |
| E7-15 | N-(6-((2-((1H-pyrazol-3-yl)methyl)-4-methyl-5-oxo-4H-thiazolo[5',4':4,5]pyrrolo[2,3-d]pyridazin-6(5H)-yl)methyl)-5-fluoropyridin-2-yl)acetamide | LCMS: (ESI) m/z 453 (M + H)+.<br>1H NMR (400 MHz, DMSO-d6) δ 12.84 (s, 1H), 10.41 (s, 1H), 8.57 (s, 1H), 8.06 (s, 1H), 7.71 (s, 2H), 6.34 (s, 1H), 5.52 (s, 2H), 4.58 (s, 2H), 4.33 (s, 3H), 2.08 (s, 3H). |
| E7-16 | 2-((1H-pyrazol-3-yl)methyl)-4-methyl-6-(thiazol-2-ylmethyl)-4H-thiazolo[5',4':4,5]pyrrolo[2,3-d]pyridazin-5(6H)-one | LC-MS: 384 [M + H]+.<br>1H NMR (400 MHz, DMSO) δ 12.78 (s, 1H), 8.58 (s, 1H), 7.75 (d, 1H), 7.70 (s, 1H), 7.64 (d, 1H), 6.27 (s, 1H), 5.65 (s, 2H), 4.48 (s, 2H), 4.27 (s, 3H). |

| Cpd No. | Structure and chemical name | Characterization |
|---|---|---|
| E7-17 | 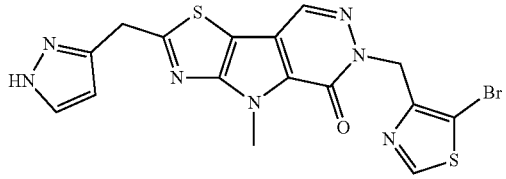 [SMILES: Cn1c2nc(Cc3cc[nH]n3)sc2c2cnn(Cc3ncsc3Br)c(=O)c21]<br>2-((1H-pyrazol-3-yl)methyl)-6-((5-bromothiazol-4-yl)methyl)-4-methyl-4H-thiazolo[5',4':4,5]pyrrolo[2,3-d]pyridazin-5(6H)-one | LCMS: m/z 462, 464 (M, M + 2H)+.<br>$^1$H NMR (400 MHz, DMSO-d$_6$)<br>δ 12.77 (s, 1H), 9.04 (s, 1H), 8.49 (s, 1H), 7.71 (s, 1H), 6.26 (d, 1H), 5.41 (s, 2H), 4.48 (s, 2H), 4.25 (s, 3H). |
| E7-18 | 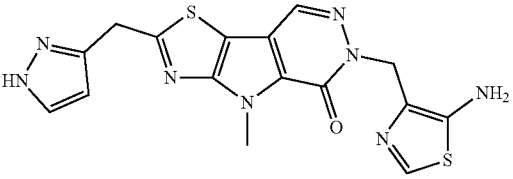 [SMILES: Cn1c2nc(Cc3cc[nH]n3)sc2c2cnn(Cc3ncsc3N)c(=O)c21]<br>2-((1H-pyrazol-3-yl)methyl)-6-((5-aminothiazol-4-yl)methyl)-4-methyl-4H-thiazolo[5',4':4,5]pyrrolo[2,3-d]pyridazin-5(6H)-one | LCMS: m/z 399 (M + H)+.<br>$^1$H NMR (400 MHz, DMSO-d$_6$) δ 12.78 (s, 1H), 8.51 (s, 1H), 7.99 (s, 1H), 7.71 (s, 1H), 6.27 (d, 1H), 5.83 (s, 2H), 5.27 (s, 2H), 4.49 (s, 2H), 4.27 (s, 3H) |
| E7-19 | 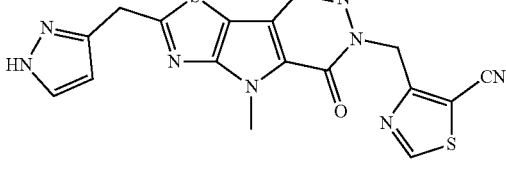<br>4-((2-((1H-pyrazol-3-yl)methyl)-4-methyl-5-oxo-4H-thiazolo[5',4':4,5]pyrrolo[2,3-d]pyridazin-6(5H)-yl)methyl)thiazole-5-carbonitrile | LCMS: m/z 409 (M + H)+.<br>$^1$H NMR (400 MHz, DMSO-d$_6$)<br>δ 12.77 (s, 1H), 9.36 (s, 1H), 8.56 (s, 1H), 7.71 (s, 1H), 6.26 (d, 1H), 5.61 (s, 2H), 4.49 (s, 2H), 4.25 (s, 3H). |
| E7-20 | 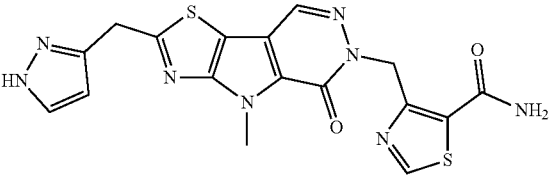 [SMILES: Cn1c2nc(Cc3cc[nH]n3)sc2c2cnn(Cc3ncsc3C(N)=O)c(=O)c21]<br>4-((2-((1H-pyrazol-3-yl)methyl)-4-methyl-5-oxo-4H-thiazolo[5',4':4,5]pyrrolo[2,3-d]pyridazin-6(5H)-yl)methyl)thiazole-5-carboxamide | LCMS: m/z 427 (M + H)+.<br>$^1$H NMR (400 MHz, DMSO-d$_6$)<br>δ 12.78 (s, 1H), 8.97 (s, 1H), 8.51 (s, 1H), 7.70 (s, 1H), 7.75 (d, 2H), 6.26 (d, 1H), 5.67 (s, 2H), 4.49 (s, 2H), 4.25 (s, 3H). |
| E7-21 | 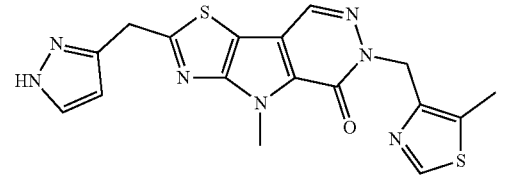 [SMILES: Cc1scnc1Cn1ncc2c3sc(Cc4cc[nH]n4)nc3n(C)c2c1=O]<br>2-((1H-pyrazol-3-yl)methyl)-4-methyl-6-((5-methylthiazol-4-yl)methyl)-4,6-dihydro-5H-thiazolo[5',4':4,5]pyrrolo[2,3-d]pyridazin-5-one | LCMS: m/z 398 (M + H)+.<br>$^1$H NMR (400 MHz, DMSO-d$_6$)<br>δ 12.77 (s, 1H), 8.74 (s, 1H), 8.47 (s, 1H), 7.70 (s, 1H), 6.26 (d, 1H), 5.39 (s, 2H), 4.49 (s, 2H), 4.26 (s, 3H), 2.49 (s, 3H). |

| Cpd No. | Structure and chemical name | Characterization |
|---|---|---|
| E7-22 | 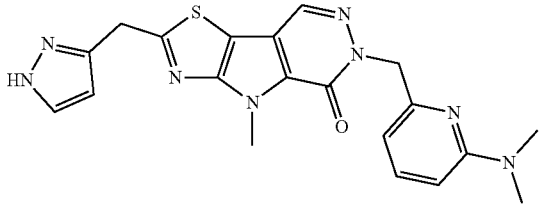 [SMILES: CN(C)c1cccc(Cn2ncc3c4sc(Cc5cc[nH]n5)nc4n(C)c3c2=O)n1]<br>2-((1H-pyrazol-3-yl)methyl)-6-((6-(dimethylamino)pyridin-2-yl)methyl)-4-methyl-4,6-dihydro-5H-thiazolo[5',4':4,5]pyrrolo[2,3-d]pyridazin-5-one | LCMS: 421 (M + H)+.<br>$^1$H NMR (400 MHz, DMSO) δ 12.78 (s, 1H), 8.53 (s, 1H), 7.68 (s, 1H), 7.39 (dd, 1H), 6.47 (d, 1H), 6.27 (d, 1H), 6.17 (d, 1H), 5.27 (s, 2H), 4.47 (m, 2H), 4.26 (s, 3H), 2.94 (s, 6H). |
| E7-23 | 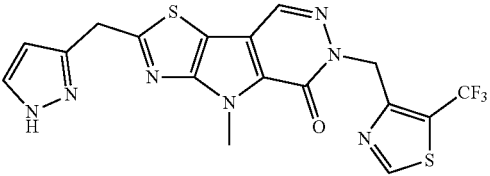 [SMILES: Cn1c2nc(Cc3cc[nH]n3)sc2c2cnn(Cc3ncsc3C(F)(F)F)c(=O)c21]<br>2-((1H-pyrazol-3-yl)methyl)-4-methyl-6-((5-(trifluoromethyl)thiazol-4-yl)methyl)-4H-thiazolo[5',4':4,5]pyrrolo[2,3-d]pyridazin-5(6H)-one | LCMS: m/z 452 (M + H)+.<br>$^1$H NMR (400 MHz, DMSO) δ 12.85 (s, 1H), 9.24 (s, 1H), 8.50 (s, 1H), 7.67 (s, 1H), 6.27 (d, 1H), 5.57 (s, 2H), 4.50 (s, 2H), 4.25 (s, 3H). |
| E7-24 | 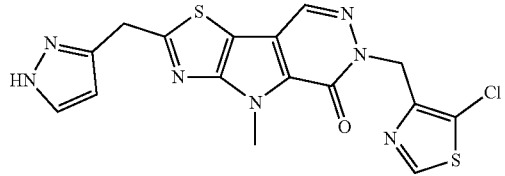 [SMILES: Cn1c2nc(Cc3cc[nH]n3)sc2c2cnn(Cc3ncsc3Cl)c(=O)c21]<br>2-((1H-pyrazol-3-yl)methyl)-6-((5-chlorothiazol-4-yl)methyl)-4-methyl-4H-thiazolo[5',4':4,5]pyrrolo[2,3-d]pyridazin-5(6H)-one | LCMS: m/z 418 (M + H)+.<br>$^1$H NMR (400 MHz, DMSO) δ 12.79 (s, 1H), 8.94 (s, 1H), 8.49 (s, 1H), 7.70 (s, 1H), 6.26 (d, 1H), 5.42 (s, 2H), 4.49 (s, 2H), 4.26 (s, 3H). |
| E7-25 | 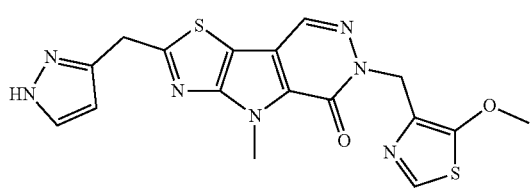 [SMILES: COc1scnc1Cn1ncc2c3sc(Cc4cc[nH]n4)nc3n(C)c2c1=O]<br>2-((1H-pyrazol-3-yl)methyl)-6-((5-methoxythiazol-4-yl)methyl)-4-methyl-4H-thiazolo[5',4':4,5]pyrrolo[2,3-d]pyridazin-5(6H)-one | LCMS (ESI): m/z 414 (M + H)+.<br>$^1$H NMR DMSO-d6 400 MHz δ 8.45 (s, 1H), 8.41 (s, 1H), 8.29 (s, 1H), 7.66 (s, 1H), 6.26 (d, 1H), 5.30 (s, 2H), 4.49 (s, 2H), 4.26 (s, 3H), 3.93 (s, 3H). |
| E7-26 | 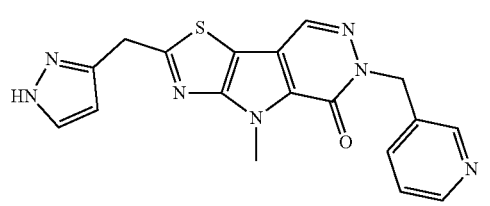 [SMILES: Cn1c2nc(Cc3cc[nH]n3)sc2c2cnn(Cc3cccnc3)c(=O)c21]<br>2-((1H-pyrazol-3-yl)methyl)-4-methyl-6-(pyridin-3-ylmethyl)-4H-thiazolo[5',4':4,5]pyrrolo[2,3-d]pyridazin-5(6H)-one | LCMS (ESI): m/z 378 (M + H).<br>$^1$H NMR (DMSO-d6 400 MHz) δ 12.79 (s, 1H), 8.57 (d, 1H), 8.54 (s, 1H), 8.48 (dd, 1H), 7.71 (ddd, 2H), 7.35 (ddd, 1H), 6.26 (d, 1H), 5.38 (s, 2H), 4.49 (s, 2H), 4.26 (s, 3H). |

| Cpd No. | Structure and chemical name | Charaterization |
|---|---|---|
| E7-27 | 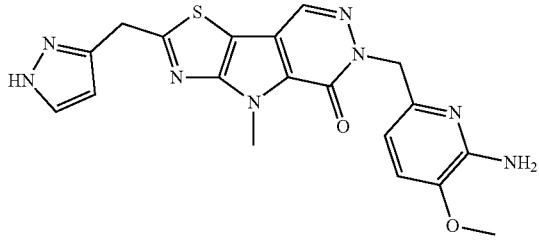 [SMILES: COc1ccc(Cn2ncc3c4sc(Cc5cc[nH]n5)nc4n(C)c3c2=O)nc1N]<br>2-((1H-pyrazol-3-yl)methyl)-6-((6-amino-5-methoxypyridin-2-yl)methyl)-4-methyl-4H-thiazolo[5',4':4,5]pyrrolo[2,3-d]pyridazin-5(6H)-one | LCMS: m/z 423 (M + H)$^+$.<br>$^1$H NMR (400 MHz, DMSO-d$_6$) δ 12.78 (s, 1H), 8.51 (s, 1H), 7.71 (s, 1H), 6.91 (d, 1H), 6.26 (d, 1H), 6.17 (d, 1H), 5.68 (s, 2H), 5.16 (s, 2H), 4.49 (s, 2H), 4.27 (s, 3H), 3.72 (s, 3H). |
| E7-28 | 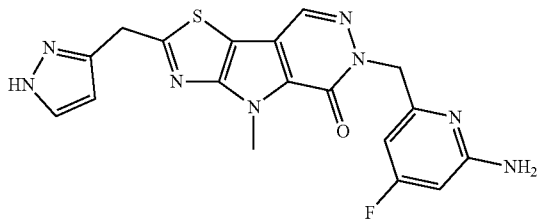 [SMILES: Cn1c2nc(Cc3cc[nH]n3)sc2c2cnn(Cc3cc(F)cc(N)n3)c(=O)c21]<br>2-((1H-pyrazol-3-yl)methyl)-6-((6-amino-4-fluoropyridin-2-yl)methyl)-4-methyl-4H-thiazolo[5',4':4,5]pyrrolo[2,3-d]pyridazin-5(6H)-one | LCMS: m/z 411 (M + H)$^+$.<br>$^1$H NMR (400 MHz, DMSO-d$_6$) δ 8.56 (s, 1H), 7.67 (s, 1H), 6.3-6.2 (m, 2H), 6.18 (d, 1H), 5.27 (s, 2H), 4.51 (s, 2H), 4.27 (s, 3H). |
| E7-29 | 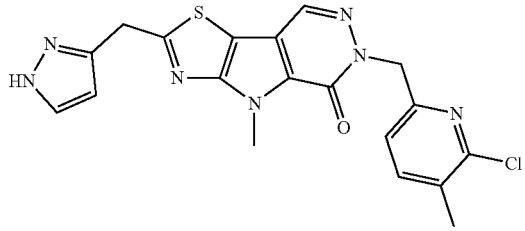 [SMILES: Cc1ccc(Cn2ncc3c4sc(Cc5cc[nH]n5)nc4n(C)c3c2=O)nc1Cl]<br>2-((1H-pyrazol-3-yl)methyl)-6-((6-chloro-5-methylpyridin-2-yl)methyl)-4-methyl-4H-thiazolo[5',4':4,5]pyrrolo[2,3-d]pyridazin-5(6H)-one | LCMS: m/z 426 (M + H)$^+$.<br>$^1$H NMR (400 MHz, DMSO) δ 8.56 (s, 1H), 7.73 (d, 1H), 7.67 (s, 1H), 7.08 (d, 1H), 6.26 (d, 1H), 5.39 (s, 2H), 4.50 (s, 2H), 4.26 (s, 3H), 2.30 (s, 3H). |
| E7-30 | 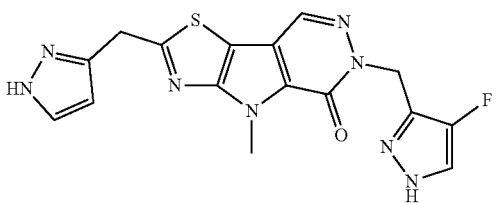 [SMILES: Cn1c2nc(Cc3cc[nH]n3)sc2c2cnn(Cc3n[nH]cc3F)c(=O)c21]<br>2-((1H-pyrazol-3-yl)methyl)-6-((4-fluoro-1H-pyrazol-3-yl)methyl)-4-methyl-4,6-dihydro-5H-thiazolo[5',4':4,5]pyrrolo[2,3-d]pyridazin-5-one | LCMS: m/z 385 (M + H)$^+$.<br>$^1$H NMR (400 MHz, DMSO) δ 12.83 (s, 1H), 12.68 (s, 1H), 8.46 (s, 1H), 7.64 (s, 2H), 6.26 (s, 1H), 5.33 (s, 2H), 4.48 (s, 2H), 4.24 (s, 3H). |

| Cpd No. | Structure and chemical name | Characterization |
|---|---|---|
| E7-31 | 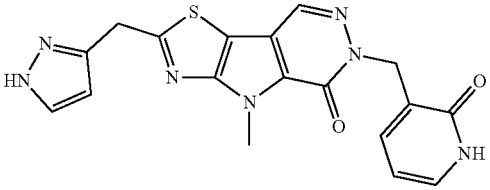 [SMILES: Cn1c2nc(Cc3cc[nH]n3)sc2c2cnn(Cc3ccc[nH]c3=O)c(=O)c21]<br>2-((1H-pyrazol-3-yl)methyl)-4-methyl-6-((2-oxo-1,2-dihydropyridin-3-yl)methyl)-4H-thiazolo[5',4':4,5]pyrrolo[2,3-d]pyridazin-5(6H)-one | LCMS: m/z 394 (M + H)$^+$.<br>$^1$H NMR (400 MHz, DMSO) δ 12.79 (s, 1H), 11.74 (s, 1H), 8.55 (s, 1H), 7.72 (s, 1H), 7.30 (d, 1H), 6.83 (d, 1H), 6.27 (d, 1H), 6.09 (t, 1H), 5.10 (s, 2H), 4.51 (s, 2H), 4.27 (s, 3H). |
| E7-32 | 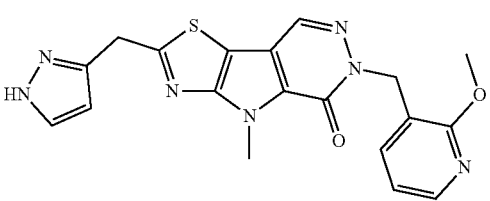 [SMILES: COc1ncccc1Cn1ncc2c3sc(Cc4cc[nH]n4)nc3n(C)c2c1=O]<br>2-((1H-pyrazol-3-yl)methyl)-6-((2-methoxy-pyridin-3-yl)methyl)-4-methyl-4H-thiazolo[5',4':4,5]pyrrolo[2,3-d]pyridazin-5(6H)-one | LCMS: m/z 408 (M + H)$^+$.<br>$^1$H NMR (400 MHz, DMSO) δ 12.78 (s, 1H), 8.56 (s, 1H), 8.08 (dd, 1H), 7.70 (s, 1H), 7.16 (d, 1H), 6.90 (dd, 1H), 6.27 (d, 1H), 5.29 (s, 2H), 4.51 (s, 2H), 4.27 (s, 3H), 3.93 (s, 3H). |
| E7-33 | 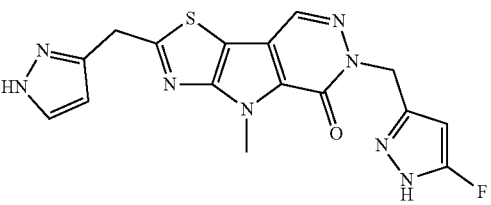 [SMILES: Cn1c2nc(Cc3cc[nH]n3)sc2c2cnn(Cc3cc(F)[nH]n3)c(=O)c21]<br>2-((1H-pyrazol-3-yl)methyl)-6-((5-fluoro-1H-pyrazol-3-yl)methyl)-4-methyl-4H-thiazolo[5',4':4,5]pyrrolo[2,3-d]pyridazin-5(6H)-one | LCMS: m/z 385 (M + H)$^+$.<br>$^1$H NMR (400 MHz, DMSO-d$_6$) δ 12.88 (s, 1H), 12.61 (s, 1H), 8.61 (d, 1H), 7.78 (s, 1H), 6.33 (d, 1H), 5.89 (d, 1H), 5.36 (s, 2H), 4.54 (d, 2H), 4.34 (s, 3H). |
| E7-34 | 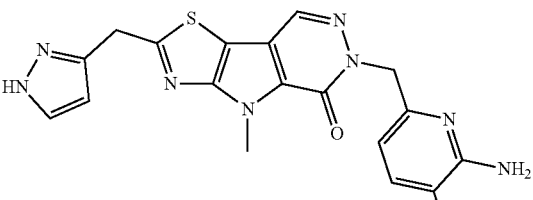<br>2-((1H-pyrazol-3-yl)methyl)-6-((6-amino-5-methylpyridin-2-yl)methyl)-4-methyl-4H-thiazolo[5',4':4,5]Pyrrolo[2,3-d]pyridazin-5(6H)-one | LCMS: m/z 407 (M + H)$^+$.<br>$^1$H NMR (400 MHz, DMSO-d$_6$) δ 12.84 (s, 1H), 8.58 (s, 1H), 7.79 (s, 1H), 7.18 (d, 1H), 6.33 (s, 1H), 6.15 (d, 1H), 5.75 (s, 2H), 5.25 (s, 2H), 4.55 (s, 2H), 4.33 (s, 3H), 2.05 (s, 3H). |

| Cpd No. | Structure and chemical name | Charaterization |
|---|---|---|
| E7-35 | 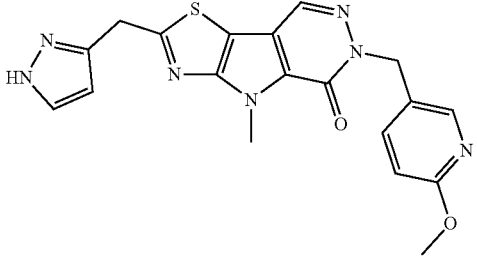 [SMILES: COc1ccc(Cn2ncc3c4sc(Cc5cc[nH]n5)nc4n(C)c3c2=O)cn1]<br>2-((1H-pyrazol-3-yl)methyl)-6-((6-methoxypyridin-3-yl)methyl)-4-methyl-4H-thiazolo[5',4':4,5]pyrrolo[2,3-d]pyridazin-5(6H)-one | LC-MS: m/z 408 (M + H)⁺.<br>¹H NMR (400 MHz, DMSO) δ 12.87 (s, 1H), 8.60 (s, 1H), 8.27 (d, 1H), 7.84-7.72 (m, 2H), 6.86 (d, 1H), 6.34 (d, 1H), 5.37 (s, 2H), 4.55 (s, 2H), 4.34 (s, 3H), 3.89 (s, 3H). |
| E7-36 | 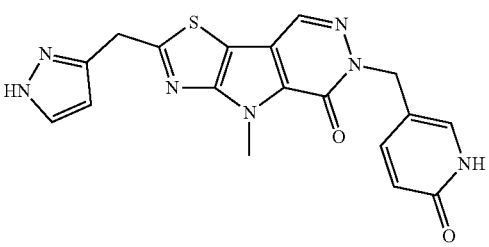 [SMILES: Cn1c2nc(Cc3cc[nH]n3)sc2c2cnn(Cc3ccc(=O)[nH]c3)c(=O)c21]<br>2-((1H-pyrazol-3-yl)methyl)-4-methyl-6-((6-oxo-1,6-dihydropyridin-3-yl)methyl)-4,6-dihydro-5H-thiazolo[5',4':4,5]pyrrolo[2,3-d]pyridazin-5-one | LC-MS: m/z 394 (M + H)⁺.<br>¹H NMR (400 MHz, DMSO) δ 12.77 (s, 1H), 11.53 (s, 1H), 8.52 (s, 1H), 7.69 (s, 1H), 7.47 (dd, 1H), 7.40 (d, 1H), 6.27 (dd, 2H), 5.07 (s, 2H), 4.49 (s, 2H), 4.26 (s, 3H). |
| E7-37 | 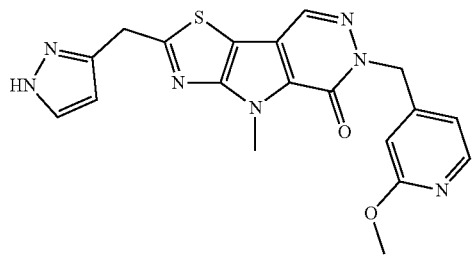 [SMILES: COc1cc(Cn2ncc3c4sc(Cc5cc[nH]n5)nc4n(C)c3c2=O)ccn1]<br>2-((1H-pyrazol-3-yl)methyl)-6-((2-methoxypyridin-4-yl)methyl)-4-methyl-4H-thiazolo[5',4':4,5]pyrrolo[2,3-d]pyridazin-5(6H)-one | LC-MS: m/z 408 (M + H)⁺.<br>¹H NMR (400 MHz, DMSO) δ 12.86 (s, 1H), 8.65 (d, 1H), 8.17 (d, 1H), 7.80 (s, 1H), 6.94-6.89 (m, 1H), 6.66 (s, 1H), 6.34 (d, 1H), 5.41 (s, 2H), 4.56 (s, 2H), 4.34 (s, 3H), 3.89 (s, 3H). |
| E7-38 | 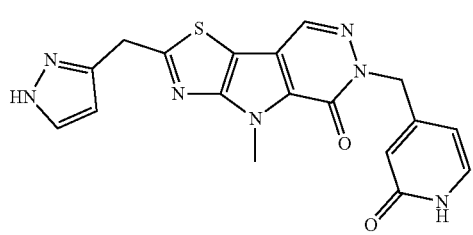 [SMILES: Cn1c2nc(Cc3cc[nH]n3)sc2c2cnn(Cc3cc[nH]c(=O)c3)c(=O)c21]<br>2-((1H-pyrazol-3-yl)methyl)-4-methyl-6-((2-oxo-1,2-dihydropyridin-4-yl)methyl)-4,6-dihydro-5H-thiazolo[5',4':4,5]pynolo[2,3-d]pyridazin-5-one | LC-MS: m/z 394 (M + H)⁺.<br>¹H NMR (400 MHz, DMSO) δ 8.57 (s, 1H), 7.68 (s, 1H), 7.31 (d, 1H), 7.23 (t, 1H), 6.27 (d, 1H), 6.07 (dd, 1H), 5.97 (s, 1H), 5.17 (s, 2H), 4.51 (s, 2H), 4.27 (s, 3H). |

| Cpd No. | Structure and chemical name | Charaterization |
|---|---|---|
| E7-39 | 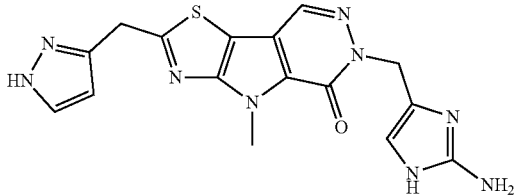 [SMILES: Cn1c2nc(Cc3cc[nH]n3)sc2c2cnn(Cc3c[nH]c(N)n3)c(=O)c21]<br>2-((1H-pyrazol-3-yl)methyl)-6-((2-amino-1H-imidazol-4-yl)methyl)-4-methyl-4H-thiazolo[5',4':4,5]pyrrolo[2,3-d]pyridazin-5(6H)-one | LCMS: m/z 382 (M + H)⁺.<br>¹H NMR (400 MHz, DMSO) δ 12.80 (s, 1H), 8.46 (s, 1H), 8.39 (s, 1H), 7.66 (s, 1H), 6.34 (s, 1H), 6.26 (d, 1H), 5.18 (s, 2H), 5.06 (s, 2H), 4.49 (s, 2H), 4.27 (s, 3H). |
| E7-40 | 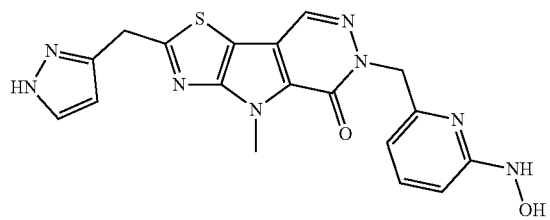 [SMILES: Cn1c2nc(Cc3cc[nH]n3)sc2c2cnn(Cc3cccc(NO)n3)c(=O)c21]<br>2-((1H-pyrazol-3-yl)methyl)-6-((6-(hydroxyamino)pyridin-2-yl)methyl)-4-methyl-4H-thiazolo[5',4':4,5]pyrrolo[2,3-d]pyridazin-5(6H)-one | LCMS: m/z 409 (M + H)⁺.<br>¹H NMR (400 MHz, DMSO) δ 12.83 (s, 1H), 8.74 (s, 1H), 8.55-8.65 (m, 2H), 7.79 (s, 1H), 7.56 (t, 1H), 6.77 (d, 1H), 6.40 (d, 1H), 6.32 (d, 1H), 5.32 (s, 2H), 4.52 (s, 2H), 4.31 (s, 3H) |
| E7-41 | 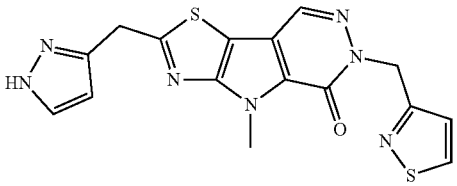 [SMILES: Cn1c2nc(Cc3cc[nH]n3)sc2c2cnn(Cc3ccsn3)c(=O)c21]<br>2-((1H-pyrazol-3-yl)methyl)-6-(isothiazol-3-ylmethyl)-4-methyl-4H-thiazolo[5',4':,5]pyrrolo[2,3-d]pyridazin 5(6H)-one | LCMS: ESI m/z 384 (M + H)⁺.<br>¹H NMR (400 MHz, DMSO-d₆) δ 9.01 (d, 1H), 8.54 (s, 1H), 7.67 (d, 1H), 7.21 (d, 1H), 6.27 (d, 1H), 5.50 (s, 2H), 4.51 (s, 2H), 4.26 (s, 3H). |
| E7-42 | 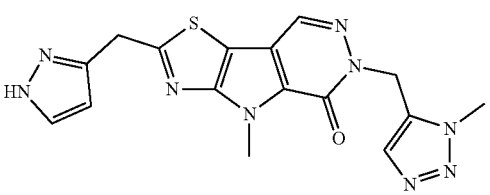 [SMILES: Cn1nncc1Cn1ncc2c3sc(Cc4cc[nH]n4)nc3n(C)c2c1=O]<br>2-((1H-pyrazol-3-yl)methyl)-4-methyl-6-((1-methyl-1H-1,2,3-triazol-5-yl)methyl)-4H-thiazolo[5',4':4,5]pyrrolo[2,3-d]pyridazin-5(6H)-one | LCMS: ESI m/z 382 (M + H)⁺.<br>¹H NMR (400 MHz, DMSO-d₆) δ 12.78 (s, 1H), 8.55 (s, 1H), 7.71 (s, 1H), 7.62 (s, 1H), 6.26 (d, 1H), 5.49 (s, 2H), 4.48 (s, 2H), 4.26 (s, 3H), 4.10 (s, 3H). |
| E7-43 | 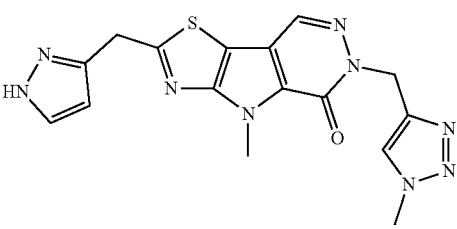 [SMILES: Cn1cc(Cn2ncc3c4sc(Cc5cc[nH]n5)nc4n(C)c3c2=O)nn1]<br>2-((1H-pyrazol-3-yl)methyl)-4-methyl-6-((1-methyl-1H-1,2,3-triazol-4-yl)methyl)-4H-thiazolo[5',4':4,5] pyrrolo[2,3-d]pyridazin-5(6H)-one | LCMS: ESI m/z 382 (M + H)⁺.<br>¹H NMR (400 MHz, DMSO-d₆) δ 12.78 (s, 1H), 8.51 (s, 1H), 7.96 (s, 1H), 7.71 (s, 1H), 6.27 (d, 1H), 5.38 (s, 2H), 4.49 (s, 2H), 4.27 (s, 3H), 3.99 (s, 3H). |

-continued

| Cpd No. | Structure and chemical name | Characterization |
|---|---|---|
| E7-44 | 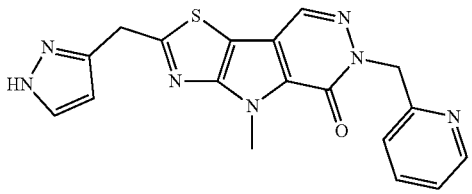 [SMILES: Cn1c2nc(Cc3cc[nH]n3)sc2c2cnn(Cc3ccccn3)c(=O)c21]<br><br>2-((1H-pyrazol-3-yl)methyl)-4-methyl-6-(pyridin-2-ylmethyl)-4H-thiazolo[5',4':4,5]pyrrolo[2,3-d]pyridazin-5(6H)-one | LCMS: ESI m/z 378 (M + H)⁺.<br>¹H NMR (400 MHz, DMSO-d₆) δ 12.94 (s, 1H), 8.64 (s, 1H), 8.57 (d, 1H), 7.82 (m, 2H), 7.36 (m, 1H), 7.23 (d, 1H), 6.36 (d, 1H), 5.55 (s, 2H), 4.58 (s, 2H), 4.36 (s, 3H). |
| E7-45 | 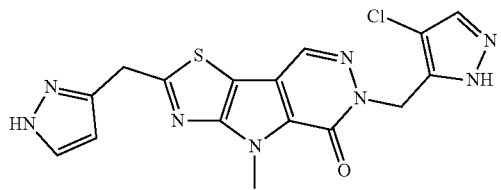 [SMILES: Cn1c2nc(Cc3cc[nH]n3)sc2c2cnn(Cc3[nH]ncc3Cl)c(=O)c21]<br><br>2-((1H-pyrazol-3-yl)methyl)-6-((4-chloro-1H-pyrazol-5-yl)methyl)-4-methyl-4H-thiazolo[5',4':4,5] pyrrolo[2,3-d]pyridazin-5(6H)-one | LCMS: m/z 401 (M + H)⁺.<br>¹H NMR (400 MHz, DMSO-d6) δ 12.96 (s, 1H), 12.77 (s, 1H), 8.48 (s, 1H), 7.91 (s, 1H), 7.71 (s, 1H), 6.26 (d, 1H), 5.33 (s, 2H), 4.49 (s, 2H), 4.27 (s, 3H). |
| E7-46 | 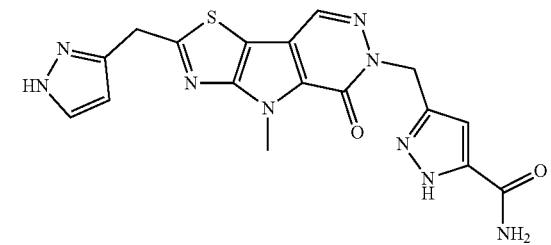 [SMILES: Cn1c2nc(Cc3cc[nH]n3)sc2c2cnn(Cc3cc(C(N)=O)[nH]n3)c(=O)c21]<br><br>3-((2-((1H-pyrazol-3-yl)methyl)-4-methyl-5-oxo-4,5-dihydro-6H-thiazolo[5',4':4,5]pyrrolo[2,3-d]pyridazin-6-yl)methyl)-1H-pyrazole-5-carboxamide | LCMS: m/z 410 (M + H)⁺.<br>¹H NMR (400 MHz, DMSO-d6) δ 13.34 (s, 1H), 12.81 (s, 1H), 8.54 (s, 1H), 7.70 (s, 2H), 7.26 (m, 1H), 6.64 (s, 1H), 6.27 (s, 1H), 5.35 (s, 2H), 4.50 (s, 2H), 4.28 (s, 3H) |
| E7-47 | 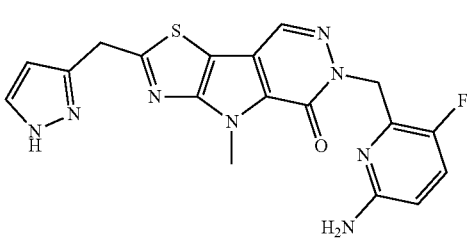 [SMILES: Cn1c2nc(Cc3cc[nH]n3)sc2c2cnn(Cc3nc(N)ccc3F)c(=O)c21]<br><br>2-((1H-pyrazol-3-yl)methyl)-6-((6-amino-3-fluoropyridin-2-yl)methyl)-4-methyl-4H-thiazolo[5',4':4,5]pyrrolo[2,3-d]pyridazin-5(6H)-one | LC-MS m/z 411.0 (M + H)⁺.<br>¹H NMR (400 MHz, DMSO) δ 12.79 (s, 1H), 8.46 (s, 1H), 7.73 (s, 1H), 7.29 (dd, 1H), 6.34 (dd, 1H), 6.27 (d, 1H), 5.74 (s, 2H), 5.30 (s, 2H), 4.46 (s, 2H), 4.26 (s, 3H) |
| E7-48 | 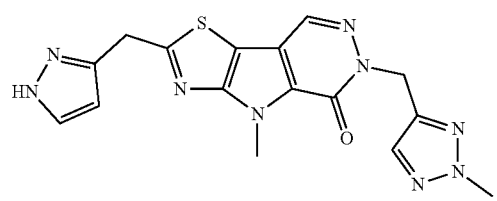 [SMILES: Cn1ncc(Cn2ncc3c4sc(Cc5cc[nH]n5)nc4n(C)c3c2=O)n1]<br><br>2-((1H-pyrazol-3-yl)methyl)-4-methyl-6-((2-methyl-2H-1,2,3-triazol-4-yl)methyl)-4H-thiazolo[5',4':4,5]pyrrolo[2,3-d]pyridazin-5(6H)-one | LC-MS m/z 382.0 (M + H)⁺.<br>¹H NMR (400 MHz, DMSO) δ 12.79 (s, 1H), 8.51 (s, 1H), 7.68 (s, 1H), 7.68 (s, 1H), 6.26 (d, 1H), 5.38 (s, 2H), 4.50 (s, 2H), 4.26 (s, 3H), 4.08 (s, 3H) |

| Cpd No. | Structure and chemical name | Charaterization |
|---|---|---|
| E7-49 | 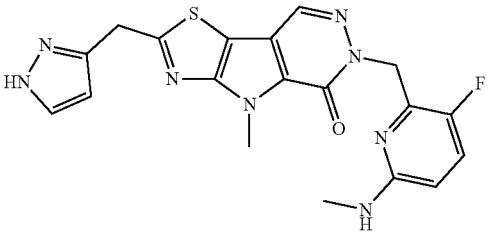 [SMILES: CNc1ccc(F)c(Cn2ncc3c4sc(Cc5cc[nH]n5)nc4n(C)c3c2=O)n1]<br>2-((1H-pyrazol-3-yl)methyl)-6-((3-fluoro-6-(methylamino)pyridin-2-yl)methyl)-4-methyl-4H-thiazolo[5',4':4,5]pyrrolo[2,3-d]pyridazin-5(6H)-one | LC-MS m/z 425 (M + H)$^+$.<br>$^1$H NMR (400 MHz, DMSO) δ 12.77 (s, 1H), 8.47 (s, 1H), 7.71 (s, 1H), 7.31 (t, 1H), 6.33-6.26 (m, 3H), 5.34 (s, 2H), 4.49 (s, 2H), 4.26 (s, 3H), 2.48 (s, 3H) |
| E7-50 | 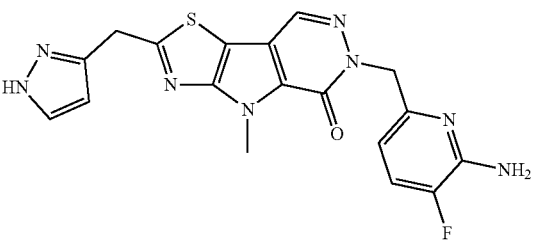 [SMILES: Cn1c2nc(Cc3cc[nH]n3)sc2c2cnn(Cc3ccc(F)c(N)n3)c(=O)c21]<br>2-((1H-pyrazol-3-yl)methyl)-6-((6-amino-5-fluoropyridin-2-yl)methyl)-4-methyl-4H-thiazolo[5',4':4,5]pyrrolo[2,3-d]pyridazin-5(6H)-one | LCMS: (ESI) m/z 411 (M + H)$^+$.<br>$^1$H NMR (400 MHz, DMSO-d$_6$) δ 8.59 (s, 1H), 7.73 (s, 1H), 7.29 (dd, 1H), 6.47-6.06 (m, 4H), 5.26 (s, 2H), 4.56 (s, 2H), 4.32 (s, 3H) |
| E7-51 | 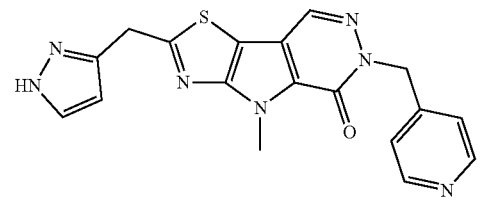 [SMILES: Cn1c2nc(Cc3cc[nH]n3)sc2c2cnn(Cc3ccncc3)c(=O)c21]<br>2-((1H-pyrazol-3-yl)methyl)-4-methyl-6-(pyridin-4-ylmethyl)-4H-thiazolo[5',4':4,5]pyrrolo[2,3-d]pyridazin-5(6H)-one | LCMS: (ESI) m/z 378 (M + H)$^+$.<br>$^1$H NMR (400 MHz, DMSO-d$_6$) δ 12.84 (s, 1H), 8.64 (s, 1H), 8.57 (d, 1H), 8.55 (d, 1H), 7.77 (s, 1H), 7.28 (d, 2H), 6.33 (d, 1H), 5.45 (s, 2H), 4.56 (s, 2H), 4.32 (s, 3H) |
| E7-52 | 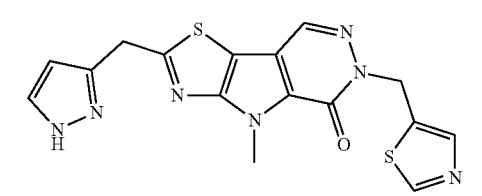 [SMILES: Cn1c2nc(Cc3cc[nH]n3)sc2c2cnn(Cc3cncs3)c(=O)c21]<br>2-((1H-pyrazol-3-yl)methyl)-4-methyl-6-(thiazol-5-ylmethyl)-4,6-dihydro-5H-thiazolo[5',4':4,5]pyrrolo[2,3-d]pyridazin-5-one | LCMS: (ESI) m/z 384 (M + H)$^+$.<br>$^1$H NMR (400 MHz, DMSO-d$_6$) δ 12.85 (s, 1H), 9.01 (s, 1H), 8.54 (d, 1H), 7.95 (d, 1H), 7.74 (s, 1H), 6.24 (s, 1H), 5.55 (s, 2H), 4.46 (s, 2H), 4.30 (s, 3H) |

-continued

| Cpd No. | Structure and chemical name | Charaterization |
|---|---|---|
| E7-53 | 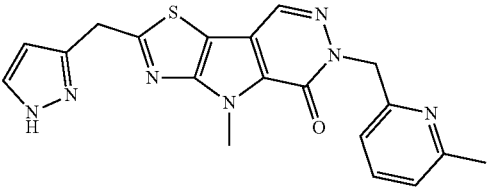 [SMILES: Cc1cccc(Cn2ncc3c4sc(Cc5cc[nH]n5)nc4n(C)c3c2=O)n1]<br>2-((1H-pyrazol-3-yl)methyl)-4-methyl-6-((6-methylpyridin-2-yl)methyl)-4,6-dihydro-5H-thiazolo[5',4':4,5]pyrrolo[2,3-d]pyridazin-5-one | LCMS: (ESI) m/z 392 (M + H)+.<br>$^1$H NMR (400 MHz, DMSO-d$_6$) δ 12.78 (s, 1H), 8.55 (s, 1H), 7.74 (s, 1H), 7.61 (dd, 1H), 7.14 (d, 1H), 6.81 (d, 1H), 6.26 (s, 1H), 5.39 (s, 2H), 4.50 (s, 2H), 4.26 (s, 3H), 2.43 (s, 3H) |
| E7-54 | 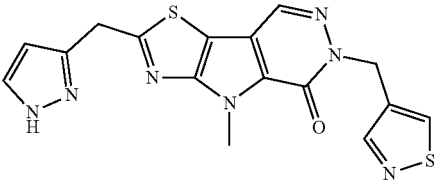 [SMILES: Cn1c2nc(Cc3cc[nH]n3)sc2c2cnn(Cc3cnsc3)c(=O)c21]<br>2-((1H-pyrazol-3-yl)methyl)-6-(isothiazol-4-ylmethyl)-4-methyl-4,6-dihydro-5H-thiazolo[5',4':4,5]pyrrolo[2,3-d]pyridazin-5-one | LCMS: (ESI) m/z 384 (M + H)+.<br>$^1$H NMR (400 MHz, DMSO-d$_6$) δ 12.78 (s, 1H), 8.91 (s, 1H), 8.56 (s, 1H), 8.53 (s, 1H), 7.71 (s, 1H), 6.26 (s, 1H), 5.48 (s, 2H), 4.49 (s, 2H), 4.31 (s, 3H) |
| E7-55 | 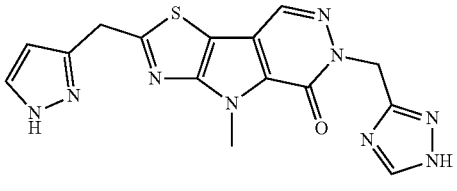 [SMILES: Cn1c2nc(Cc3cc[nH]n3)sc2c2cnn(Cc3nc[nH]n3)c(=O)c21]<br>6-((1H-1,2,4-triazol-3-yl)methyl)-2-((1H-pyrazol-3-yl)methyl)-4-methyl-4,6-dihydro-5H-thiazolo[5',4':4,5]pyrrolo[2,3-d]pyridazin-5-one | LCMS: (ESI) m/z 368 (M + H)+.<br>$^1$H NMR (400 MHz, DMSO-d$_6$) δ 13.85 (s, 1H), 12.78 (s, 1H), 8.51 (s, 1H), 8.49-8.21(m, 1H), 7.71 (s, 1H), 6.27 (d, 1H), 5.41 (s, 2H), 4.49 (s, 2H), 4.26 (s, 3H) |
| E7-56 | 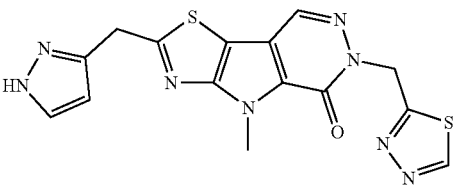 [SMILES: Cn1c2nc(Cc3cc[nH]n3)sc2c2cnn(Cc3nncs3)c(=O)c21]<br>6-((1,3,4-thiadiazol-2-yl)methyl)-2-((1H-pyrazol-3-yl)methyl)-4-methyl-4,6-dihydro-5H-thiazolo[5',4':4,5]pyrrolo[2,3-d]pyridazin-5-one | LCMS: (ESI) m/z 385 (M + H)+.<br>$^1$H NMR (400 MHz, DMSO-d$_6$) δ 12.79 (s, 1H), 9.57 (s, 1H), 8.61 (s, 1H), 7.71 (s, 1H), 6.26 (d, 1H), 5.80 (s, 2H), 4.49 (s, 2H), 4.27 (s, 3H) |
| E7-57 | 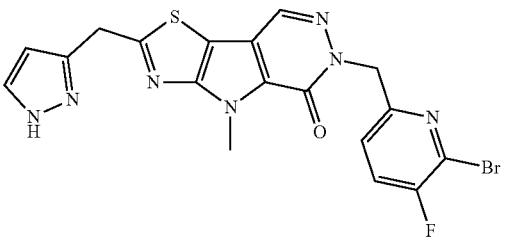 [SMILES: Cn1c2nc(Cc3cc[nH]n3)sc2c2cnn(Cc3ccc(F)c(Br)n3)c(=O)c21]<br>2-((1H-pyrazol-3-yl)methyl)-6-((6-bromo-5-fluoropyridin-2-yl)methyl)-4-methyl-4,6-dihydro-5H-thiazolo[5',4':4,5]pyrrolo[2,3-d]pyridazin-5-one | LCMS: (ESI) m/z 476 (M + 2H)+.<br>$^1$H NMR (400 MHz, DMSO-d$_6$) δ 12.78 (s, 1H), 8.57 (s, 1H), 7.81 (dd, 1H), 7.71 (s, 1H), 7.30 (dd, 1H), 6.26 (d, 1H), 5.43 (s, 2H), 4.49 (s, 2H), 4.26 (s, 3H) |

| Cpd No. | Structure and chemical name | Charaterization |
|---|---|---|
| E7-58 | 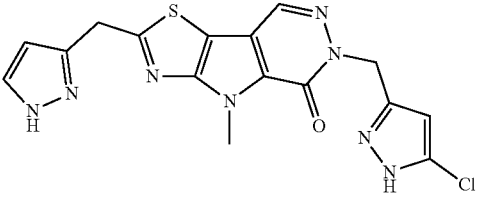 [SMILES: Cn1c2nc(Cc3cc[nH]n3)sc2c2cnn(Cc3cc(Cl)[nH]n3)c(=O)c21]<br>2-((1H-pyrazol-3-yl)methyl)-6-((5-chloro-1H-pyrazol-3-yl)methyl)-4-methyl-4,6-dihydro-5H-thiazolo[5',4':4,5]pyrrolo[2,3-d]pyridazin-5-one | LCMS: (ESI) m/z 401 (M + H)+.<br>$^1$H NMR (400 MHz, DMSO-d$_6$) δ 13.01 (s, 1H), 12.95 (s, 1H), 8.53 (s, 1H), 7.68 (dd, 1H), 6.26 (d, 1H), 6.17 (s, 1H), 5.32 (s, 2H), 4.50 (s, 2H), 4.26 (s, 3H) |
| E7-59 | 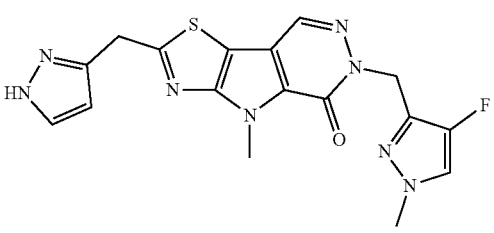 [SMILES: Cn1cc(F)c(Cn2ncc3c4sc(Cc5cc[nH]n5)nc4n(C)c3c2=O)n1]<br>2-((1H-pyrazol-3-yl)methyl)-6-((4-fluoro-1-methyl-1H-pyrazol-3-yl)methyl)-4-methyl-4,6-dihydro-5H-thiazolo[5',4':4,5]pyrrolo[2,3-d]pyridazin-5-one | LCMS: (ESI) m/z 399 (M + H)+.<br>$^1$H NMR (400 MHz, DMSO-d$_6$) δ 12.77 (s, 1H), 8.47 (s, 1H), 7.75 (d, 1H), 7.71 (s, 1H), 6.26 (s, 1H), 5.29 (s, 2H), 4.47 (s, 2H), 4.26 (s, 3H), 3.70 (s, 3H) |
| E7-60 | 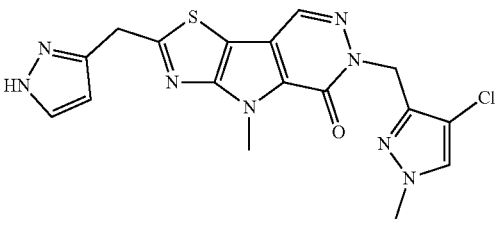 [SMILES: Cn1cc(Cl)c(Cn2ncc3c4sc(Cc5cc[nH]n5)nc4n(C)c3c2=O)n1]<br>2-((1H-pyrazol-3-yl)methyl)-6-((4-chloro-1-methyl-1H-pyrazol-3-yl)methyl)-4-methyl-4,6-dihydro-5H-thiazolo[5',4':4,5]pyrrolo[2,3-d]pyridazin-5-one | LCMS: (ESI) m/z 415 (M + H)+.<br>$^1$H NMR (400 MHz, DMSO-d$_6$) δ 12.82 (s, 1H), 8.52 (s, 1H), 7.92 (s, 1H), 7.76 (s, 1H), 6.31 (s, 1H), 5.34 (s, 2H), 4.53 (s, 2H), 4.31 (s, 3H), 3.79 (s, 3H) |
| E7-61 | 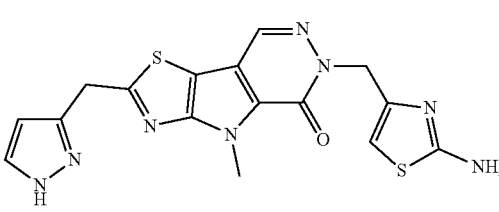<br>2-((1H-pyrazol-3-yl)methyl)-6-((2-aminothiazol-4-yl)methyl)-4-methyl-4,6-dihydro-5H-thiazolo[5',4':4,5]pyrrolo[2,3-d]pyridazin-5-one | LCMS: (ESI) m/z 399 (M + H)+.<br>$^1$H NMR (400 MHz, DMSO-d$_6$) δ 12.79 (s, 1H), 8.49 (s, 1H), 7.71 (s, 1H), 6.91 (s, 2H), 6.27 (s, 1H), 6.18 (s, 1H), 5.12 (s, 2H), 4.49 (s, 2H), 4.27 (s, 3H). |

-continued

| Cpd No. | Structure and chemical name | Charaterization |
|---|---|---|
| E7-62 | 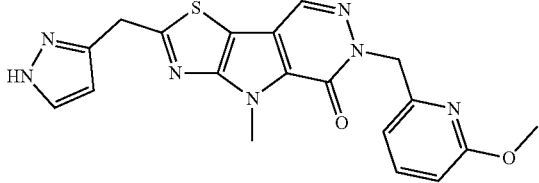 [SMILES: COc1cccc(Cn2ncc3c4sc(Cc5cc[nH]n5)nc4n(C)c3c2=O)n1]<br>2-((1H-pyrazol-3-yl)methyl)-6-((6-methoxypyridin-2-yl)methyl)-4-methyl-4,6-dihydro-5H-thiazolo[5',4':4,5]pyrrolo[2,3-d]pyridazin-5-one | LCMS: (ESI) m/z 408 (M + H)+. 1H NMR (400 MHz, DMSO-d6) δ 12.79 (s, 1H), 8.56 (s. 1H), 7.71 (s, 1H), 7.63 (dd, 1H), 6.68 (d, 1H), 6.60 (d, 1H), 6.27 (d, 1H), 5.36 (s, 2H), 4.51 (s, 2H), 4.26 (s, 3H), 3.76 (s, 3H). |
| E7-63 | 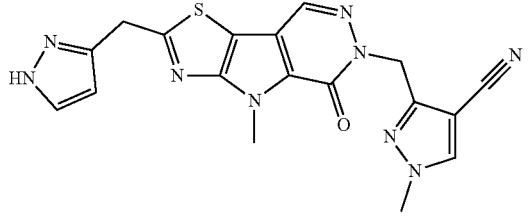 [SMILES: Cn1cc(C#N)c(Cn2ncc3c4sc(Cc5cc[nH]n5)nc4n(C)c3c2=O)n1]<br>3-((2-((1H-pyrazol-3-yl)methyl)-4-methyl-5-oxo-4H-thiazolo[5',4':4,5]pyrrolo[2,3-d]pyridazin-6(5H)-yl)methyl)-1-methyl-1H-pyrazole-4-carbonitrile | LC-MS: m/z 406 (M + H)+. 1H NMR (400 MHz, DMSO-d6) δ: 12.79 (s, 1H), 8.53 (s, 1H), 8.44 (s, 1H), 7.72 (s, 1H), 6.27 (s, 1H), 5.40 (s, 2H), 4.48 (s, 2H), 4.26 (s, 3H), 3.83 (s, 3H). |
| E7-64 | 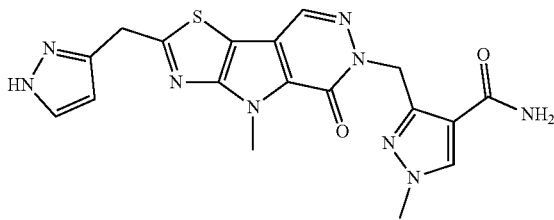 [SMILES: Cn1cc(C(N)=O)c(Cn2ncc3c4sc(Cc5cc[nH]n5)nc4n(C)c3c2=O)n1]<br>3-((2-((1H-pyrazol-3-yl)methyl)-4-methyl-5-oxo-4H-thiazolo[5',4':4,5]pyrrolo[2,3-d]pyridazin-6(5H) yl)methyl) 1 methyl-1H-pyrazole-4-carboxamide | LC-MS: m/z 424 (M + H)+. 1H NMR (400 MHz, DMSO-d6) δ: 12.79 (s, 1H), 8.46 (s, 1H), 8.10 (s, 1H), 7.72 (s, 1H), 7.57 (s, 1H), 7.02 (s, 1H), 6.27 (s, 1H), 5.53 (s, 2H), 4.48 (s, 2H), 4.26 (s, 3H), 3.69 (s, 3H). |
| E7-65 | 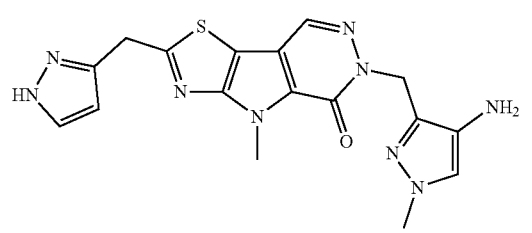 [SMILES: Cn1cc(N)c(Cn2ncc3c4sc(Cc5cc[nH]n5)nc4n(C)c3c2=O)n1]<br>2-((1H-pyrazol-3-yl)methyl)-6-((4-amino-1-methyl-1H-pyrazol-3-yl)methyl)-4-methyl-4H-thiazolo[5',4':4,5]pyrrolo[2,3-d]pyridazin-5(6H)-one | LC-MS: m/z 396 (M + H)+. 1H NMR (400 MHz, DMSO-d6) δ: 8.51 (s, 1H), 7.67 (s, 1H), 6.95 (s, 1H), 6.27 (d, 1H), 5.17 (s, 2H), 4.50 (s, 2H), 4.27 (s, 3H), 3.61 (s, 3H). |

| Cpd No. | Structure and chemical name | Characterization |
|---|---|---|
| E7-66 | 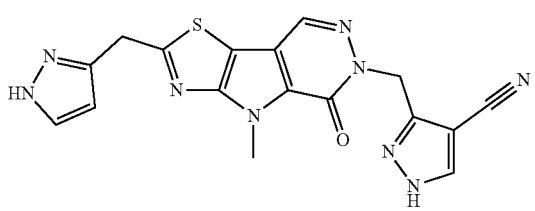 [SMILES: Cn1c2nc(Cc3cc[nH]n3)sc2c2cnn(Cc3n[nH]cc3C#N)c(=O)c21]<br>3-((2-((1H-pyrazol-3-yl)methyl)-4-methyl-5-oxo-4H-thiazolo[5',4':4,5]pyrrolo[2,3-d]pyridazin-6(5H)-yl)methyl)-1H-pyrazole-4-carbonitrile | LC-MS: m/z 392 (M + H)+. 1H NMR (400 MHz, DMSO-d6) δ: 13.62 (s, 1H), 12.79 (s, 1H), 8.54 (m, 2H), 7.71 (s, 1H), 6.27 (d, 1H), 5.45 (s, 2H), 4.49 (s, 2H), 4.26 (s, 3H). |
| E7-67 | 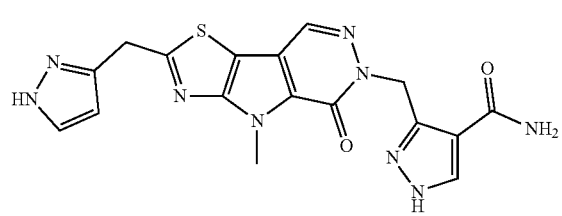 [SMILES: Cn1c2nc(Cc3cc[nH]n3)sc2c2cnn(Cc3n[nH]cc3C(N)=O)c(=O)c21]<br>3-((2-((1H-pyrazol-3-yl)methyl)-4-methyl-5-oxo-4H-thiazolo[5',4':4,5]pyrrolo[2,3-d]pyridazin-6(5H)-yl)methyl)-1H-pyrazole-4-carboxamide | LC-MS: m/z 410 (M + H)+. 1H NMR (400 MHz, DMSO-d6) δ: 12.75 (s, 2H), 8.48 (s, 1H), 8.17 (s, 1H), 7.68 (s, 1H), 7.56 (s, 1H), 7.01 (s, 1H), 6.27 (d, 1H), 5.57 (s, 2H), 4.50 (s, 2H), 4.26 (s, 3H). |
| E7-68 | 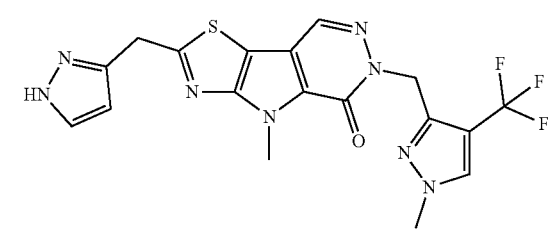 [SMILES: Cn1cc(C(F)(F)F)c(Cn2ncc3c4sc(Cc5cc[nH]n5)nc4n(C)c3c2=O)n1]<br>2-((1H-pyrazol-3-yl)methyl)-4-methyl-6-((1-methyl-4-(trifluoromethyl)-1H-pyrazol-3-yl)methyl)-4H-thiazolo[5',4':4,5]pyrrolo[2,3-d]pyridazin-5(6H)-one | LC-MS: m/z 449 (M + H)+. 1H NMR (400 MHz, DMSO-d6) δ: 12.85 (s, 1H), 8.54 (s, 1H), 8.34 (d, 1H), 7.77 (s, 1H), 6.32 (s, 1H), 5.44 (d, 2H), 4.54 (s, 2H), 4.32 (s, 3H), 3.83 (s, 3H). |
| E7-69 | 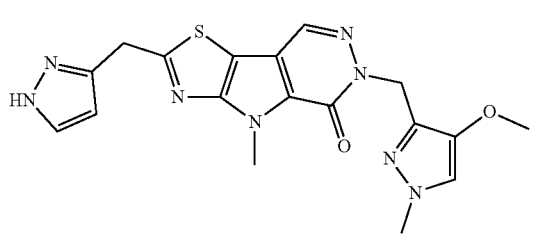 [SMILES: COc1cn(C)nc1Cn1ncc2c3sc(Cc4cc[nH]n4)nc3n(C)c2c1=O]<br>2-((1H-pyrazol-3-yl)methyl)-6-((4-methoxy-1-methyl-1H-pyrazol-3-yl)methyl)-4-methyl-4H-thiazolo[5',4':4,5]pyrrolo[2,3-d]pyridazin-5(6H)-one | LC-MS: m/z 411 (M + H)+. 1H NMR (400 MHz, DMSO-d6) δ: 12.77 (s, 1H), 8.43 (s, 1H), 7.71 (s, 1H), 7.41 (s, 1H), 6.26 (d, 1H), 5.20 (s, 2H), 4.48 (s, 2H), 4.26 (s, 3H), 3.65 (s, 3H), 3.61 (s, 3H). |

| Cpd No. | Structure and chemical name | Characterization |
|---|---|---|
| E7-70 | 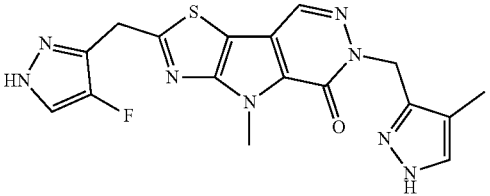 [SMILES: Cc1c[nH]nc1Cn1ncc2c3sc(Cc4n[nH]cc4F)nc3n(C)c2c1=O]<br>2-((4-fluoro-1H-pyrazol-3-yl)methyl)-4-methyl-6-((4-methyl-1H-pyrazol-3-yl)methyl)-4H-thiazolo[5',4':4,5]pyrrolo[2,3-d]pyridazin-5(6H)-one | LC-MS: m/z 399 (M + H)$^+$. $^1$H NMR (400 MHz, DMSO-d6) δ: 12.90-12.30 (m, 2H), 8.49 (s, 1H), 7.81 (s, 1H), 7.34 (s, 1H), 5.30 (s, 2H), 4.50 (s, 2H), 4.26 (s, 3H), 1.96 (s, 3H). |
| E7-71 | 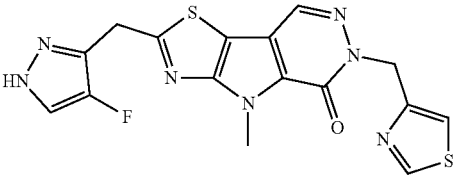 [SMILES: Cn1c2nc(Cc3n[nH]cc3F)sc2c2cnn(Cc3cscn3)c(=O)c21]<br>2-((4-fluoro-1H-pyrazol-3-yl)methyl)-4-methyl-6-(thiazol-4-ylmethyl)-4,6-dihydro-5H-thiazolo[5',4':4,5]pyrrolo[2,3-d]pyridazin-5-one | LC-MS: m/z 402 (M + H)$^+$. $^1$H NMR (400 MHz, DMSO-d6) δ: 12.80 (s, 1H), 9.04 (d, 1H), 8.54 (s, 1H), 7.88 (s, 1H), 7.49-7.39 (m, 1H), 5.48 (s, 2H), 4.50 (s, 2H), 4.26 (s, 3H). |
| E7-72 | 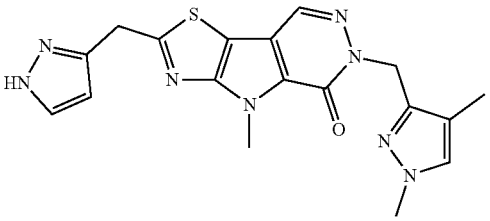 [SMILES: Cc1cn(C)nc1Cn1ncc2c3sc(Cc4cc[nH]n4)nc3n(C)c2c1=O]<br>2-((1H-pyrazol-3-yl)methyl)-6-((1,4-dimethyl-1H-pyrazol-3-yl)methyl)-4-methyl-4H-thiazolo[5',4':4,5]pyrrolo[2,3-d]pyridazin-5(6H)-one | LC-MS: m/z 395 (M + H)$^+$. $^1$H NMR (400 MHz, DMSO-d6) δ: 12.86 (s, 1H), 8.51 (s, 1H), 7.72 (s, 1H), 7.41 (s, 1H), 6.32 (s, 1H), 5.29 (s, 2H), 4.55 (s, 2H), 4.32 (s, 3H), 3.74 (s, 3H), 1.99 (s, 3H). |
| E7-73 | 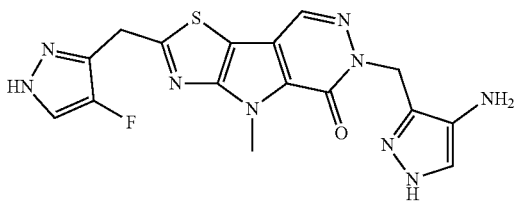 [SMILES: Cn1c2nc(Cc3n[nH]cc3F)sc2c2cnn(Cc3n[nH]cc3N)c(=O)c21]<br>6-((4-amino-1H-pyrazol-3-yl)methyl)-2-((4-fluoro-1H-pyrazol-3-yl)methyl)-4-methyl-4H-thiazolo[5',4':4,5]pyrrolo[2,3-d]pyridazin-5(6H)-one | LC-MS: m/z 400 (M + H)$^+$. $^1$H NMR (400 MHz, DMSO-d6) δ: 8.53 (s, 1 H), 7.80 (s, 1 H), 6.96 (s, 1 H), 5.23 (s, 2 H), 4.50 (s, 2 H), 4.27 (s, 3 H). |

| Cpd No. | Structure and chemical name | Charaterization |
|---|---|---|
| E7-74 | 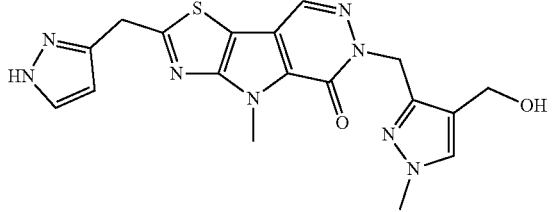 [SMILES: Cn1cc(CO)c(Cn2ncc3c4sc(Cc5cc[nH]n5)nc4n(C)c3c2=O)n1]<br>2-((1H-pyrazol-3-yl)methyl)-6-((4-(hydroxymethyl)-1-methyl-1H-pyrazol-3-yl)methyl)-4-methyl-4H-thiazolo[5',4':4,5]pyrrolo[2,3-d]pyridazin-5(6H)-one | LC-MS: m/z 411 (M + H)$^+$. $^1$H NMR (400 MHz, DMSO-d6) δ: 12.82 (s, 1H), 8.48 (s, 1H), 7.67 (s, 1H), 7.50 (s, 1H), 6.27 (d, 1H), 5.28 (s, 2H), 4.50 (s, 2H), 4.38 (s, 2H), 4.27 (s, 3H), 3.71 (s, 3H). |
| E7-75 | 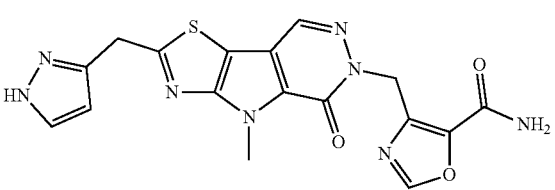 [SMILES: Cn1c2nc(Cc3cc[nH]n3)sc2c2cnn(Cc3ncoc3C(N)=O)c(=O)c21]<br>4-((2-((1H-pyrazol-3-yl)methyl)-4-methyl-5-oxo-4H-thiazolo[5',4':4,5]pyrrolo[2,3-d]pyridazin-6(5H)-yl)methyl)oxazole-5-carboxamide | LC-MS: m/z 411 (M + H)$^+$. $^1$H NMR (400 MHz, DMSO-d6) δ: 12.80 (s, 1H), 8.49 (s, 1H), 8.38 (s, 1H), 8.09 (s, 1H), 7.80 (s, 1H), 7.72 (s, 1H), 6.27 (d, 1H), 5.56 (s, 2H), 4.49 (s, 2H), 4.26 (s, 3H). |
| E7-76 | 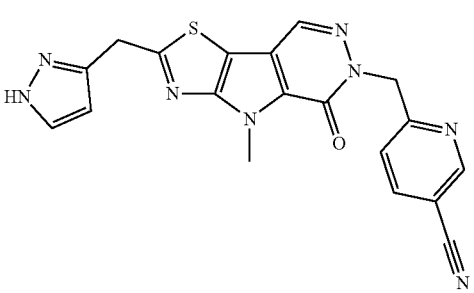 [SMILES: Cn1c2nc(Cc3cc[nH]n3)sc2c2cnn(Cc3ccc(C#N)cn3)c(=O)c21]<br>6-((2-((1H-pyrazol-3-yl)methyl)-4-methyl-5-oxo-4H-thiazolo[5',4':4,5]pyrrolo[2,3-d]pyridazin-6(5H)-yl)methyl)nicotinonitrile | LC-MS: m/z 403 (M + H)$^+$. $^1$H NMR (400 MHz, DMSO-d6) δ: 12.82 (s, 1H), 8.94 (d, 1H), 8.57 (s, 1H), 8.26 (dd, 1H), 7.69 (s, 1H), 7.42 (d, 1H), 6.27 (d, 1H), 5.55 (s, 2H), 4.51 (s, 2H), 4.25 (s, 3H). |
| E7-77 | 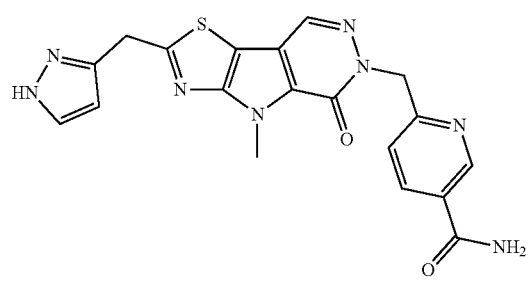 [SMILES: Cn1c2nc(Cc3cc[nH]n3)sc2c2cnn(Cc3ccc(C(N)=O)cn3)c(=O)c21]<br>6-((2-((1H-pyrazol-3-yl)methyl)-4-methyl-5-oxo-4H-thiazolo[5',4':4,5]pyrrolo[2,3-d]pyridazin-6(5H)-yl)methyl)nicotinamide | LC-MS: m/z 421 (M + H)$^+$. $^1$H NMR (400 MHz, DMSO-d6) δ: 12.82 (s, 1H), 8.92 (d, 1H), 8.56 (s, 1H), 8.14 (dd, 2H), 7.69 (s, 1H), 7.57 (s, 1H), 7.23 (d, 1H), 6.27 (d, 1H), 5.50 (s, 2H), 4.51 (s, 2H), 4.26 (s, 3H). |

-continued

| Cpd No. | Structure and chemical name | Characterization |
|---|---|---|
| E7-78 | 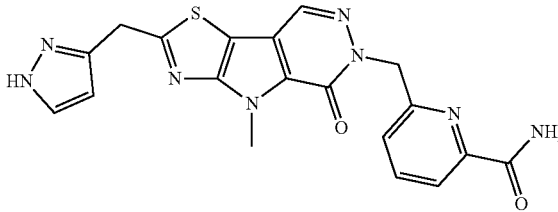<br>6-((2-((1H-pyrazol-3-yl)methyl)-4-methyl-5-oxo-4H-thiazolo[5',4':4,5]pyrrolo[2,3-d]pyridazin-6(5H)-yl)methyl)picolinamide | LC-MS: m/z 421 (M + H)+. 1H NMR (400 MHz, DMSO-d6) δ: 12.79 (s, 1H), 8.59 (s, 1H), 7.97-7.82 (m, 3H), 7.75-7.60 (m, 2H), 7.26 (dd, 1H), 6.27 (d, 1H), 5.53 (s, 2H), 4.51 (s, 2H), 4.26 (s, 3H). |
| E7-79 | 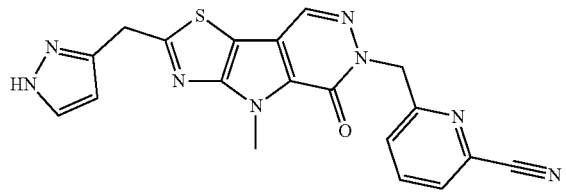 [SMILES: Cn1c2nc(Cc3cc[nH]n3)sc2c2cnn(Cc3cccc(C#N)n3)c(=O)c21]<br>6-((2-((1H-pyrazol-3-yl)methyl)-4-methyl-5-oxo-4H-thiazolo[5',4':4,5]pyrrolo[2,3-d]pyridazin-6(5H)-yl)methyl)picolinonitrile | LC-MS: m/z 403 (M + H)+. 1H NMR (400 MHz, DMSO-d6) δ: 8.64 (s, 1H), 8.12-7.98 (m, 2H), 7.74 (s, 1H), 7.60 (d, 1H), 6.33 (d, 1H), 5.57 (s, 2H), 4.57 (s, 2H), 4.32 (s, 3H). |
| E7-80 | 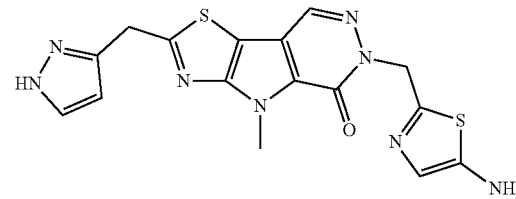<br>2-((1H-pyrazol-3-yl)methyl)-6-((5-aminothiazol-2-yl)methyl)-4-methyl-4H-thiazolo[5',4':4,5]pyrrolo[2,3-d]pyridazin-5(6H)-one | LC-MS: m/z 399 (M + H)+. 1H NMR (400 MHz, DMSO-d6) δ: 12.79 (s, 1H), 8.55 (s, 1H), 7.68 (s, 1H), 6.89 (s, 1H), 6.27 (s, 1H), 5.58 (s, 2H), 5.36 (s, 2H), 4.50 (s, 2H), 4.27 (s, 3H). |
| E7-81 | 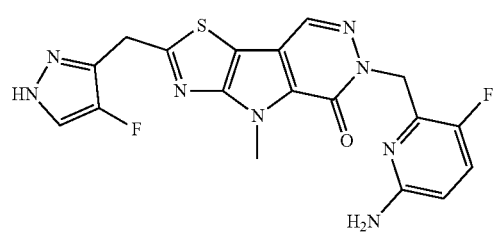 [SMILES: Cn1c2nc(Cc3n[nH]cc3F)sc2c2cnn(Cc3nc(N)ccc3F)c(=O)c21]<br>6-((6-amino-3-fluoropyridin-2-yl)methyl)-2-((4-fluoro-1H-pyrazol-3-yl)methyl)-4-methyl-4H-thiazolo[5',4':4,5]pyrrolo[2,3-d]pyridazin-5(6H)-one | LC-MS: m/z 429 (M + H)+. 1H NMR (400 MHz, DMSO-d6) δ: 12.84 (s, 1H), 8.48 (s, 1H), 7.88 (d, 1H), 7.29 (t, 1H), 6.34 (dd, 1H), 5.76 (s, 2H), 5.31 (s, 2H), 4.51 (s, 2H), 4.23 (s, 3H). |
| E7-82 | 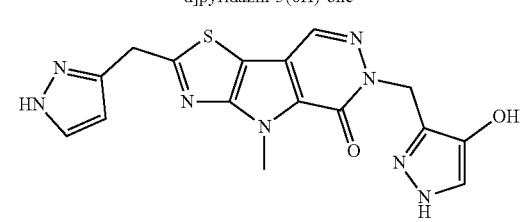<br>2-((1H-pyrazol-3-yl)methyl)-6-((4-hydroxy-1H-pyrazol-3-yl)methyl)-4-methyl-4H-thiazolo[5',4':4,5]pyrrolo[2,3-d]pyridazin-5(6H)-one | LC-MS: m/z 383 (M + H)+. 1H NMR (400 MHz, DMSO-d6) δ: 12.85 (s, 1H), 12.10 (s, 1H), 8.57 (s, 1H), 8.32 (s, 1H), 7.77 (s, 1H), 7.21 (s, 1H), 6.33 (d, 1H), 5.32 (s, 2H), 4.55 (s, 2H), 4.34 (s, 3H). |

-continued

| Cpd No. | Structure and chemical name | Charaterization |
|---|---|---|
| E7-83 | 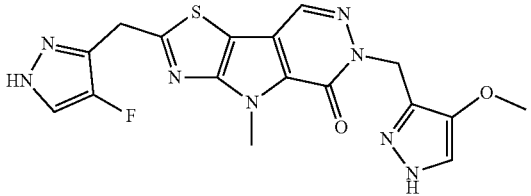 [SMILES: COc1c[nH]nc1Cn1ncc2c3sc(Cc4n[nH]cc4F)nc3n(C)c2c1=O]<br>2-((4-fluoro-1H-pyrazol-3-yl)methyl)-6-((4-methoxy-1H-pyrazol-3-yl)methyl)-4-methyl-4H-thiazolo[5',4':4,5]pyrrolo[2,3-d]pyridazin-5(6H)-one | LC-MS: m/z 415 (M + H)+. 1H NMR (400 MHz, DMSO-d6) δ: 12.76 (s, 1H), 12.13 (s, 1H), 8.45 (s, 1H), 7.87 (s, 1H), 7.39 (s, 1H), 5.25 (s, 2H), 4.49 (s, 2H), 4.26 (s, 3H), 3.63 (s, 3H). |
| E7-84 | 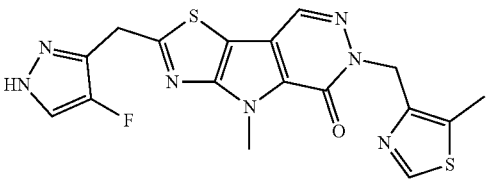 [SMILES: Cc1scnc1Cn1ncc2c3sc(Cc4n[nH]cc4F)nc3n(C)c2c1=O]<br>2-((4-fluoro-1H-pyrazol-3-yl)methyl)-4-methyl-6-((5-methylthiazol-4-yl)methyl)-4H-thiazolo[5',4':4,5]pyrrolo[2,3-d]pyridazin-5(6H)-one | LC-MS: m/z 416 (M + H)+. 1H NMR (400 MHz, DMSO-d6) 5: 12.78 (s, 1H), 8.75 (s, 1H), 8.49 (s, 1H), 7.85 (s, 1H), 5.39 (s, 2H), 4.50 (s, 2H), 4.26 (s, 3H), 2.51 (s, 3H). |
| E7-85 | 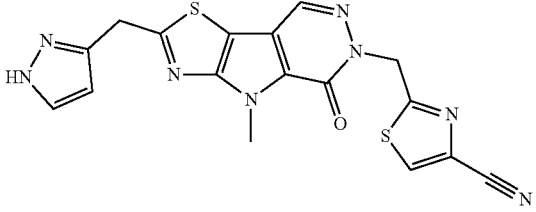 [SMILES: Cn1c2nc(Cc3cc[nH]n3)sc2c2cnn(Cc3nc(C#N)cs3)c(=O)c21]<br>2-((2-((1H-pyrazol-3-yl)methyl)-4-methyl-5-oxo-4H-thiazolo[5',4':4,5]pyrrolo[2,3-d]pyridazin-6(5H)-yl)methyl)thiazole-4-carbonitrile | LC-MS: m/z 409 (M + H)+. 1H NMR (400 MHz, DMSO-d6) δ: 12.80 (s, 1H), 8.82 (s, 1H), 8.63 (s, 1H), 7.69 (s, 1H), 6.27 (d, 1H), 5.69 (s, 2H), 4.51 (s, 2H), 4.27 (s, 3H). |
| E7-86 | 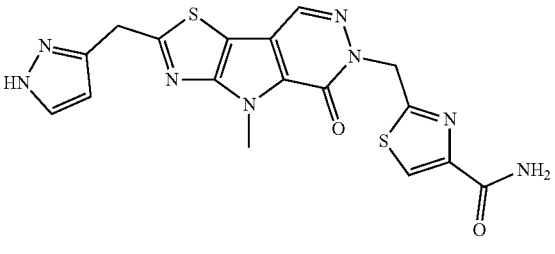 [SMILES: Cn1c2nc(Cc3cc[nH]n3)sc2c2cnn(Cc3nc(C(N)=O)cs3)c(=O)c21]<br>2-((2-((1H-pyrazol-3-yl)methyl)-4-methyl-5-oxo-4H-thiazolo[5',4':4,5]pyrrolo[2,3-d]pyridazin-6(5H)-yl)methyl)thiazole-4-carboxamide | LC-MS: m/z 427 (M + H)+. 1H NMR (400 MHz, DMSO-d6) δ: 8.63 (s, 1H), 8.19 (s, 1H), 7.76-7.63 (m, 2H), 7.57 (s, 1H), 6.27 (s, 1H), 5.67 (s, 2H), 4.51 (s, 2H), 4.28 (s, 3H). |
| E7-87 | 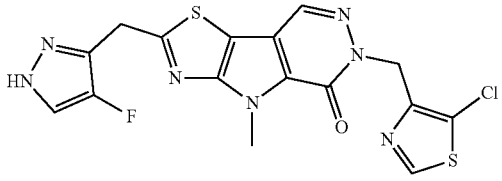 [SMILES: Cn1c2nc(Cc3n[nH]cc3F)sc2c2cnn(Cc3ncsc3Cl)c(=O)c21]<br>6-(5-chlorothiazol-4-yl)methyl)-2-((4-fluoro-1H-pyrazol-3-yl)methyl)-4-methyl-4H-thiazolo[5',4':4,5]pyrrolo[2,3-d]pyridazin-5(6H)-one | LC-MS: m/z 436 (M + H)+. 1H NMR (400 MHz, DMSO-d6) δ: 12.83 (s, 1H), 8.94 (s, 1H), 8.51 (s, 1H), 7.83 (s, 1H), 5.43 (s, 2H), 4.51 (s, 2H), 4.26 (s, 3H). |

| Cpd No. | Structure and chemical name | Characterization |
|---|---|---|
| E7-88 | 2-((1H-pyrazol-3-yl)methyl)-6-((2-aminooxazol-5-yl)methyl)-4-methyl-4H-thiazolo[5',4':4,5]pyrrolo[2,3-d]pyridazin-5(6H)-one | LC-MS: m/z 383 (M + H)+ $^1$H NMR (400 MHz, DMSO-d6) δ: 12.79 (s, 1H), 8.50 (s, 1H), 7.70 (s, 1H), 6.65 (s, 1H), 6.57 (s, 2H), 6.23 (d, 1H), 5.21 (s, 2H), 4.49 (s, 2H), 4.27 (s, 3H). |
| E7-89 | 2-((1H-pyrazol-3-yl)methyl)-4-methyl-6-((1-methyl-4-(trifluoromethoxy)-1H-pyrazol-3-yl)methyl)-4H-thiazolo[5',4':4,5]pyrrolo[2,3-d]pyridazin-5(6H)-one | LC-MS: m/z 465 (M + H). $^1$H NMR (400 MHz, DMSO-d6) δ: 12.78 (s, 1H), 8.48 (s, 1H), 7.99 (s, 1H), 7.72 (s, 1H), 6.27 (d, 1H), 5.31 (s, 2H), 4.49 (s, 2H), 4.27 (s, 3H), 3.76 (s, 3H). |
| E7-90 | 5-((2-((1H-pyrazol-3-yl)methyl)-4-methyl-5-oxo-4H-thiazolo[5',4':4,5]pyrrolo[2,3-d]pyridazin-6(5H)-yl)methyl)oxazole-2-carboxamide | LC-MS: m/z 411 (M + H)+. $^1$H NMR (400 MHz, DMSO-d6) δ: 12.78 (s, 1H), 8.56 (s, 1H), 8.17 (s, 1H), 7.84 (s, 1H), 7.72 (s, 1H), 7.34 (s, 1H), 6.27 (d, 1H), 5.48 (s, 2H), 4.49 (s, 2H), 4.27 (s, 3H). |
| E7-91 | 2-((1H-pyrazol-3-yl)methyl)-6-((5-fluorothiazol-4-yl)methyl)-4-methyl-4H-thiazolo[5',4':4,5]pyrrolo[2,3-d]pyridazin-5(6H)-one | LC-MS: m/z 402 (M + H)+. $^1$H NMR (400 MHz, DMSO-d6) δ: 12.78 (s, 1H), 8.57 (d, 1H), 8.50 (s, 1H), 7.71 (s, 1H), 6.26 (d, 1H), 5.38 (d, 2H), 4.49 (s, 2H), 4.26 (s, 3H). |

-continued

| Cpd No. | Structure and chemical name | Charaterization |
|---|---|---|
| E7-92 | 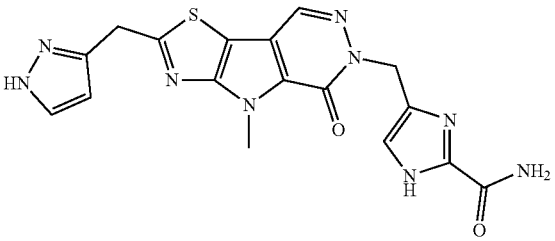 [SMILES: Cn1c2nc(Cc3cc[nH]n3)sc2c2cnn(Cc3c[nH]c(C(N)=O)n3)c(=O)c21]<br>4-((2-((1H-pyrazol-3-yl)methyl)-4-methyl-5-oxo-4H-thiazolo[5',4':4,5]pyrrolo[2,3-d]pyridazin-6(5H)-yl)methyl)-1H-imidazole-2-carboxamide | LC-MS: m/z 410 (M + H)$^+$. $^1$H NMR (400 MHz, DMSO-d6) δ: 12.83 (s, 1H), 8.49 (s, 1H), 7.67 (s, 2H), 7.38 (s, 1H), 7.06 (s, 1H), 6.26 (d, 1H), 5.30 (s, 2H), 4.49 (s, 2H), 4.27 (s, 3H). |
| E7-93 | 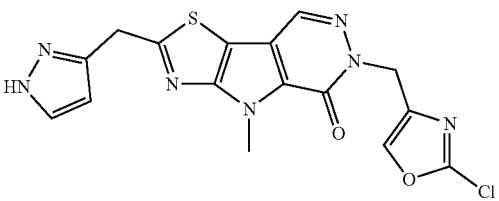<br>2-((1H-pyrazol-3-yl)methyl)-6-((2-chlorooxazol-4-yl)methyl)-4-methyl-4H-thiazolo[5',4':4,5]pyrrolo[2,3-d]pyridazin-5(6H)-one | LC-MS: m/z 402 (M + H)$^+$. $^1$H NMR (400 MHz, DMSO-d6) δ: 12.79 (s, 1H), 8.52 (s, 1H), 8.17 (s, 1H), 7.71 (s, 1H), 6.26 (d, 1H), 5.23 (s, 2H), 4.49 (s, 2H), 4.27 (s, 3H). |
| E7-94 | 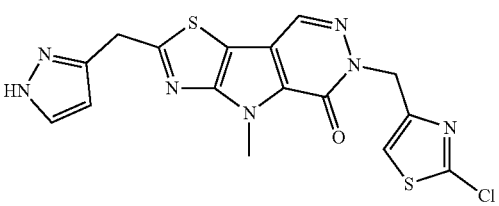 [SMILES: Cn1c2nc(Cc3cc[nH]n3)sc2c2cnn(Cc3csc(Cl)n3)c(=O)c21]<br>2-((1H-pyrazol-3-yl)methyl)-6-((2-chlorothiazol-4-yl)methyl)-4-methyl-4H-thiazolo[5',4':4,5]pynolo[2,3-d]pyridazin-5(6H)-one | LC-MS: m/z 418 (M + H)$^+$. $^1$H NMR (400 MHz, DMSO-d6) δ: 12.82 (s, 1H), 8.58 (s, 1H), 7.75 (s, 1H), 7.49 (s, 1H), 6.31 (d, 1H), 5.42 (s, 2H), 4.54 (s, 2H), 4.31 (s, 3H). |
| E7-95 | 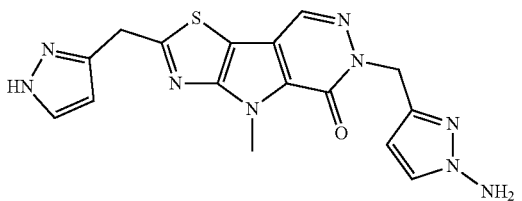 [SMILES: Cn1c2nc(Cc3cc[nH]n3)sc2c2cnn(Cc3ccn(N)n3)c(=O)c21]<br>2-((1H-pyrazol-3-yl)methyl)-6-((1-amino-1H-pyrazol-3-yl)methyl)-4-methyl-4H-thiazolo[5',4':4,5]pyrrolo[2,3-d]pyridazin-5(6H)-one | LC-MS: m/z 382 (M + H)$^+$. $^1$H NMR (400 MHz, DMSO-d6) δ: 8.48 (s, 1H), 7.67 (s, 1H), 7.37 (d, 1H), 6.34 (d, 2H), 6.27 (d, 1H), 6.00 (d, 1H), 5.24 (s, 2H), 4.50 (s, 2H), 4.27 (s, 3H). |

-continued

| Cpd No. | Structure and chemical name | Charaterization |
|---|---|---|
| E7-96 | 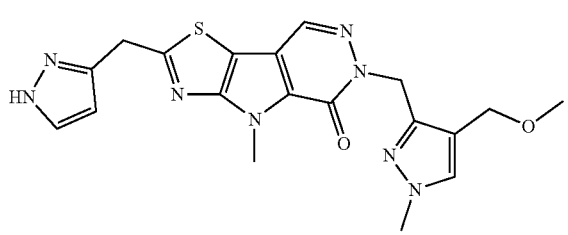 [SMILES: COCc1cn(C)nc1Cn1ncc2c3sc(Cc4cc[nH]n4)nc3n(C)c2c1=O]<br>2-((1H-pyrazol-3-yl)methyl)-6-((4-(methoxymethyl)-1-methyl-1H-pyrazol-3-yl)methyl)-4-methyl-4H-thiazolo[5',4':4,5]pyrrolo[2,3-d]pyridazin-5(6H)-one | LC-MS: m/z 425 (M + H)$^+$. $^1$H NMR (400 MHz, DMSO-d6) δ: 12.79 (s, 1H), 8.46 (s, 1H), 7.72 (s, 1H), 7.59 (s, 1H), 6.27 (s, 1H), 5.28 (s, 2H), 4.48 (s, 2H), 4.29-4.25 (m, 5H), 3.73 (s, 3H), 3.11 (s, 3H). |
| E7-97 | 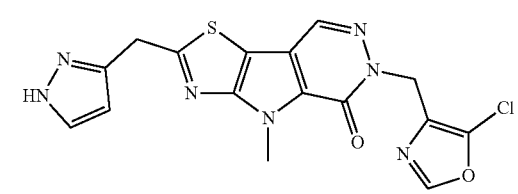 [SMILES: Cn1c2nc(Cc3cc[nH]n3)sc2c2cnn(Cc3ncoc3Cl)c(=O)c21]<br>2-((1H-pyrazol-3-yl)methyl)-6-((5-chlorooxazol-4-yl)methyl)-4-methyl-4H-thiazolo[5',4':4,5]pyrrolo[2,3-d]pyridazin-5(6H)-one | LC-MS: m/z 402 (M + H)$^+$. $^1$H NMR (400 MHz, DMSO-d6) δ: 12.78 (s, 1H), 8.52 (s, 1H), 8.39 (s, 1H), 7.68 (s, 1H), 6.27 (d, 1H), 5.24 (s, 2H), 4.50 (s, 2H), 4.26 (s, 3H). |
| E7-98 | 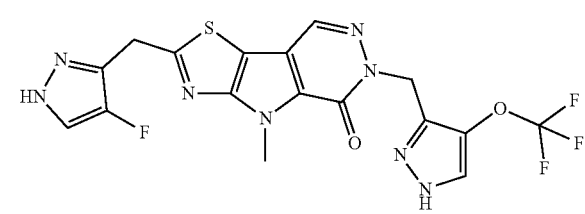 [SMILES: Cn1c2nc(Cc3n[nH]cc3F)sc2c2cnn(Cc3n[nH]cc3OC(F)(F)F)c(=O)c21]<br>2-((4-fluoro-1H-pyrazol-3-yl)methyl)-4-methyl-6-((4-(trifluoromethoxy)-1H-pyrazol-3-yl)methyl)-4H-thiazolo[5',4':4,5]pyrrolo[2,3-d]pyridazin-5(6H)-one | LC-MS: m/z 469 (M + H)$^+$. $^1$H NMR (400 MHz, DMSO-d6) δ: 13.37-12.75 (m, 2H), 8.65-8.50 (m, 1H), 8.15-7.58 (m, 2H), 5.49-5.36 (m, 2H), 4.67-4.50 (m, 2H), 4.32 (s, 3H). |
| E7-99 | 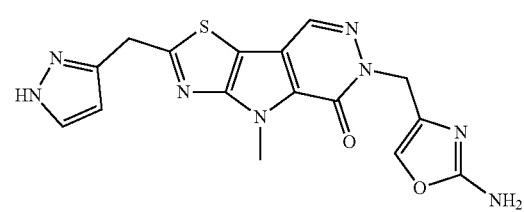 [SMILES: Cn1c2nc(Cc3cc[nH]n3)sc2c2cnn(Cc3coc(N)n3)c(=O)c21]<br>2-((1H-pyrazol-3-yl)methyl)-6-((2-aminooxazol-4-yl)methyl)-4-methyl-4H-thiazolo[5',4':4,5]pyrrolo[2,3-d]pyridazin-5(6H)-one | LC-MS: m/z 383 (M + H)$^+$. $^1$H NMR (400 MHz, DMSO-d6) δ: 12.84 (s, 1H), 8.53 (s, 1H), 7.77 (s, 1H), 7.25 (s, 1H), 6.58 (s, 2H), 6.32 (d, 1H), 5.10 (s, 2H), 4.54 (s, 2H), 4.32 (s, 3H). |

-continued

| Cpd No. | Structure and chemical name | Charaterization |
|---|---|---|
| E7-100 | 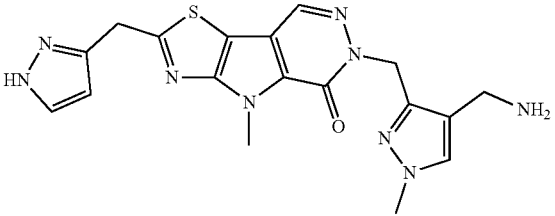 [SMILES: Cn1cc(CN)c(Cn2ncc3c4sc(Cc5cc[nH]n5)nc4n(C)c3c2=O)n1]<br>2-((1H-pyrazol-3-yl)methyl)-6-((4-(aminomethyl)-1-methyl-1H-pyrazol-3-yl)methyl)-4-methyl-4H-thiazolo[5',4':4,5]pyrrolo[2,3-d]pyridazin-5(6H)-one | LC-MS: m/z 410 (M + H)⁺. ¹H NMR (400 MHz, DMSO-d6) δ: 12.89 (s, 1H), 8.58 (s, 1H), 8.45 (s, 1H), 7.77-7.64 (m, 2H), 6.33 (d, 1H), 5.39 (s, 2H), 4.57 (s, 2H), 4.33 (s, 3H), 3.96 (s, 2H), 3.82 (s, 3H). |
| E7-101 | 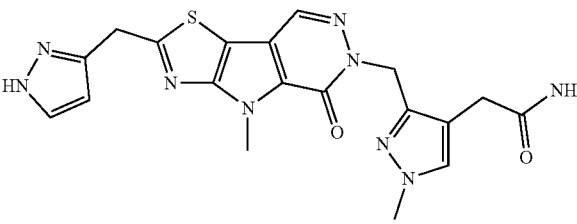<br>2-(3-((2-((1H-pyrazol-3-yl)methyl)-4-methyl-5-oxo-4H-thiazolo[5',4':4,5]pyrrolo[2,3-d]pyridazin-6(5H)-yl)methyl)-1-methyl-1H-pyrazol-4-yl)acetamide | LC-MS: m/z 438 (M + H)⁺. ¹H NMR (400 MHz, DMSO-d6) δ: 12.78 (s, 1H), 8.46 (s, 1H), 7.72 (s, 1H), 7.44 (s, 1H), 7.25 (s, 1H), 6.80 (s, 1H), 6.26 (d, 1H), 5.26 (s, 2H), 4.48 (s, 2H), 4.26 (s, 3H), 3.70 (s, 3H), 3.31 (s, 2H). |
| E7-102 | 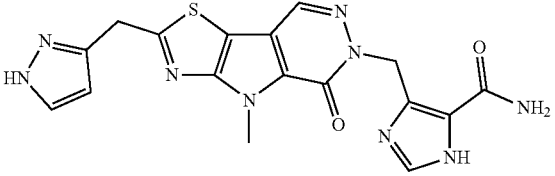 [SMILES: Cn1c2nc(Cc3cc[nH]n3)sc2c2cnn(Cc3nc[nH]c3C(N)=O)c(=O)c21]<br>4-((2-((1H-pyrazol-3-yl)methyl)-4-methyl-5-oxo-4,5-dihydro-6H-thiazolo[5',4':4,5]pyrrolo[2,3-d]pyridazin-6-yl)methyl)-1H-imidazole-5-carboxamide | LC-MS: m/z 410 (M + H)⁺. ¹H NMR (400 MHz, DMSO-d6) δ: 12.79 (s, 1H), 12.10 (s, 1H), 8.51 (s, 1H), 7.72 (s, 1H), 7.53 (s, 1H), 7.29 (s, 1H), 7.08 (s, 1H), 6.27 (d, 1H), 5.72 (s, 2H), 4.50 (s, 2H), 4.30 (s, 3H) |
| E7-103 | 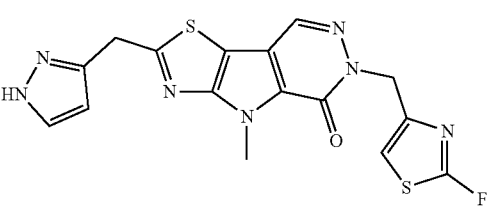 [SMILES: Cn1c2nc(Cc3cc[nH]n3)sc2c2cnn(Cc3csc(F)n3)c(=O)c21]<br>2-((1H-pyrazol-3-yl)methyl)-6-((2-fluorothiazol-4-yl)methyl)-4-methyl-4,6-dihydro-5H-thiazolo[5',4':4,5]pyrrolo[2,3-d]pyridazin-5-one | LC-MS: m/z 402 (M + H)⁺. ¹H NMR (400 MHz, DMSO-d6) δ: 12.85 (s, 1H), 8.59 (s, 1H), 7.80 (d, 1H), 7.14 (s, 1H), 6.33 (d, 1H), 5.36 (d, 2H), 4.53 (d, 2H), 4.33 (s, 3H) |

-continued

| Cpd No. | Structure and chemical name | Characterization |
|---|---|---|
| E7-104 | 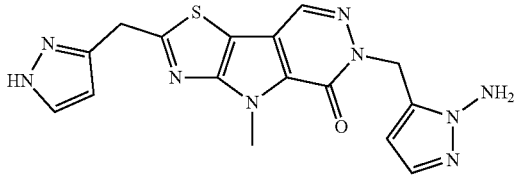 [SMILES: Cn1c2nc(Cc3cc[nH]n3)sc2c2cnn(Cc3ccnn3N)c(=O)c21]<br>2-((1H-pyrazol-3-yl)methyl)-6-((1-amino-1H-pyrazol-5-yl)methyl)-4-methyl-4,6-dihydro-5H-thiazolo[5',4':4,5]pyrrolo[2,3-d]pyridazin-5-one | LC-MS: m/z 382 (M + H)+. 1H NMR (400 MHz, DMSO-d6) δ: 12.80 (s, 1H), 8.53 (s, 1H), 7.69 (s, 1H), 7.16 (d, 1H), 6.30 (s, 2H), 6.27 (s, 1H), 5.88 (s, 1H), 5.41 (s, 2H), 4.50 (s, 2H), 4.27 (s, 3H). |
| E7-105 | 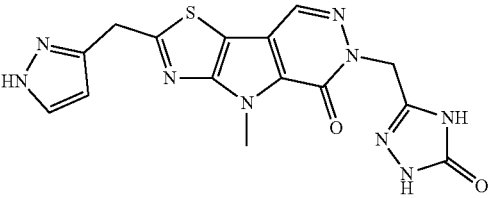 [SMILES: Cn1c2nc(Cc3cc[nH]n3)sc2c2cnn(Cc3n[nH]c(=O)[nH]3)c(=O)c21]<br>2-((1H-pyrazol-3-yl)methyl)-4-methyl-6-((5-oxo-4,5-dihydro-1H-1,2,4-triazol-3-yl)methyl)-4,6-dihydro-5H-thiazolo[5',4':4,5]pyrrolo[2,3-d]pyridazin-5-one | LC-MS: m/z 384 (M + H)+. 1H NMR (400 MHz, DMSO-d6) δ: 12.79 (s, 1H), 11.31 (s, 1H), 8.54 (d, 1H), 7.69 (s, 1H), 6.27 (d, 1H), 5.17 (d, 2H), 4.51 (s, 2H), 4.27 (s, 3H). |
| E7-106 | 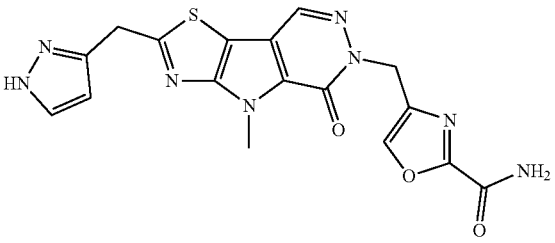 [SMILES: Cn1c2nc(Cc3cc[nH]n3)sc2c2cnn(Cc3coc(C(N)=O)n3)c(=O)c21]<br>4-((2-((1H-pyrazol-3-yl)methyl)-4-methyl-5-oxo-4,5-dihydro-6H-thiazolo[5',4':4,5]pyrrolo[2,3-d]pyridazin-6-yl)methyl)oxazole-2-carboxamide | LC-MS: m/z 411 (M + H)+. 1H NMR (400 MHz, DMSO-d6) δ: 12.78 (s, 1H), 8.52 (s, 1H), 8.25-8.12 (m, 2H), 7.84 (s, 1H), 7.70 (s, 1H), 6.26 (d, 1H), 5.30 (s, 2H), 4.48 (s, 2H), 4.26 (s, 3H) |
| E7-107 | 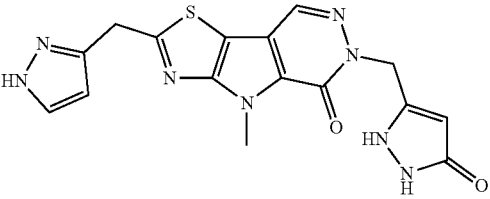 [SMILES: Cn1c2nc(Cc3cc[nH]n3)sc2c2cnn(Cc3cc(=O)[nH][nH]3)c(=O)c21]<br>2-((1H-pylazol-3-yl)methyl)-4-methyl-6-((5-oxo-2,5-dihydro-1H-pyrazol-3-yl)methyl)-4,6-dihydro-5H-thiazolo[5',4':4,5]pyrrolo[2,3-d]pyridazin-5-one | LC-MS: m/z 383 (M + H)+. 1H NMR (400 MHz, DMSO-d6) δ: 12.79 (s, 1H), 8.51 (s, 1H), 8.36 (s, 2H), 7.67 (s, 1H), 6.26 (d, 1H), 5.31 (s, 1H), 5.19 (s, 2H), 4.49 (s, 2H), 4.27 (s, 3H). |
| E7-108 | 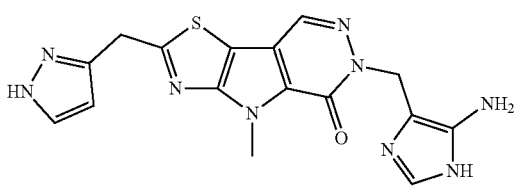 [SMILES: Cn1c2nc(Cc3cc[nH]n3)sc2c2cnn(Cc3nc[nH]c3N)c(=O)c21]<br>2-((1H-pyrazol-3-yl)methyl)-6-((5-amino-1H-imidazol-4-yl)methyl)-4-methyl-4,6-dihydro-5H-thiazolo[5',4':4,5]pyrrolo[2,3-d]pyridazin-5-one | LC-MS: m/z 382 (M + H)+. 1H NMR (400 MHz, DMSO-d6) δ: 12.79 (s, 1H), 11.47 (s, 1H), 8.52 (s, 1H), 7.68 (s, 1H), 7.04 (s, 1H), 6.27 (s, 1H), 5.17 (s, 2H), 4.50 (s, 2H), 4.28 (s, 3H) |

| Cpd No. | Structure and chemical name | Characterization |
|---|---|---|
| E7-109 | 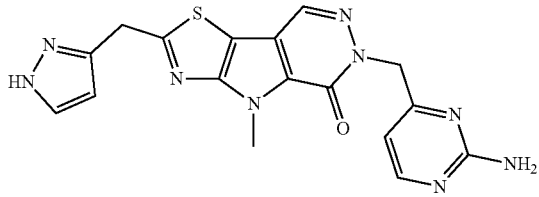 [SMILES: Cn1c2nc(Cc3cc[nH]n3)sc2c2cnn(Cc3ccnc(N)n3)c(=O)c21]<br>2-((1H-pyrazol-3-yl)methyl)-6-((2-aminopyrimidin-4-yl)methyl)-4-methyl-4,6-dihydro-5H-thiazolo[5',4':4,5]pyrrolo[2,3-d]pyridazin-5-one | LC-MS: m/z 394 (M + H)⁺. ¹H NMR (400 MHz, DMSO-d6) δ: 12.78 (s, 1H), 8.56 (s, 1H), 8.11 (d, 1H), 7.71 (s, 1H), 6.60 (s, 2H), 6.27 (d, 1H), 6.18 (d, 1H), 5.19 (s, 2H), 4.50 (s, 2H), 4.26 (s, 3H) |
| E7-110 | 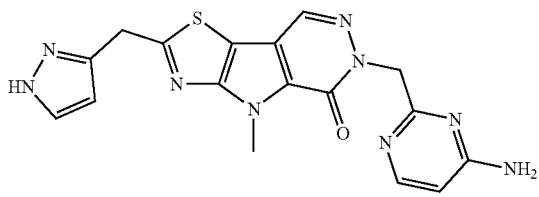 [SMILES: Cn1c2nc(Cc3cc[nH]n3)sc2c2cnn(Cc3nccc(N)n3)c(=O)c21]<br>2-((1H-pyrazol-3-yl)methyl)-6-((4-aminopyrimidin-2-yl)methyl)-4-methyl-4,6-dihydro-5H-thiazolo[5',4':4,5]pyrrolo[2,3-d]pyridazin-5-one | LC-MS: m/z 394 (M + H)⁺. ¹H NMR (400 MHz, DMSO-d6) δ: 12.84 (s, 1H), 8.55 (s, 1H), 7.99 (d, 1H), 7.77 (s, 1H), 6.86 (s, 2H), 6.44-6.16 (m, 2H), 5.28 (s, 2H), 4.57 (s, 2H), 4.32 (s, 3H) |

Example 8. Synthesis of Compounds E8-v, E8-vi, and E8-viii

Scheme E8

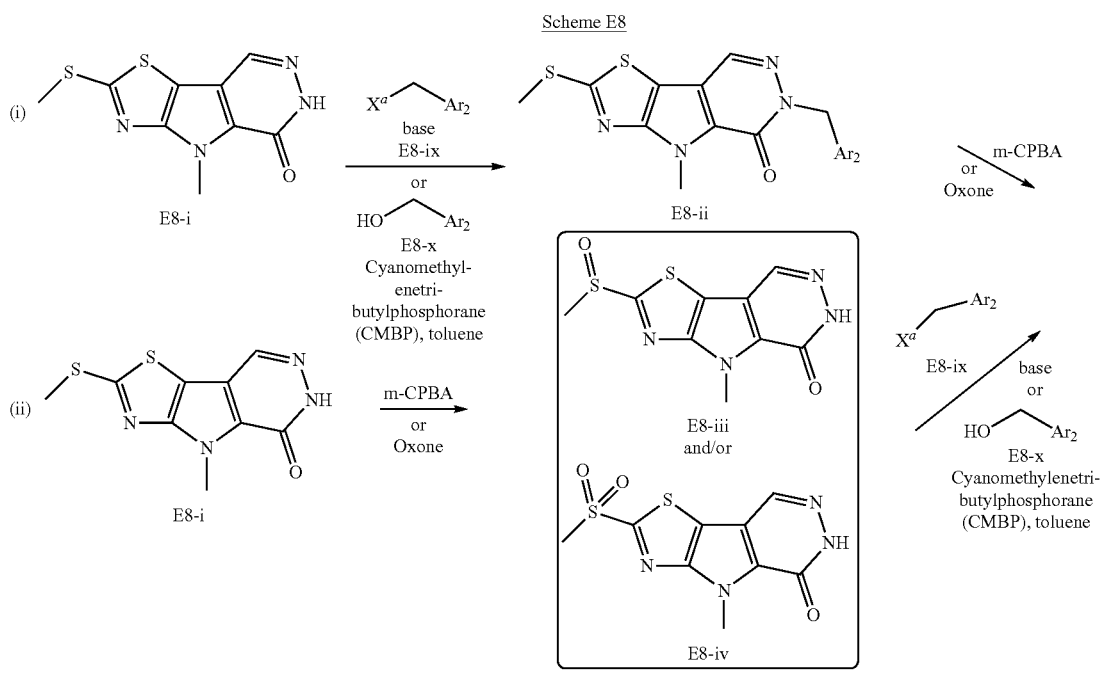

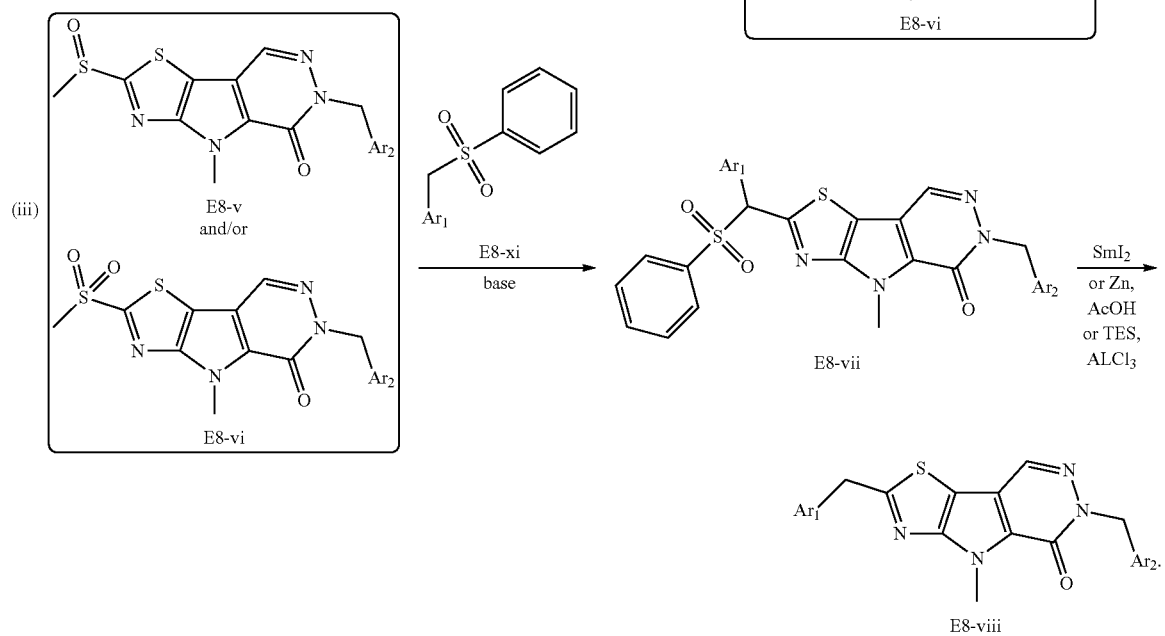

Compound E8-i can be converted to intermediate E8-ii through either alkylation or Mitsunobu reaction similar to Example E7-iii to E7-vi (see route (i) in Scheme E8). Oxidation of E8-ii with either mCPBA or oxone generate compounds E8-v and/or E8-vi. Both compounds of E8-v and E8-vi can also be formed from E8-i by oxidation first followed by alkylation or Mitsumobu reaction (see route (ii) in Scheme E8). Wherein $X^a$ is a leaving group (e.g. Cl, Br, I, OMs, OTs); Compound E8-v and/or E8-vi can be converted to intermediate E8-vii through nucleophilic aromatic substitution reaction with compound E8-xi, using a base such as LiHMDS or t-BuOK. Compound E8-viii can be synthesized from compound E8-vii using either $SmI_2$, or Zn in AcOH, or TES in $AlCl_3$. As used herein, Ar1 and Ar2 are each independently optionally substituted 5-membered or 6-membered heteroaryl.

Example 8A. Synthesis of 2-((1H-pyrazol-3-yl)methyl)-6-((6-aminopyridin-2-yl)methyl)-4-methyl-4H-thiazolo[5',4':4,5]pyrrolo[2,3-d]pyridazin-5(6H)-one and 6-((6-aminopyridin-2-yl)methyl)-4-methyl-2-(1H-pyrazole-3-carbonyl)-4H-thiazolo[5',4':4,5]pyrrolo[2,3-d]pyridazin-5(6H)-one

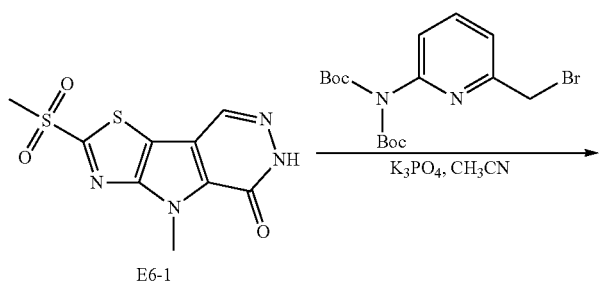

-continued

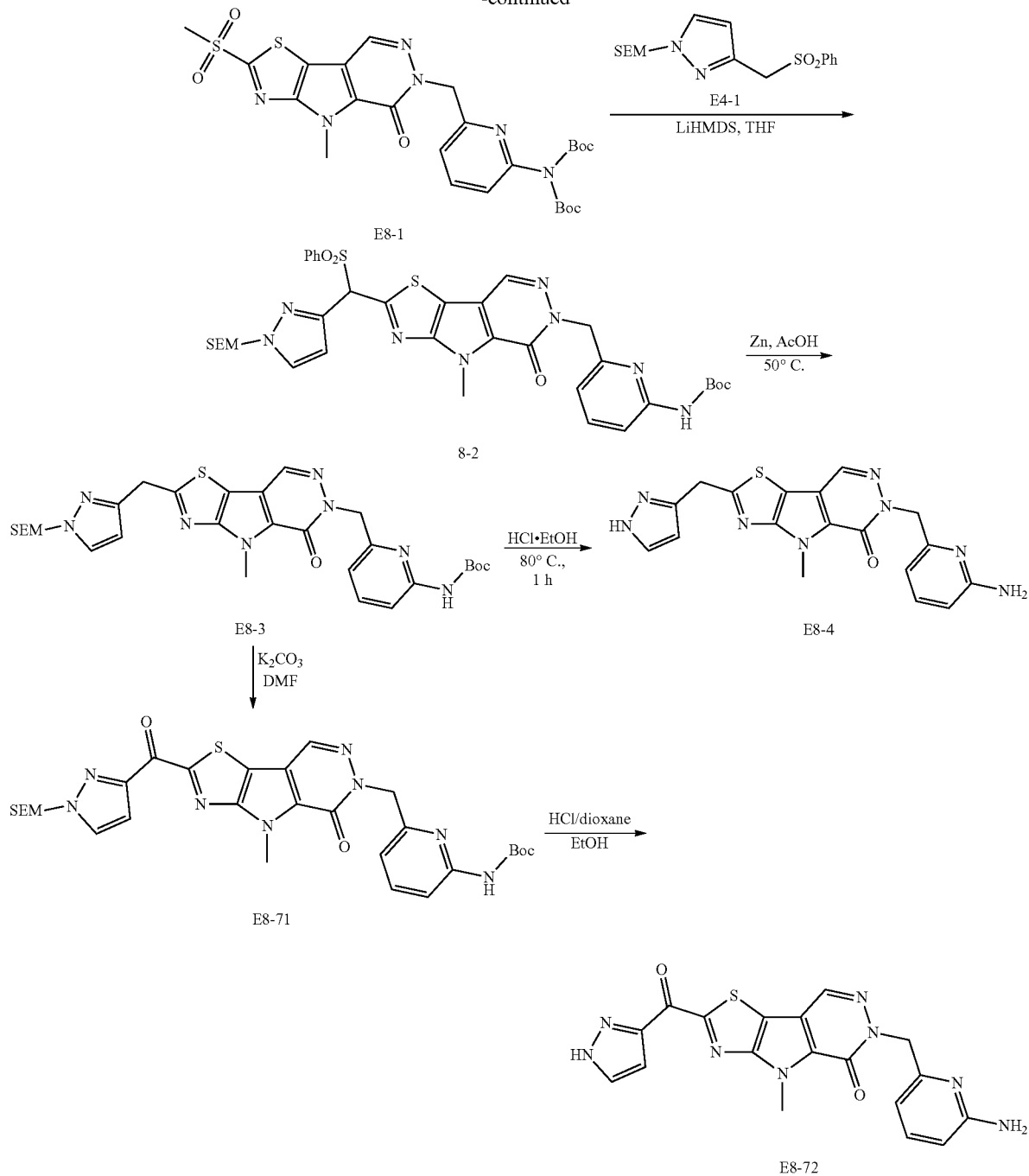

Step A tert-butyl N-[(tert-butoxy)carbonyl]-N-[6-({4-methanesulfonyl-7-methyl-9-oxo-3-thia-5,7,10,11-tetraazatricyclo[6.4.0.0{2,6}]dodeca-1(8),2(6),4,11-tetraen-10-yl}methyl)pyridin-2-yl]carbamate A mixture of 4-methyl-2-(methylsulfonyl)-4H-thiazolo[5',4':4,5]pyrrolo[2,3-d]pyridazin-5(6H)-one (7.5 g, 26.4 mmol) and $K_3PO_4$ (8.3 g, 39.3 mmol) in anhydrous MeCN (300 mL) was stirred at 70° C. for 1 hr under $N_2$. Followed a solution of tert-butyl N-[(tert-butoxy)carbonyl]-N-[6-(bromomethyl)pyridin-2-yl]carbamate (11.2 g, 29.0 mmol) in MeCN (30 mL) was added. After stirred at 70° C. for 2.5 hr under $N_2$, the reaction mixture was quenched with sat. $NH_4Cl$ and extracted with EA (300 mL×3). The combined organic layers were washed with water and brine, dried over $Na_2SO_4$, filtered and the organic phase was concentrated. The crude product was purified by flash chromatography (silica gel, 0~50% ethyl acetate in petroleum ether) to give tert-butyl N-[(tert-butoxy)carbonyl]-N-[6-({4-methanesulfonyl-7-methyl-9-oxo-3-thia-5,7,10,11-tetraazatricyclo[6.4.0.0{2,6}]dodeca-1(8),2(6),4,11-tetraen-10-yl} methyl)pyridin-2-yl]carbamate (5.5 g). LC-MS (ESI) found: 591.1 $(M+H)^+$.

Step B. tert-Butyl (6-((4-methyl-5-oxo-2-((phenylsulfonyl)(1-((2-(trimethylsilyl)ethoxy)methyl)-1H-pyrazol-3-yl)methyl)-4H-thiazolo[5',4':4,5]pyrrolo[2,3-d]pyridazin-6(5H)-yl)methyl)pyridin-2-yl)carbamate To a stirred mixture of 3-((phenylsulfonyl)methyl)-1-((2-(trimethylsilyl)ethoxy)methyl)-1H-pyrazole (11.9 g, 33.8 mmol) in anhydrous THF (200 mL) was added LiHMDS (50 mL, 1 M in THF) at −40° C. under argon. After 10 min, the mixture was warmed up to 10° C. and stirred for 1 hr, then tert-butyl N-[(tert-butoxy)carbonyl]-N-[6-({4-methanesulfonyl-7-methyl-9-oxo-3-thia-5,7,10,11-tetraazatricyclo[6.4.0.0{2,6}]dodeca-1(8),2(6),4,11-tetraen-10-yl} methyl) pyridin-2-yl]carbamate (9.1 g, 15.4 mmol in 35 mL THF) was added. The reaction was stirred at 10° C. for another 30 min. The reaction mixture was poured into aq. NH$_4$Cl, extracted with EtOAc (200 mL×3). The combined organic layers were washed with water and brine, dried over anhydrous Na$_2$SO$_4$ and concentrated. The crude product was purified by flash chromatography (silica gel, 0~50% ethyl acetate in petroleum ether) to give tert-butyl (6-((4-methyl-5-oxo-2-((phenylsulfonyl)(1-((2-(trimethylsilyl)ethoxy)methyl)-1H-pyrazol-3-yl)methyl)-4H-thiazolo[5',4':4,5]pyrrolo [2,3-d]pyridazin-6(5H)-yl)methyl)pyridin-2-yl)carbamate (6.6 g). LC-MS (ESI) found: 763.2 (M+H)$^+$.

Step C. tert-Butyl (6-((4-methyl-5-oxo-2-((1-((2-(trimethylsilyl)ethoxy)methyl)-1H-pyrazol-3-yl)methyl)-4H-thiazolo[5',4':4,5]pyrrolo[2,3-d]pyridazin-6(5H)-yl)methyl)pyridin-2-yl)carbamate A solution of tert-butyl (6-((4-methyl-5-oxo-2-((phenylsulfonyl)(1-((2-(trimethylsilyl)ethoxy)methyl)-1H-pyrazol-3-yl)methyl)-4H-thiazolo[5',4':4,5]pyrrolo[2,3-d]pyridazin-6(5H)-yl)methyl)pyridin-2-yl)carbamate (6.0 g, 7.86 mmol) in EtOH/AcOH (35 mL/50 mL) was heated to 50° C. with vigorously stirred in the presence of Zn (2.55 g, 117.9 mmol) for 40 min. Additional zinc were added every 40 min (2.55 g, twice, monitor the reaction by TLC/LC-MS to avoid the by-product and over reduced product). The solution was filtered and the filter cake was washed with DCM. The filtrate was partly evaporated, neutralized with saturated NaHCO$_3$ solution, dried over MgSO$_4$ and the solvent was removed under vacuum. The crude product was purified by flash chromatography (silica gel, DCM: MeOH=40:1) to give tert-butyl (6-((4-methyl-5-oxo-2-((1-((2-(trimethylsilyl)ethoxy)methyl)-1H-pyrazol-3-yl)methyl)-4H-thiazolo[5',4':4,5]pyrrolo[2,3-d]pyridazin-6(5H)-yl)methyl)pyridin-2-yl)carbamate (3.1 g). LC-MS (ESI) found: 623.3 (M+H)$^+$.

Step D. 2-((1H-pyrazol-3-yl)methyl)-6-((6-aminopyridin-2-yl)methyl)-4-methyl-4H-thiazolo[5',4':4,5]pyrrolo[2,3-d]pyridazin-5(6H)-one To a mixture of tert-butyl (6-((4-methyl-5-oxo-2-((1-((2-(trimethylsilyl)ethoxy)methyl)-1H-pyrazol-3-yl)methyl)-4H-thiazolo[5',4':4,5]pyrrolo[2,3-d]pyridazin-6(5H)-yl)methyl)pyridin-2-yl)carbamate (3.0 g, 4.8 mmol) in ethanol (30 mL) was added HCl (30 mL, 4 M in dioxane). The reaction mixture was stirred at 80° C. for 40 min. The reaction mixture was cooled down to r.t., filtered and the solid was collected, suspended in water and neutralized with aqueous NaHCO$_3$ at 10° C. Filtered to give the desire compound 2-((1H-pyrazol-3-yl)methyl)-6-((6-aminopyridin-2-yl)methyl)-4-methyl-4H-thiazolo[5',4':4,5]pyrrolo[2,3-d]pyridazin-5(6H)-one (1.5 g). LC-MS (ESI) found: 393.2 (M+H)$^+$. $^1$HNMR (400 MHz, DMSO-d$_6$) δ 12.78 (s, 1H), 8.53 (s, 1H), 7.72 (s, 1H), 7.25 (dd, 1H), 6.33-6.24 (m, 2H), 6.08 (d, 1H), 5.90 (s, 2H), 5.19 (s, 2H), 4.49 (s, 2H), 4.26 (s, 3H).

Step E. Synthesis of tert-butyl (6-((4-methyl-5-oxo-2-(1-((2-(trimethylsilyl)ethoxy) methyl)-1H-pyrazole-3-carbonyl)-4H-thiazolo[5',4':4,5]pyrrolo[2,3-d]pyridazin-6(5H)-yl)methyl)pyridin-2-yl)carbamate To a solution of tert-butyl (6-((4-methyl-5-oxo-2-((1-((2-(trimethylsilyl)ethoxy)methyl)-1H-pyrazol-3-yl)methyl)-4H-thiazolo[5',4':4,5]pyrrolo[2,3-d]pyridazin-6(5H)-yl)methyl)pyridin-2-yl)carbamate (100 mg, 0.16 mmol) in DMF (2 mL) was added K$_2$CO$_3$ (88 mg, 0.64 mmol). The mixture was stirred at 70° C. for 8 hr. The mixture was poured into water, the precipitate was collected by filtration and purified by pre-TLC (2% MeOH in DCM) to afford tert-butyl (6-((4-methyl-5-oxo-2-(1-((2-(trimethylsilyl)ethoxy)methyl)-1H-pyrazole-3-carbonyl)-4H-thiazolo[5',4':4,5]pyrrolo[2,3-d]pyridazin-6(5H)-yl)methyl)pyridin-2-yl)carbamate (20 mg). LC-MS (ESI): m/z 637 (M+H)$^+$.

Step F. Synthesis of 6-((6-aminopyridin-2-yl)methyl)-4-methyl-2-(1H-pyrazole-3-carbonyl)-4H-thiazolo[5',4':4,5]pyrrolo[2,3-d]pyridazin-5(6H)-one To a solution of tert-butyl (6-((4-methyl-5-oxo-2-(1-((2-(trimethylsilyl)ethoxy)methyl)-1H-pyrazole-3-carbonyl)-4H-thiazolo[5',4':4,5]pyrrolo[2,3-d]pyridazin-6(5H)-yl)methyl)pyridin-2-yl)carbamate (20 mg, 0.03 mmol) in EtOH (1 mL) was added HCl (1 mL, 4 mol/L in dioxane). The mixture was stirred at 80° C. for 1 hr and cooled down. The precipitate was collected by filtration and neutralized with sat. NaHCO$_3$, washed with water and dried to afford 5 mg of 6-((6-aminopyridin-2-yl)methyl)-4-methyl-2-(1H-pyrazole-3-carbonyl)-4H-thiazolo[5',4':4,5]pyrrolo[2,3-d]pyridazin-5(6H)-one. LC-MS (ESI): m/z 407 (M+H)$^+$. 1H NMR (400 MHz, DMSO-d$_6$) δ: 8.75 (s, 1H), 7.96 (s, 1H), 7.50 (s, 1H), 7.31-7.22 (m, 1H), 6.31 (d, 1H), 6.14 (d, 1H), 5.91 (s, 2H), 5.23 (s, 2H), 4.38 (s, 3H).

Example 8B. Synthesis of 6-((1H-pyrazol-3-yl)methyl)-2-((6-(dimethylamino)pyridin-2-yl)methyl)-4-methyl-4,6-dihydro-5H-thiazolo[5',4':4,5]pyrrolo[2,3-d]pyridazin-5-one

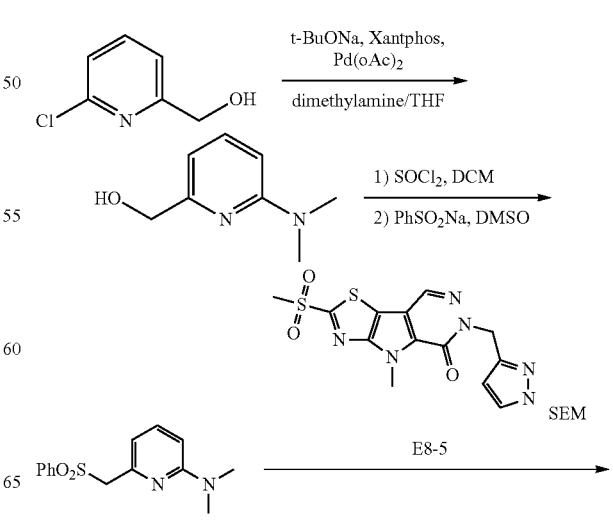

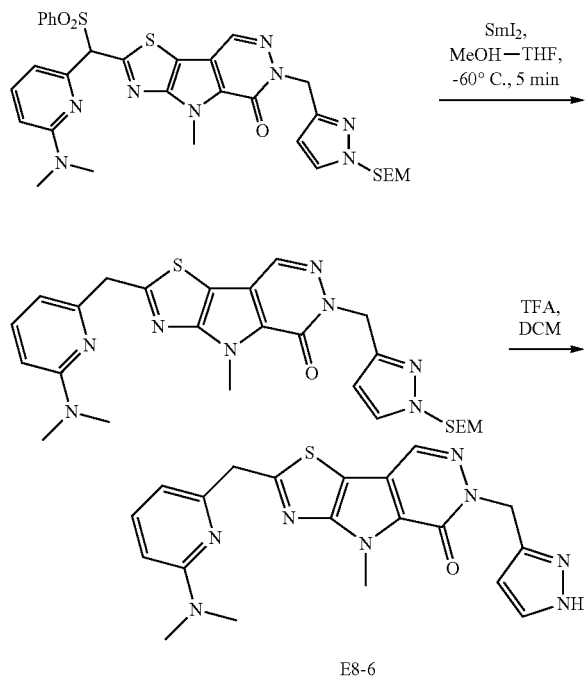

E8-6

Step A. (6-(dimethylamino)pyridin-2-yl)methanol

To a solution of (6-chloropyridin yl)methanol (500 mg, 2.67 mmol) in dimethylamine in THF (35 mL) was added Pd(OAc)$_2$ (78 mg, 0.35 mmol), Xantphos (170 mg, 0.29 mmol) and t-BuONa (385 mg, 4.01 mmol). The reaction mixture was stirred at 100° C. for 18 h. The reaction mixture was filtered and concentrated under reduced pressure. The residue was purified by flash chromatography (silica gel, 0~35% ethyl acetate in petroleum ether) to afford (6-(dimethylamino)pyridin-2-yl)methanol (180 mg). LCMS: 153 (M+H)$^+$.

Step B. 6-(chloromethyl)-N,N-dimethylpyridin-2-amine

To a stirred mixture of (6-(dimethylamino)pyridin-2-yl)methanol (170 mg, 1.1 mmol) in DCM (10 mL) was added SOCl$_2$ (665 mg, 5.6 mmol) at 0° C. The reaction mixture was stirred at r.t for 1 hr. The reaction mixture was adjusted at pH=7-8 with aq. NaHCO$_3$. Then the mixture was extracted with DCM, washed with water and brine. The organic layer was dried over Na$_2$SO$_4$, concentrated under reduced pressure to afford 6-(chloromethyl)-N,N-dimethylpyridin-2-amine (70 mg). LCMS: 171 (M+H)$^+$.

Step C. N,N-dimethyl-6-((phenylsulfonyl)methyl)pyridin-2-amine

To a stirred mixture of 6-(chloromethyl)-N,N-dimethylpyridin-2-amine (500 mg, 2.94 mmol) in DMSO (10 mL) was added PhSO$_2$Na (1.44 g, 8.82 mmol) at r.t. The mixture was stirred at r.t for 18 hr. The reaction mixture was poured into water and extracted with DCM. The mixture was washed with water and the organic layer was concentrated under reduced pressure. The residue was purified by flash chromatography (silica gel, 0~20% ethyl acetate in petroleum ether) to afford N,N-dimethyl-6-((phenylsulfonyl)methyl) pyridine-2-amine (380 mg). LCMS: 277 (M+H)$^+$.

Step D. 24(6-(dimethylamino)pyridin-2-yl)(phenylsulfonyl)methyl)-4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one To a stirred mixture of 4-methyl-2-(methylsulfonyl)-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (180 mg, 0.36 mmol), which was synthesized similar to compound E8-1 in Example 8A, in dry THF (10 mL) was added N,N-dimethyl-6-((phenylsulfonyl)methyl)pyridin-2-amine (120 mg, 0.44 mmol) and t-BuOK (122 mg, 1.1 mmol) at 60° C. under N$_2$. The mixture was stirred at 60° C. for 2 h under N$_2$. Then the mixture was poured into the water and extracted with EtOAc, washed with water and brine. The organic layer was dried over Na$_2$SO$_4$, concentrated under reduced pressure and purified by Prep-TLC (PE:EtOAc=1:1.5) to afford 2-((6-(dimethylamino)pyridin yl)(phenylsulfonyl)methyl)-4-methyl-6-((1-((2-(trimethylsilyl)ethoxy)methyl)-1H-pyrazol yl)methyl)-4H-thiazolo[5',4':4,5] pyrrolo[2,3-d]pyridazin-5(6H)-one (50 mg). LCMS: 691 (M+H)$^+$.

Step E. 2-((6-(dimethylamino)pyridin-2-yl)methyl)-4-methyl-6-((1-((2-(trimethylsilyl)ethoxy)methyl)-1H-pyrazol-3-yl)methyl)-4H-thiazolo [5',4':4,5]pyrrolo[2,3-d]pyridazin-5(6H)-one To a mixture of 24(6-(dimethylamino)pyridin-2-yl)(phenylsulfonyl)methyl)-4-methyl-6-((1-((2-(trimethylsilyl) ethoxy)methyl)-1H-pyrazol-3-yl)methyl)-4H-thiazolo[5',4':4,5] pyrrolo[2,3-d]pyridazin-5(6H)-one (50 mg, 0.07 mmol) in THF (5 mL) and MeOH (5 mL) at r.t under N$_2$ was added SmI$_2$ (5 mL, 0.1M in THF) at −40° C. The reaction mixture was stirred at −40° C. for 10 min and then quenched with water. The following mixture was extracted with EtOAc twice. The combined organic layers were washed with brine (30 mL), dried over anhydrous Na$_2$SO$_4$ and concentrated under reduced pressure. The residue was purified by prep-TLC (PE/EtOAc=1/1.5) to give the desired product (10 mg). LCMS: m/z 551 (M+H)+.

Step F. 6-((1H-pyrazol-3-yl)methyl)-2-((6-(dimethylamino)pyridin-2-yl)methyl)-4-methyl-4H-thiazolo [5',4':4,5]pyrrolo[2,3-d]pyridazin-5(6H)-one A mixture of 24(6-(dimethylamino)pyridin-2-yl)methyl)-4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (10 mg, 0.018 mmol) in DCM/TFA (2 mL/2 mL) was stirred at r.t for 1 hour. The reaction mixture was concentrated. The residue was purified by prep-HPLC to afford desired product (1.4 mg). LCMS: 421 (M+H)$^+$.
$^1$NMR (400 MHz, DMSO) δ 8.51 (s, 1H), 7.55 (s, 1H), 7.48 (dd, 1H), 6.64 (d, 1H), 6.54 (d, 1H), 6.11 (d, 1H), 5.32 (s, 2H), 4.44 (s, 2H), 4.26 (s, 3H), 3.05 (s, 6H). The following compounds were synthesized according to Scheme E8 and Example 8C using the appropriate starting material. Standard protection and deprotection can be used when necessary.

| Cpd No. | Structure and chemical name | Characterization |
|---|---|---|
| E8-7 | 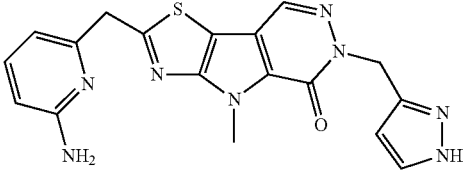 [SMILES: Cn1c2nc(Cc3cccc(N)n3)sc2c2cnn(Cc3cc[nH]n3)c(=O)c21]<br>6-((1H-pyrazol-3-yl)methyl)-2-((6-aminopyridin-2-yl)methyl)-4-methyl-4H-thiazolo[5',4':4,5]pyrrolo[2,3-d]pyridazin-5(6H)-one | LCMS: 393(M + H)$^+$.<br>$^1$H-NMR(400 MHz, DMSO) δ 12.67 (s, 1H), 8.50 (s, 1H), 7.62 (s, 1H), 7.46 (s, 1H), 6.60 (d, 1H), 6.45 (s, 1H), 6.11 (d, 1H), 5.33 (s, 2H), 4.42 (s, 2H), 4.26 (s, 3H) |
| E8-8 | 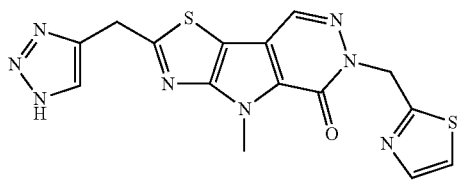 [SMILES: Cn1c2nc(Cc3c[nH]nn3)sc2c2cnn(Cc3nccs3)c(=O)c21]<br>2-((1H-1,2,3-triazol-4-yl)methyl)-4-methyl-6-(thiazol-2-ylmethyl)-4H-thiazolo[5',4':4,5]pyrrolo[2,3-d]pyridazin-5(6H)-one | LCMS: m/z 385 (M + H)$^+$.<br>1H NMR (400 MHz, DMSO-d6) δ 8.60 (s, 1H), 7.89 (s, 1H), 7.75 (d, 1H), 7.67 (d, 1H), 5.65 (s, 2H), 4.63 (s, 2H), 4.27 (s, 3H). |
| E8-9 | 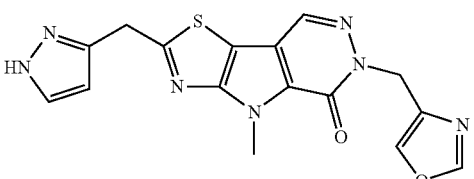<br>2-((1H-pyrazol-3-yl)methyl)-4-methyl-6-(oxazol-4-ylmethyl)-4H-thiazolo[5',4':4,5]pyrrolo[2,3-d]pyridazin-5(6H)-one | LCMS: m/z 368 (M + H)$^+$.<br>1H NMR (400 MHz, DMSO-d6) δ 12.79 (s, 1H), 8.51 (s, 1H), 8.29 (s, 1H), 8.00 (s, 1H), 7.68 (s, 1H), 6.26 (s, 1H), 5.26 (s, 2H), 4.49 (s, 2H), 4.27 (s, 3H). |
| E8-10 | 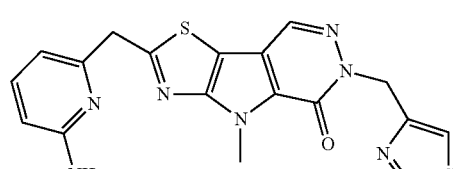<br>2-((6-aminopyridin-2-yl)methyl)-4-methyl-6-(thiazol-4-ylmethyl)-4H-thiazolo[5',4':4,5]pyrrolo[2,3-d]pyridazin-5(6H)-one | LCMS: m/z 410 (M + H)$^+$.<br>1H NMR (400 MHz, DMSO-d6) δ 9.03 (d, 1H), 8.52 (s, 1H), 7.42(d, 1H), 7.36 (t, 1H), 6.55 (d, 1H), 6.35 (d, 1H), 5.98 (s, 2H), 5.48 (s, 2H), 4.37 (s, 2H), 4.26 (s, 3H) |
| E8-11 | 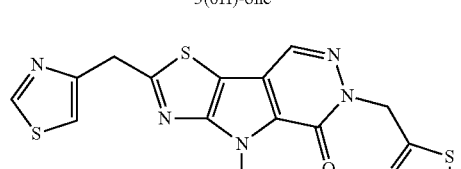<br>4-methyl-6-(thiazol-2-ylmethyl)-2-(thiazol-4-ylmethyl)-4H-thiazolo[5',4':4,5]pyrrolo[2,3-d]pyridazin-5(6H)-one | LC-MS: m/z 401 (M + H)$^+$.<br>1H NMR (400 MHz, DMSO) δ 9.13 (d, 1H), 8.60 (s, 1H), 7.75 (d, 1H), 7.72 (d, 1H), 7.67 (d, 1H), 5.65 (s, 2H), 4.71 (s, 2H), 4.27 (s, 3H). |

| Cpd No. | Structure and chemical name | Characterization |
|---|---|---|
| E8-12 | 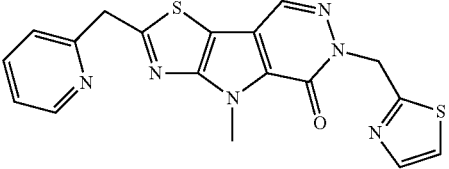 [SMILES: Cn1c2nc(Cc3ccccn3)sc2c2cnn(Cc3nccs3)c(=O)c21]<br>4-methyl-2-(pyridin-2-ylmethyl)-6-(thiazol-2-ylmethyl)-4H-thiazolo[5',4':4,5]pyrrolo[2,3-d]pyridazin-5(6H)-one | LC-MS: m/z 395 (M + H)+.<br>1H NMR (400 MHz, DMSO) δ 8.60 (s, 1H), 8.57 (dd, 1H), 7.81 (td, 1H), 7.74 (d, 1H), 7.67 (d, 1H), 7.51 (d, 1H), 7.36-7.30 (m, 1H), 5.65 (s, 2H), 4.68 (s, 2H), 4.26 (s, 3H) |
| E8-13 | 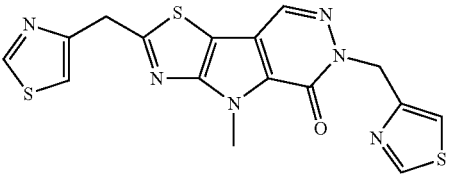 [SMILES: Cn1c2nc(Cc3cscn3)sc2c2cnn(Cc3cscn3)c(=O)c21]<br>4-methyl-2,6-bis(thiazol-4-ylmethyl)-4H-thiazolo[5',4':4,5]pyrrolo[2,3-d]pyridazin-5(6H)-one | LC-MS: m/z 401 (M + H)+.<br>1H NMR (400 MHz, DMSO) δ 9.13 (d, 1H), 9.03 (d, 1H), 8.54 (s, 1H), 7.72 (d, 1H), 7.44-7.41 (m, 1H), 5.48 (s, 2H), 4.71 (s, 2H), 4.27 (s, 3H). |
| E8-14 | 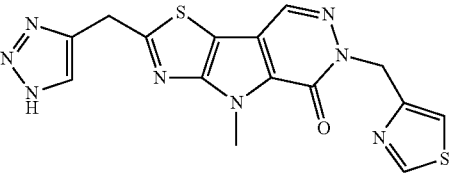 [SMILES: Cn1c2nc(Cc3c[nH]nn3)sc2c2cnn(Cc3cscn3)c(=O)c21]<br>2-((1H-1,2,3-triazol-4-yl)methyl)-4-methyl-6-(thiazol-4-ylmethyl)-4H-thiazolo[5',4':4,5]pyrrolo[2,3-d]pyridazin-5(6H)-one | LC-MS: m/z 385 (M + H)+.<br>1H NMR (400 MHz, DMSO) δ 9.03 (d, 1H), 8.54 (s, 1H), 7.89 (s, 1H), 7.42 (d, 1H), 5.48 (s, 2H), 4.63 (s, 2H), 4.26 (s, 3H). |
| E8-15 | 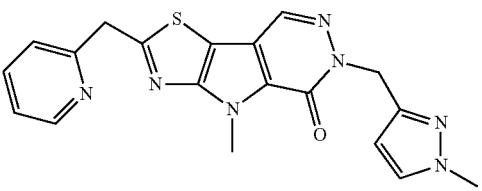 [SMILES: Cn1ccc(Cn2ncc3c4sc(Cc5ccccn5)nc4n(C)c3c2=O)n1]<br>4-methyl-6-((1-methyl-1H-pyrazol-3-yl)methyl)-2-(pyridin-2-ylmethyl)-4H-thiazoio[5',4':4,5]pyirolo[2,3-d]pyridazin-5(6H)-one | LCMS: m/z 392 (M + H)+.<br>1H NMR (400 MHz, DMSO) δ 8.56 (d, 1H), 8.50 (s, 1H), 7.81 (td, 1H), 7.55 (d, 1H), 7.50 (d, 1H), 7.32 (dd, 1H), 6.07 (d, 1H), 5.26 (s, 2H), 4.67 (s, 2H), 4.26 (s, 3H), 3.76 (s, 3H). |
| E8-16 | 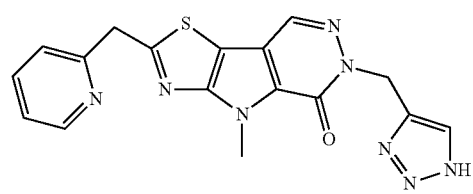 [SMILES: Cn1c2nc(Cc3ccccn3)sc2c2cnn(Cc3c[nH]nn3)c(=O)c21]<br>6-((1H-1,2,3-triazol-4-yl)methyl)-4-methyl-2-(pyridin-2-ylmethyl)-4H-thiazoio[5',4':4,5]pyrrolo[2,3-d]pyridazin-5(6H)-one | LCMS: m/z 379 (M + H)+.<br>1H NMR (400 MHz, DMSO) δ 8.56 (d, 1H), 8.52 (s, 1H), 7.84-7.78 (m, 1H), 7.71 (s, 1H), 7.50 (d, 1H), 7.36-7.28 (m, 1H), 5.42 (s, 2H), 4.67 (s, 2H), 4.26 (s, 3H). |

| Cpd No. | Structure and chemical name | Characterization |
|---|---|---|
| E8-17 | 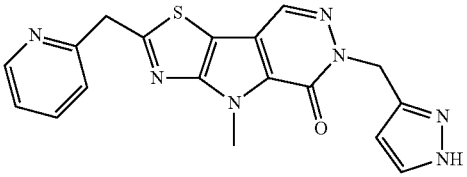 [SMILES: Cn1c2nc(Cc3ccccn3)sc2c2cnn(Cc3cc[nH]n3)c(=O)c21]<br>6-((1H-pyrazol-3-yl)methyl)-4-methyl-2-(pyridin-2-ylmethyl)-4H-thiazolo[5',4':4,5]pyrrolo[2,3-d]pyridazin-5(6H)-one | LCMS: m/z 378 (M + H)$^+$.<br>1H NMR (400 MHz, DMSO-d6) δ 12.63 (s, 1H), 8.57-8.55 (m, 1H), 8.51 (s, 1H), 7.81 (dd, 1H), 7.59 (s, 1H), 7.50 (d, 1H), 7.34-7.30 (m, 1H), 6.11 (d, 1H), 5.32 (s, 2H), 4.67 (s, 2H), 4.26 (s, 3H). |
| E8-18 | 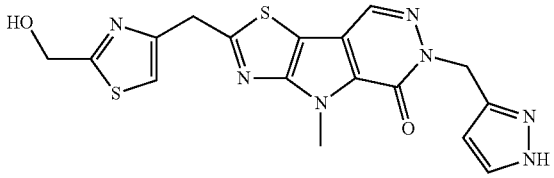 [SMILES: Cn1c2nc(Cc3csc(CO)n3)sc2c2cnn(Cc3cc[nH]n3)c(=O)c21]<br>6-((1H-pyrazol-3-yl)methyl)-2-((2-(hydroxymethyl)thiazol-4-yl)methyl)-4-methyl-4H-thiazolo[5',4':4,5]pyrrolo[2,3-d]pyridazin-5(6H)-one | LC-MS: m/z 414(M + 1)+.<br>1H NMR (400 MHz, DMSO) δ 12.63 (s, 1H), 8.51 (s, 1H), 7.61 (s, 1H), 7.56 (s, 1H), 6.11 (s, 1H), 6.06 (t, 1H), 5.32 (s, 2H), 4.70 (d, 2H), 4.60 (s, 2H), 4.27 (s, 3H). |
| E8-19 | 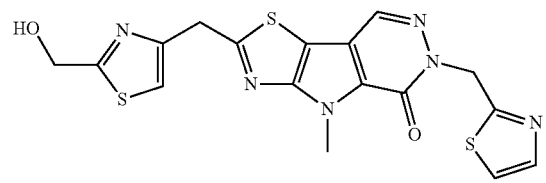 [SMILES: Cn1c2nc(Cc3csc(CO)n3)sc2c2cnn(Cc3nccs3)c(=O)c21]<br>2-((2-(hydroxymethyl)thiazol-4-yl)methyl)-4-methyl-6-(thiazol-2-ylmethyl)-4H-thiazolo[5',4':4,5]pyrrolo[2,3-d]pyridazin-5(6H)-one | LC-MS: m/z 431(M + 1)+.<br>1H NMR (400 MHz, DMSO) δ 8.60 (s, 1H), 7.75 (d, 1H), 7.67 (d, 1H), 7.57 (s, 1H), 6.10-5.97 (m, 1H), 5.65 (s, 2H), 4.70 (d, 2H), 4.61 (s, 2H), 4.26 (s, 3H). |
| E8-20 | 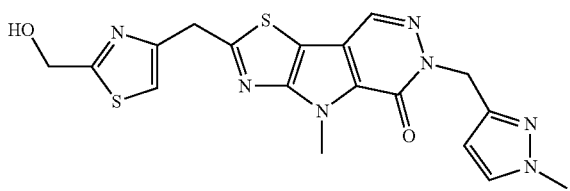 [SMILES: Cn1ccc(Cn2ncc3c4sc(Cc5csc(CO)n5)nc4n(C)c3c2=O)n1]<br>2-((2-(hydroxymethyl)thiazol-4-yl)methyl)-4-methyl-6-((1-methyl-1H-pyrazol-3-yl)methyl)-4H-thiazolo[5',4':4,5]pyrrolo[2,3-d]pyridazin-5(6H)-one | LC-MS: m/z 428(M + 1)$^+$.<br>1H NMR (400 MHz, DMSO) δ 8.49 (s, 1H), 7.62-7.58 (m, 2H), 6.07-6.03 (m, 2H), 5.26 (s, 2H), 4.70 (d, 2H), 4.60 (s, 2H), 4.26 (s, 3H), 3.76 (s, 3H). |
| E8-21 | 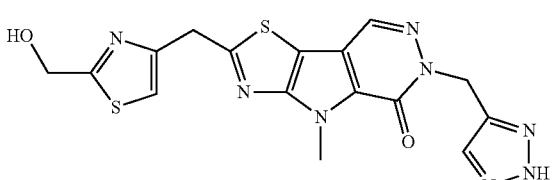<br>6-((2H-1,2,3-triazol-4-yl)methyl)-2-((2-(hydroxymethyl)thiazol-4-yl)methyl)-4-methyl-4H-thiazolo[5',4':4,5]pyrrolo[2,3-d]pyridazin-5(6H)-one | LC-MS: m/z 415(M + 1)+.<br>1H NMR (400 MHz, DMSO) δ 14.77 (s, 1H), 8.52 (s, 1H), 7.65 (s, 1H), 7.56 (s, 1H), 6.05 (t, 1H), 5.42 (s, 2H), 4.70 (d, 2H), 4.60 (s, 2H), 4.26 (s, 3H). |

| Cpd No. | Structure and chemical name | Characterization |
|---|---|---|
| E8-22 | 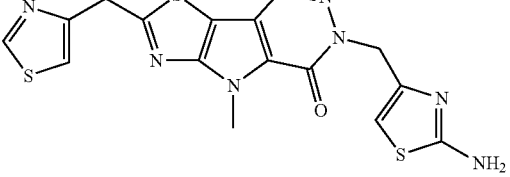<br>6-((2-aminothiazol-4-yl)methyl)-4-methyl-2-(thiazol-4-ylmethyl)-4H-thiazolo[5',4':4,5]pyrrolo[2,3-d]pyridazin-5(6H)-one | LCMS: m/z 416 (M + H)+. 1H NMR (400 MHz, DMSO) δ 9.13 (d, 1H), 8.51 (s, 1H), 7.72 (d, 1H), 7.03 (br s, 2H), 6.22 (s, 1H), 5.13 (s, 2H), 4.71 (s, 2H), 4.27 (s, 3H). |
| E8-23 | 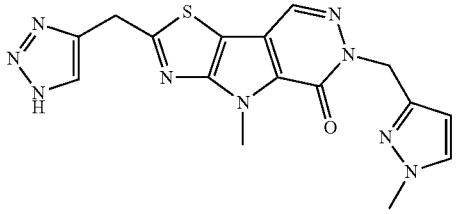 [SMILES: Cn1ccc(Cn2ncc3c4sc(Cc5c[nH]nn5)nc4n(C)c3c2=O)n1]<br>2-((1H-1,2,3-triazol-4-yl)methyl)-4-methyl-6-((1-methyl-1H-pyrazol-3-yl)methyl)-4H-thiazolo[5',4':4,5]pyrrolo[2,3-d]pyridazin-5(6H)-one | LCMS: m/z 382 (M + H)+. 1H NMR (400 MHz, DMSO-d6) δ 8.50 (s, 1H), 7.89 (s, 1H), 7.56 (d, 1H), 6.07 (d, 1H), 5.26 (s, 2H), 4.63 (s, 2H), 4.26 (s, 3H), 3.76 (s, 3H). |
| E8-24 | 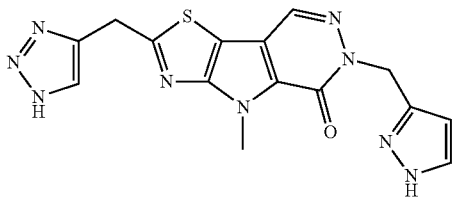 [SMILES: Cn1c2nc(Cc3c[nH]nn3)sc2c2cnn(Cc3cc[nH]n3)c(=O)c21]<br>2-((1H-1,2,3-triazol-4-yl)methyl)-6-((1H-pyrazol-3-yl)methyl)-4-methyl-4H-thiazolo[5',4':4,5]pyrrolo[2,3-d]pyridazin-5(6H)-one | LCMS: m/z 368 (M + H)+. 1H NMR (400 MHz, DMSO-d6) δ 14.73 (s, 1H), 12.64 (s, 1H), 8.51 (s, 1H), 7.89 (s, 1H), 7.61 (s, 1H), 6.11 (d, 1H), 5.33 (s, 2H), 4.63 (s, 2H), 4.26 (s, 3H). |
| E8-25 | 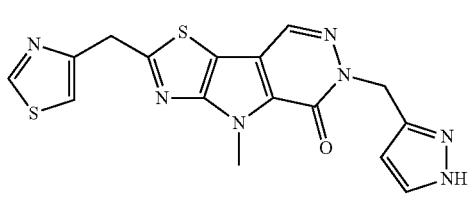 [SMILES: Cn1c2nc(Cc3cscn3)sc2c2cnn(Cc3cc[nH]n3)c(=O)c21]<br>6-((1H-pyrazol-3-yl)methyl)-4-methyl-2-(thiazol-4-ylmethyl)-4,6-dihydro-5H-thiazolo[5',4':4,5]pyrrolo[2,3-d]pyridazin-5-one | LC-MS: m/z 384.0 (M + H)+. 1H NMR (400 MHz, DMSO) δ 12.62 (s, 1H), 9.12 (d, 1H), 8.51 (s, 1H), 7.72 (d, 1H), 7.61 (s, 1H), 6.11 (s, 1H), 5.32 (s, 2H), 4.70 (s, 2H), 4.27 (s, 3H). |
| E8-26 | 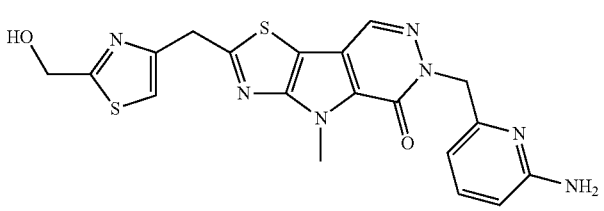 [SMILES: Cn1c2nc(Cc3csc(CO)n3)sc2c2cnn(Cc3cccc(N)n3)c(=O)c21]<br>6-((6-aminopyridin-2-yl)methyl)-2-((2-(hydroxymethyl)thiazol-4-yl)methyl)-4-methyl-4H-thiazolo[5',4':4,5]pyrrolo[2,3-d]pyridazin-5(6H)-one | LC-MS: 440.0 [M + H]+ 1H NMR (400 MHz, DMSO) δ 8.55 (s, 1H), 7.57 (s, 1H), 7.29-7.21 (m, 1H), 6.29 (d, 1H), 6.13-6.07 (m, 2H), 5.92 (s, 2H), 5.19 (s, 2H), 4.70 (d, 2H), 4.61 (s, 2H), 4.26 (s, 3H). |

| Cpd No. | Structure and chemical name | Characterization |
|---|---|---|
| E8-27 | 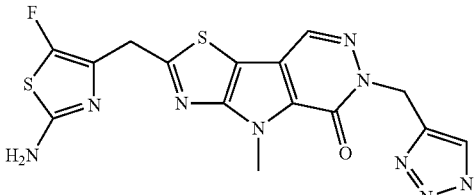<br>6-((1H-1,2,3-triazol-4-yl)methyl)-2-((2-amino-5-fluorothiazol-4-yl)methyl)-4-methyl-4H-thiazolo[5',4':4,5]pyrrolo[2,3-d]pyridazin-5(6H)-one | LCMS: 418 (M + H)+.<br>$^{1}$H NMR (400 MHz, DMSO) δ 8.53 (s, 1H), 7.74 (s, 1H), 6.92 (s, 2H), 5.43 (s, 2H), 4.27 (s, 2H), 4.26 (s, 3H). |
| E8-28 | 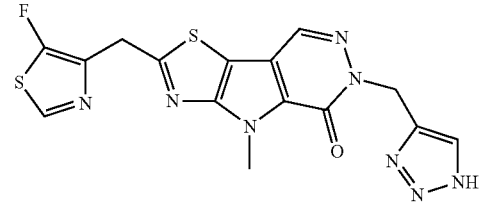 [SMILES: Cn1c2nc(Cc3ncsc3F)sc2c2cnn(Cc3c[nH]nn3)c(=O)c21]<br>6-((1H-1,2,3-triazol-4-yl)methyl)-2-((5-fluorothiazol-4-yl)methyl)-4-methyl-4,6-dihydro-5H-thiazolo[5',4':4,5]pyrrolo[2,3-d]pyridazin-5-one | LCMS: 403 (M + H)+.<br>$^{1}$H NMR (400 MHz, DMSO) δ 8.70 (d, 1H), 8.54 (s, 1H), 7.73 (s, 1H), 5.42 (s, 2H), 4.60 (d, 2H), 4.25 (s, 3H). |
| E8-29 | 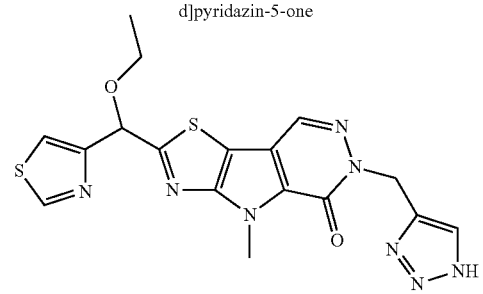<br>6-((1H-1,2,3-triazol-4-yl)methyl)-2-(ethoxy(thiazol-4-yl)methyl)-4-methyl-4H-thiazolo[5',4':4,5]pyrrolo[2,3-d]pyridazin-5(6H)-one | LCMS: 429 (M + H)+.<br>$^{1}$H NMR (400 MHz, DMSO) δ 9.09 (d, 1H), 8.57 (s, 1H), 7.88 (d, 1H), 7.73 (s, 1H), 6.12 (s, 1H), 5.54-5.34 (m, 2H), 4.23 (s, 3H), 3.76-3.61 (m, 2H), 1.20 (q, 3H). |
| E8-30 | 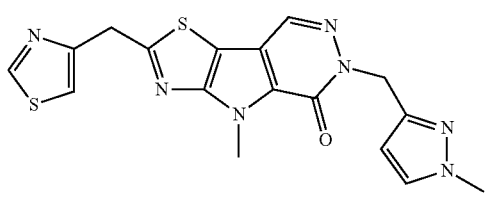 [SMILES: Cn1ccc(Cn2ncc3c4sc(Cc5cscn5)nc4n(C)c3c2=O)n1]<br>4-methyl-6-((1-methyl-1H-pyrazol-3-yl)methyl)-2-(thiazol-4-ylmethyl)-4H-thiazolo[5',4':4,5]pyrrolo[2,3-d]pyridazin-5(6H)-one | LCMS: m/z 398 (M + H)+.<br>$^{1}$H NMR (400 MHz, DMSO) δ 9.12 (d, 1H), 8.50 (s, 1H), 7.72 (d, 1H), 7.56 (d, 1H), 6.07 (d, 1H), 5.26 (s, 2H), 4.70 (s, 2H), 4.26 (s, 3H), 3.76 (s, 3H). |
| E8-31 | 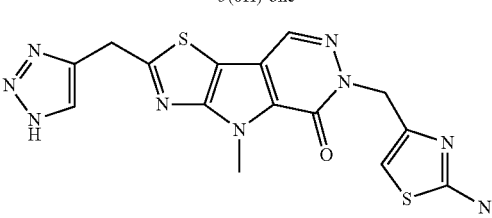<br>2-((1H-1,2,3-triazol-4-yl)methyl)-6-((2-aminothiazol-4-yl)methyl)-4-methyl-4H-thiazolo[5',4':4,5]pyrrolo[2,3-d]pyridazin-5(6H)-one | LCMS: m/z 400 (M + H)+.<br>$^{1}$H NMR (400 MHz, DMSO) δ 8.50 (s, 1H), 7.89 (s, 1H), 6.90 (s, 2H), 6.18 (s, 1H), 5.02 (s, 2H), 4.63 (s, 2H) 4.26 (s, 3H). |

-continued

| Cpd No. | Structure and chemical name | Characterization |
|---|---|---|
| E8-32 | 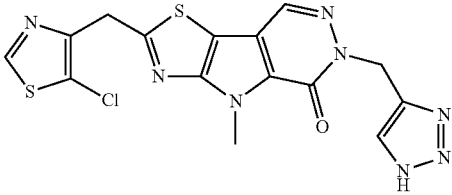 [SMILES: Cn1c2nc(Cc3ncsc3Cl)sc2c2cnn(Cc3c[nH]nn3)c(=O)c21]<br>6-((1H-1,2,3-triazol-4-yl)methyl)-2-((5-chlorothiazol-4-yl)methyl)-4-methyl-4H-thiazolo[5',4':4,5]pyrrolo[2,3-d]pyridazin-5(6H)-one | LCMS: m/z 419 (M + H)+.<br>$^1$H NMR (400 MHz, DMSO) δ 9.09 (s, 1H), 8.53 (s, 1H), 7.73 (s, 1H), 5.42 (s, 2H), 4.65 (s, 2H), 4.25 (s, 3H). |
| E8-33 | 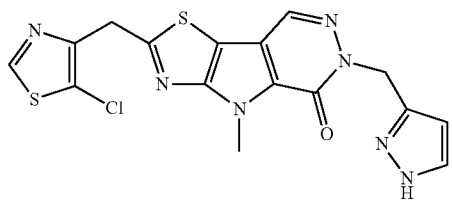 [SMILES: Cn1c2nc(Cc3ncsc3Cl)sc2c2cnn(Cc3cc[nH]n3)c(=O)c21]<br>6-((1H-pyrazol-3-yl)methyl)-2-((5-chlorothiazol-4-yl)methyl)-4-methyl-4H-thiazolo[5',4':4,5]pyrrolo[2,3-d]pyridazin-5(6H)-one | LCMS: m/z 418 (M + H)+.<br>$^1$H NMR (400 MHz, DMSO) δ 9.09 (s, 1H), 8.51 (s, 1H), 7.55 (s, 1H), 6.11 (d, 1H), 5.32 (s, 2H), 4.65 (s, 2H), 4.26 (s, 3H). |
| E8-34 | 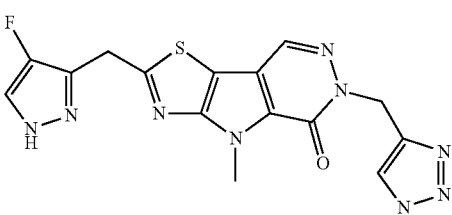<br>6-((1H-1,2,3-triazol-4-yl)methyl)-2-((4-fluoro-1H-pyrazol-3-yl)methyl)-4-methyl-4,6-dihydro-5H-thiazolo[5',4':4,5]pyrrolo[2,3-d]pyridazin-5-one | LC-MS m/z 386.0 (M + H)+.<br>$^1$H NMR (400 MHz, DMSO) δ 14.82 (s, 1H), 12.82 (s, 1H), 8.57 (s, 1H), 7.95 (s, 1H), 7.70 (s, 1H), 5.47 (s, 2H), 4.54 (s, 2H), 4.31 (s, 3H) |
| E8-35 | 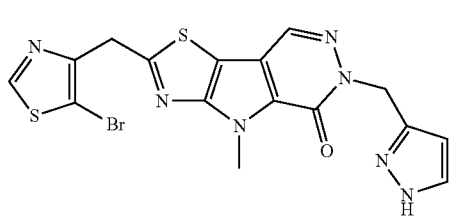<br>6-((1H-pyrazol-3-yl)methyl)-2-((5-bromothiazol-4-yl)methyl)-4-methyl-4H-thiazolo[5',4':4,5]pyrrolo[2,3-d]pyridazin-5(6H)-one | LCMS: m/z 462 (M + H)+.<br>$^1$H NMR (400 MHz, DMSO-d$_6$) δ 12.64(s, 1H), 9.19 (s, 1H), 8.51 (s, 1H), 7.57 (s, 1H), 6.11 (d, 1H), 5.33(s, 2H), 4.65 (s, 2H), 4.26(s, 3H). |
| E8-36 | 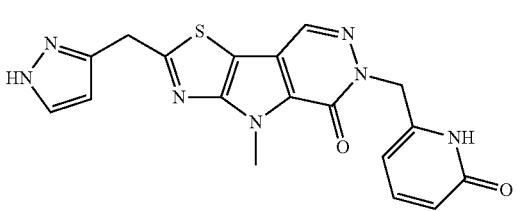 [SMILES: Cn1c2nc(Cc3cc[nH]n3)sc2c2cnn(Cc3cccc(=O)[nH]3)c(=O)c21]<br>2-((1H-pyrazol-3-yl)methyl)-4-methyl-6-((6-oxo-1,6-dihydropyridin-2-yl)methyl)-4H-thiazolo[5',4':4,5]pyrrolo[2,3-d]pyridazin-5(6H)-one | LCMS: m/z 394 (M + H)+.<br>$^1$H NMR (400 MHz, DMSO) δ 12.77 (s, 1H), 11.71 (s, 1H), 8.58 (s, 1H), 7.70 (s, 1H), 7.32 (s, 1H), 6.25-6.05 (m, 2H), 5.75 (s, 1H), 5.19 (s, 2H), 4.50 (s, 2H), 4.26 (s, 3H). |

| Cpd No. | Structure and chemical name | Charaterization |
|---|---|---|
| E8-37 | 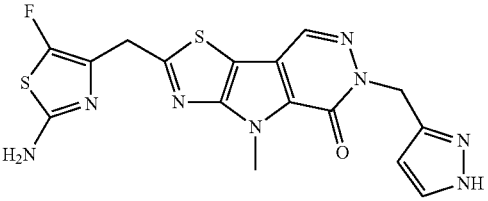 [SMILES: Cn1c2nc(Cc3nc(N)sc3F)sc2c2cnn(Cc3cc[nH]n3)c(=O)c21]<br>6-((1H-pyrazol-3-yl)methyl)-2-((2-amino-5-fluorothiazol-4-yl)methyl)-4-methyl-4,6-dihydro-5H-thiazolo[5',4':4,5]pyrrolo[2,3-d]pyridazin-5-one | LCMS: m/z 417 (M + H)+.<br>1H NMR DMSO-d6 400 MHz<br>δ 12.65 (s, 1H), 8.51 (s, 1H), 7.57 (s, 1H), 6.92 (s, 2H), 6.12 (d, 1H), 5.33 (s, 2H), 4.26 (s, 5H). |
| E8-38 | 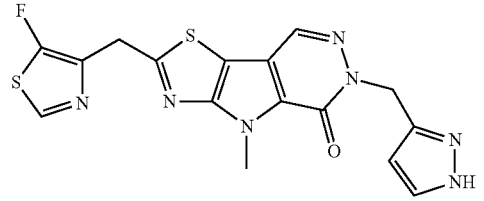 [SMILES: Cn1c2nc(Cc3ncsc3F)sc2c2cnn(Cc3cc[nH]n3)c(=O)c21]<br>6-((1H-pyrazol-3-yl)methyl)-2-((5-fluorothiazol-4-yl)methyl)-4-methyl-4H-thiazolo[5',4':4,5]pyrrolo[2,3-d]pyridazin-5(6H)-one | LCMS: m/z 402 (M + H)+.<br>1H NMR DMSO-d6 400 MHz<br>δ12.70 (s, 1H), 8.70 (d, 1H), 8.52 (s, 1H), 7.55 (s, 1H), 6.11 (d, 1H), 5.33 (s, 2H), 4.60 (d, 2H), 4.26 (s, 3H). |
| E8-39 | 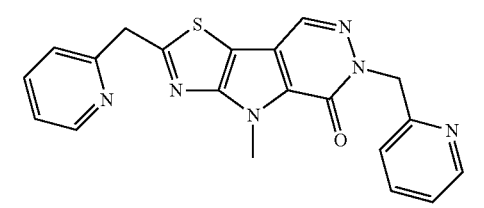 [SMILES: Cn1c2nc(Cc3ccccn3)sc2c2cnn(Cc3ccccn3)c(=O)c21]<br>4-methyl-2,6-bis(pyridin-2-ylmethyl)-4H-thiazolo[5',4':4,5]pyrrolo[2,3-d]pyridazin-5(6H)-one | LCMS: m/z 389 (M + H)+.<br>1H NMR DMSO-d6 400 MHz<br>δ 8.61-8.54 (m, 2H), 8.51-8.46 (m, 1H), 7.82 (td, 1H), 7:73 (td, 1H), 7.52 (d, 1H), 7.34 (ddd, 1H), 7.27 (dd, 1H), 7.14 (d, 1H), 5.46 (s, 2H), 4.69 (s, 2H), 4.26 (s, 3H). |
| E8-40 | 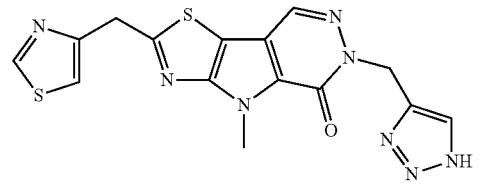 [SMILES: Cn1c2nc(Cc3cscn3)sc2c2cnn(Cc3c[nH]nn3)c(=O)c21]<br>6-((1H-1,2,3-triazol-4-yl)methyl)-4-methyl-2-(thiazol-4-ylmethyl)-4H-thiazolo[5',4':4,5]pyrrolo[2,3-d]pyridazin-5(6H)-one | LCMS: m/z 385 (M + H)+.<br>1H NMR (400 MHz, DMSO-d6) δ 9.13 (d, 1H), 8.53 (s, 1H), 7.74 (s, 1H), 7.72 (d, 1H), 5.42 (s, 2H), 4.70 (s, 2H), 4.26 (s, 3H). |
| E8-41 | 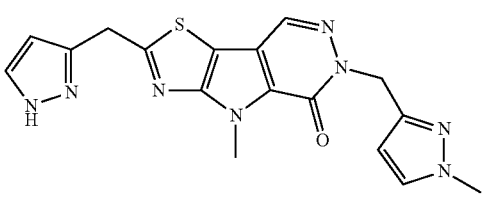 [SMILES: Cn1ccc(Cn2ncc3c4sc(Cc5cc[nH]n5)nc4n(C)c3c2=O)n1]<br>2-((1H-pyrazol-3-yl)methyl)-4-methyl-6-((1-methyl-1H-pyrazol-3-yl)methyl)-4H-thiazolo[5',4':4,5]pyrrolo[2,3-d]pyridazin-5(6H)-one | LCMS: m/z 381 (M + H)+.<br>1H NMR (400 MHz, DMSO-d6) δ 12.77 (s, 1H), 8.48 (s, 1H), 7.71 (s, 1H), 7.55 (d, 1H), 6.26 (d, 1H), 6.07 (d, 1H), 5.26 (s, 2H), 4.47 (s, 2H), 4.27 (s, 3H), 3.76 (s, 3H). |

| Cpd No. | Structure and chemical name | Characterization |
|---|---|---|
| E8-42 | 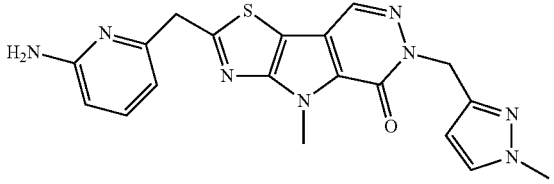 [SMILES: Cn1ccc(Cn2ncc3c4sc(Cc5cccc(N)n5)nc4n(C)c3c2=O)n1]<br>2-((6-aminopyridin-2-yl)methyl)-4-methyl-6-((1-methyl-1H-pyrazol-3-yl)methyl)-4H-thiazolo[5',4':4,5]pyrrolo[2,3-d]pyridazin-5(6H)-one | LCMS: m/z 407 (M + H)+.<br>1H NMR (400 MHz, DMSO-$d_6$) δ 8.48 (s, 1H), 7.55 (d, 1H), 7.35 (t, 1H), 6.55 (d, 1H), 6.35 (d, 1H), 6.07 (d, 1H), 5.97 (s, 2H), 5.26 (s, 2H), 4.36 (s, 2H), 4.26 (s, 3H), 3.76 (s, 3H). |
| E8-43 | 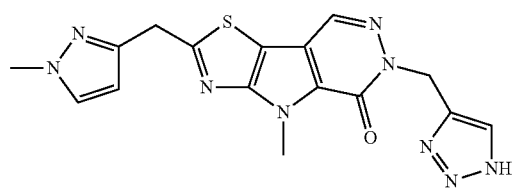 [SMILES: Cn1ccc(Cc2nc3c(s2)c2cnn(Cc4c[nH]nn4)c(=O)c2n3C)n1]<br>6-((1H-1,2,3-triazol-4-yl)methyl)-4-methyl-2-((1-methyl-1H-pyrazol-3-yl)methyl)-4H-thiazolo[5',4':4,5]pyrrolo[2,3-d]pyridazin-5(6H)-one | LCMS: m/z 382 (M + H)+.<br>1H NMR (400 MHz, DMSO-$d_6$) δ 14.70 (s, 1H), 8.51 (s, 1H), 7.74 (s, 1H), 7.65 (d, 1H), 6.22 (d, 1H), 5.42 (s, 2H), 4.43 (s, 2H), 4.26 (s, 3H), 3.81 (s, 3H). |
| E8-44 | 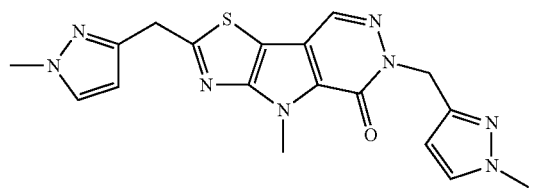<br>4-methyl-2,6-bis((1-methyl-1H-pyrazol-3-yl)methyl)-4H-thiazolo[5',4':4,5]pyrrolo[2,3-d]pyridazin-5(6H)-one | LCMS: m/z 395 (M + H)+.<br>1H NMR (400 MHz, DMSO-$d_6$) δ 8.48 (s, 1H), 7.65 (d, 1H), 7.55 (d, 1H), 6.22 (d, 1H), 6.07 (d, 1H), 5.26 (s, 2H), 4.43 (s, 2H), 4.26 (s, 3H), 3.82 (s, 3H), 3.76 (s, 3H). |
| E8-45 | 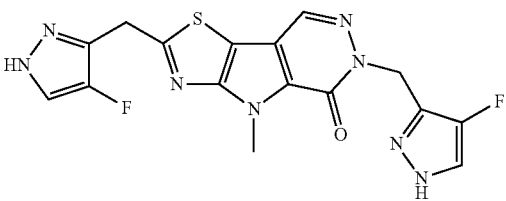 [SMILES: Cn1c2nc(Cc3n[nH]cc3F)sc2c2cnn(Cc3n[nH]cc3F)c(=O)c21]<br>2,6-bis((4-fluoro-1H-pyrazol-3-yl)methyl)-4-methyl-4H-thiazolo[5',4':4,5]pyrrolo[2,3-d]pyridazin-5(6H)-one | LCMS: m/z 403 (M + H)+.<br>1H NMR (400 MHz, DMSO-$d_6$) δ 13.02-12.57 (m, 2H), 8.49 (s, 1H), 7.6-7.8 (m, 2H), 5.33 (s, 2H), 4.49 (s, 2H), 4.27 (s, 3H). |
| E8-46 | 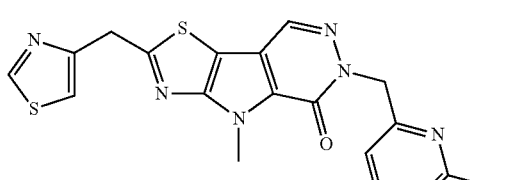<br>6-((6-aminopyridin-2-yl)methyl)-4-methyl-2-(thiazol-4-ylmethyl)-4H-thiazolo[5',4':4,5]pyrrolo[2,3-d]pyridazin-5(6H)-one | LCMS: m/z 410 (M + H)+.<br>1H NMR (400 MHz, DMSO-$d_6$) δ 9.13 (d, 1H), 8.55 (s, 1H), 7.72 (d, 1H), 7.25 (t, 1H), 6.29 (d, 1H), 6.07 (d, 1H), 5.92 (s, 2H), 5.19 (s, 2H), 4.71 (s, 2H), 4.26 (s, 3H). |

-continued

| Cpd No. | Structure and chemical name | Characterization |
|---|---|---|
| E8-47 | 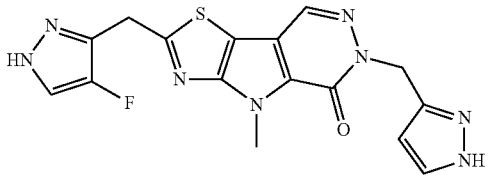 [SMILES: Cn1c2nc(Cc3n[nH]cc3F)sc2c2cnn(Cc3cc[nH]n3)c(=O)c21]<br>6-((1H-pyrazol-3-yl)methyl)-2-((4-fluoro-1H-pyrazol-3-yl)methyl)-4-methyl-4H-thiazolo[5',4':4,5]pyrrolo[2,3-d]pyridazin-5(6H)-one | LCMS: m/z 385 (M + H)⁺.<br>¹H NMR (400 MHz, DMSO) δ 12.77 (s, 1H), 12.62 (s, 1H), 8.50 (s, 1H), 7.87 (d, 1H), 7.61 (s, 1H), 6.11 (s, 1H), 5.32 (s, 2H), 4.49 (s, 2H), 4.26 (s, 3H). |
| E8-48 | 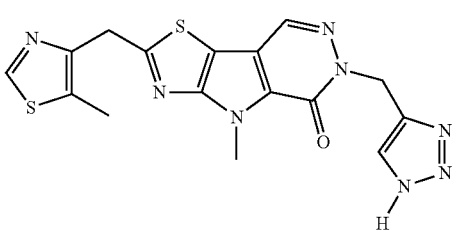 [SMILES: Cc1scnc1Cc1nc2c(s1)c1cnn(Cc3c[nH]nn3)c(=O)c1n2C]<br>6-((1H-1,2,3-triazol-4-yl)methyl)-4-methyl-2-((5-methylthiazol-4-yl)methyl)-4H-thiazolo[5',4':4,5]pyrrolo[2,3-d]pyridazin-5(6H)-one | LCMS: m/z 399 (M + H)+.<br>¹H NMR (400 MHz, DMSO-d6) δ 8.95 (s, 1H), 8.55 (s, 1H), 7.79 (s, 1H), 5.47 (s, 2H), 4.66 (s, 2H), 4.31 (s, 3H), 2.55 (s, 3H). |
| E8-49 | 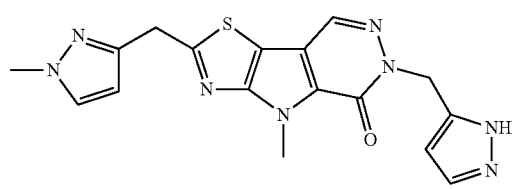 [SMILES: Cn1ccc(Cc2nc3c(s2)c2cnn(Cc4ccn[nH]4)c(=O)c2n3C)n1]<br>6-((1H-pyrazol-5-yl)methyl)-4-methyl-2-((1-methyl-1H-pyrazol-3-yl)methyl)-4H-thiazolo[5',4':4,5]pyrrolo[2,3-d]pyridazin-5(6H)-one | LCMS: m/z 381 (M + H)⁺.<br>¹H NMR (400 MHz, DMSO-d6) δ 12.64 (s, 1H), 8.49 (s, 1H), 7.65 (s, 1H), 7.56 (s, 1H), 6.23 (d, 1H), 6.11 (d, 1H), 5.32 (s, 2H), 4.43 (s, 2H), 4.26 (s, 3H), 3.82 (s, 2H). |
| E8-50 | 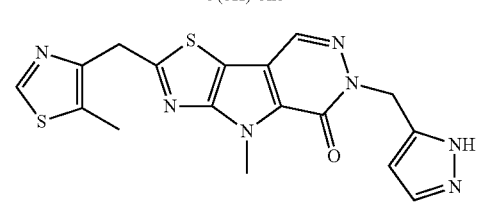<br>6-((1H-pyrazol-5-yl)methyl)-4-methyl-2-((5-methylthiazol-4-yl)methyl)-4H-thiazolo[5',4':4,5]pyrrolo[2,3-d]pyridazine-5(6H)-one | LCMS: m/z 398 (M + H)⁺.<br>¹H NMR (400 MHz, DMSO-d6) δ 12.63 (s, 1H), 8.90 (s, 1H), 8.48 (s, 1H), 7.60 (s, 1H), 6.11 (d, 1H), 5.32 (s, 2H), 4.61 (s, 2H), 4.26 (s, 3H) 2.50 (s, 3H overlap with DMSO-d6). . |
| E8-51 | 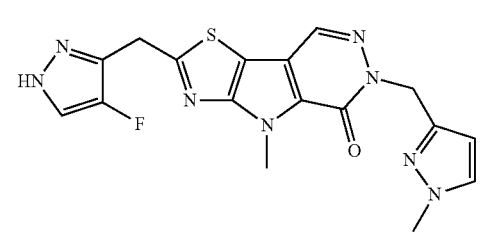 [SMILES: Cn1ccc(Cn2ncc3c4sc(Cc5n[nH]cc5F)nc4n(C)c3c2=O)n1]<br>2-((4-fluoro-1H-pyrazol-3-yl)methyl)-4-methyl-6-((1-methyl-1H-pyrazol-3-yl)methyl)-4H-thiazolo[5',4':4,5]pyrrolo[2,3-d]pyridazin-5(6H)-one | LCMS: m/z 399 (M + H)⁺.<br>¹H NMR (400 MHz, DMSO-d6) δ 12.83 (s, 1H), 8.54 (s, 1H), 7.91 (s, 1H), 7.61 (s, 1H), 6.13 (s, 1H), 5.32 (s, 2H), 4.54 (s, 2H), 4.34 (s, 3H), 3.81 (s, 3H). |

| Cpd No. | Structure and chemical name | Characterization |
|---|---|---|
| E8-52 | 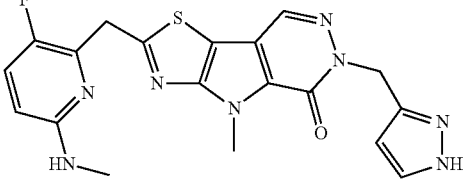<br>6-((1H-pyrazol-3-yl)methyl)-2-((3-fluoro-6-(methylamino)pyridin-2-yl)methyl)-4-methyl-4H-thiazolo[5',4':4,5]pyrrolo[2,3-d]pyridazin-5(6H)-one | LCMS: m/z 425 (M + H)+.<br>$^1$H NMR (400 MHz, DMSO) δ 12.68 (s, 1H), 8.56 (s, 1H), 7.65 (s, 1H), 7.43 (t, 1H), 6.62 (d, 1H), 6.46 (dd, 1H), 6.16 (s, 1H), 5.37 (s, 2H), 4.52 (s, 2H), 4.31 (s, 3H), 2.83 (d, 3H) |
| E8-53 | 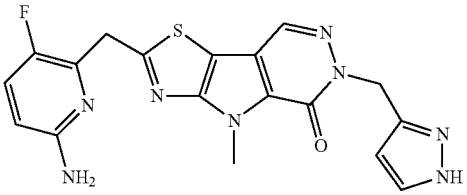 [SMILES: Cn1c2nc(Cc3nc(N)ccc3F)sc2c2cnn(Cc3cc[nH]n3)c(=O)c21]<br>6-((1H-pyrazol-3-yl)methyl)-2-((6-amino-3-fluoropyridin-2-yl)methyl)-4-methyl-4H-thiazolo[5',4':4,5]pyrrolo[2,3-d]pyridazin-5(6H)-one | LC-MS: m/z 411 (M + H)+.<br>$^1$H NMR (400 MHz, DMSO-d$_6$) δ 12.64 (s, 1H), 8.50 (s, 1H), 7.57 (s, 1H), 7.36 (t, 1H), 6.41 (dd, 1H), 6.11 (d, 1H), 5.96 (s, 2H), 5.32 (s, 2H), 4.44 (d, 2H), 4.26 (s, 3H) |
| E8-54 | 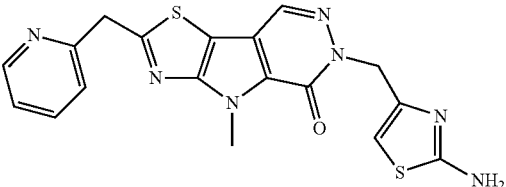<br>6-((2-aminothiazol-4-yl)methyl)-4-methyl-2-(pyridin-2-ylmethyl)-4,6-dihydro-5H-thiazolo[5',4':4,5]pyrrolo[2,3-d]pyridazin-5-one | LC-MS: m/z 410 (M + H)+.<br>$^1$H NMR (400 MHz, DMSO-d$_6$) δ 8.52 (s, 1H), 8.49 (s, 1H), 7.83 (d, 1H), 7.51 (d, 1H), 7.40-7.25 (m, 1H), 6.91 (s, 2H), 6.17 (s, 1H), 5.12 (s, 2H), 4.67 (s, 2H), 4.26 (s, 3H) |
| E8-55 | 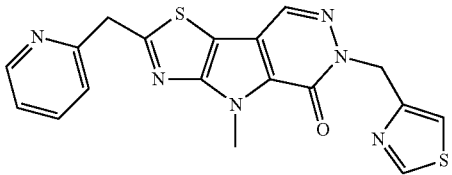 [SMILES: Cn1c2nc(Cc3ccccn3)sc2c2cnn(Cc3cscn3)c(=O)c21]<br>4-methyl-2-(pyridin-2-ylmethyl)-6-(thiazol-4-ylmethyl)-4,6-dihydro-5H-thiazolo[5',4':4,5]pyrrolo[2,3-d]pyridazin-5-one | LC-MS: m/z 395 (M + H)+.<br>$^1$H NMR (400MHz, DMSO-d$_6$) δ 9.09 (d, 1H), 8.63 (m, 1H), 8.59 (s, 1H), 7.88 (m, 1H), 7.57 (d 1H), 7.51 (s, 1H), 7.39 (dd, 1H), 5.54 (s, 2H), 4.73 (s, 2H), 4.32 (s, 3H) |
| E8-56 | 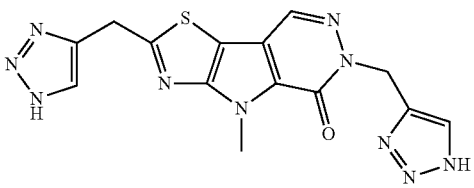 [SMILES: Cn1c2nc(Cc3c[nH]nn3)sc2c2cnn(Cc3c[nH]nn3)c(=O)c21]<br>2,6-bis((1H-1,2,3-triazol-4-yl)methyl)-4-methyl-4,6-dihydro-5H-thiazolo[5',4':4,5]pyrrolo[2,3-d]pyridazin-5-one | LC-MS: m/z 369 (M + H)+.<br>$^1$H NMR (400 MHz, DMSO-d$_6$) δ 8.53 (s, 1H), 7.89 (s, 1H), 7.74 (s 1H), 5.43 (s, 2H), 4.63 (s, 2H), 4.26 (s, 3H) |

| Cpd No. | Structure and chemical name | Characterization |
|---|---|---|
| E8-57 | 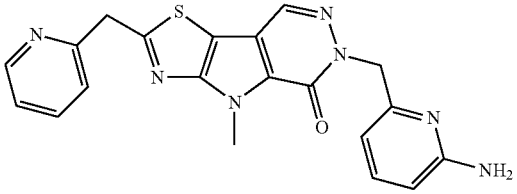 [SMILES: Cn1c2nc(Cc3ccccn3)sc2c2cnn(Cc3cccc(N)n3)c(=O)c21]<br>6-((6-aminopyridin-2-yl)methyl)-4-methyl-2-(pyridin-2-ylmethyl)-4,6-dihydro-5H-thiazolo[5',4':4,5]pyrrolo[2,3-d]pyridazin-5-one | LC-MS: m/z 404 (M + H)$^+$.<br>$^1$H NMR (400 MHz, DMSO-$d_6$) δ 8.57 (s, 1H), 8.54 (s, 1H), 7.82 (dd, 1H), 7.51 (d 1H), 7.33 (dd, 1H), 7.27-7.22 (m, 1H), 6.29 (d 1H), 6.07 (d 1H), 5.90 (s, 2H), 5.19 (s, 2H), 4.68 (s, 2H), 4.26 (s, 3H) |
| E8-58 | 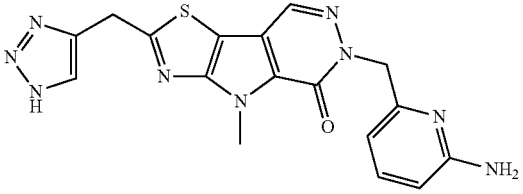 [SMILES: Cn1c2nc(Cc3c[nH]nn3)sc2c2cnn(Cc3cccc(N)n3)c(=O)c21]<br>2-((1H-1,2,3-triazol-4-yl)methyl)-6-((6-aminopyridin-2-yl)methyl)-4-methyl-4,6-dihydro-5H-thiazolo[5',4':4,5]pyrrolo[2,3-d]pyridazin-5-one | LC-MS: m/z 394 (M + H)$^+$.<br>$^1$H NMR (400 MHz, DMSO-$d_6$) δ 8.55 (s, 1H), 7.90 (s, 1H), 7.26 (dd 1H), 6.30 (d, 1H), 6.07 (d 1H), 5.91 (s, 2H), 5.19 (s, 2H), 4.64 (s, 2H), 4.26 (s, 3H) |
| E8-59 | 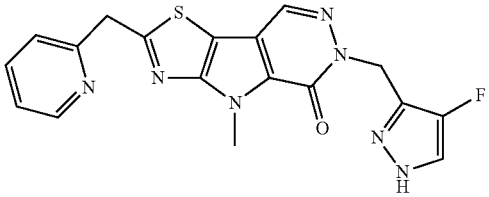 [SMILES: Cn1c2nc(Cc3ccccn3)sc2c2cnn(Cc3n[nH]cc3F)c(=O)c21]<br>6-((4-fluoro-1H-pyrazol-3-yl)methyl)-4-methyl-2-(pyridin-2-ylmethyl)-4,6-dihydro-5H-thiazolo[5',4':4,5]pyrrolo[2,3-d]pyridazin-5-one | LC-MS: m/z 396 (M + H)$^+$.<br>$^1$H NMR (400 MHz, DMSO-$d_6$) δ 12.60 (s, 1H), 8.57 (s, 1H), 8.55 (s, 1H), 7.90-7.80 (m, 1H), 7.68 (s, 1H), 7.49 (d 1H), 7.31 (dd, 1H), 5.32 (s, 2H), 4.65 (s, 2H), 4.24 (s, 3H) |
| E8-60 | 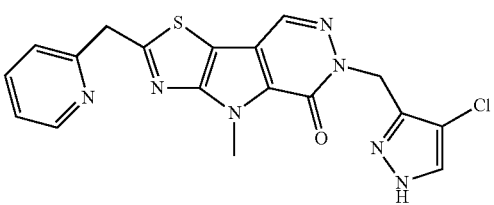 [SMILES: Cn1c2nc(Cc3ccccn3)sc2c2cnn(Cc3n[nH]cc3Cl)c(=O)c21]<br>6-((4-chloro-1H-pyrazol-3-yl)methyl)-4-methyl-2-(pyridin-2-ylmethyl)-4,6-dihydro-5H-thiazolo[5',4':4,5]pyrrolo[2,3-d]pyridazin-5-one | LC-MS: m/z 412 (M + H)$^+$.<br>$^1$H NMR (400 MHz, DMSO-$d_6$) δ 13.00 (s, 1H), 8.67 (d, 1H), 8.46 (s, 1H), 7.86 (s, 1H), 7.82 (dd, 1H), 7.51 (d, 1H), 7.33 (dd, 1H), 5.34 (s, 2H), 4.67 (s, 2H), 4.26 (s, 3H |
| E8-61 | 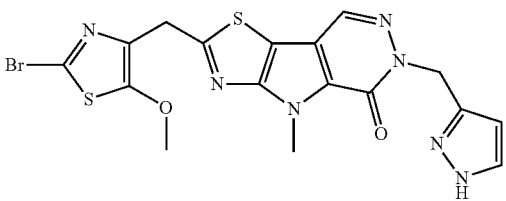 [SMILES: COc1sc(Br)nc1Cc1nc2c(s1)c1cnn(Cc3cc[nH]n3)c(=O)c1n2C]<br>6-((1H-pyrazol-3-yl)methyl)-2-((2-bromo-5-methoxythiazol-4-yl)methyl)-4-methyl-4H-thiazolo[5',4':4,5]pyrrolo[2,3-d]pyridazin-5(6H)-one | LC-MS: m/z 492 (M + H)$^+$.<br>$^1$H NMR (400 MHz, DMSO-d6) δ: 12.64 (s, 1H), 8.52 (s, 1H), 7.61 (s, 1H), 6.11 (s, 1H), 5.32 (s, 2H), 4.44 (s, 2H), 4.26 (s, 3H), 3.99 (s, 3H). |

| Cpd No. | Structure and chemical name | Characterization |
|---|---|---|
| E8-62 | 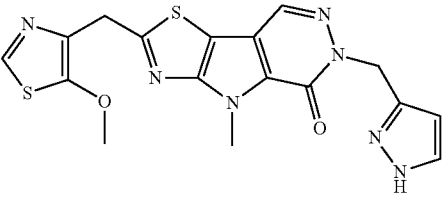 [SMILES: COc1scnc1Cc1nc2c(s1)c1cnn(Cc3cc[nH]n3)c(=O)c1n2C]<br>6-((1H-pyrazol-3-yl)methyl)-2-((5-methoxythiazol-4-yl)methyl)-4-methyl-4H-thiazolo[5',4':4,5]pyrrolo[2,3-d]pyridazin-5(6H)-one | LC-MS: m/z 414 (M + H)⁺.<br>¹H NMR (400 MHz, DMSO-d6) δ: 12.63 (s, 1H), 8.57 (s, 1H), 8.50 (s, 1H), 7.60 (s, 1H), 6.11 (d, 1H), 5.32 (s, 2H), 4.47 (s, 2H), 4.26 (s, 3H), 3.97 (s, 3H). |
| E8-63 | 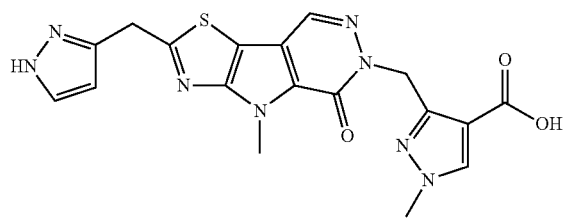 [SMILES: Cn1cc(C(=O)O)c(Cn2ncc3c4sc(Cc5cc[nH]n5)nc4n(C)c3c2=O)n1]<br>3-((2-((1H-pyrazol-3-yl)methyl)-4-methyl-5-oxo-4H-thiazolo[5',4':4,5]pyrrolo[2,3-d]pyridazin-6(5H)-yl)methyl)-1-methyl-1H-pyrazole-4-carboxylic acid | LC-MS: m/z 425 (M + H)⁺.<br>¹H NMR (400 MHz, DMSO-d6) δ: 9.12 (s, 1H), 8.19 (s, 1H), 7.66 (s, 1H), 6.25 (s, 1H), 5.59 (s, 2H), 4.49 (s, 2H), 4.31 (s, 3H), 3.81 (s, 3H). |
| E8-64 | 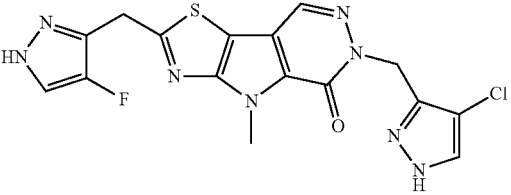 [SMILES: Cn1c2nc(Cc3n[nH]cc3F)sc2c2cnn(Cc3n[nH]cc3Cl)c(=O)c21]<br>6-((4-chloro-1H-pyrazol-3-yl)methyl)-2-((4-fluoro-1H-pyrazol-3-yl)methyl)-4-methyl-4H-thiazolo[5',4':4,5]pyrrolo[2,3-d]pyridazin-5(6H)-one | LC-MS: m/z 419 (M + H)⁺.<br>¹H NMR (400 MHz, DMSO-d6) δ: 13.28-12.57 (m, 2H), 8.49 (s, 1H), 7.90-7.50 (m, 2H), 5.34 (s, 2H), 4.50 (s, 2H), 4.26 (s, 3H). |
| E8-65 | 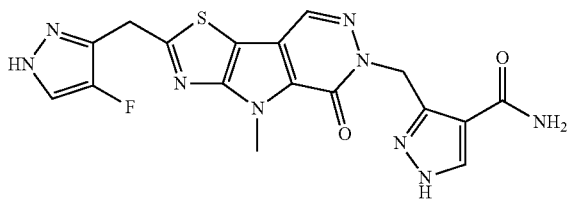 [SMILES: Cn1c2nc(Cc3n[nH]cc3F)sc2c2cnn(Cc3n[nH]cc3C(N)=O)c(=O)c21]<br>3-((2-((4-fluoro-1H-pyrazol-3-yl)methyl)-4-methyl-5-oxo-4H-thiazolo[5',4':4,5]pyrrolo[2,3-d]pyridazin-6(5H)-yl)methyl)-1H-pyrazole-4-carboxamide | LC-MS: m/z 428 (M + H)⁺.<br>¹H NMR (400 MHz, DMSO-d6) δ: 12.89-12.76 (m, 2H), 8.49 (s, 1H), 8.22 (s, 1H), 7.86 (s, 1H), 7.60 (s, 1H), 7.00 (s, 1H), 5.57 (s, 2H), 4.51 (s, 2H), 4.26 (s, 3H). |
| E8-66 | 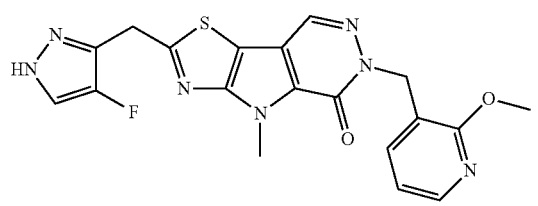 [SMILES: COc1ncccc1Cn1ncc2c3sc(Cc4n[nH]cc4F)nc3n(C)c2c1=O]<br>2-((4-fluoro-1H-pyrazol-3-yl)methyl)-6-((2-methoxypyridin-3-yl)methyl)-4-methyl-4H-thiazolo[5',4':4,5]pyrrolo[2,3-d]pyridazin-5(6H)-one | LC-MS: m/z 426 (M + H)⁺.<br>¹H NMR (400 MHz, DMSO-d6) δ: 12.80 (s, 1H), 8.57 (d, 1H), 8.08 (dd, 1H), 7.92 (d, 1H), 7.16 (d, 1H), 6.90 (dd, 1H), 5.29 (s, 2H), 4.50 (s, 2H), 4.26 (s, 3H), 3.92 (s, 3H). |

| Cpd No. | Structure and chemical name | Characterization |
|---|---|---|
| E8-67 | 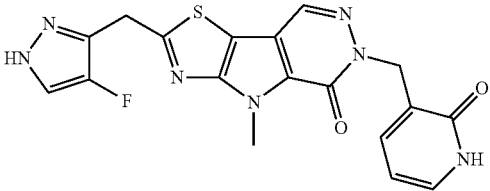 [SMILES: Cn1c2nc(Cc3n[nH]cc3F)sc2c2cnn(Cc3ccc[nH]c3=O)c(=O)c21]<br>2-((4-fluoro-1H-pyrazol-3-yl)methyl)-4-methyl-6-((2-oxo-1,2-dihydropyridin-3-yl)methyl)-4H-thiazolo[5',4':4,5]pyrrolo[2,3-d]pyridazin-5(6H)-one | LC-MS: m/z 412 (M + H)⁺.<br>¹H NMR (400 MHz, DMSO-d6) δ: 12.78 (s, 1H), 11.71 (s, 1H), 8.56 (s, 1H), 7.87 (s, 1H), 7.30 (d, 1H), 6.82 (d, 1H), 6.08 (dd, 1H), 5.10 (s, 2H), 4.50 (s, 2H), 4.26 (s, 3H). |
| E8-68 | 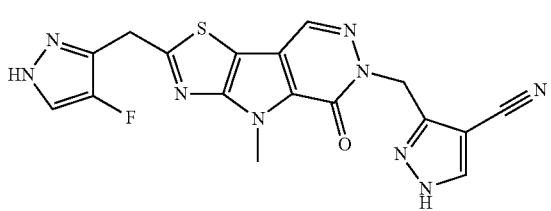 [SMILES: Cn1c2nc(Cc3n[nH]cc3F)sc2c2cnn(Cc3n[nH]cc3C#N)c(=O)c21]<br>3-((2-((4-fluoro-1H-pyrazol-3-yl)methyl)-4-methyl-5-oxo-4H-thiazolo[5',4':4,5]pyrrolo[2,3-d]pyridazin-6(5H)-yl)methyl)-1H-pyrazole-4-carbonitrile | LC-MS: m/z 410 (M + H)⁺.<br>¹H NMR (400 MHz, DMSO-d6) δ: 13.63 (s, 1H), 12.81 (s, 1H), 8.55 (s, 1H), 8.37 (s, 1H), 7.81 (s, 1H), 5.45 (s, 2H), 4.51 (s, 2H), 4.25 (s, 3H). |
| E8-69 | 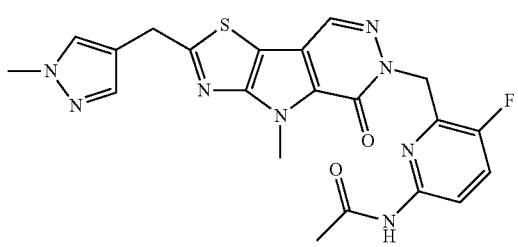 [SMILES: CC(=O)Nc1ccc(F)c(Cn2ncc3c4sc(Cc5cnn(C)c5)nc4n(C)c3c2=O)n1]<br>N-(5-fluoro-6-((4-methyl-2-((1-methyl-1H-pyrazol-4-yl)methyl)-5-oxo-4,5-dihydro-6H-thiazolo[5',4':4,5]pyrrolo[2,3-d]pyridazin-6-yl)methyl)pyridin-2-yl)acetamide | LC-MS: m/z 467 (M + H)⁺.<br>¹H NMR (400 MHz, DMSO-d6) δ: δ10.35 (s, 1H), 8.49 (s, 1H), 8.00 (s, 1H), 7.70 (dd, 2H), 7.45 (s, 1H), 5.45 (s, 2H), 4.34 (s, 2H), 4.26 (s, 3H), 3.83 (s, 3H), 2.01 (s, 3H) |
| E8-70 | 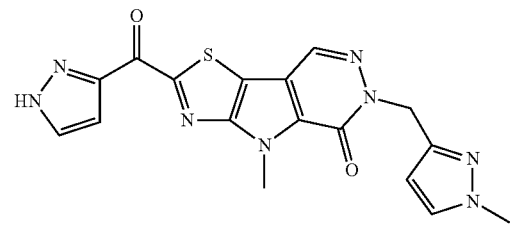 [SMILES: Cn1ccc(Cn2ncc3c4sc(C(=O)c5cc[nH]n5)nc4n(C)c3c2=O)n1]<br>4-methyl-6-((1-methyl-1H-pyrazol-3-yl)methyl)-2-(1H-pyrazole-3-carbonyl)-4H-thiazolo[5',4':4,5]pyrrolo[2,3-d]pyridazin-5(6H)-one | LC-MS: m/z 395 (M + H)⁺.<br>¹H NMR (400 MHz, DMSO-d₆) δ 13.85 (s, 1H), 8.70 (s, 1H), 8.04 (s, 1H), 7.58 (d, 1H), 7.38 (s, 1H), 6.12 (d, 1H), 5.30 (s, 2H), 4.38 (s, 3H), 3.77 (s, 3H). |

Example 9. Synthesis of Compounds E9-vi and E9-vii
Scheme E9
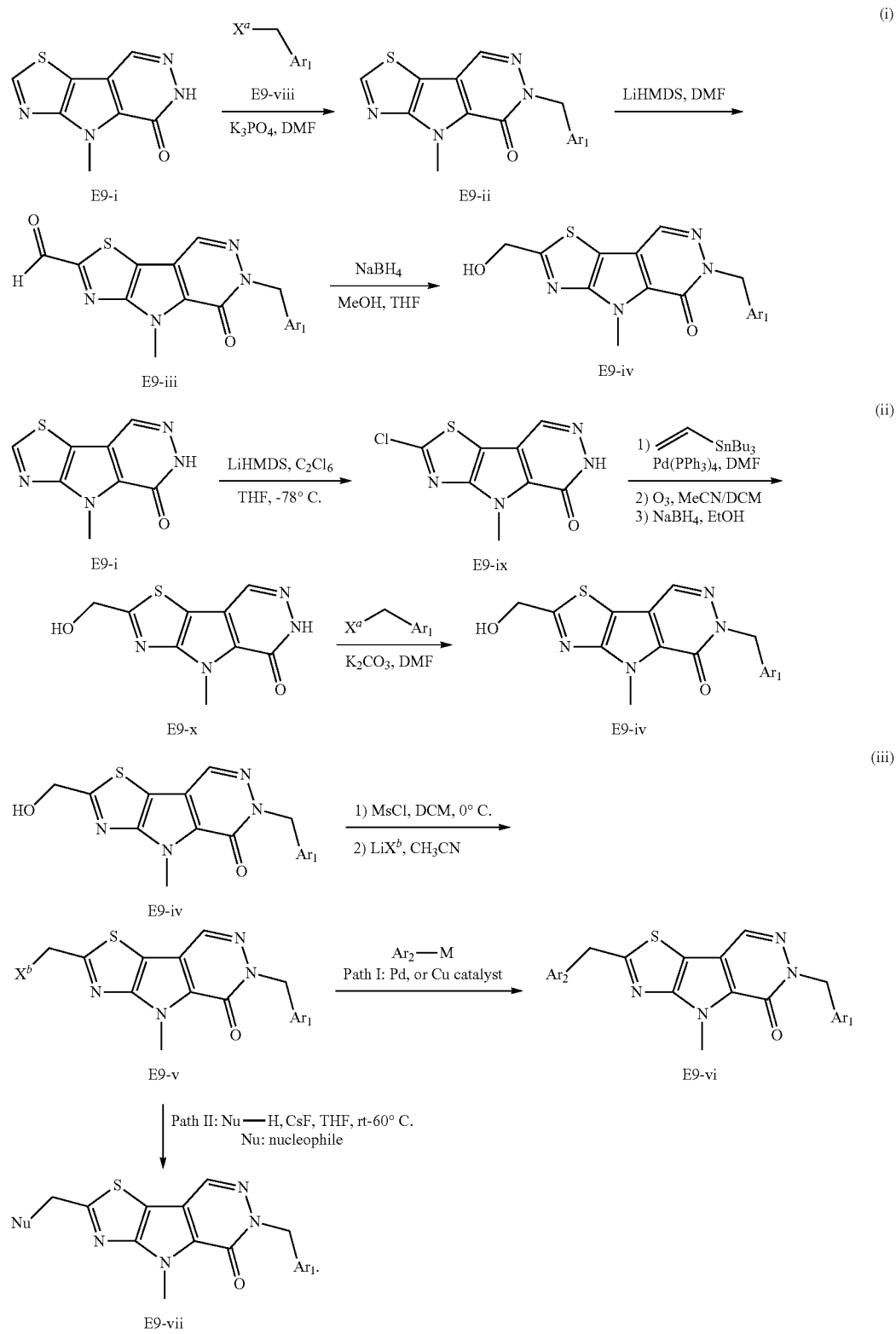

Compound E9-iv can be synthesized by two approaches, (i) and (ii) in Scheme 9. For approach (i), compound E9-ii can be synthesized from compound E9-i through alkylation reaction as showed in Example 7 or Example 8. As used herein, $X^a$ is a leaving group. Formylation reaction of compound E9-ii with LiHMDS and DMF provides intermediate E9-iii. E9-iii reacts with a reducing agent (e.g. NaBH$_4$) to provide compound E9-iv. Alternatively in approach (ii), haloagenation of compound E9-i generates compound E9-ix. Compound E9-ix undergoes Stille reaction, ozonolysis, and reduction to furnish compound E9-x. Compound E9-x can be alkylated with E9-viii to provide compound E9-iv. In Scheme 9, (iii), Compound E9-iv undergoes halogenation to give intermediate E9-v ($X^b$ is halogen such as Cl or Br). A metal (e.g. Pd or Cu) catalyzed coupling of E9-v with organic Tin, boron, zinc or magnesium provides compound E9-vi. As used herein, M is an organic metal complex (e.g. organoboron complex such as boronic acid or pinaco boron complex, organotin complex such as —Sn(Bu$^t$)$_3$; organozinc complex such as —Zn(halogen)); Compound E9-v can also react with some nucleophiles such as nitrogen in a heterocycle to give product E9-vii. As used herein, Ar$_1$ and Ar$_2$ are each independently optionally substituted 5-membered or 6-membered heteroaryl, $X^a$ is a leaving group (e.g. Br, I, OMs, or OTs); and $X^b$ is halogen.

Example 9A. Synthesis of 6-((1H-indazol-4-yl)methyl)-4-methyl-2-(thiazol-4-ylmethyl)-4H-thiazolo[5',4':4,5]pyrrolo[2,3-d]pyridazin-5(6H)-one

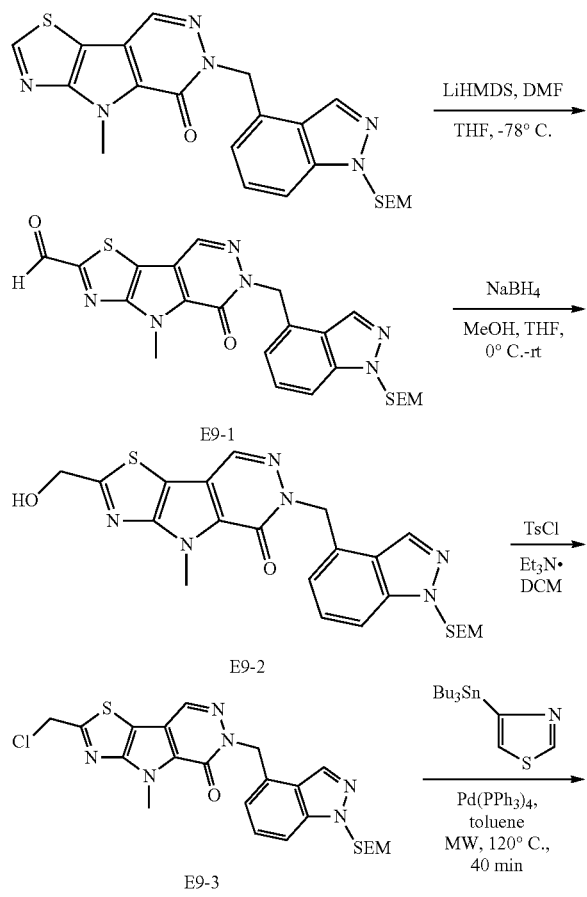

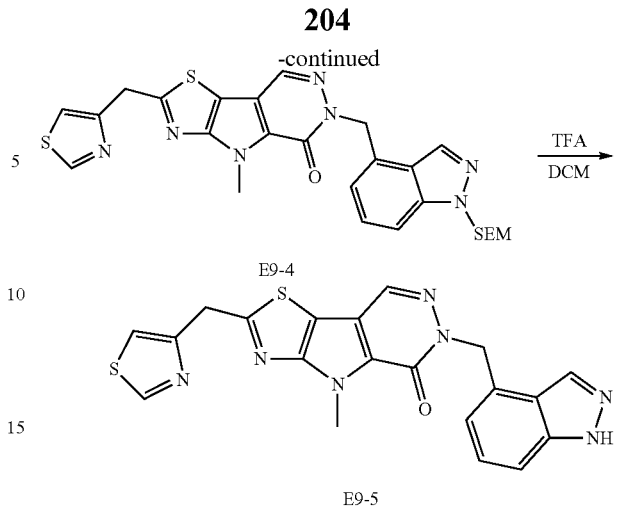

Step A. Synthesis of 4-methyl-5-oxo-6-((1-((2-(trimethylsilyl)ethoxy)methyl)-1H-indazol-4-yl)methyl)-5,6-dihydro-4H-thiazolo[5',4':4,5]pyrrolo[2,3-d]pyridazine-2-carbaldehyde To a mixture of 4-methyl-6-((1-((2-(trimethylsilyl)ethoxy)methyl)-1H-indazol-4-yl)methyl)-4H-thiazolo[5',4':4,5]pyrrolo[2,3-d]pyridazin-5(6H)-one (2.6 g, 5.57 mmol, 1 eq) in dry THF (30 mL) was added LiHMDS (1 M, 11.14 mL, 2.0 eq) at −78° C. The mixture was stirred at −78° C. for 2 hr. Then DMF (2.04 g, 27.86 mmol, 2.14 mL, 5.0 eq) was added dropwise to the above mixture. The mixture was stirred at −78° C. for 2 hr. TLC (PE:EA=2:1, UV=254 nm) showed that one main new spot was formed. The mixture was poured into cold sat. NH$_4$Cl (20 mL). Then the mixture was warmed to room temperature. The mixture was extracted with EtOAc (40 mL×3). The organic layer was washed by water (20 mL×3) and concentrated in vacuo to give the desired product (2.6 g, crude). LCMS: m/z 495.2 [M+H]$^+$ Step B. Synthesis of 2-(hydroxymethyl)-4-methyl-6-((1-((2-(trimethylsilyl)ethoxy) methyl)-1H-indazol-4-yl)methyl)-4H-thiazolo[5',4':4,5]pyrrolo[2,3-d]pyridazin-5(6H)-one To a mixture of crude 4-methyl-5-oxo-6-((1-((2-(trimethylsilyl)ethoxy) methyl)-1H-indazol-4-yl)methyl)-5,6-dihydro-4H-thiazolo[5',4':4,5]pyrrolo[2,3-d]pyridazine-2-carbaldehyde (1.0 g, 2.02 mmol, 1 eq) in THF (10 mL) and MeOH (10 mL) was added NaBH$_4$ (152.97 mg, 4.04 mmol, 2 eq). The mixture was stirred at 30° C. for 14 hr. TLC (DCM:MeOH=10:1, UV=254 nm) showed that the starting material was consumed completely and one main new spot was formed. The reaction was quenched by addition of water (20 mL) and extracted with EtOAc (30 mL×3). The combined organic layers were washed with brine (20 mL). The organic phase was concentrated in vacuo. The residue was purified by flash silica gel chromatography (ISCO®; 40 g SepaFlash® Silica Flash Column, Eluent of 0~5% MeOH/DCM @ 30 mL/min). The eluent was concentrated in vacuo to give the desired product (382 mg). LCMS: m/z 497.1 [M+H]$^+$. $^1$H NMR (400 MHz, DMSO-d$_6$) δ ppm 8.61 (s, 1H), 8.25 (s, 1H), 7.66 (d, 1H), 7.38 (t, 1H), 7.05 (d, 1H), 6.36 (t, 1H), 5.74 (s, 2H), 5.68 (s, 2H), 4.89 (d, 2H), 4.26 (s, 3H), 3.50 (t, 2H), 0.78 (t, 2H), −0.12 (s, 9H).

Step C. Synthesis of 2-(chloromethyl)-4-methyl-6-((1-((2-(trimethylsilyl)ethoxy) methyl)-1H-indazol-4-yl)methyl)-4H-thiazolo[5',4':4,5]pyrrolo[2,3-d]pyridazin-5(6H)-one To a mixture of 2-(hydroxymethyl)-4-methyl-6-((1-((2-(trimethylsilyl) ethoxy)methyl)-1H-indazol-4-yl)methyl)-4H-thiazolo[5',4':4,5]pyrrolo[2,3-d]pyridazin-5(6H)-one (150.0 mg, 302.02 umol, 1 eq) and Et$_3$N (61.12 mg, 604.04 umol, 84.08 uL, 2.0 eq) in DCM (5 mL) was added 4-methylbenzenesulfonyl chloride (75.0 mg, 393.40 umol, 1.30 eq). The mixture was stirred at 30° C. for 5 hr. TLC (PE:EA=4:1, UV=254 nm) showed the starting material was consumed completely. Water (10 mL) and DCM (20 mL) was added to the mixture. The organic layers were concentrated in vacuo to give a yellow gum (0.1 g). The residue was purified by flash silica gel chromatography (ISCO®; 4 g SepaFlash® Silica Flash Column, Eluent of 0~20% Ethyl acetate/Petroleum ether gradient @ 30 mL/min). The desired fraction was concentrated in vacuo to give the desired product (40.0 mg, 76.88 umol). LCMS: m/z 515.1 [M+H]$^+$. $^1$H NMR (400 MHz, CHLOROFORM-d) δ ppm 8.27 (d, 1H), 8.26 (s, 1H), 7.52 (d, 1H), 7.39 (dd, 1H), 7.25 (s, 1H), 5.76 (s, 2H), 5.72 (s, 2H), 4.96 (s, 2H), 4.40 (s, 3H), 3.50-3.57 (m, 2H), 0.84-0.90 (m, 2H), −0.09 to −0.06 (m, 9H).

Step D. Synthesis of 4-methyl-2-(thiazol-4-ylmethyl)-6-((1-((2-(trimethylsilyl)ethoxy) methyl)-1H-indazol-4-yl)methyl)-4,6-dihydro-5H-thiazolo[5',4':4;5]pyrrolo[2,3-d]pyridazin-5-one To a solution of 2-(chloromethyl)-4-methyl-6-((1-((2-(trimethylsilyl)ethoxy)methyl)-1H-indazol-4-yl)methyl)-4H-thiazolo[5',4':4,5] pyrrolo[2,3-d]pyridazin-5(6H)-one (50 mg, 0.97 mmol) and 4-(tributylstannyl)thiazole (114 mg, 2.91 mmol) in toluene (4 mL) was added Pd(PPh$_3$)$_4$ (402 mg, 2.91 mmol). Then the mixture was heated in MW reactor at 120° C. for 30 min under N$_2$. The solution was poured into water and extracted with EtOAc, dried over anhydrous Na$_2$SO$_4$. The organic layer was concentrated under reduced pressure. The residue was purified by flash chromatography (silica gel, 0~50% ethyl acetate in petroleum ether) to give 4-methyl-2-(thiazol-4-ylmethyl)-6-((1-((2-(trimethylsilyl)ethoxy)methyl)-1H-indazol-4-yl) methyl)-4H-thiazolo[5',4':4,5]pyrrolo[2,3-d]pyridazin-5(6H)-one (30 mg). LCMS: 564 (M+H)$^+$.

Step E. Synthesis of 6-((1H-indazol-4-yl)methyl)-4-methyl-2-(thiazol-4-ylmethyl)-4,6-dihydro-5H-thiazolo[5',4':4,5]pyrrolo[2,3-d]pyridazin-5-one To a mixture of compound E9-4 (30 mg, 0.05 mmol) in DCM (3 mL) at r.t. under N$_2$ was added TFA (3 mL). The reaction mixture was stirred at r.t. for 1 h. The mixture was concentrated under reduced pressure. The residue was purified by prep-HPLC (C18, 0~90% acetonitrile in H$_2$O with 0.1% formic acid) to give the desired product (3.9 mg). LCMS: 434 (M+H)$^+$. $^1$H NMR (400 MHz, DMSO) δ 13.12 (s, 1H), 9.12 (d, 1H), 8.56 (s, 1H), 8.14 (s, 1H), 7.71 (d, 1H), 7.45 (d, 1H), 7.35-7.24 (m, 1H), 6.96 (d, 1H), 5.65 (s, 2H), 4.70 (s, 2H), 4.27 (s, 3H).

Example 9B. Synthesis of 4-methyl-2-(pyridin-2-ylmethyl)-6-(pyridin-3-ylmethyl)-4H-thiazolo[5',4':4,5]pyrrolo[2,3-d]pyridazin-5(6H)-one

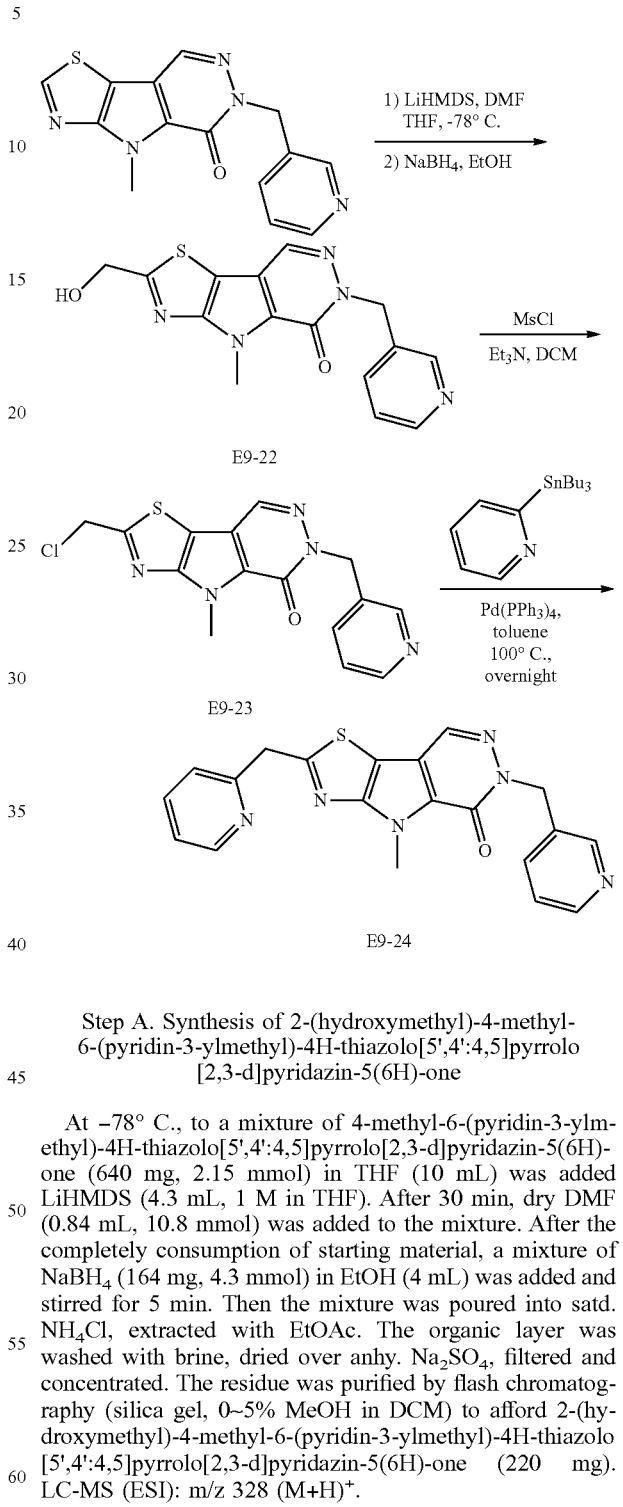

Step A. Synthesis of 2-(hydroxymethyl)-4-methyl-6-(pyridin-3-ylmethyl)-4H-thiazolo[5',4':4,5]pyrrolo[2,3-d]pyridazin-5(6H)-one At −78° C., to a mixture of 4-methyl-6-(pyridin-3-ylmethyl)-4H-thiazolo[5',4':4,5]pyrrolo[2,3-d]pyridazin-5(6H)-one (640 mg, 2.15 mmol) in THF (10 mL) was added LiHMDS (4.3 mL, 1 M in THF). After 30 min, dry DMF (0.84 mL, 10.8 mmol) was added to the mixture. After the completely consumption of starting material, a mixture of NaBH$_4$ (164 mg, 4.3 mmol) in EtOH (4 mL) was added and stirred for 5 min. Then the mixture was poured into satd. NH$_4$Cl, extracted with EtOAc. The organic layer was washed with brine, dried over anhy. Na$_2$SO$_4$, filtered and concentrated. The residue was purified by flash chromatography (silica gel, 0~5% MeOH in DCM) to afford 2-(hydroxymethyl)-4-methyl-6-(pyridin-3-ylmethyl)-4H-thiazolo[5',4':4,5]pyrrolo[2,3-d]pyridazin-5(6H)-one (220 mg). LC-MS (ESI): m/z 328 (M+H)$^+$.

Step B. Synthesis of 2-(chloromethyl)-4-methyl-6-(pyridin-3-ylmethyl)-4H-thiazolo[5',4':4,5]pyrrolo[2,3-d]pyridazin-5(6H)-one To a mixture of 2-(hydroxymethyl)-4-methyl-6-(pyridin-3-ylmethyl)-4H-thiazolo[5',4':4,5]pyrrolo[2,3-d]pyridazin-5

(6H)-one (100 mg, 0.31 mmol) in DCM (5 mL) were added Et₃N (0.43 mL, 3.1 mmol) and MsCl (0.12 mL, 1.5 mmol). The reaction was stirred at room temperature for 6 hr. Then the mixture was washed with satd. NH₄Cl (aq.), dried over anhy. Na₂SO₄, filtered and concentrated. The residue was purified by flash chromatography (silica gel, 0~50% EtOAc in PE) to afford 65 mg of 2-(chloromethyl)-4-methyl-6-(pyridin-3-ylmethyl)-4H-thiazolo[5',4':4,5]pyrrolo[2,3-d]pyridazin-5(6H)-one. LC-MS (ESI): m/z 346 (M+H)⁺.

Step C. Synthesis of 4-methyl-2-(pyridin-2-ylmethyl)-6-(pyridin-3-ylmethyl)-4H-thiazolo[5',4':4,5]pyrrolo[2,3-d]pyridazin-5(6H)-one Under nitrogen, to a mixture of 2-(chloromethyl)-4-methyl-6-(pyridin-3-ylmethyl)-4H-thiazolo[5',4':4,5]pyrrolo[2,3-d]pyridazin-5(6H)-one (50 mg, 0.14 mmol) and 2-(tributylstannyl)pyridine (0.14 mL, 0.43 mmol) in toluene (3 mL) was added Pd(PPh₃)₄ (17 mg, 0.014 mmol). The reaction mixture was stirred at 100° C. overnight. Then the mixture was cooled, concentrated under reduced pressure and the residue was purified by prep-TLC (eluant: 10% MeOH in DCM) to afford 2 mg of 4-methyl-2-(pyridin-2-ylmethyl)-6-(pyridin-3-ylmethyl)-4H-thiazolo[5',4':4,5]pyrrolo[2,3-d]pyridazin-5(6H)-one. LC-MS (ESI): m/z 389 (M+H)⁺. ¹H NMR (400 MHz, DMSO-d6) δ 8.56 (m, 3H), 8.48 (dd, 1H), 7.81 (td, 1H), 7.71 (d, 1H), 7.50 (d, 1H), 7.37-7.30 (m, 2H), 5.38 (s, 2H), 4.67 (s, 2H), 4.25 (s, 3H).

Example 9C. Synthesis of 2-((1H-1,2,4-triazol-1-yl)methyl)-6-((1H-pyrazol-3-yl)methyl)-4-methyl-4H-thiazolo[5',4':4,5]pyrrolo[2,3-d]pyridazin-5(6H)-one and 6-((1H-pyrazol-3-yl)methyl)-2-((4H-1,2,4-triazol-4-yl)methyl)-4-methyl-4H-thiazolo[5',4':4,5]pyrrolo[2,3-d]pyridazin-5(6H)-one

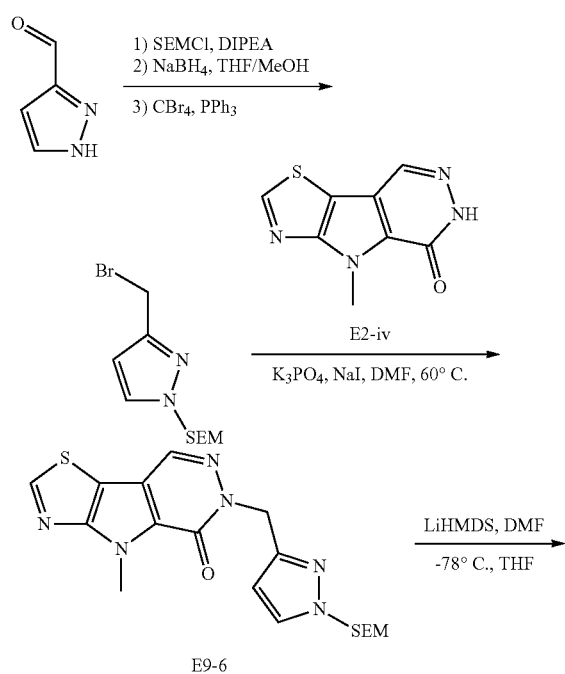

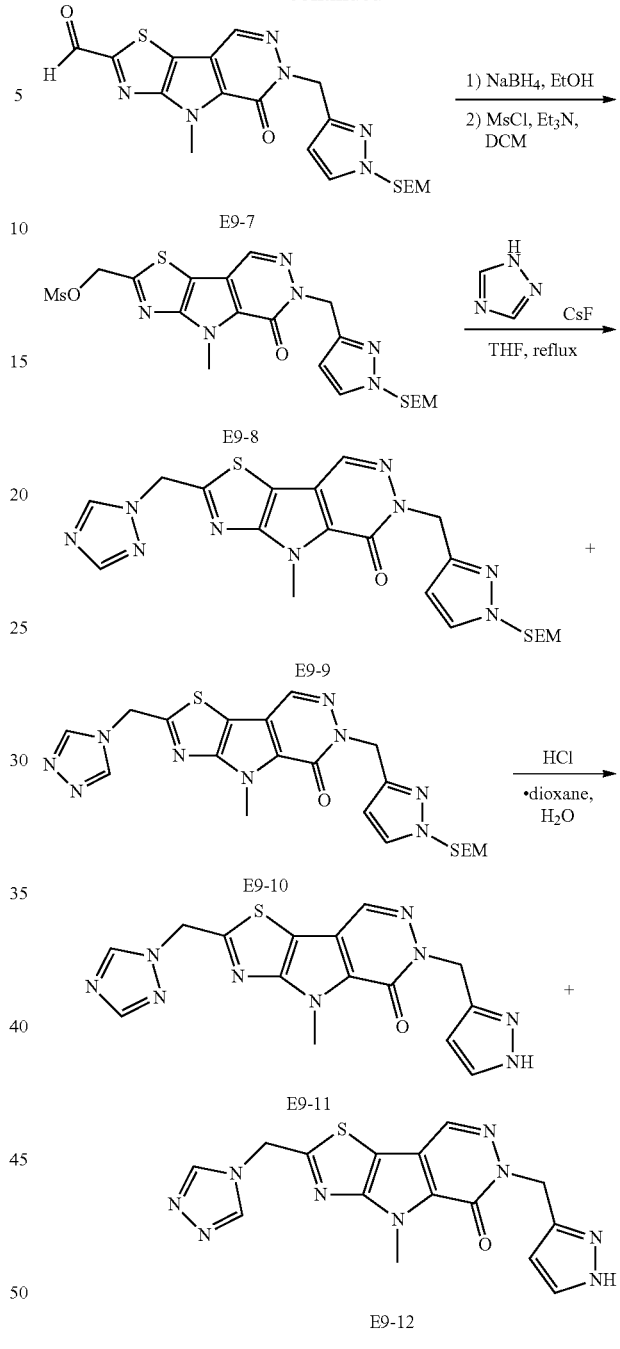

Step A. Synthesis of 1-((2-(trimethylsilyl)ethoxy)methyl)-1H-pyrazole-3-carbaldehyde To a suspension of 1H-pyrazole-3-carbaldehyde (10.0 g, 104.07 mmol, 1 eq) and DIPEA (33.63 g, 260.18 mmol, 45.32 mL, 2.5 eq) in DCM (500 mL) was added dropwise 2-(chloromethoxy)ethyl-trimethyl-silane (26.03 g, 156.11 mmol, 27.63 mL, 1.5 eq) at −40° C. Then the reaction mixture was warmed to room temperature and stirred for 16 hr. TLC (petroleum ether:EtOAc=5:1) showed the starting material was consumed completely, and two new spots were formed. The reaction mixture was concentrated in vacuo. The residue was combined with another 2 batches (10.0 g each) and purified by Combiflash (from 100% of petroleum ether to 40% of EtOAc in petroleum ether) to give desired product 60.0 g. (note: mixture of 2 regioisomers with ~5/4 ratio). $^{1}$H NMR (400 MHz, CHLOROFORM-d) δ ppm 10.06 (s, 1H), 10.00 (s, 1H), 7.68 (d, 1H), 7.67 (d, 1H), 7.03 (d, 1H), 6.92 (d, 1H), 5.87 (s, 2H), 5.56 (s, 2H), 3.61-3.67 (m, 4H), 0.91-1.01 (m, 4H), −0.09-0.05 (m, 18H).

Step B. Synthesis of (1-((2-(trimethylsilyl)ethoxy) methyl)-1H-pyrazol-3-yl)methanol To a solution of 1-((2-(trimethylsilyl)ethoxy)methyl)-1H-pyrazole-3-carbaldehyde (30 g, 132.54 mmol, 1 eq, mixture of 2 regioisomers with ~5/4 ratio) in THF (200 mL)/MeOH (100 mL) was added NaBH$_4$ (7.52 g, 198.81 mmol, 1.50 eq) in portions at 0° C., the reaction mixture was stirred at 0° C. to room temperature for 18 hr. TLC (petroleum ether:EtOAc=2:1) showed the starting materials were consumed completely, and two new spots were formed. The solvent was concentrated in vacuo. The residue was purified by Combiflash (100% of petroleum ether to 100% of EtOAc) to give 25 g of the desired product. (Note: mixture of 2 regioisomers ratio ~3/2). $^{1}$H NMR (400 MHz, CHLOROFORM-d) δ ppm 7.55 (d, 1H), 7.47 (brs, 1H), 6.36 (d, 1H), 6.34 (d, 1H), 5.57 (s, 2H), 5.42 (s, 2H), 4.74-4.76 (m, 4H), 3.55-3.60 (m, 4H), 0.85-0.96 (m, 4H), 0.00-0.06 (m, 18H).

Step C. Synthesis of 3-(bromomethyl)-1-((2-(trimethylsilyl)ethoxy)methyl)-1H-pyrazole To a solution of (1-((2-(trimethylsilyl)ethoxy)methyl)-1H-pyrazol-3-yl)methanol (23 g, 100.72 mmol, 1 eq, mixture of 2 regioisomers ratio ~3/2) and PPh$_3$ (36.98 g, 141.00 mmol, 1.4 eq) in DCM (200 mL) was added CBr$_4$ (46.76 g, 141.00 mmol, 1.4 eq) at 0° C. and the reaction mixture was stirred at 0° C. for 3 hr. TLC (petroleum ether:EtOAc=5:1) showed the starting materials were consumed completely, and a new spot was formed. The reaction mixture was concentrated in vacuo. The residue was combined with another batch (2.0 g) and purified by Combiflash (from 100% of petroleum ether to 50% of EtOAc in petroleum ether) to give desired product 22.0 g (75.53 mmol). $^{1}$H NMR (400 MHz, CHLOROFORM-d) δ ppm 7.51 (d, 1H), 6.39 (d, 1H), 5.38 (s, 2H), 4.50 (s, 2H), 3.52-3.57 (m, 2H), 0.86-0.96 (m, 2H), −0.03-0.02 (m, 9H).

Step D. Synthesis of 4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one A suspension of 4-methyl-4H-thiazolo[5',4':4,5]pyrrolo [2,3-d]pyridazin-5(6H)-one (1.0 g, 4.85 mmol, 1 eq), 3-(bromomethyl)-1-((2-(trimethylsilyl)ethoxy)methyl)-1H-pyrazole (2.12 g, 7.27 mmol, 1.5 eq), K$_3$PO$_4$ (2.57 g, 12.12 mmol, 2.5 eq) and NaI (218.05 mg, 1.45 mmol, 0.3 eq) in DMF (15 mL) was stirred at 60° C. for 18 hr under N$_2$. TLC (petroleum ether:EtOAc=1:1) showed the starting material was consumed completely, and a new spot was formed. The reaction mixture was combined with another 3 batches (1.0 g each) and poured into ice-water (250 mL). The mixture was extracted with EtOAc (150 mL×3). The combined organic layers were washed with water (120 mL×2), brine (120 mL), and dried over Na$_2$SO$_4$. The solvent was concentrated in vacuo. The crude product was purified by combiflash (form 100% of petroleum ether to 80% of EtOA in petroleum ether) to give the desired product (3.6 g). $^{1}$H NMR (400 MHz, CHLOROFORM-d) δ ppm 8.91 (s, 1H), 8.27 (s, 1H), 7.49 (d, 1H), 6.36 (d, 1H), 5.51 (s, 2H), 5.40 (m, 2H), 4.45 (s, 3H), 3.52-3.58 (m, 2H), 0.85-0.90 (m, 2H), −0.05 (s, 9H).

Step E. Synthesis of 4-methyl-5-oxo-6-((1-((2-(trimethylsilyl)ethoxy)methyl)-1H-pyrazol-3-yl) methyl)-5,6-dihydro-4H-thiazolo[5',4':4,5]pyrrolo[2,3-d]pyridazine-2-carbaldehyde Under argon, to a solution of 4-methyl-6-((1-((2-(trimethylsilyl)ethoxy) methyl)-1H-pyrazol-3-yl)methyl)-4H-thiazolo[5',4':4,5]pyrrolo[2,3-d]pyridazin-5(6H)-one (1.7 g, 4.09 mmol, 1 eq) in THF (30 mL) was slowly added LiHMDS (1.0 M, 8.18 mL, 2 eq) at −78° C., the reaction mixture was stirred at −70° C. for 1 hr. Then a solution of DMF (1.49 g, 20.45 mmol, 1.57 mL, 5 eq) in THF (3 mL) was added dropwise to the mixture. The resulting mixture was stirred at −70° C. for 1 h. TLC (petroleum ether:EtOAc=1:1) showed a new spot was formed. The reaction mixture was drop-wise added to aq. NH$_4$Cl (50 mL) at 0° C., then the mixture was extracted with EtOAc (30 mL×3). The combined organic layers were washed with brine (40 mL), and dried over Na$_2$SO$_4$. The solvent was removed in vacuo to afford crude desired product (1.8 g) which was used for the next step without further purification.

Step F. Synthesis of 2-(hydroxymethyl)-4-methyl-6-((1-((2-(trimethylsilyl)ethoxy) methyl)-1H-pyrazol-3-yl)methyl)-4H-thiazolo[5',4':4,5]pyrrolo[2,3-d] pyridazin-5(6H)-one To a solution of 4-methyl-5-oxo-6-((1-((2-(trimethylsilyl) ethoxy)methyl)-1H-pyrazol-3-yl)methyl)-5,6-dihydro-4H-thiazolo[5',4':4,5]pyrrolo[2,3-d]pyridazine-2-carbaldehyde (1.8 g, 3.24 mmol, 1 eq) in THF (20 mL) MeOH (10 mL) was added NaBH$_4$ (245.08 mg, 6.48 mmol, 2 eq) at 0° C. and the reaction mixture was stirred at room temperature for 18 hr. TLC (petroleum ether:EtOAc=1:2) showed the starting material was consumed completely, and a new spot was formed. The reaction mixture was concentrated in vacuo, the residue was purified by combiflash (from 100% DCM to 5% of MeOH in DCM). The desired product (1.1 g) was obtained. $^{1}$H NMR (400 MHz, DMSO-d$_6$) δ ppm 8.63 (s, 1H), 7.86 (d, 1H), 6.44 (t, 1H), 6.27 (d, 1H), 5.40-5.42 (m, 4H), 4.98 (d, 2H), 4.34 (s, 3H), 3.55-3.61 (m, 2H), 0.86-0.91 (m, 2H), 0.00 (s, 9H).

Step G. Synthesis of (4-methyl-5-oxo-6-((1-((2-(trimethylsilyl)ethoxy)methyl)-1H-pyrazol-3-yl) methyl)-5,6-dihydro-4H-thiazolo[5',4':4,5]pyrrolo[2,3-d]pyridazin-2-yl)methyl methanesulfonate To a solution of 2-(hydroxymethyl)-4-methyl-6-((1-((2-(trimethylsilyl)ethoxy)methyl)-1H-pyrazol-3-yl)methyl)-4H-thiazolo[5',4':4,5] pyrrolo[2,3-d]pyridazin-5(6H)-one (700 mg, 1.57 mmol, 1 eq) and Et$_3$N (317.21 mg, 3.13 mmol, 436.33 uL, 2.0 eq) in DCM (15 mL) was added dropwise MsCl (269.32 mg, 2.35 mmol, 181.97 uL, 1.5 eq) at 0° C. and the reaction mixture was stirred at room temperature for 1 h. TLC (petroleum ether:EtOAc=1:1) showed the starting material was consumed completely, and a new spot was formed. The reaction mixture was diluted with EtOAc (80 mL), and washed with water (30 mL×4), brine (40 mL), and dried over Na$_2$SO$_4$. The solvent was removed in vacuo to afford crude product (700 mg). LCMS: (m/z 525.5 (M+H).

Step H. Synthesis of 2-((1H-1,2,4-triazol-1-yl) methyl)-4-methyl-6-((1-((2-(trimethylsilyl)ethoxy) methyl)-1H-pyrazol-3-yl)methyl)-4H-thiazolo[5',4': 4,5] pyrrolo[2,3-d]pyridazin-5(6H)-one and 2-((4H-1,2,4-triazol-4-yl)methyl)-4-methyl-6-((1-((2-(trimethylsilyl)ethoxy)methyl)-1H-pyrazol-3-yl) methyl)-4H-thiazolo[5',4':4,5]pyrrolo[2,3-d] pyridazin-5(6H)-one A mixture of (4-methyl-5-oxo-6-((1-((2-(trimethylsilyl) ethoxy)methyl)-1H-pyrazol-3-yl)methyl)-5,6-dihydro-4H-thiazolo[5',4':4,5]pyrrolo[2,3-d]pyridazin-2-yl)methyl methanesulfonate (150 mg, 285.88 umol, 1 eq) 1H-1,2,4-triazole (197.45 mg, 2.86 mmol, 10 eq) and CsF (86.85 mg, 571.77 umol, 21.08 uL, 2 eq) in MeCN (8 mL) was stirred at 60° C. under $N_2$ for 18 hr. LCMS showed the starting material was consumed completely, and two new peaks were formed. The reaction mixture was concentrated in vacuo, and the residue was purified by Combiflash (from 100% of DCM to 8% of MeOH in DCM). The product 2-((1H-1,2,4-triazol-1-yl)methyl)-4-methyl-6-((1-((2-(trimethylsilyl) ethoxy)methyl)-1H-pyrazol-3-yl)methyl)-4H-thiazolo[5',4': 4,5]pyrrolo[2,3-d]pyridazin-5(6H)-one (55 mg) and 2-((4H-1,2,4-triazol-4-yl)methyl)-4-methyl-6-(0-((2-(trimethylsilyl)ethoxy)methyl)-1H-pyrazol-3-yl)methyl)-4H-thiazolo[5',4':4,5]pyrrolo[2,3-d]pyridazin-5(6H)-one (30 mg) were obtained.

Step I. Synthesis of 2-((1H-1,2,4-triazol-1-yl) methyl)-6-((1H-pyrazol-3-yl)methyl)-4-methyl-4H-thiazolo[5',4':4,5]pyrrolo[2,3-d]pyridazin-5(6H)-one To a suspension of 2-((1H-1,2,4-triazol-1-yl)methyl)-4-methyl-6-((1-((2-(trimethylsilyl)ethoxy)methyl)-1H-pyrazol-3-yl)methyl)-4H-thiazolo[5',4':4,5]pyrrolo[2,3-d] pyridazin-5(6H)-one (55 mg, 110.52 umol, 1 eq) and HCl/dioxane (4 M, 1 mL, 36.19 eq) in DCM (3 mL) was added $H_2O$ (1.99 mg, 110.52 umol, 0.05 mL, 1 eq) and the reaction mixture was stirred at room temperature for 18 hr. LCMS showed the starting material was consumed completely, and 84% of desired product was found. The reaction mixture was concentrated in vacuo, and the residue was purified by Prep-HPLC to give the desired product (24.1 mg, 65.60 umol, 59.35% yield). Column: Xtimate C18 150*25 mm*5 um, mobile phase: [water (0.225% FA)-ACN]; B %: 13%-43%, 11.2 min. LCMS: m/z 367.9 (M+H)$^+$ $^1$H NMR (400 MHz, METHANOL-$d_4$) δ ppm 8.72 (s, 1H), 8.35 (s, 1H), 8.05 (s, 1H), 7.52 (brs, 1H), 6.26 (d, 1H), 5.92 (s, 2H), 5.43 (s, 2H), 4.30 (s, 3H).

Step J. Synthesis of 6-((1H-pyrazol-3-yl)methyl)-2-((4H-1,2,4-triazol-4-yl)methyl) methyl-4H-thiazolo [5',4':4,5]pyrrolo[2,3-d]pyridazin-5(6H)-one To a suspension of 2-((4H-1,2,4-triazol-4-yl)methyl)-4-methyl-6-((1-((2-(trimethylsilyl)ethoxy)methyl)-1H-pyrazol-3-yl)methyl)-4H-thiazolo[5',4':4,5]pyrrolo[2,3-d] pyridazin-5(6H)-one (30 mg, 60.28 umol, 1 eq) and HCl/dioxane (4 M, 1 mL, 66.35 eq) in DCM (3 mL) was added $H_2O$ (50.00 mg, 2.78 mmol, 0.05 mL, 46.04 eq) and the reaction mixture was stirred at room temperature for 18 hr. LCMS showed the starting material was consumed completely, the desired product was found. The reaction mixture was concentrated in vacuo, and the residue was purified by Prep-HPLC to give the desired product (2.1 mg, 5.72 umol). Column: Xtimate C18 150*25 mm*5 um; mobile phase: [water (0.225% FA)-ACN]; B %: 13%-43%, 11.2 min. LCMS: m/z 368.0 (M+H)$^+$. $^1$H NMR (400 MHz, METHANOL-$d_4$) δ ppm 8.74 (s, 2H), 8.38 (s, 1H), 7.52 (d, 1H), 6.26 (d, 1H), 5.84 (s, 2H), 5.44 (s, 2H), 4.31 (s, 3H).

The following compounds were synthesized according to Scheme E9 and the procedure of Examples 9A-9B using the appropriate starting material. Standard protection and deprotection can be used when necessary.

| Cpd No. | Structure and chemical name | Charaterization |
|---|---|---|
| E9-13 | 2-((1H-pyrazol-1-yl)methyl)-6-((1H-pyrazol-3-yl)methyl)-4-methyl-4H-thiazolo[5',4':4,5]pyrrolo[2,3-d]pyridazin-5(6H)-one | LCMS: m/z 367.0 [M + H]$^+$. $^1$H NMR (400 MHz, METHANOL-$d_4$) δ ppm 8.39 (s, 1H), 7.90 (d, 1H), 7.63 (d, 1H), 7.59 (brs, 1H), 6.43 (t, 1H), 6.29 (brs, 1H), 5.85 (s, 2H), 5.48 (s, 2H), 4.37 (s, 3H). |
| E9-14 | 6-((1H-pyrazol-3-yl)methyl)-4-methyl-2-((2-oxo-2,3-dihydro-1H-imidazol-1-yl)methyl)-4H-thiazolo[5',4':4,5]pyrrolo[2,3-d]pyridazin-5(6H)-one | LCMS: m/z 383.0 [M + H]$^+$. $^1$H NMR (400 MHz, METHANOL-$d_4$) δ ppm 8.41 (s, 1H), 7.55-7.57 (m, 1H), 6.64 (d, 1H), 6.51 (d, 1H), 6.30 (s, 1H), 5.48 (s, 2H), 5.28 (s, 2H), 4.37 (s, 3H). |

-continued

| Cpd No. | Structure and chemical name | Charaterization |
|---|---|---|
| E9-15 | 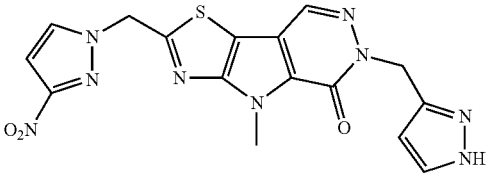 [SMILES: Cn1c2nc(Cn3ccc([N+](=O)[O-])n3)sc2c2cnn(Cc3cc[nH]n3)c(=O)c21]<br>6-((1H-pyrazol-3-yl)methyl)-4-methyl-2-((3-nitro-1H-pyrazol-1-yl)methyl)-4,6-dihydro-5H-thiazolo[5',4':4,5]pyrrolo[2,3-d]pyridazin-5-one | LCMS: m/z 412.0 [M + H]$^+$.<br>$^1$H NMR (400 MHz, DMSO-d$_6$) δ ppm 12.61 (brs, 1H), 8.55 (s, IH), 8.28 (d, 1H), 7.58 (brs, 1H), 7.13 (d, 1H), 6.08 (d, 1H), 6.03 (s, 2H), 5.30 (brs, 2H), 4.24 (s, 3H). |
| E9-16 | 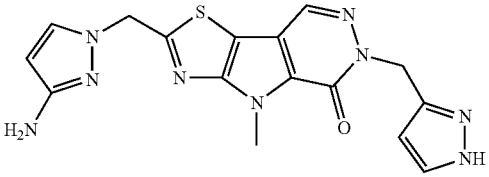<br>6-((1H-pyrazol-3-yl)methyl)-2-((3-amino-1H-pyrazol-1-yl)methyl)-4-methyl-4H-thiazolo[5',4':4,5]pyrrolo[2,3-d]pyridazin-5(6H)-one | LCMS: m/z 382.0 [M + H]$^+$<br>$^1$H NMR (400 MHz, METHANOL-d$_4$) δ ppm 8.35 (s, 1H), 7.53 (d, 2H), 6.26 (brs, 1H), 5.71 (d, 1H), 5.54 (s, 2H), 5.44 (s, 2H), 4.33 (s, 3H). |
| E9-17 | 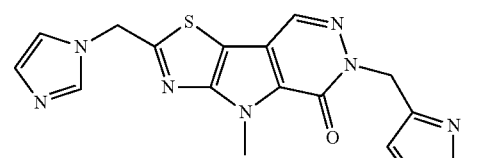<br>2-((1H-imidazol-1-yl)methyl)-6-((1H-pyrazol-3-yl)methyl)-4-methyl-4H-thiazolo[5',4':4,5]pyrrolo[2,3-d]pyridazin-5(6H)-one | LCMS: m/z 366.9 [M + H]$^+$.<br>$^1$HNMR (400 MHz, METHANOL-d$_4$) δ ppm 8.36 (s, 1H), 7.89 (s, 1H), 7.54 (brs, 1H), 7.30 (s, 1H), 7.03 (s, 1H), 6.26 (s, 1H), 5.72 (s, 2H), 5.44 (s, 2H), 4.33 (s, 3H). |
| E9-18 | 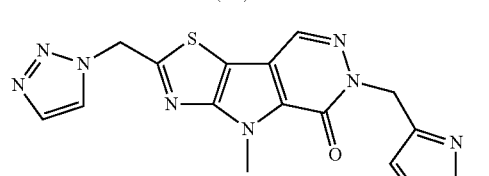<br>2-((1H-1,2,3-triazol-1-yl)methyl)-6-((1H-pyrazol-3-yl)methyl)-4-methyl-4H-thiazolo[5',4':4,5]pyrrolo[2,3-d]pyridazin-5(6H)-one | LCMS: m/z 368 [M + H]$^+$.<br>$^1$H NMR (400 MHz, DMSO-d$_6$) δ ppm 8.53 (brs, 1H), 8.32 (s, 1H), 7.81 (s, 1H), 7.58 (brs, 1H), 6.17 (s, 2H), 6.07 (brs, 1H), 5.29 (brs, 2H), 4.23 (s, 3H). |
| E9-19 | 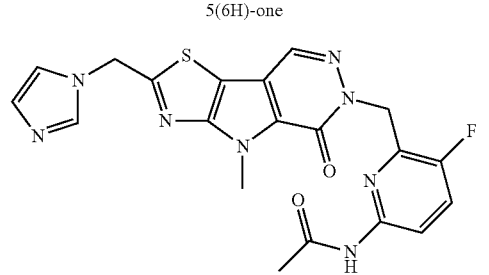<br>N-(6-((2-((1H-imidazol-1-yl)methyl)-4-methyl-5-oxo-4,5-dihydro-6H-thiazolo[5',4':4,5]pyrrolo[2,3-d]pyridazin-6-yl)methyl)-5-fluoropyridin-2-yl)acetamide | LC-MS: m/z 453 (M + H)$^+$.<br>$^1$H NMR (400 MHz, DMSO-d6) δ: 10.36 (s, 1H), 8.55 (s, 1H), 8.07-7.84 (m, 2H), 7.70 (t, 1H), 7.37 (s, 1H), 7.00 (s, 1H), 5.79 (s, 2H), 5.45 (s, 2H), 4.26 (s, 3H), 2.01 (s, 3H) |

Example 9D Synthesis of 2-((1H-1,2,4-triazol-1-yl)methyl)-6-((2-aminopyrimidin-4-yl)methyl)-4-methyl-4H-thiazolo[5',4':4,5]pyrrolo[2,3-d]pyridazin-5(6H)-one

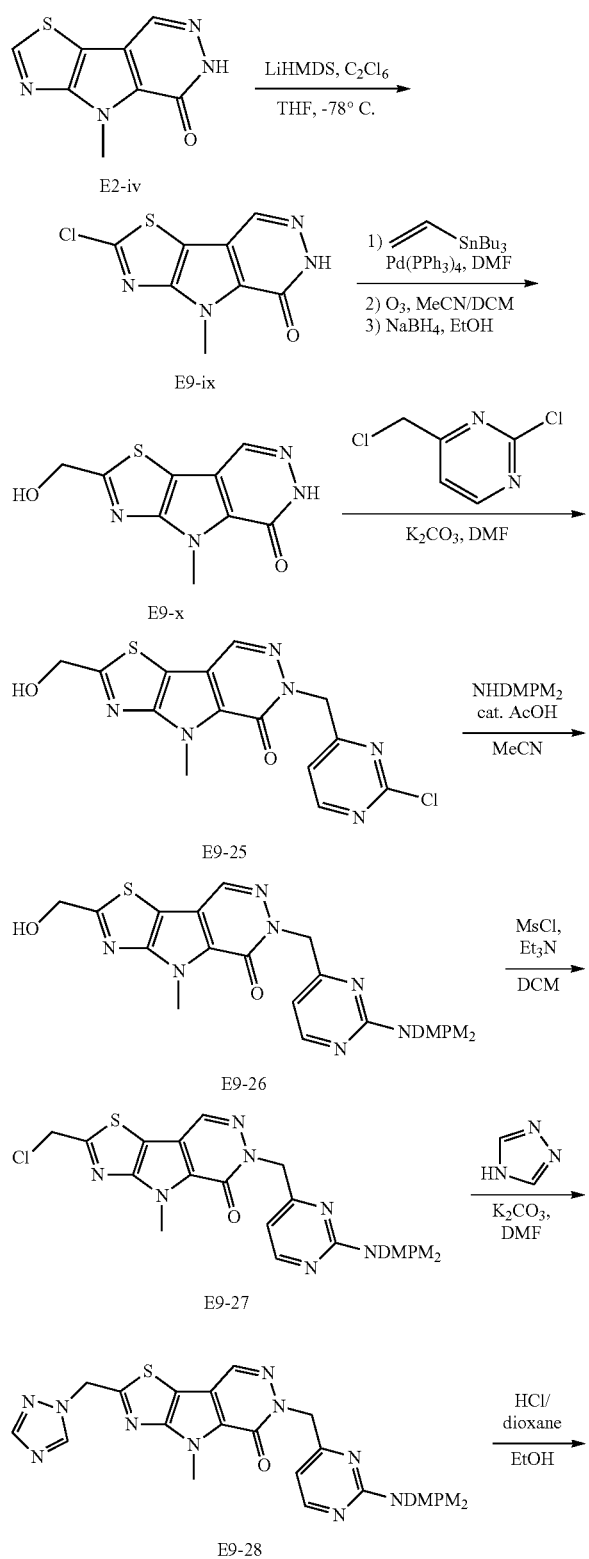

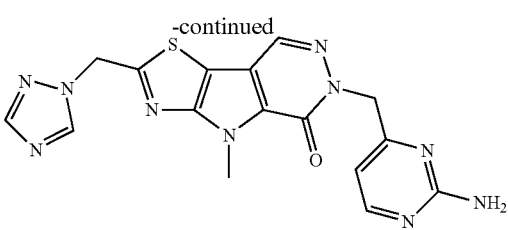

Step A. Synthesis of 2-chloro-4-methyl-4H-thiazolo[5',4':4,5]pyrrolo[2,3-d]pyridazin-5(6H)-one To a mixture of 4-methyl-4H-thiazolo[5',4':4,5]pyrrolo[2,3-d]pyridazin-5(6H)-one (3 g, 14.5 mmol) in dry THF (80 mL) was added LiHMDS (30.5 mL) at −65° C. by dropwise. After stirred for 1 hr, a solution of hexachloroethane (1.8 mL, 16 mmol) in dry THF (20 mL) was added. The reaction mixture was raised to −20° C. over 3 hr. Then the mixture was quenched with satd. NH$_4$Cl and stirred at r.t. for 20 min. The precipitate was collected by filtration and washed with EtOAc to give 3.5 g of 2-chloro-4-methyl-4H-thiazolo[5',4':4,5]pyrrolo[2,3-d]pyridazin-5(6H)-one. LC-MS (ESI): m/z 241 (M+H)$^+$.

Step B. Synthesis of 4-methyl-2-vinyl-4H-thiazolo[5',4':4,5]pyrrolo[2,3-d]pyridazin-5(6H)-one Under nitrogen, to a mixture of 2-chloro-4-methyl-4H-thiazolo[5',4':4,5]pyrrolo[2,3-d]pyridazin-5(6H)-one (1.5 g, 6.2 mmol) and tributyl(ethenyl)stannane (5.5 mL, 18.7 mmol) in DMF (30 mL) was added Pd(PPh$_3$)$_4$ (0.36 g, 0.31 mmol). The reaction mixture was stirred at 100° C. for 2 hr. Then the mixture was cooled down and diluted with EtOAc, washed with water and brine, dried over anhy. Na$_2$SO$_4$ and concentrated. The residue was purified by flash chromatography (silica gel, 0~10% MeOH in DCM) to give 1.4 g of 4-methyl-2-vinyl-4H-thiazolo[5',4':4,5]pyrrolo[2,3-d]pyridazin-5(6H)-one. LC-MS (ESI): m/z 233 (M+H)$^+$.

Step C. Synthesis of 4-methyl-5-oxo-5,6-dihydro-4H-thiazolo[5',4':4,5]pyrrolo[2,3-d]pyridazine-2-carbaldehyde Under −60° C., a mixture of 4-methyl-2-vinyl-4H-thiazolo[5',4':4,5]pyrrolo[2,3-d]pyridazin-5(6H)-one (500 mg, 2.15 mmol) in DCM/MeCN (500 mL, 1:1 volume) was purged with O$_3$ for 20 min. Then the reaction was quenched with dimethylsolfane and concentrated to give 500 mg of 4-methyl-5-oxo-5,6-dihydro-4H-thiazolo[5',4':4,5]pyrrolo[2,3-d]pyridazine-2-carbaldehyde. LC-MS (ESI): m/z 235 (M+H)$^+$.

Step D. Synthesis of 2-(hydroxymethyl)-4-methyl-4H-thiazolo[5',4':4,5]pyrrolo[2,3-d]pyridazin-5(6H)-one To a mixture of 4-methyl-5-oxo-5,6-dihydro-4H-thiazolo[5',4':4,5]pyrrolo[2,3-d]pyridazine-2-carbaldehyde (500 mg, 2.13 mmol) in EtOH (3 mL) was added NaBH$_4$ (81 mg, 2.13 mmol) at 0° C. The reaction was stirred at room temperature for 5 min. Then the mixture was poured into satd. NH$_4$Cl, extracted with EtOAc. The organic layer was washed with brine, dried over anhy. Na$_2$SO$_4$ and concentrated. The residue was purified by flash chromatography (silica gel, 0~8%

MeOH in DCM) to give 120 mg of 2-(hydroxymethyl)-4-methyl-4H-thiazolo[5',4':4,5]pyrrolo[2,3-d]pyridazin-5(6H)-one. LC-MS (ESI): m/z 237 (M+H)+.

Step E. Synthesis of 6-((2-chloropyrimidin-4-yl)methyl)-2-(hydroxymethyl)-4-methyl-4H-thiazolo[5',4':4,5]pyrrolo[2,3-d]pyridazin-5(6H)-one To a mixture of 2-(hydroxymethyl)-4-methyl-4H-thiazolo[5',4':4,5]pyrrolo[2,3-d]pyridazin-5(6H)-one (200 mg, 0.85 mmol) in DMF (8 mL) was added K$_2$CO$_3$ (351 mg, 2.54 mmol). After stirred at 60° C. for 30 min, a solution of 2-chloro-4-(chloromethyl)pyrimidine (276 mg, 1.7 mmol) in DMF (2 mL) was added. The reaction mixture was stirred for another 4 hr, poured into satd. NH$_4$Cl, extracted with EtOAc. The organic layer was washed with brine, dried over anhy. Na$_2$SO$_4$ and concentrated. The residue was purified by flash chromatography (silica gel, 0~8% MeOH in DCM) to give 160 mg of 6-((2-chloropyrimidin-4-yl)methyl)-2-(hydroxymethyl)-4-methyl-4H-thiazolo[5',4':4,5]pyrrolo[2,3-d]pyridazin-5(6H)-one. LC-MS (ESI): m/z 363 (M+H)+.

Step F. Synthesis of 6-((2-(bis(2,4-dimethoxybenzyl)amino)pyrimidin-4-yl)methyl)-2-(hydroxymethyl)-4-methyl-4H-thiazolo[5',4':4,5]pyrrolo[2,3-d]pyridazin-5(6H)-one To a mixture of 6-((2-chloropyrimidin-4-yl)methyl)-2-(hydroxymethyl)-4-methyl-4H-thiazolo[5',4':4,5]pyrrolo[2,3-d]pyridazin-5(6H)-one (160 mg, 0.44 mmol) in MeCN (5 mL) was added bis(2,4-dimethoxybenzyl)amine (280 mg, 0.88 mmol) and AcOH (1 drop). The reaction mixture was stirred at 80° C. overnight. The reaction mixture was evaporated and the residue was purified by prep-TLC (eluant: 5% MeOH in DCM) to give 75 mg of 6-((2-(bis(2,4-dimethoxybenzyl)amino)pyrimidin-4-yl)methyl)-2-(hydroxymethyl)-4-methyl-4H-thiazolo[5',4':4,5]pyrrolo[2,3-d]pyridazin-5(6H)-one. LC-MS (ESI): m/z 644 (M+H)+.

Step G. Synthesis of 6-((2-(bis(2,4-dimethoxybenzyl)amino)pyrimidin-4-yl)methyl)-2-(chloromethyl)-4-methyl-4H-thiazolo[5',4':4,5]pyrrolo[2,3-d]pyridazin-5(6H)-one Under 0° C., to a solution of 6-((2-(bis(2,4-dimethoxybenzyl)amino)pyrimidin-4-yl)methyl)-2-(hydroxymethyl)-4-methyl-4H-thiazolo[5',4':4,5]pyrrolo[2,3-d]pyridazin-5(6H)-one (75 mg, 0.12 mmol) in DCM (5 mL) was added Et$_3$N (0.16 mL, 1.16 mmol) and MsCl (0.05 mL, 0.58 mmol). The mixture was stirred at r.t. overnight. The reaction mixture was diluted with DCM, washed with satd. NH$_4$Cl and brine, dried over anhy. Na$_2$SO$_4$ and concentrated to give 70 mg of crude product of 6-((2-(bis(2,4-dimethoxybenzyl)amino)pyrimidin-4-yl)methyl)-2-(chloromethyl)-4-methyl-4H-thiazolo[5',4':4,5]pyrrolo[2,3-d]pyridazin-5(6H)-one. LC-MS (ESI): m/z 662 (M+H)+.

Step H. Synthesis of 2-((1H-1,2,4-triazol-1-yl)methyl)-6-((2-(bis(2,4-dimethoxybenzyl)amino)pyrimidin-4-yl)methyl)-4-methyl-4H-thiazolo[5',4':4,5]pyrrolo[2,3-d]pyridazin-5(6H)-one A mixture of 4H-1,2,4-triazole (39 mg, 0.57 mmol) and K$_2$CO$_3$ (78 mg, 0.57 mmol) in DMF (3 mL) was stirred at 60° C. for 30 min. 6-((2-(bis(2,4-dimethoxybenzyl)amino)pyrimidin-4-yl)methyl)-2-(chloromethyl) methyl-4H-thiazolo[5',4':4,5]pyrrolo[2,3-d]pyridazin-5(6H)-one (75 mg, 0.11 mmol) was added and stirred for another 30 min. The suspension was poured into satd. NH$_4$Cl, extracted with EtOAc. The organic layer was washed with brine, dried over anhy. Na$_2$SO$_4$ and concentrated. The residue was purified by flash chromatography (silica gel, 0~10% DCM in MeOH) to give 60 mg of 2-((1H-1,2,4-triazol-1-yl)methyl)-6-((2-(bis(2,4-dimethoxybenzyl)amino)pyrimidin-4-yl)methyl)-4-methyl-4H-thiazolo[5',4':4,5]pyrrolo[2,3-d]pyridazin-5(6H)-one. LC-MS (ESI): m/z 695 (M+H)+.

Step G. Synthesis of 2-((1H-1,2,4-triazol-1-yl)methyl)-6-((2-aminopyrimidin-4-yl)methyl)-4-methyl-4H-thiazolo[5',4':4,5]pyrrolo[2,3-d]pyridazin-5(6H)-one To a mixture of 2-((1H-1,2,4-triazol-1-yl)methyl)-6-((2-(bis(2,4-dimethoxybenzyl)amino) pyrimidin-4-yl)methyl)-4-methyl-4H-thiazolo[5',4':4,5]pyrrolo[2,3-d]pyridazin-5(6H)-one (30 mg, 0.043 mmol) in EtOH (2 mL) was added HCl (0.5 mL, 4 M in dioxane). The reaction mixture was stirred at 80° C. overnight. Then the mixture was cooled down and poured into satd. NaHCO$_3$, extracted with EtOAc. The organic layer was washed with brine, dried over anhy. Na$_2$SO$_4$ and concentrated. The residue was purified by prep-HPLC to give 8 mg of 2-((1H-1,2,4-triazol-1-yl)methyl)-6-((2-aminopyrimidin-4-yl)methyl)-4-methyl-4H-thiazolo[5',4':4,5]pyrrolo[2,3-d]pyridazin-5(6H)-one. LC-MS (ESI): m/z 395 (M-1-H)+. $^1$H NMR (400 MHz, DMSO-d6) δ 8.80 (s, 1H), 8.62 (s, 1H), 8.12-8.10 (m, 2H), 6.60 (s, 2H), 6.19 (d, 1H), 6.01 (s, 2H), 5.19 (s, 2H), 4.26 (s, 3H).

| Cpd No. | Structure and chemical name | Characterization |
|---|---|---|
| E9-31 | 2-((1H-imidazol-1-yl)methyl)-6-((2-aminopyrimidin-4-yl)methyl)-4-methyl-4H-thiazolo[5',4':4,5]pyrrolo[2,3-d]pyridazin-5(6H)-one | LC-MS: m/z 394 (M + H)+. $^1$H NMR (400 MHz, DMSO-d6) δ: 8.62 (s, 1H), 8.11 (d, 1H), 7.88 (s, 1H), 7.36 (s, 1H), 6.99 (s, 1H), 6.61 (s, 2H), 6.18 (d, 1H), 5.79 (s, 2H), 5.19 (s, 2H), 4.26 (s, 3H). |

| Cpd No. | Structure and chemical name | Characterization |
|---|---|---|
| E9-32 | 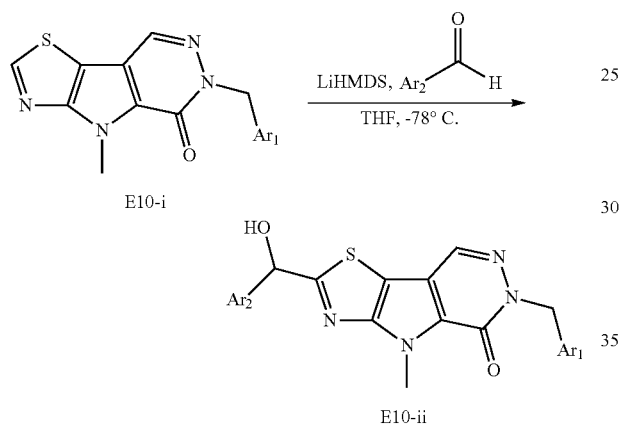

2-((1H-1,2,4-triazol-1-yl)methyl)-4-methyl-6-((5-oxo-4,5-dihydro-1H-1,2,4-triazol-3-yl)methyl)-4H-thiazolo[5',4':4,5]pyrrolo[2,3-d]pyridazin-5(6H)-one | LC-MS: m/z 385 (M + H)+.
1H NMR (400 MHz, DMSO-d6) δ: 11.32-11.28 (m, 2H), 8.80 (s, 1H), 8.59 (s, 1H), 8.11 (s, 1H), 6.01 (s, 2H), 5.14 (s, 2H), 4.26 (s, 3H). |

Example 10. Synthesis of Compounds E10-ii

Scheme E10

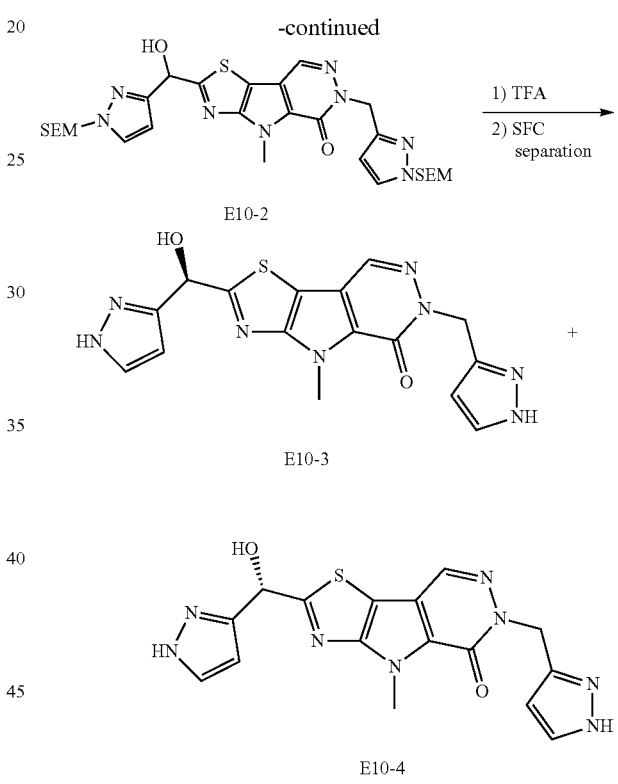

Reaction of E10-i with LiHMDS and an aldehyde generates compound E10-ii, which can be separated with chiral HPLC or SFC to give two enantiomers. As used herein, Ar$_1$ and Ar$_2$ are each independently optionally substituted 5- or 6-membered monocyclic heteroaryl.

Example 10A. Synthesis of (R)-6-((1H-pyrazol-3-yl)methyl)-2-(hydroxy(1H-pyrazol-3-yl)methyl)-4-methyl-4H-thiazolo[5',4':4,5]pyrrolo[2,3-d]pyridazin-5(6H)-one and (S)-6-((1H-pyrazol-3-yl)methyl)-2-(hydroxy(1H-pyrazol-3-yl)methyl)-4-methyl-4H-thiazolo[5',4':4,5]pyrrolo[2,3-d]pyridazin-5(6H)-one

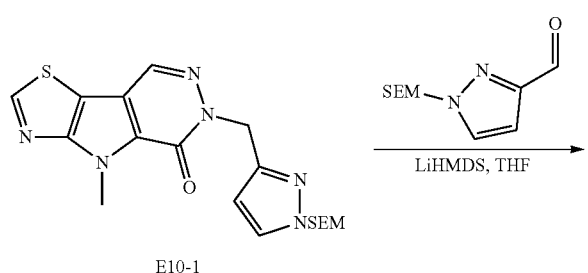

Step A. Synthesis of 2-(hydroxy(1-((2-(trimethylsilyl)ethoxy)methyl)-1H-pyrazol-3-yl)methyl)-4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one Under argon, to a solution of 4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (0.5 g, 1.20 mmol, 1 eq) in THF (10 mL) was slowly added LiHMDS (1.0 M, 2.41 mL, 2 eq) at −78° C., and the reaction mixture was stirred at −70° C. for 1 hr. Then a solution of 1-(2-trimethylsilylethoxymethyl) pyrazole-3-carbaldehyde (816.97 mg, 3.61 mmol, 3 eq) in THF (1 mL) was added to the reaction mixture. The resulting mixture was stirred at −70° C. for 1 hr. TLC (petroleum ether:EtOAc=1:1) showed two new spot was formed. The reaction mixture was quenched by aq NH₄Cl (5 mL) at −70° C., and then warmed to room temperature. The mixture was diluted with water (10 mL), and extracted with EtOAc (8 mL×3). The combined organic layers were washed with brine (10 mL), and dried over Na₂SO₄. The solvent was concentrated in vacuo. The residue was purified by Combiflash (from 100% of petroleum ether to 100% of EtOAc) to give crude product (130 mg) as pale brown gum, which was used for the next step without further purification. LCMS: m/z 643.2 [M+H]⁺

Step B. Synthesis of 6-((1H-pyrazol-3-yl)methyl)-2-(hydroxy(1H-pyrazol-3-yl)methyl) methyl-4H-thiazolo[5',4':4,5]pyrrolo[2,3-d]pyridazin-5(6H)-one To a solution of 2-(hydroxy(1-((2-(trimethylsilyl)ethoxy)methyl)-1H-pyrazol-3-yl)methyl)-4-methyl-6-((1-((2-(trimethylsilyl)ethoxy)methyl)-1H-pyrazol-3-yl)methyl)-4H-thiazolo[5',4':4,5]pyrrolo[2,3-d]pyridazin-5(6H)-one (0.13 g, 202.20 umol, 1 eq) in DCM (8 mL) was added TFA (4.62 g, 40.52 mmol, 3 mL, 200.38 eq), followed by H₂O (500.00 mg, 27.75 mmol, 0.5 mL, 137.26 eq), then the reaction mixture was stirred at room temperature for 18 hr, then heated to 40° C. for 18 hr. LCMS showed the starting material was consumed completely. The reaction mixture was concentrated in vacuo, and the residue was purified by Prep-HPLC to give the desired product (20.5 mg). LCMS: m/z 382.9 [M+H]'. NMR (400 MHz, DMSO-d₆) δ ppm 12.72 (brs, 1H), 12.61 (brs, 1H), 8.52 (s, 1H), 7.56-7.62 (m, 2H), 6.82 (brs, 1H), 6.18 (d, 1H), 5.99-6.09 (m, 2H), 5.24-5.32 (m, 2H), 4.19 (s; 3H).

Step C. Synthesis of (R)-6-((1H-pyrazol-3-yl)methyl)-2-(hydroxy(1H-pyrazol-3-yl)methyl)-4-methyl-4H-thiazolo[5',4':4,5]pyrrolo[2,3-d]pyridazin-5(6H)-one and (S)-6-((1H-pyrazol-3-yl)methyl)-2-(hydroxy(1H-pyrazol-3-yl)methyl)-4-methyl-4H-thiazolo[5',4':4,5]pyrrolo[2,3-d]pyridazin-5(6H)-one The compound 6-((1H-pyrazol-3-yl)methyl)-2-(hydroxy(1H-pyrazol-3-yl)methyl)-4-methyl-4H-thiazolo[5',4':4,5]pyrrolo[2,3-d]pyridazin-5(6H)-one was separated by SFC. SFC condition: Column is DAICEL CHIRALCEL OJ-H (250 mm*30 mm, 5 um); mobile phase: A: 55% of CO2; B: 45% [0.1. % NH₃H₂O in EtOH]/min. The SFC separation afforded 2-[(R)-hydroxy(1H-pyrazol-3-yl)methyl]-4-methyl-6-(1H-pyrazol-3-ylmethyl)thiazolo[3,4]pyrrolo[1,3-d]pyridazin-5-one and 2-[(S)-hydroxy(1H-pyrazol-3-yl)methyl]-4-methyl-6-(1H-pyrazol-3-ylmethyl)thiazolo[3,4]pyrrolo[1,3-d]pyridazin-5-one. One isomer (4.4 mg): LCMS: m/z 383 [M+H]⁺. ¹H NMR (400 MHz, Methanol-d₄) δ ppm 8.39 (s, 1H), 7.61 (brs, 1H), 7.55 (brs, 1H), 6.34 (brs, 1H), 6.25 (brs, 1H), 6.18 (brs, 1H), 5.44 (s, 2H), 4.29 (s, 3H). Another isomer (4.1 mg): LCMS: m/z 383 (M+H)⁺. NMR (400 MHz, METHANOL-d₄) δ ppm 8.40 (s, 1H), 7.59 (brs, 1H), 7.54 (brs, 1H), 6.34 (brs, 1H), 6.26 (brs, 1H), 6.19 (brs, 1H), 5.44 (s, 2H), 4.29 (s, 3H).

Example 10B: Synthesis of 6-((1H-pyrazol-3-yl)methyl)-2-(difluoro(1H-pyrazol yl)methyl)-4-methyl-4,6-dihydro-5H-thiazolo[5',4':4,5]pyrrolo[2,3-d]pyridazin-5-one

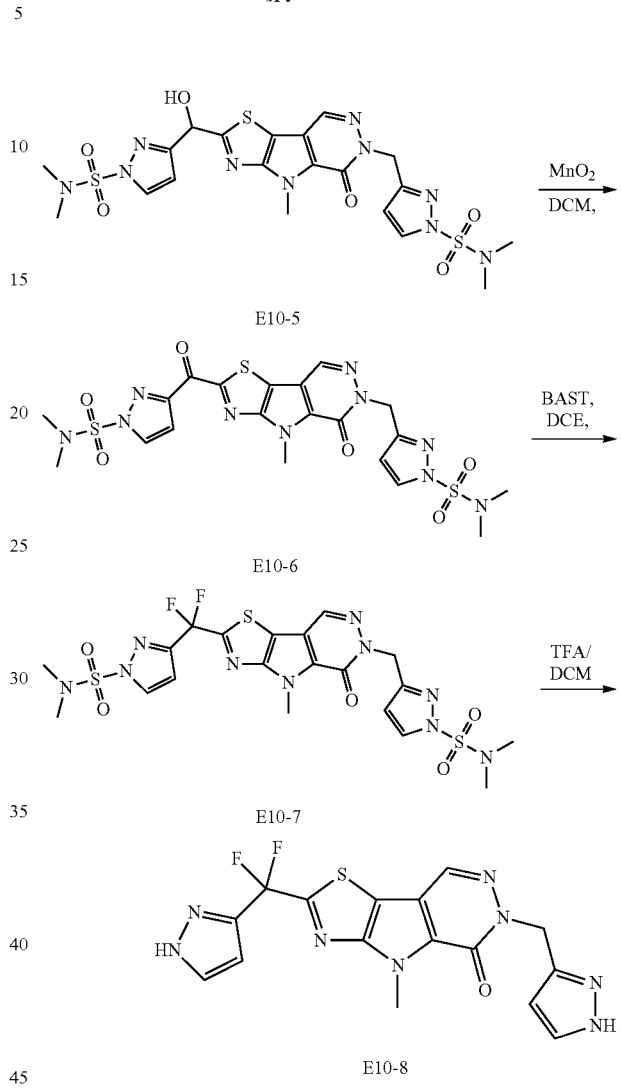

Step A. 3-(6-((1-(N,N-dimethylsulfamoyl)-1H-pyrazol-3-yl)methyl)-4-methyl-5-oxo-5,6-dihydro-4H-thiazolo[5',4':4,5]pyrrolo[2,3-d]pyridazine-2-carbonyl)-N,N-dimethyl-1H-pyrazole-1-sulfonamide To a mixture of 3-((2-((1-(N,N-dimethylsulfamoyl)-1H-pyrazol-3-yl)(hydroxy)methyl)-4-methyl-5-oxo-4,5-dihydro-6H-thiazolo[5',4':4,5]pyrrolo[2,3-d]pyridazin-6-yl)methyl)-N,N-dimethyl-1H-pyrazole-1-sulfonamide (50 mg, 83.80 umol, made similarly to E10-1) in DCM (1.5 mL) was added MnO₂ (72.85 mg, 838.00 umol) and the mixture was stirred at 15° C. for 1.5 hours. The reaction mixture was filtered and concentrated under reduced pressure to give a crude product (60 mg, crude). LCMS: m/z 595.1 (M+H)⁺. ¹H NMR (400 MHz, CDCl₃) δ 8.34 (s, 1H), 8.12 (d, 1H), 7.90 (d, 1H), 7.41 (d, 1H), 6.38 (d, 1H), 5.54 (s, 2H), 4.49 (s, 3H), 3.10 (s, 6H) 2.93 (s, 6H).

Step B. 3-((2-((1-(N,N-dimethylsulfamoyl)-1H-pyrazol-3-yl)difluoromethyl)-4-methyl-5-oxo-4,5-dihydro-6H-thiazolo[5',4':4,5]pyrrolo[2,3-d]pyridazin-6-yl)methyl)-N,N-dimethyl-1H-pyrazole-1-sulfonamide To a solution of 3-(6-((1-(N,N-dimethylsulfamoyl)-1H-pyrazol-3-yl)methyl)-4-methyl-5-oxo-5,6-dihydro-4H-thiazolo[5',4':4,5]pyrrolo[2,3-d]pyridazine-2-carbonyl)-N,N-dimethyl-1H-pyrazole-1-sulfonamide (240 mg, 403.60 umol) in DCE (4 mL) was added BAST (1.34 g, 6.05 mmol, 1.33 mL), and the mixture was stirred at 50° C. for 12 h. The reaction mixture was diluted with dichloromethane (20 mL) and washed with saturated NaHCO₃ (10 mL*2), dried over anhydrous Na₂SO₄, filtered and concentrated under reduced pressure to give a crude product (300 mg, crude) which was used in the next step without further purification. LCMS: m/z 617.1 (M+H)⁺.

Step C. 6-((1H-pyrazol-3-yl)methyl)-2-(difluoro(1H-pyrazol-3-yl)methyl)-4-methyl-4,6-dihydro-5H-thiazolo[5',4':4,5]pyrrolo[2,3-d]pyridazin-5-one To a mixture of 3-((2-((1-(N,N-dimethylsulfamoyl)-1H-pyrazol-3-yl)difluoromethyl)-4-methyl-5-oxo-4,5-dihydro-6H-thiazolo[5',4':4,5]pyrrolo[2,3-d]pyridazin-6-yl)methyl)-N,N-dimethyl-1H-pyrazole-1-sulfonamide (240 mg, 163.47 umol) in DCM (2 mL) was added TFA (2.07 g, 18.15 mmol, 1.34 mL) and the mixture was warmed up to 50° C. for 5 h. The reaction mixture was concentrated under reduced pressure. The residue was purified by prep-HPLC (column: Agela ASB 150*25 mm*5 um; mobile phase: [water (0.05% HCl)-ACN]; B %: 30%-60%, 8 min) to give desired product (3.9 mg, 5.45% yield, 92% purity) as a white solid. LCMS: m/z 403.1 (M+H)⁺. ¹H NMR (400 MHz, DMSO-d₆) δ 8.67 (s, 1H), 7.95 (s, 1H), 7.61 (s, 1H), 6.72 (s, 1H), 6.16 (s, 1H), 5.36 (s, 2H), 4.28 (s, 3H).

Example 10C: Synthesis of 2-(1-(1H-pyrazol-3-yl)ethyl)-6-((1H-pyrazol-3-yl)methyl)-4-methyl-4,6-dihydro-5H-thiazolo[5',4':4,5]pyrrolo[2,3-d]pyridazin-5-one

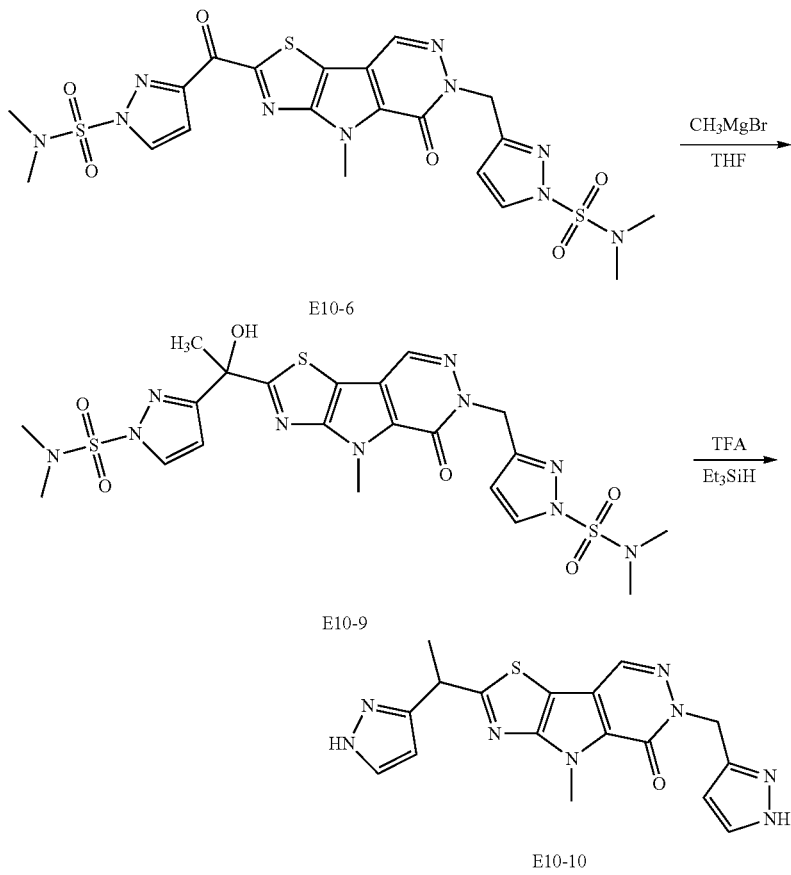

Step A: 3-((2-(1-(1-(N,N-dimethylsulfamoyl)-1H-pyrazol-3-yl)-1-hydroxyethyl)-4-methyl-5-oxo-4,5-dihydro-6H-thiazolo[5',4':4,5]pyrrolo[2,3-d]pyridazin-6-yl)methyl)-N,N-dimethyl-1H-pyrazole-1-sulfonamide To a solution of 3-(6-((1-(N,N-dimethylsulfamoyl)-1H-pyrazol-3-yl)methyl)-4-methyl-5-oxo-5,6-dihydro-4H-thiazolo[5',4':4,5]pyrrolo[2,3-d]pyridazine-2-carbonyl)-N,N-dimethyl-1H-pyrazole-1-sulfonamide (160 mg, 269.07 umol) in THF (3 mL) was added CH₃MgBr (3 M, 179.38 uL) and the reaction mixture was stirred at 0° C. for 3 h. The reaction mixture was poured into saturated NH$_4$Cl (10 mL) at 0° C., extracted with ethyl acetate (20 mL*3). The combined organic layers were washed with brine (10 mL), dried over anhydrous Na2SO4, filtered and concentrated under reduced pressure. The residue was purified by flash silica gel chromatography (ISCO®; 12 g SepaFlash® Silica Flash Column, Eluent of 0~90% Ethyl acetate/Petroleum ether gradient @ 40 mL/min) to give desired product (50 mg, 81.87 umol). LCMS: m/z 611.1 (M+H)$^+$.

Step B: 2-(1-(1H-pyrazol-3-yl)ethyl)-6-((1H-pyrazol-3-yl)methyl)-4-methyl-4,6-dihydro-5H-thiazolo[5',4':4,5]pyrrolo[2,3-d]pyridazin-5-one To a mixture of 3-((2-(1-(1-(N,N-dimethylsulfamoyl)-1H-pyrazol-3-yl)-1-hydroxyethyl)-4-methyl-5-oxo-4,5-dihydro-6H-thiazolo[5',4':4,5]pyrrolo[2,3-d]pyridazin-6-yl)methyl)-N,N-dimethyl-1H-pyrazole sulfonamide (50 mg, 81.87 umol) in DCE (0.5 mL) was added Et3SiH (19.04 mg, 163.75 umol, 26.15 uL) at 0° C., followed by TFA (1.54 g, 13.51 mmol, 1 mL, 164.96 eq) and stirred at 0° C. for 1 h. The mixture was warmed up to 50° C. for another 1 h. The reaction mixture was concentrated under reduced pressure. The residue was purified by prep-HPLC (column: Agela ASB 150*25 mm*5 um; mobile phase: [water (0.05% HCl)-ACN]; B %: 25%-55%, 7 min) to give 7.0 mg of desired product. LCMS: m/z 381.2 (M+H)$^+$. $^1$H NMR (400 MHz, CD$_3$OD) δ 8.46 (s, 1H), 8.15 (d, 2H), 6.78 (d, 1H), 6.74 (d, 1H), 5.60 (s, 2H), 5.00 (q, 1H), 4.33 (s, 3H), 1.94 (d, 3H).

Example 10D: Synthesis of 6-((1H-pyrazol-3-yl)methyl)-4-methyl-2-(1H-pyrazole-3-carbonyl)-4,6-dihydro-5H-thiazolo[5',4':4,5]pyrrolo[2,3-d]pyridazin-5-one

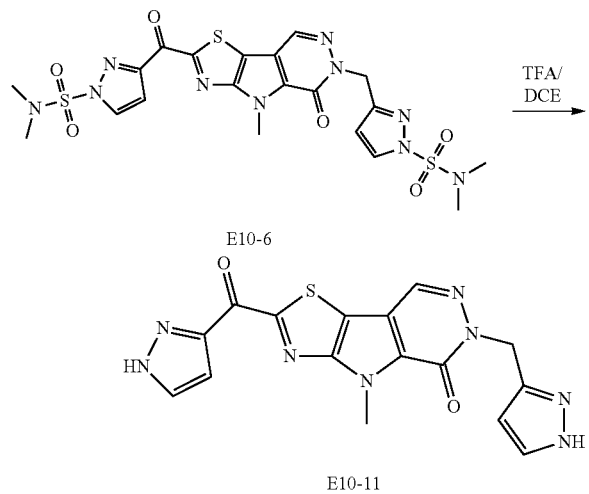

Step A. 4-methyl-2-(1H-pyrazole-3-carbonyl)-6-(1H-pyrazol-3-ylmethyl)thiazolo[3,4] pyrrolo[1,3-d]pyridazin-5-one To a solution of 3-(6-((1-(N,N-dimethylsulfamoyl)-1H-pyrazol-3-yl)methyl)-4-methyl-5-oxo-5,6-dihydro-4H-thiazolo[5',4':4,5]pyrrolo[2,3-d]pyridazine-2-carbonyl)-N,N-dimethyl-1H-pyrazole-1-sulfonamide (50 mg, 84.08 umol) in DCE (1.5 mL) was added TFA (2.31 g, 20.26 mmol, 1.5 mL) and the reaction mixture was warmed up to 50° C. for 12 h. The reaction mixture was concentrated under vacuum. The residue was purified by prep-HPLC to give 6.0 mg of desired product. LCMS: m/z 381.1 (M+H)$^+$. $^1$H NMR (400 MHz, DMSO-d$_6$) δ 8.72 (s, 1H), 7.96 (d, 1H), 7.64 (d, 1H), 7.49 (d, 1H), 6.19 (d, 1H), 5.37 (s, 2H), 4.38 (s, 3H).

Example 11. PKR Mutant Assay

Procedure:

PKR or PKR mutant enzyme solution was diluted into a reaction mix, which contains 1× buffer (100 mM KCl, 50 mM Tris pH 7.5, 5 mM MgCl$_2$) as well as PEP (cont depends on enzyme), 180 μM NADH, 0.5 units LDH, 1 mM DTT, 0.03% BSA; final assay concentrations after 1.11 fold dilution are indicated.

2 μL of test compound was added into wells first, and then 180 μL reaction mix was added.

Reactions mixture with test compound was assembled except for ADP, and plates were stored for 60 minutes at room temperature.

20 uL ADP was added to start reaction at room temperature and reaction progress was measured as changes in absorbance at 340 nm wavelength at room temperature.

Test Compound Preparation:

Test compound stock was made at 100× concentration in 100% DMSO (10 mM) 1 to 3 dilutions were made for 11 points (i.e. 50 μl of first concentration added to 100 μl 100% DMSO to yield 3.33 mM, 50 μl of this added to 100 μl DMSO to yield 1.11 mM, and so forth)

1 to 100 dilution into assay (2 μl in 200 μl) yielded starting concentration of 100 μM, decreasing 3 fold for 11 points.

Assay Buffer: 100 mM KCl, 50 mM Tris 7.5, 5 mM MgCl2, 1 mM DTT, 0.03% BSA

Reaction Mixture: PKR mutant enzyme: 40-400 ng/well; ADP: 0.2-1.65 mM; PEP: 0.1-0.5 mM; NADH: 180 μM; LDH: 0.5 units (Sigma #59023); DTT: 1 mM; BSA: 0.03%.

Example 12. PKR WT Single Point Percent Activation Assay

A compound described herein was diluted with DMSO and tested at concentration. The enzyme was diluted in an enzyme solution, which contains 1× buffer (100 mM KCl, 50 mM Tris pH 7.5, 5 mM MgCl$_2$) as well as PEP (conc depends on enzyme), 180 μM NADH, 0.5 units LDH, 1 mM DTT, 0.03% BSA; final assay concentrations after 1.11 fold dilution are indicated.

2 μL of compound solution was first added into wells, and then 180 μL of enzyme solution was added. Assays were assembled except for ADP, and plates were stored for 60 minutes at RT. 20 μL ADP was added to start the assay and assay output was evaluated using OD340. The assay was run at room temperature.

Final concentration: PKR wt (100 ng/well), Tris pH 7.5 (50 mM), KCl (100 mM), MgCl$_2$ (5 mM), ADP (0.48 mM), PEP (0.15 mM), NADH (180 μM), LDH (0.5 units, Sigma 59023), DTT (1 mM) and BSA (0.03%).

Example 13. PKR R510Q Single Point Percent Activation Assay

A compound described herein was diluted with DMSO and tested at 1 μM concentration. The enzyme was diluted in into an enzyme solution, which contains 1× buffer (100 mM KCl, 50 mM Tris pH 7.5, 5 mM MgCl2) as well as PEP (conc depends on enzyme), 180 µM NADH, 0.5 units LDH, 1 mM DTT, 0.03% BSA; final assay concentrations after 1.11 fold dilution are indicated.

2 µL of compound solution was first added into wells, and then 180 µL of enzyme. solution was added. Assays were assembled except for ADP, and plates were stored for 60 minutes at RT. 20 µL ADP was added to start the assay and assay output was evaluated using OD340. The assay was run at room temperature.

Final concentration: PKR R510Q (40 ng/well), Tris pH 7.5 (50 mM), KCl (100 mM), MgCl$_2$ (5 mM), ADP (0.2 mM), PEP (0.11 mM), NADH (180 µM), LDH (0.5 units, Sigma 59023), DTT (1 mM) and BSA (0.03%).

Example 14. PKR R532W Single Point Percent Activation Assay

A compound described herein was diluted with DMSO and tested at 1 µM concentration. The enzyme was diluted in an enzyme solution, which contains 1× buffer (100 mM KCl, 50 mM Tris pH 7.5, 5 mM MgCl2) as well as PEP (conc depends on enzyme), 180 µM NADH, 0.5 units LDH, 1 mM DTT, 0.03% BSA; final assay concentrations after 1.11 fold dilution are indicated.

2 µL of compound solution was first added into wells, and then 180 µL of enzyme solution was added. Assays were assembled except for ADP, and plates were stored for 60 minutes at RT. 20 µL ADP was added to start the assay and assay output was evaluated using OD340. The assay was run at room temperature.

Final concentration: PKR R532W (100 ng/well), Tris pH 7.5 (50 mM), KCl (100 mM), MgCl2 (5 mM), ADP (0.36 mM), PEP (0.1 mM), NADH (180 µM), LDH (0.5 units, Sigma 59023), DTT (1 mM) and BSA (0.03%).

Example 15. PKR T384M Single Point Percent Activation Assay

A compound described herein was diluted with DMSO and tested at 1 µM concentration. The enzyme was diluted in into an enzyme solution, which contains 1× buffer (100 mM KCl, 50 mM Tris pH 7.5, 5 mM MgCl2) as well as PEP (conc depends on enzyme), 180 µM NADH, 0.5 units LDH, 1 mM DTT, 0.03% BSA; final assay concentrations after 1.11 fold dilution are indicated.

2 µL of compound solution was first added into wells, and then 180 µL enzyme solution was added. Assays were assembled except for ADP, and plates were stored for 60 minutes at RT. 20 µL ADP was added to start the assay and assay output was evaluated using OD340. The assay was run at room temperature.

Final concentration: PKR T384M soluble (300 ng/well), Tris pH 7.5 (50 mM), KCl (100 mM), MgCl2 (5 mM), ADP (0.08 mM), PEP (0.23 mM), NADH (180 µM), LDH (0.5 units, Sigma 59023), DTT (1 mM) and BSA (0.03%).

Example 16. Red Blood Cell (RBC) Purification

Fresh blood drawn from healthy volunteers into K$_2$EDTA tubes was collected. Whole blood was pelleted by spinning at 500 g for 10 minutes. Cut transfusion bag port off of Purecell leukocyte reduction neofilter (Fisher NCO267633) one (1) inch above filter. Attach a 10 ml syringe barrel to the remaining cut tubing attached to neofilter. The plasma layer was removed from the pellet of the whole blood and the pellet was resuspended in 2× volume of phosphate buffered saline (PBS). Transfer 9 ml re-suspended blood cell pellet to prepared 10 ml syringe that is attached to the neofilter. Allow whole blood to gravity flow through filter until all fluid runs through upper tubing into filter disc. Add plunger to the syringe, remove syringe from clamp and invert the filter, then plunge air through the syringe filter system. Using a new 5 ml syringe, remove filtered RBCs from the bag by the syringe port and transfer purified RBCs to a 5 ml snap cap tube that has been incubated on ice. Spin 5 ml snap cap tube at 500 g for 10 minutes at 15 C, aspirate supernatant and resuspend in AGAM (1×PBS, 1% glucose, 170 mg/L adenine, 5.25 g/L mannitol) at a density of 4×10$^9$ cells/mL.

Example 17. Cell Based ATP Assay

For cell based ATP assays, the compound as described herein was prepared in 100% DMSO as a 10 mM stock. Serial dilutions (1:4) were performed in 96-well V-bottom storage plate and then added 1:100 to 96-well V-bottom plates containing AGAM. RBCs were diluted in AGAM media to a density of 1×10$^7$ cells/mL before added 90 µL/well to black clear bottom assay plates (final compound concentration at 0.1% DMSO concentration). Assay plates were sealed using aluminum foil seals and incubated overnight at 37° C. in a humidified chamber. ATP levels were read out using Cell-Titer-Glo (Promega).

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A compound represented by the following structural formula:

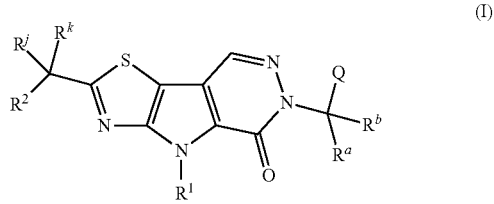

or a pharmaceutically acceptable salt thereof, wherein:
 R$^1$ is hydrogen, an optionally substituted alkyl, an optionally substituted haloalkyl, an optionally substituted alkenyl, an optionally substituted alkynyl, an optionally substituted cycloalkyl, an optionally substituted heterocyclyl, an optionally substituted aryl, —OR$^{o1}$, —C(=O)R$^{c1}$, or a nitrogen protecting group; wherein:
  R$^{o1}$ is hydrogen, optionally substituted alkyl, or an oxygen protecting group;
  R$^{c1}$ is optionally substituted alkyl or —N(R$^{cn}$)$_2$, wherein each instance of R$^{cn}$ is independently hydrogen, —C$_{1-6}$ alkyl, or a nitrogen protecting group;
 R$^2$ is an optionally substituted 5- or 6-membered monocyclic heteroaryl;
 Q is an optionally substituted 5-membered monocyclic heteroaryl;
 R$^a$ and R$^b$ are each independently hydrogen, a halogen, —CN, —NO$_2$, —N$_3$, an optionally substituted alkyl, —OR$^{o3}$, —N(R$^{n1}$)$_2$, —C(=O)N(R$^{n1}$)$_2$, or —C(=O)R$^{c2}$; or alternatively R$^a$ and R$^b$ can be taken together with the carbon atom to which they are attached to form an optionally substituted cycloalkyl or an optionally substituted heterocyclyl; wherein:

each instance of R$^{n1}$ is independently hydrogen, an optionally substituted —C$_1$-C$_6$ alkyl, or a nitrogen protecting group;

R$^{o3}$ is hydrogen, an optionally substituted —C$_1$-C$_6$ alkyl, or an oxygen protecting group; and R$^{c2}$ is an optionally substituted —C$_1$-C$_6$ alkyl; and R$^j$ and R$^k$ are each independently hydrogen, a halogen, —CN, —OR$^{o7}$, —N(R$^{n5}$)$_2$, —N(R$^{n5}$)C(=O) R$^{c5}$, —C(=O)N(R$^{n5}$)$_2$, —C(=O)R$^{c5}$, —C(=O)OR$^{o7}$, —SR$^{js}$, —S(=O)$_2$R$^{js}$, —S(=O)R$^{js}$, or an optionally substituted —C$_1$-C$_6$ alkyl; or alternatively R$^j$ and R$^k$ can be taken together with the carbon atom to which they are attached to form C=O, an optionally substituted C$_1$-C$_6$ monocyclic cycloalkyl ring, or an optionally substituted C$_3$-C$_6$ monocyclic heterocyclyl ring; wherein:

each instance of R$^{n5}$ is independently hydrogen, an optionally substituted —C$_1$-C$_6$ alkyl, —OR$^{o8}$, or a nitrogen protecting group, wherein R$^{o8}$ is hydrogen, an optionally substituted —C$_1$-C$_6$ alkyl, or an oxygen protecting group;

each instance of R$^{o7}$ is independently hydrogen, an optionally substituted —C$_1$-C$_6$ alkyl, or an oxygen protecting group;

each instance of R$^{c5}$ is independently an optionally substituted —C$_1$-C$_6$ alkyl; and each instance of R$^{js}$ is independently an optionally substituted —C$_1$-C$_6$ alkyl, an optionally substituted C$_{6-12}$ aryl, an optionally substituted heteroaryl, or a sulfur protecting group.

2. The compound according to claim 1 or a pharmaceutically acceptable salt thereof, wherein the 5- or 6-membered monocyclic heteroaryl represented by R$^2$ is optionally substituted at each substitutable ring carbon atom by R$^p$ and optionally substituted at each substitutable ring nitrogen atom by R$^{n6}$; wherein:

each instance of R$^p$ is independently hydrogen, a halogen, —CN, —NO$_2$, —N$_3$, an optionally substituted alkyl, an optionally substituted alkenyl, an optionally substituted alkynyl, an optionally substituted cycloalkyl, an optionally substituted aryl, an optionally substituted heterocyclyl, an optionally substituted heteroaryl, —OR$^{o6}$, —SR$^{s2}$, —N(R$^{n3}$)$_2$, —C(=O)N(R$^{n3}$)$_2$, —N(R$^{n3}$)C(=O)R$^{c4}$, —C(=O)R$^{c4}$, —C(=O)OR$^{o6}$, —OC(=O)R$^{c4}$, —S(=O)R$^{s2}$, —S(=O)$_2$R$^{s2}$, —S(=O)OR$^{o6}$, —OS(=O)R$^{c4}$, —S(=O)$_2$OR$^{o6}$, —OS(=O)$_2$R$^{c4}$, —S(=O)N(R$^{n3}$)$_2$, —S(=O)$_2$N(R$^{n3}$)$_2$, —N(R$^{n3}$)S(=O)R$^{s2}$, —N(R$^{n3}$)S(=O)$_2$R$^{s2}$, —N(R$^{n3}$)C(=O)OR$^{o6}$, —OC(=O)N(R$^{n3}$)$_2$, —N(R$^{n3}$)C(=O)N(R$^{n3}$)$_2$, —N(R$^{n3}$)S(=O)N(R$^{n3}$)$_2$, —N(R$^{n3}$)S(=O)$_2$N(R$^{n3}$)$_2$, —N(R$^{n3}$)S(=O)OR$^{o6}$, —N(R$^{n3}$)S(=O)$_2$OR$^{o6}$, —OS(=O)N(R$^{n3}$)$_2$, or —OS(=O)$_2$N(R$^{n3}$)$_2$; or alternatively two instances of R$^p$ attached to the same or adjacent carbon atoms, can be taken together with the carbon atom(s) to which they are attached to form an optionally substituted cycloalkyl or a heterocycloalkyl; wherein:

each instance of R$^{n3}$ is independently hydrogen, an optionally substituted —C$_1$-C$_6$ alkyl, or a nitrogen protecting group;

each instance of R$^{o6}$ is independently hydrogen, an optionally substituted —C$_1$-C$_6$ alkyl, or an oxygen protecting group; and each instance of R$^{c4}$ is an optionally substituted —C$_1$-C$_6$ alkyl;

each instance of R$^{s2}$ is independently an optionally substituted —C$_1$-C$_6$ alkyl or a sulfur protecting group; and R$^{n6}$ is hydrogen, an optionally substituted —C$_1$-C$_6$ alkyl, or a nitrogen protecting group.

3. The compound according to claim 2 or a pharmaceutically acceptable salt thereof, wherein the 5- or 6-membered monocyclic heteroaryl represented by R$^2$ is selected from one of the following:

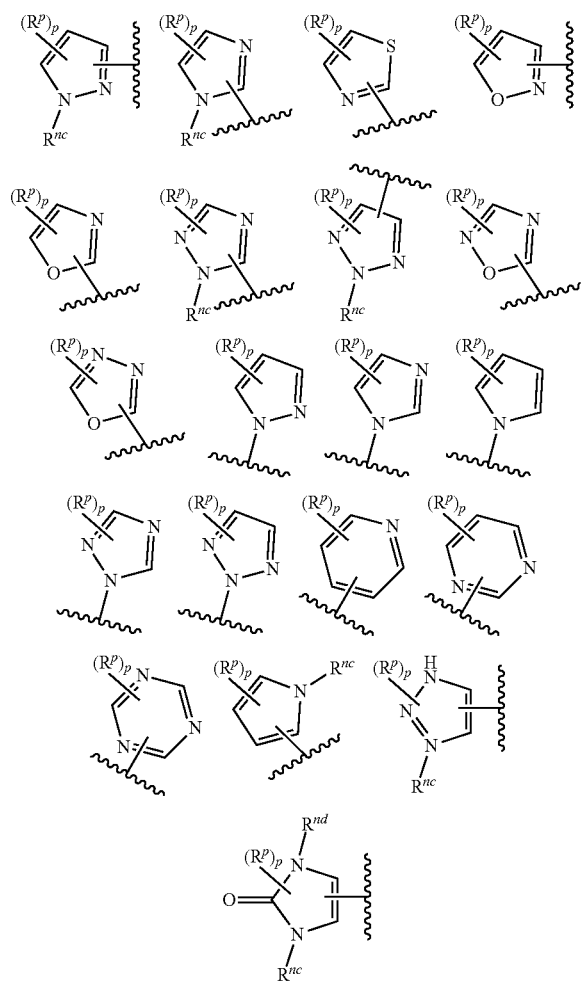

wherein:

each instance of R$^{nc}$ and R$^{nd}$ is independently hydrogen, optionally substituted —C$_1$-C$_6$ alkyl, or a nitrogen protecting group; and p is 0, 1, 2, 3, or 4, as valency permits.

4. The compound according to claim 1 or a pharmaceutically acceptable salt thereof, wherein the 5-membered monocyclic heteroaryl represented by Q is selected from the following:

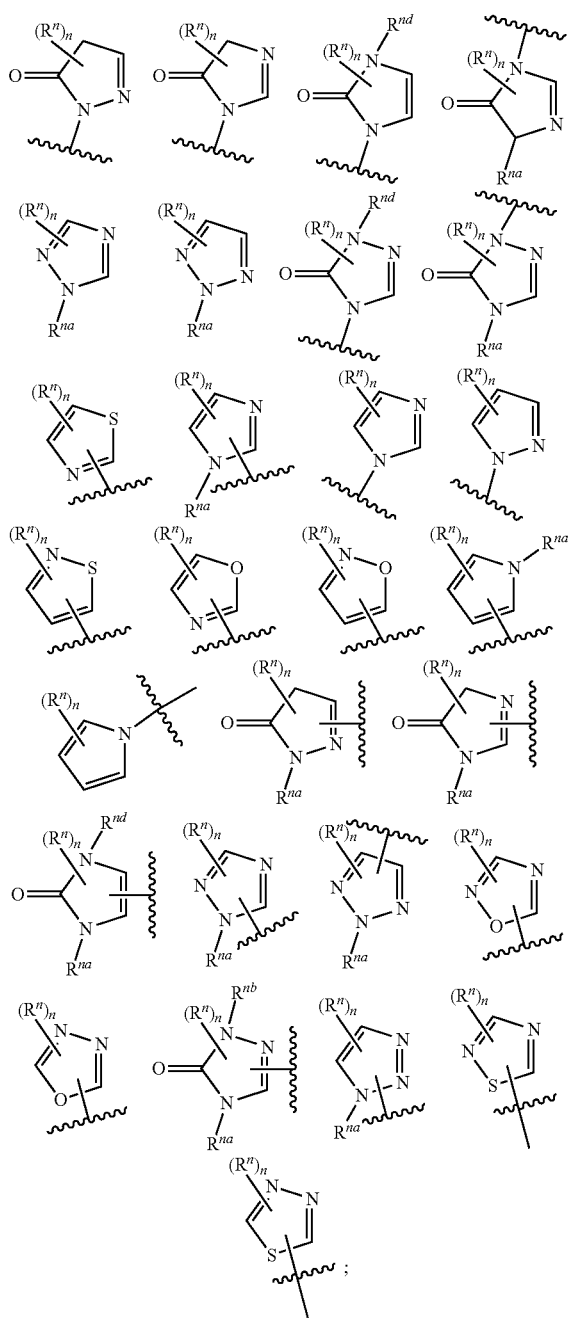

wherein:

each instance of $R^n$ is independently hydrogen, a halogen, —CN, —NO$_2$, —N$_3$, an optionally substituted alkyl, an optionally substituted alkenyl, an optionally substituted alkynyl, an optionally substituted cycloalkyl, an optionally substituted aryl, an optionally substituted heterocyclyl, an optionally substituted heteroaryl, —OR$^4$, —SR$^{s1}$, —N(R$^{n2}$)$_2$, —C(=O)N(R$^{n2}$)$_2$, —N(R$^{n2}$)C(=O)R$^{c3}$, —C(=O)R$^{c3}$, —C(=O)OR$^{o4}$, —OC(=O)R$^{c3}$, —S(=O)R$^{s1}$, —S(=O)$_2$R$^{s1}$, —S(=O)OR$^{o4}$, —OS(=O)R$^{c3}$, —S(=O)$_2$OR$^{o4}$, —OS(=O)$_2$R$^{c3}$, —S(=O)N(R$^{n2}$)$_2$, —S(=O)$_2$N(R$^{n2}$)$_2$, —N(R$^{n2}$)S(=O)R$^{s1}$, —N(R$^{n2}$)S(=O)$_2$R$^{s1}$, —N(R$^{n2}$)C(=O)OR$^{o4}$, —OC(=O)N(R$^{n2}$)$_2$, —N(R$^{n2}$)C(=O)N(R$^{n2}$)$_2$, —N(R$^{n2}$)S(=O)N(R$^{n2}$)$_2$, —N(R$^{n2}$)S(=O)$_2$N(R$^{n2}$)$_2$, —N(R$^{n2}$)S(=O)OR$^{o4}$, —N(R$^{n2}$)S(=O)$_2$OR$^{o4}$, —OS(=O)N(R$^{n2}$)$_2$, or —OS(=O)$_2$N(R$^{n2}$)$_2$; or two instances of $R^n$ attached to the same or adjacent carbon atoms, taken together with the carbon atoms to which they are attached to form an optionally substituted cycloalkyl or a heterocycloalkyl; wherein:

each instance of $R^{n2}$ is independently hydrogen, an optionally substituted —C$_1$-C$_6$ alkyl, or a nitrogen protecting group;

each instance of $R^{o4}$ is independently hydrogen, an optionally substituted —C$_1$-C$_6$ alkyl, or an oxygen protecting group;

each instance of $R^{c3}$ is independently an optionally substituted —C$_1$-C$_6$ alkyl;

each instance of $R^{s1}$ is independently an optionally substituted —C$_1$-C$_6$ alkyl or a sulfur protecting group;

n is 0, 1, 2, or 3, as valency permits; and each of $R^{na}$, $R^{nb}$, and $R^{nd}$ is independently hydrogen, an optionally substituted —C$_1$-C$_6$ alkyl, or a nitrogen protecting group.

5. The compound according to claim 4 or a pharmaceutically acceptable salt thereof, wherein each instance of $R^n$ is independently hydrogen, halogen, optionally substituted C$_{1-4}$ alkyl, —CN, —NO$_2$, —N$_3$, —OR$^{o4}$, —N(R$^{n2}$)$_2$, —C(=O)N(R$^{n2}$)$_2$, —C(=O)R$^{c3}$, or —C(=O)OR$^{o4}$.

6. The compound according to claim 1 or a pharmaceutically acceptable salt thereof, wherein R$^1$ is hydrogen or a —C$_1$-C$_4$ alkyl;

R$^j$ and R$^k$ are each hydrogen; and

R$^a$ and R$^b$ are each hydrogen.

7. The compound according to claim 1 or pharmaceutically acceptable salt thereof, wherein the compound is selected from the following compounds:

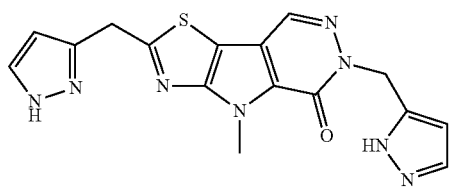 [SMILES: Cn1c2nc(Cc3cc[nH]n3)sc2c2cnn(Cc3ccn[nH]3)c(=O)c21]

-continued
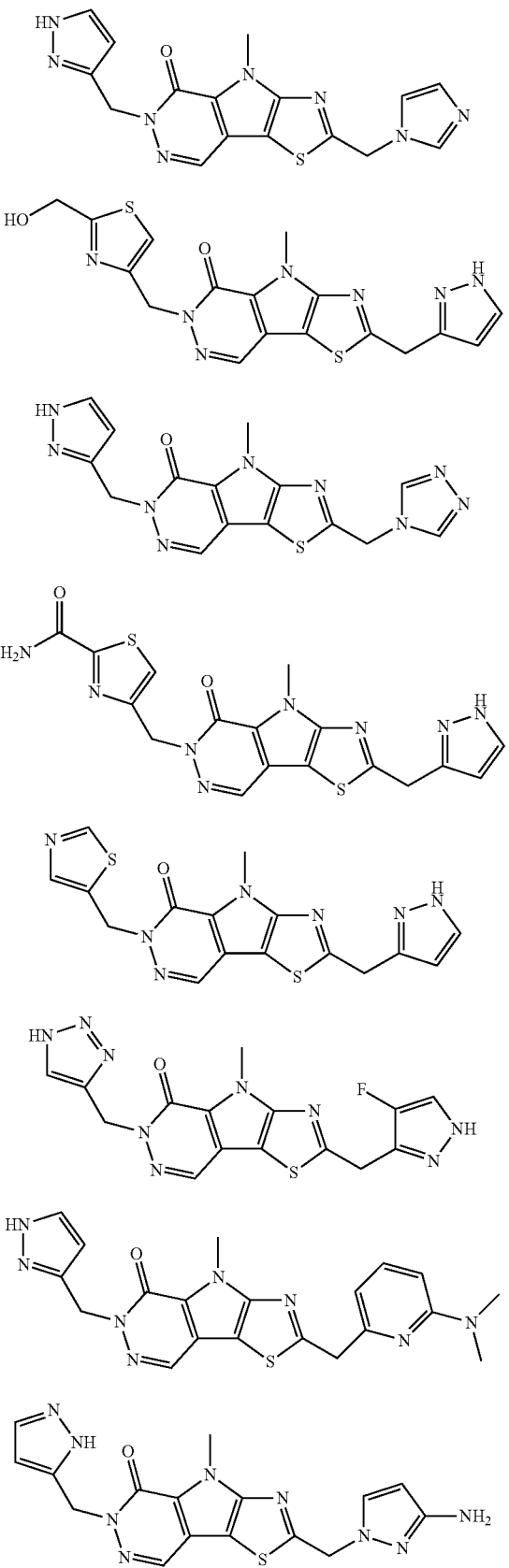

-continued
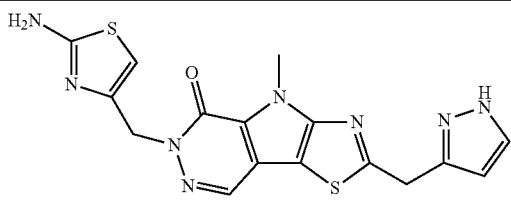
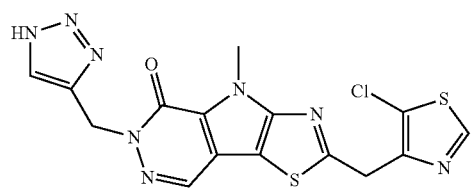
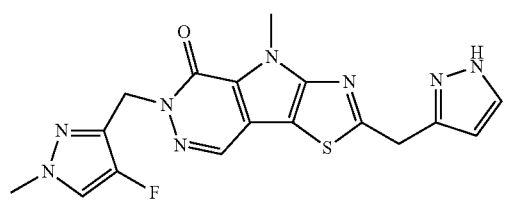 [SMILES: Cn1cc(F)c(Cn2ncc3c4sc(Cc5cc[nH]n5)nc4n(C)c3c2=O)n1]
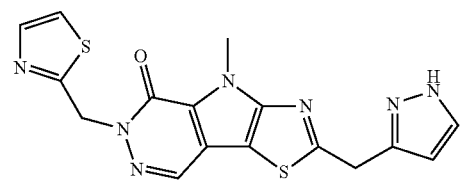 [SMILES: Cn1c2nc(Cc3cc[nH]n3)sc2c2cnn(Cc3nccs3)c(=O)c21]
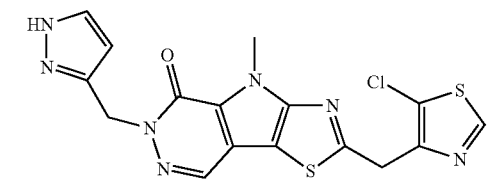 [SMILES: Cn1c2nc(Cc3ncsc3Cl)sc2c2cnn(Cc3cc[nH]n3)c(=O)c21]
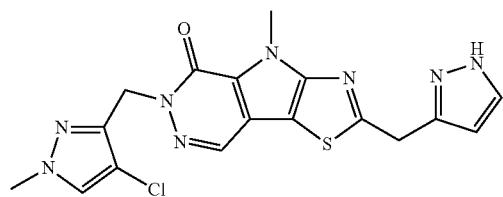
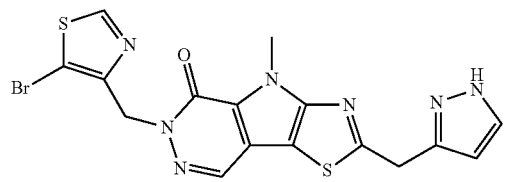
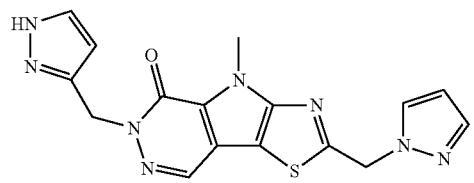 [SMILES: Cn1c2nc(Cn3cccn3)sc2c2cnn(Cc3cc[nH]n3)c(=O)c21]

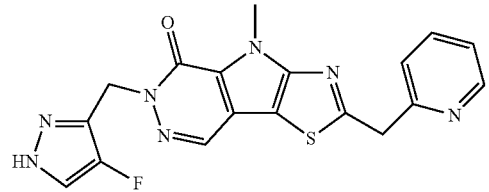 [SMILES: Cn1c2nc(Cc3ccccn3)sc2c2cnn(Cc3n[nH]cc3F)c(=O)c21]
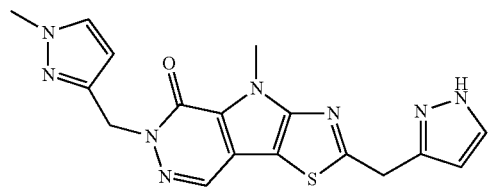 [SMILES: Cn1ccc(Cn2ncc3c4sc(Cc5cc[nH]n5)nc4n(C)c3c2=O)n1]
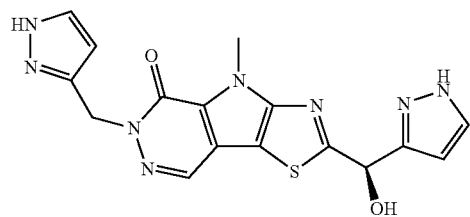 [SMILES: Cn1c2nc([C@H](O)c3cc[nH]n3)sc2c2cnn(Cc3cc[nH]n3)c(=O)c21]
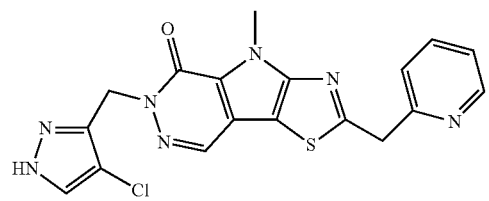 [SMILES: Cn1c2nc(Cc3ccccn3)sc2c2cnn(Cc3n[nH]cc3Cl)c(=O)c21]
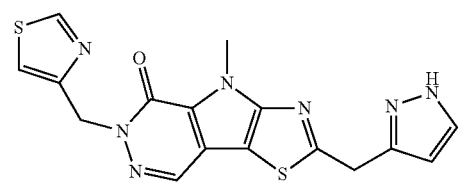 [SMILES: Cn1c2nc(Cc3cc[nH]n3)sc2c2cnn(Cc3cscn3)c(=O)c21]
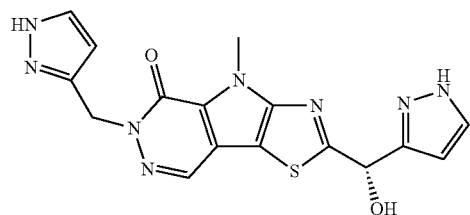 [SMILES: Cn1c2nc([C@@H](O)c3cc[nH]n3)sc2c2cnn(Cc3cc[nH]n3)c(=O)c21]
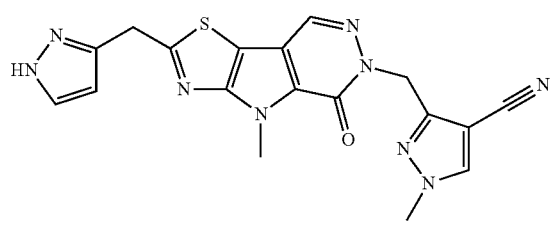 [SMILES: Cn1cc(C#N)c(Cn2ncc3c4sc(Cc5cc[nH]n5)nc4n(C)c3c2=O)n1]

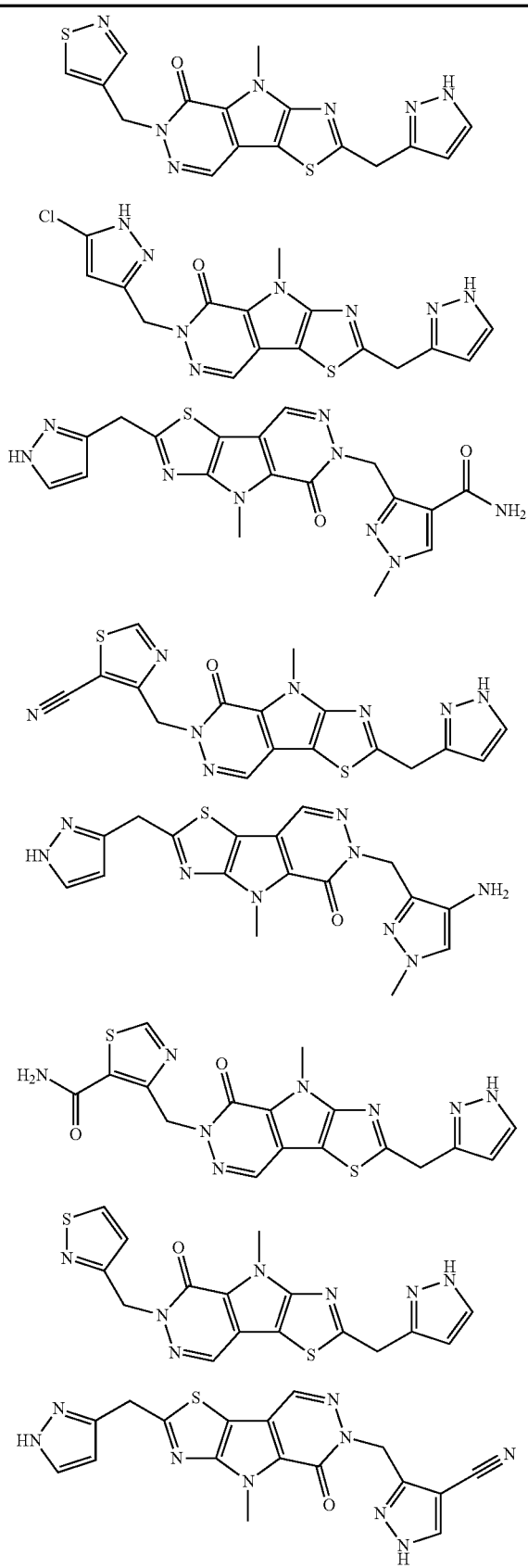

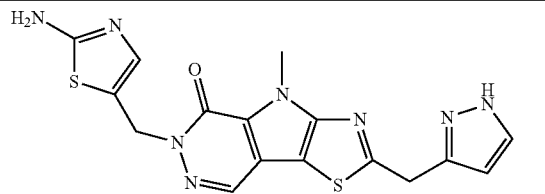
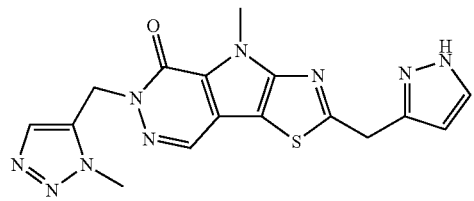 [SMILES: Cn1nncc1Cn1ncc2c3sc(Cc4cc[nH]n4)nc3n(C)c2c1=O]
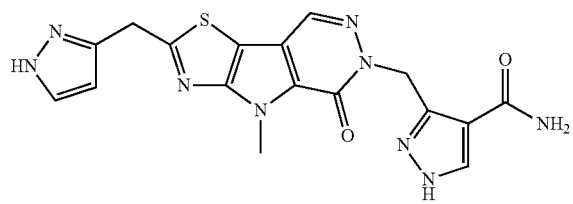 [SMILES: Cn1c2nc(Cc3cc[nH]n3)sc2c2cnn(Cc3n[nH]cc3C(N)=O)c(=O)c21]
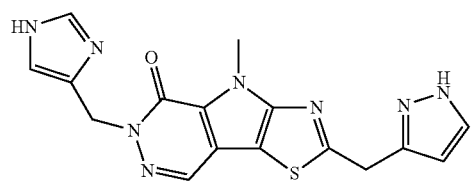
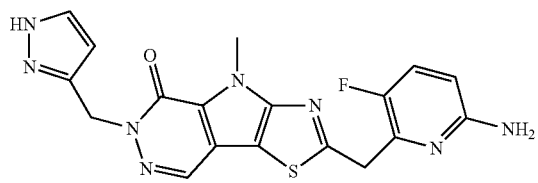 [SMILES: Cn1c2nc(Cc3nc(N)ccc3F)sc2c2cnn(Cc3cc[nH]n3)c(=O)c21]
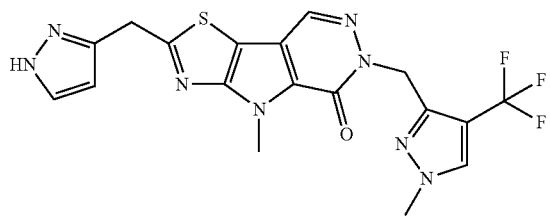 [SMILES: Cn1cc(C(F)(F)F)c(Cn2ncc3c4sc(Cc5cc[nH]n5)nc4n(C)c3c2=O)n1]
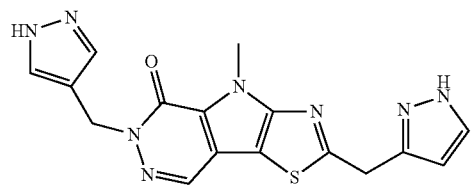 [SMILES: Cn1c2nc(Cc3cc[nH]n3)sc2c2cnn(Cc3cn[nH]c3)c(=O)c21]
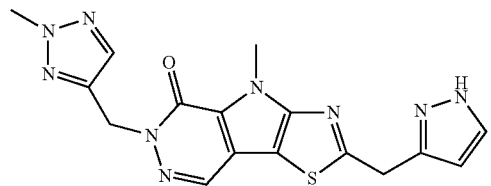

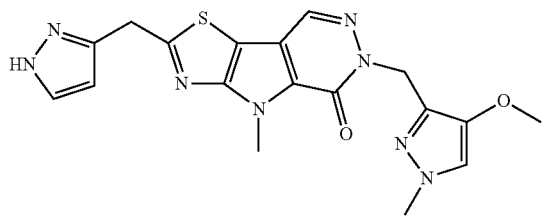 [SMILES: COc1cn(C)nc1Cn1ncc2c3sc(Cc4cc[nH]n4)nc3n(C)c2c1=O]
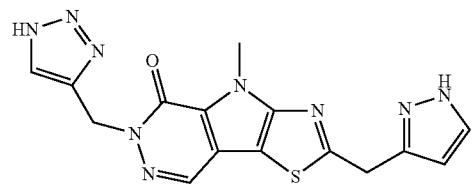 [SMILES: Cn1c2nc(Cc3cc[nH]n3)sc2c2cnn(Cc3c[nH]nn3)c(=O)c21]
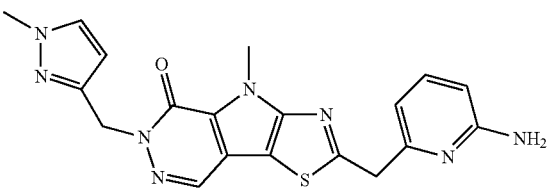 [SMILES: Cn1ccc(Cn2ncc3c4sc(Cc5cccc(N)n5)nc4n(C)c3c2=O)n1]
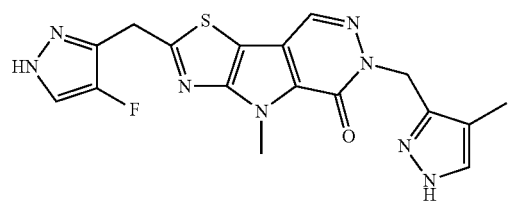 [SMILES: Cc1c[nH]nc1Cn1ncc2c3sc(Cc4n[nH]cc4F)nc3n(C)c2c1=O]
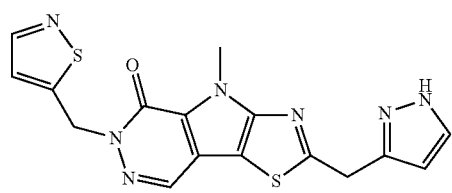 [SMILES: Cn1c2nc(Cc3cc[nH]n3)sc2c2cnn(Cc3ccns3)c(=O)c21]
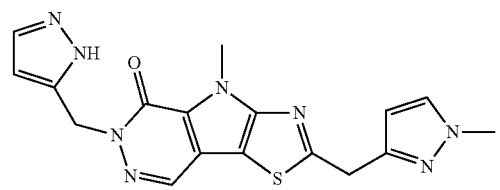 [SMILES: Cn1ccc(Cc2nc3c(s2)c2cnn(Cc4ccn[nH]4)c(=O)c2n3C)n1]
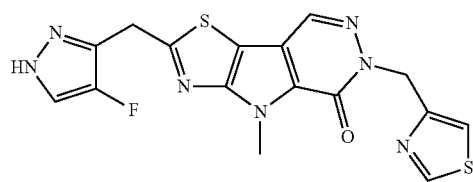 [SMILES: Cn1c2nc(Cc3n[nH]cc3F)sc2c2cnn(Cc3cscn3)c(=O)c21]
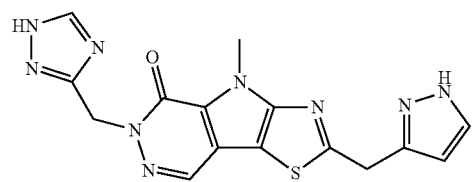 [SMILES: Cn1c2nc(Cc3cc[nH]n3)sc2c2cnn(Cc3nc[nH]n3)c(=O)c21]

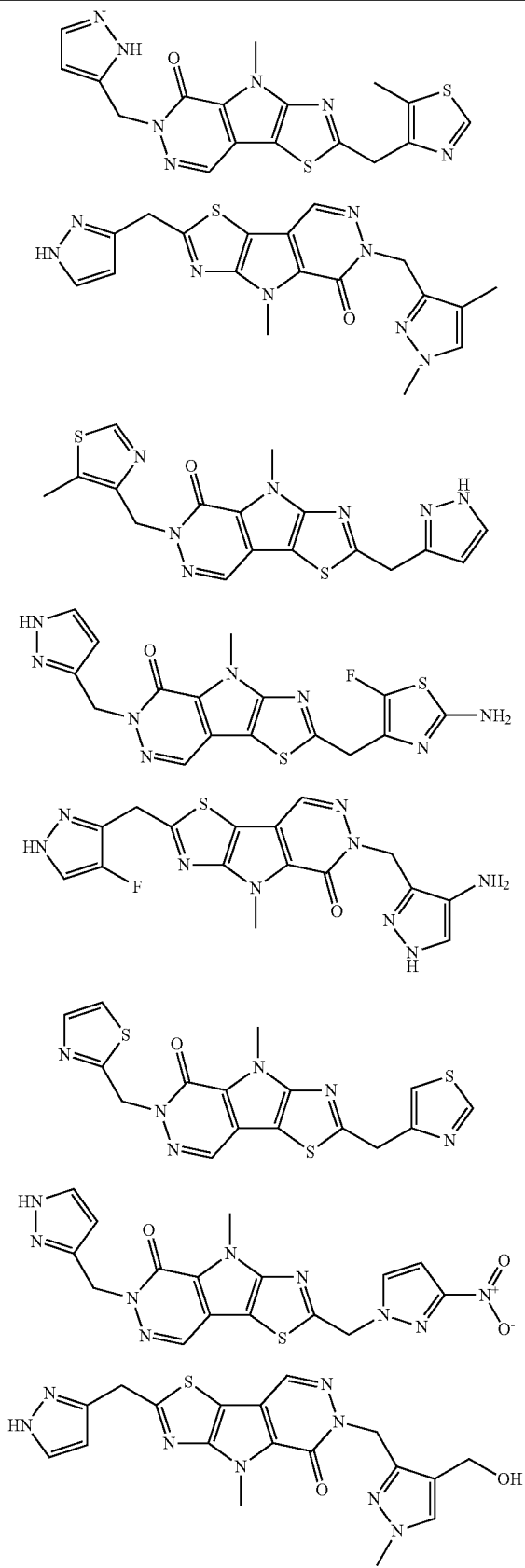

-continued
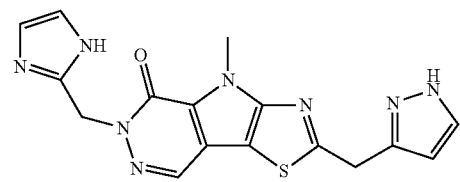 [SMILES: Cn1c2nc(Cc3cc[nH]n3)sc2c2cnn(Cc3ncc[nH]3)c(=O)c21]
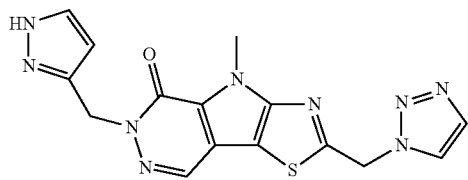 [SMILES: Cn1c2nc(Cn3ccnn3)sc2c2cnn(Cc3cc[nH]n3)c(=O)c21]
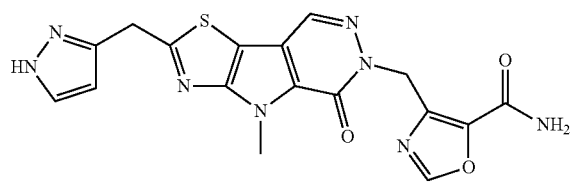 [SMILES: Cn1c2nc(Cc3cc[nH]n3)sc2c2cnn(Cc3ncoc3C(N)=O)c(=O)c21]
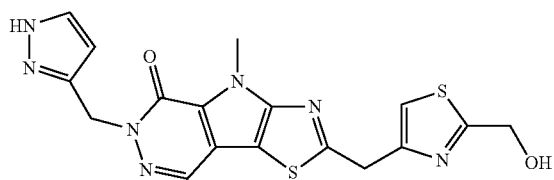 [SMILES: Cn1c2nc(Cc3csc(CO)n3)sc2c2cnn(Cc3cc[nH]n3)c(=O)c21]
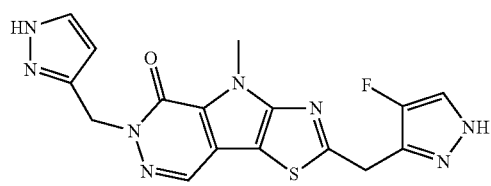 [SMILES: Cn1c2nc(Cc3n[nH]cc3F)sc2c2cnn(Cc3cc[nH]n3)c(=O)c21]
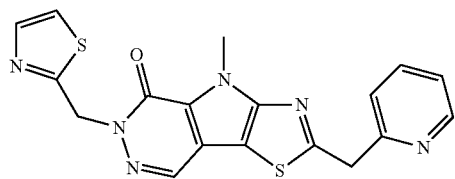 [SMILES: Cn1c2nc(Cc3ccccn3)sc2c2cnn(Cc3nccs3)c(=O)c21]
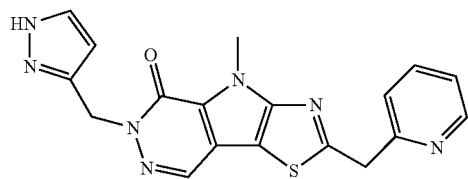 [SMILES: Cn1c2nc(Cc3ccccn3)sc2c2cnn(Cc3cc[nH]n3)c(=O)c21]
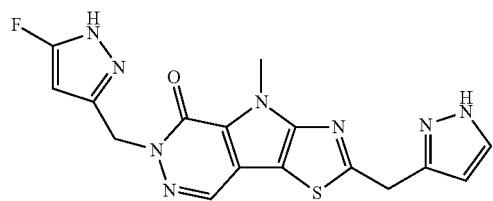 [SMILES: Cn1c2nc(Cc3cc[nH]n3)sc2c2cnn(Cc3cc(F)[nH]n3)c(=O)c21]

-continued
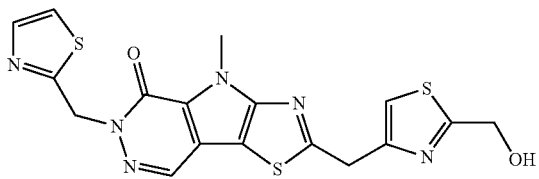 [SMILES: Cn1c2nc(Cc3csc(CO)n3)sc2c2cnn(Cc3nccs3)c(=O)c21]
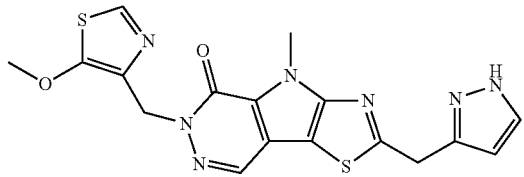 [SMILES: COc1scnc1Cn1ncc2c3sc(Cc4cc[nH]n4)nc3n(C)c2c1=O]
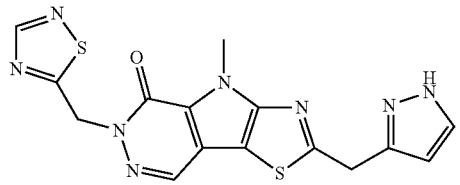 [SMILES: Cn1c2nc(Cc3cc[nH]n3)sc2c2cnn(Cc3ncns3)c(=O)c21]
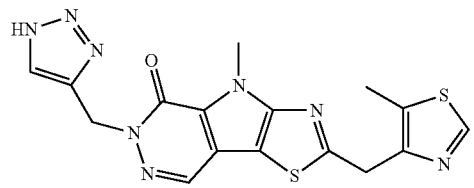 [SMILES: Cc1scnc1Cc1nc2c(s1)c1cnn(Cc3c[nH]nn3)c(=O)c1n2C]
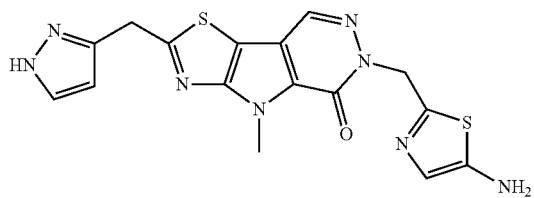 [SMILES: Cn1c2nc(Cc3cc[nH]n3)sc2c2cnn(Cc3ncc(N)s3)c(=O)c21]
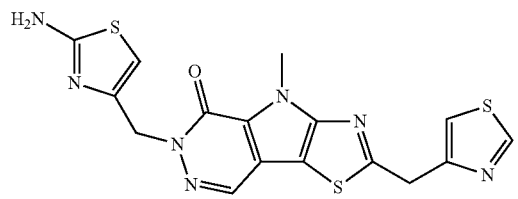 [SMILES: Cn1c2nc(Cc3cscn3)sc2c2cnn(Cc3csc(N)n3)c(=O)c21]
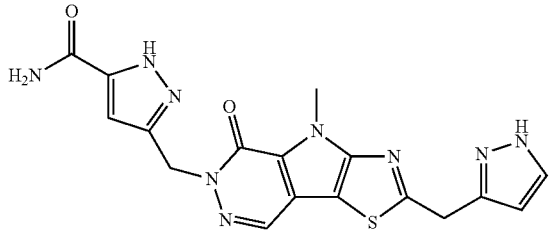 [SMILES: Cn1c2nc(Cc3cc[nH]n3)sc2c2cnn(Cc3cc(C(N)=O)[nH]n3)c(=O)c21]
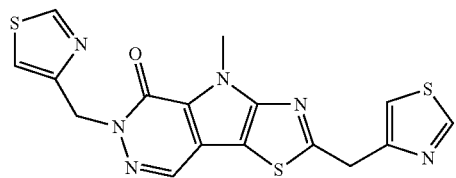 [SMILES: Cn1c2nc(Cc3cscn3)sc2c2cnn(Cc3cscn3)c(=O)c21]

-continued
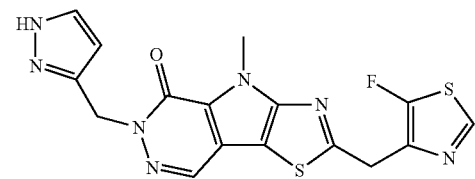 [SMILES: Cn1c2nc(Cc3ncsc3F)sc2c2cnn(Cc3cc[nH]n3)c(=O)c21]
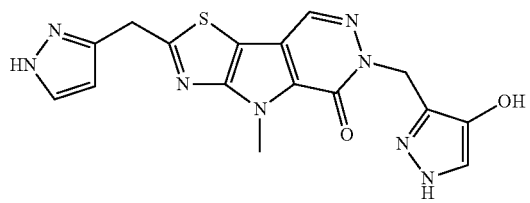 [SMILES: Cn1c2nc(Cc3cc[nH]n3)sc2c2cnn(Cc3n[nH]cc3O)c(=O)c21]
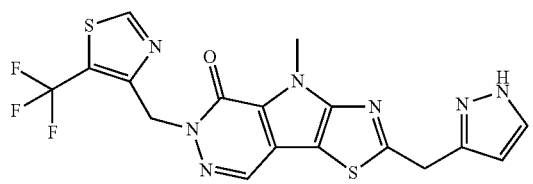 [SMILES: Cn1c2nc(Cc3cc[nH]n3)sc2c2cnn(Cc3ncsc3C(F)(F)F)c(=O)c21]
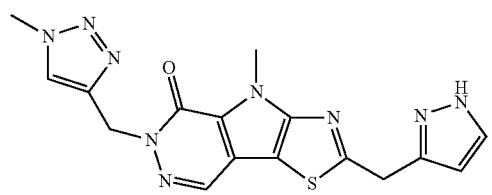 [SMILES: Cn1cc(Cn2ncc3c4sc(Cc5cc[nH]n5)nc4n(C)c3c2=O)nn1]
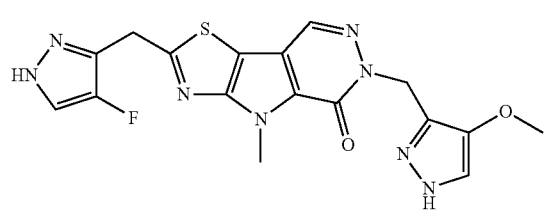 [SMILES: COc1c[nH]nc1Cn1ncc2c3sc(Cc4n[nH]cc4F)nc3n(C)c2c1=O]
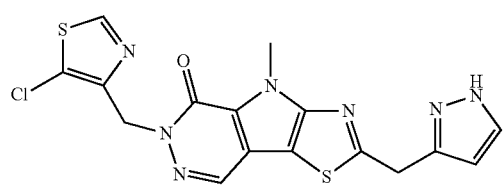 [SMILES: Cn1c2nc(Cc3cc[nH]n3)sc2c2cnn(Cc3ncsc3Cl)c(=O)c21]
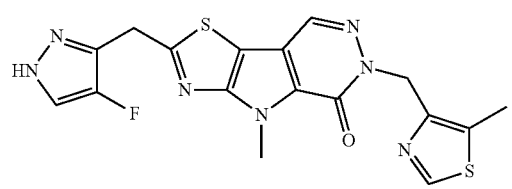 [SMILES: Cc1scnc1Cn1ncc2c3sc(Cc4n[nH]cc4F)nc3n(C)c2c1=O]
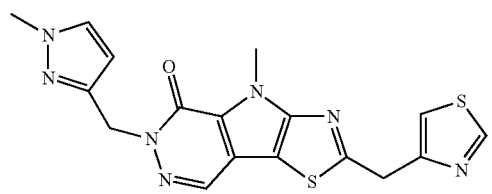 [SMILES: Cn1ccc(Cn2ncc3c4sc(Cc5cscn5)nc4n(C)c3c2=O)n1]

-continued
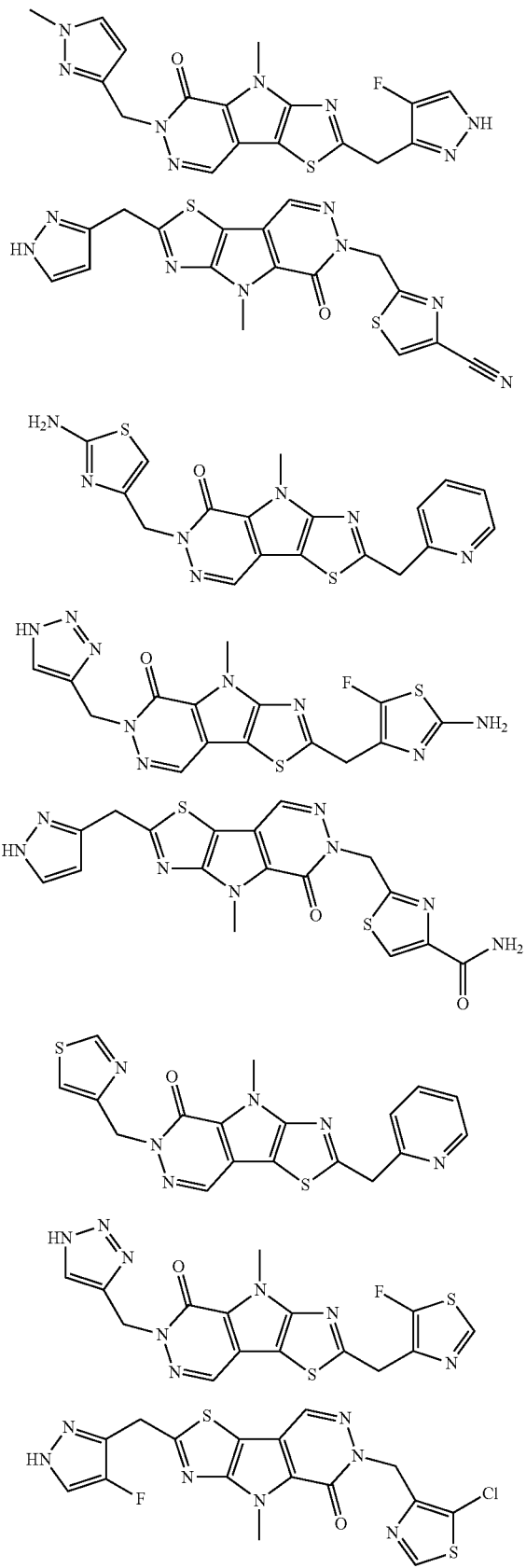

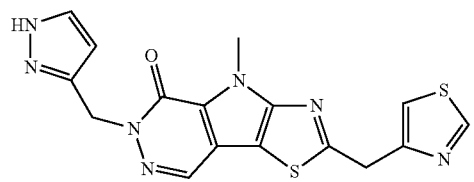 [SMILES: Cn1c2nc(Cc3cscn3)sc2c2cnn(Cc3cc[nH]n3)c(=O)c21]
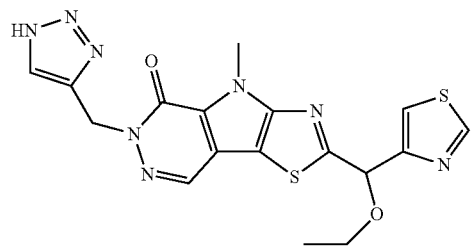 [SMILES: CCOC(c1cscn1)c1nc2c(s1)c1cnn(Cc3c[nH]nn3)c(=O)c1n2C]
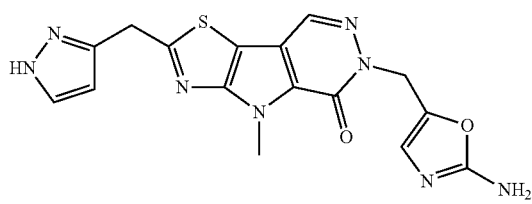 [SMILES: Cn1c2nc(Cc3cc[nH]n3)sc2c2cnn(Cc3cnc(N)o3)c(=O)c21]
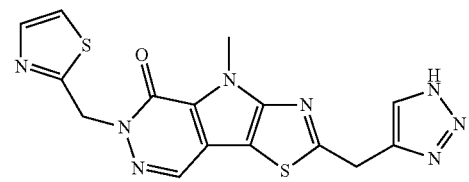 [SMILES: Cn1c2nc(Cc3c[nH]nn3)sc2c2cnn(Cc3nccs3)c(=O)c21]
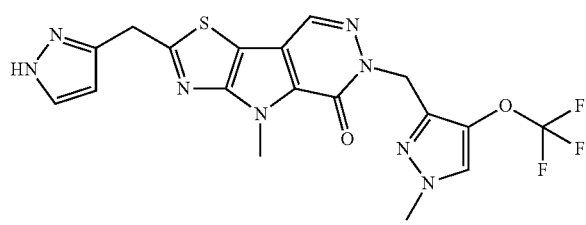 [SMILES: Cn1cc(OC(F)(F)F)c(Cn2ncc3c4sc(Cc5cc[nH]n5)nc4n(C)c3c2=O)n1]
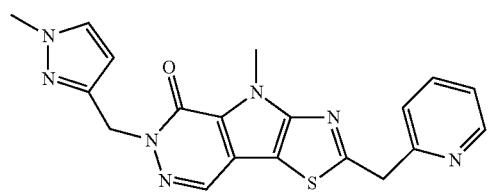 [SMILES: Cn1ccc(Cn2ncc3c4sc(Cc5ccccn5)nc4n(C)c3c2=O)n1]
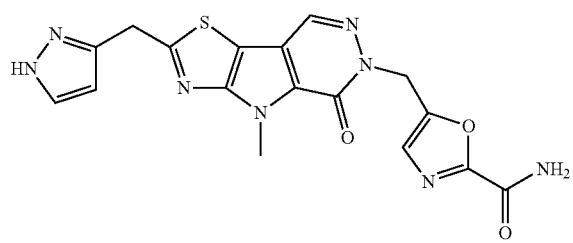 [SMILES: Cn1c2nc(Cc3cc[nH]n3)sc2c2cnn(Cc3cnc(C(N)=O)o3)c(=O)c21]

-continued
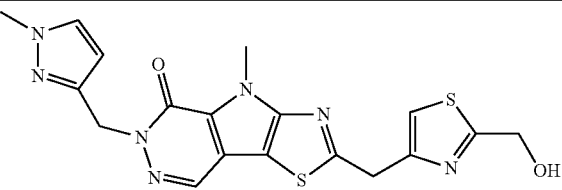
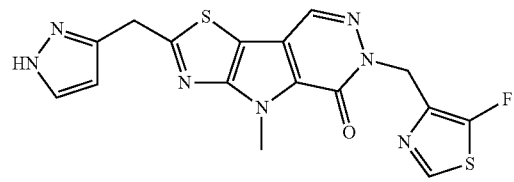 [SMILES: Cn1c2nc(Cc3cc[nH]n3)sc2c2cnn(Cc3ncsc3F)c(=O)c21]
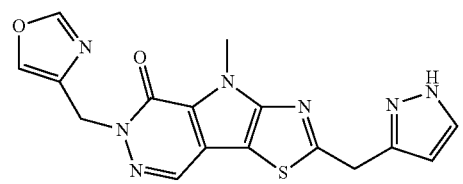 [SMILES: Cn1c2nc(Cc3cc[nH]n3)sc2c2cnn(Cc3cocn3)c(=O)c21]
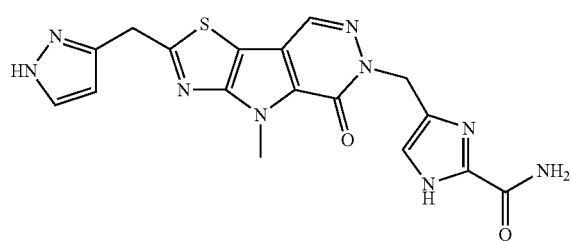 [SMILES: Cn1c2nc(Cc3cc[nH]n3)sc2c2cnn(Cc3c[nH]c(C(N)=O)n3)c(=O)c21]
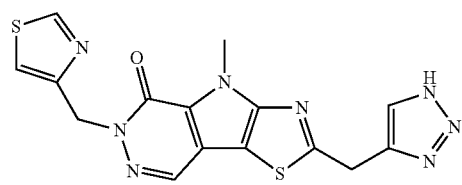 [SMILES: Cn1c2nc(Cc3c[nH]nn3)sc2c2cnn(Cc3cscn3)c(=O)c21]
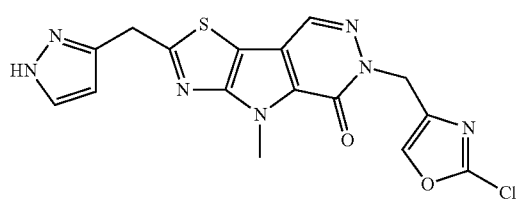 [SMILES: Cn1c2nc(Cc3cc[nH]n3)sc2c2cnn(Cc3coc(Cl)n3)c(=O)c21]
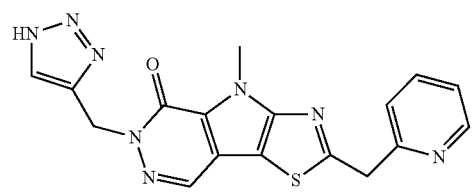 [SMILES: Cn1c2nc(Cc3ccccn3)sc2c2cnn(Cc3c[nH]nn3)c(=O)c21]
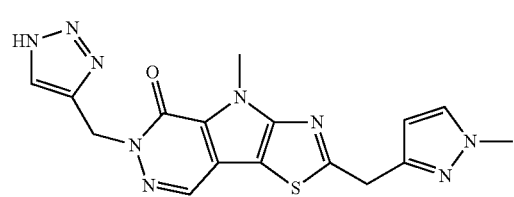 [SMILES: Cn1ccc(Cc2nc3c(s2)c2cnn(Cc4c[nH]nn4)c(=O)c2n3C)n1]

-continued
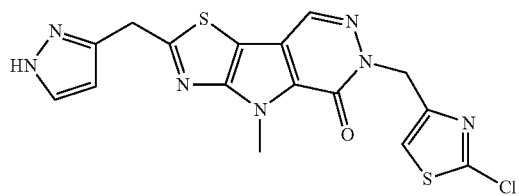
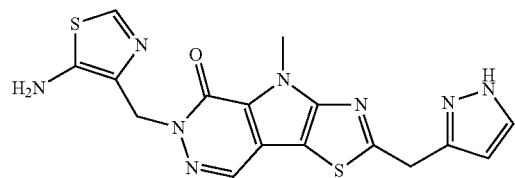 [SMILES: Cn1c2nc(Cc3cc[nH]n3)sc2c2cnn(Cc3ncsc3N)c(=O)c21]
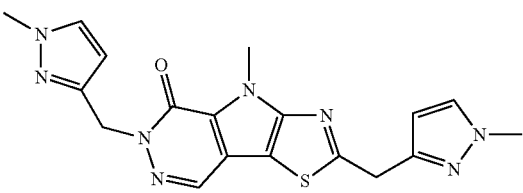
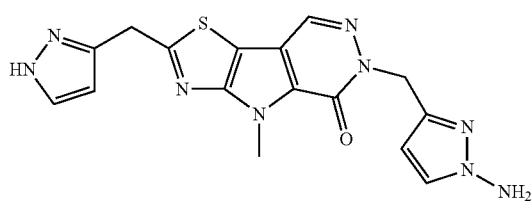 [SMILES: Cn1c2nc(Cc3cc[nH]n3)sc2c2cnn(Cc3ccn(N)n3)c(=O)c21]
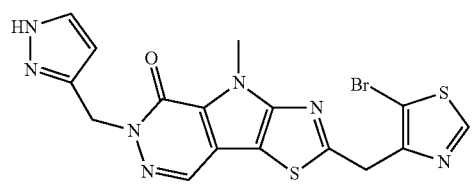
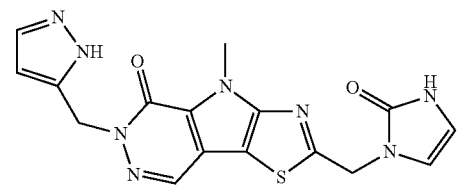 [SMILES: Cn1c2nc(Cn3cc[nH]c3=O)sc2c2cnn(Cc3ccn[nH]3)c(=O)c21]
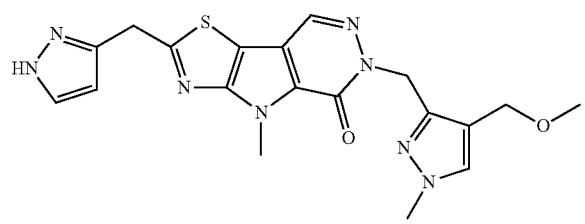 [SMILES: COCc1cn(C)nc1Cn1ncc2c3sc(Cc4cc[nH]n4)nc3n(C)c2c1=O]
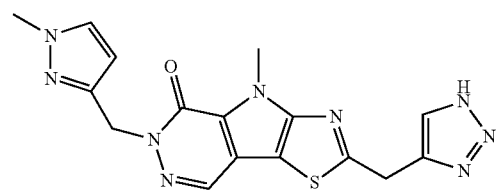 [SMILES: Cn1ccc(Cn2ncc3c4sc(Cc5c[nH]nn5)nc4n(C)c3c2=O)n1]

-continued
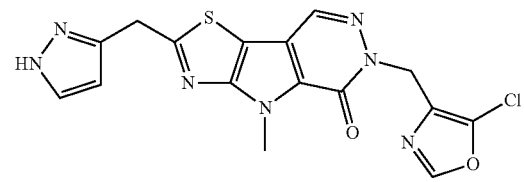 [SMILES: Cn1c2nc(Cc3cc[nH]n3)sc2c2cnn(Cc3ncoc3Cl)c(=O)c21]
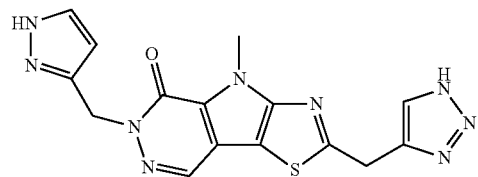 [SMILES: Cn1c2nc(Cc3c[nH]nn3)sc2c2cnn(Cc3cc[nH]n3)c(=O)c21]
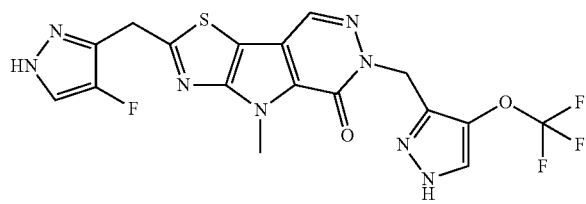 [SMILES: Cn1c2nc(Cc3n[nH]cc3F)sc2c2cnn(Cc3n[nH]cc3OC(F)(F)F)c(=O)c21]
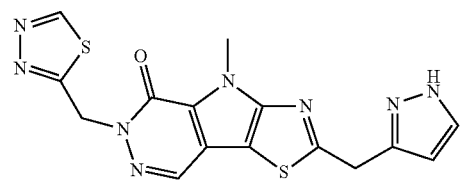
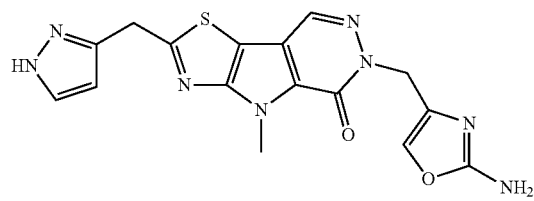 [SMILES: Cn1c2nc(Cc3cc[nH]n3)sc2c2cnn(Cc3coc(N)n3)c(=O)c21]
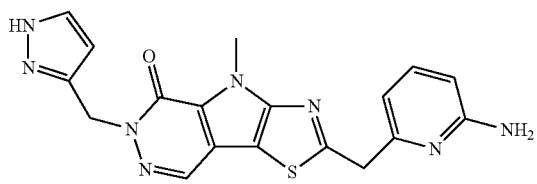 [SMILES: Cn1c2nc(Cc3cccc(N)n3)sc2c2cnn(Cc3cc[nH]n3)c(=O)c21]
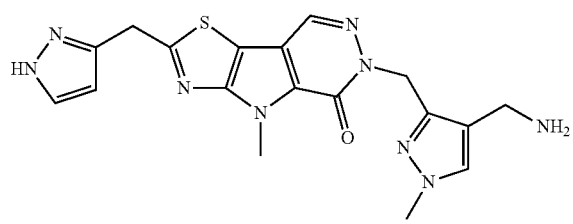 [SMILES: Cn1cc(CN)c(Cn2ncc3c4sc(Cc5cc[nH]n5)nc4n(C)c3c2=O)n1]
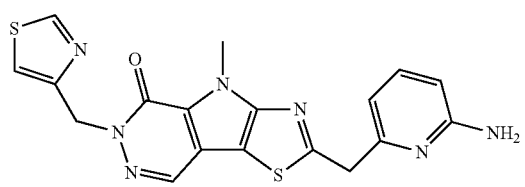 [SMILES: Cn1c2nc(Cc3cccc(N)n3)sc2c2cnn(Cc3cscn3)c(=O)c21]

-continued
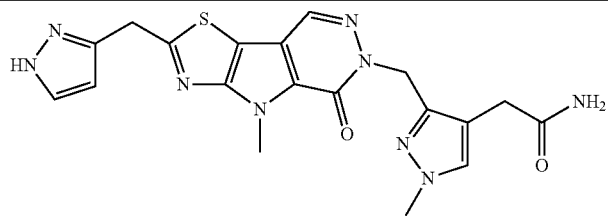
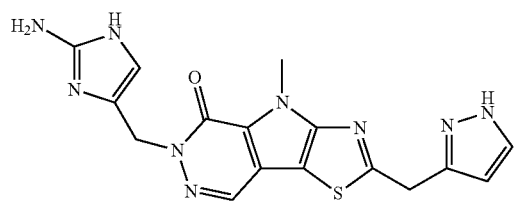 [SMILES: Cn1c2nc(Cc3cc[nH]n3)sc2c2cnn(Cc3c[nH]c(N)n3)c(=O)c21]
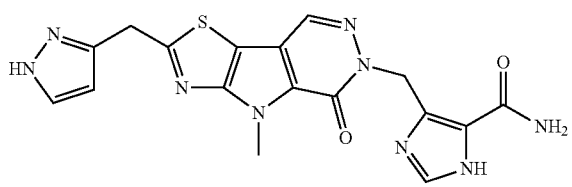 [SMILES: Cn1c2nc(Cc3cc[nH]n3)sc2c2cnn(Cc3nc[nH]c3C(N)=O)c(=O)c21]
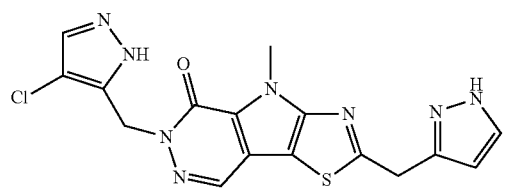 [SMILES: Cn1c2nc(Cc3cc[nH]n3)sc2c2cnn(Cc3[nH]ncc3Cl)c(=O)c21]
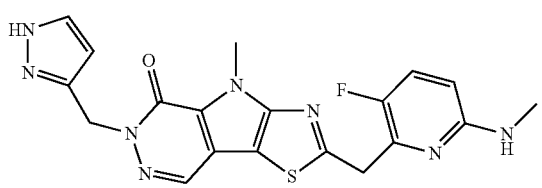 [SMILES: CNc1ccc(F)c(Cc2nc3c(s2)c2cnn(Cc4cc[nH]n4)c(=O)c2n3C)n1]
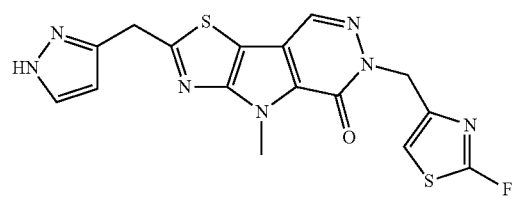 [SMILES: Cn1c2nc(Cc3cc[nH]n3)sc2c2cnn(Cc3csc(F)n3)c(=O)c21]
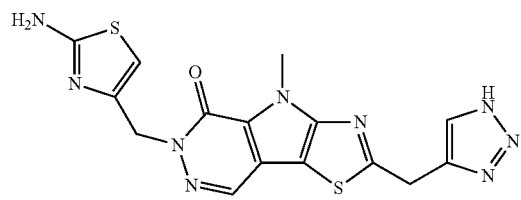 [SMILES: Cn1c2nc(Cc3c[nH]nn3)sc2c2cnn(Cc3csc(N)n3)c(=O)c21]
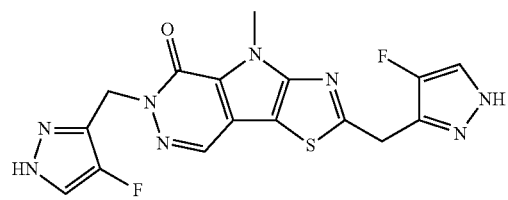 [SMILES: Cn1c2nc(Cc3n[nH]cc3F)sc2c2cnn(Cc3n[nH]cc3F)c(=O)c21]

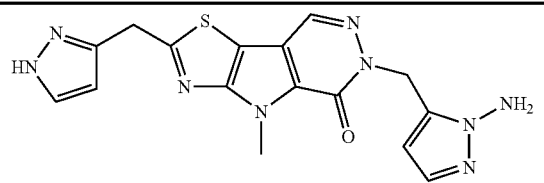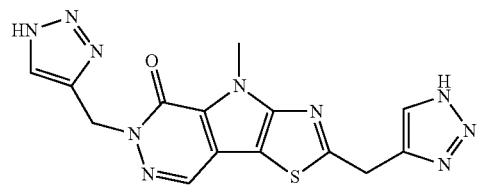 [SMILES: Cn1c2nc(Cc3c[nH]nn3)sc2c2cnn(Cc3c[nH]nn3)c(=O)c21]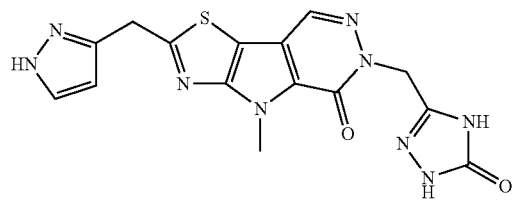 [SMILES: Cn1c2nc(Cc3cc[nH]n3)sc2c2cnn(Cc3n[nH]c(=O)[nH]3)c(=O)c21]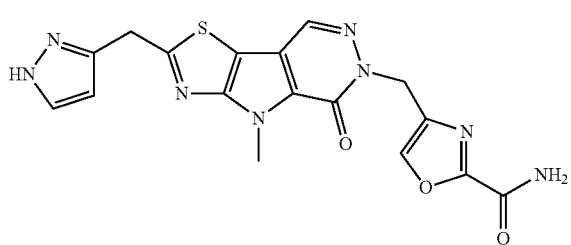 [SMILES: Cn1c2nc(Cc3cc[nH]n3)sc2c2cnn(Cc3coc(C(N)=O)n3)c(=O)c21]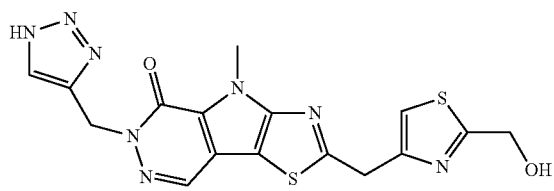 [SMILES: Cn1c2nc(Cc3csc(CO)n3)sc2c2cnn(Cc3c[nH]nn3)c(=O)c21]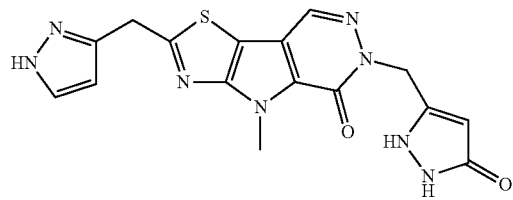 [SMILES: Cn1c2nc(Cc3cc[nH]n3)sc2c2cnn(Cc3cc(=O)[nH][nH]3)c(=O)c21]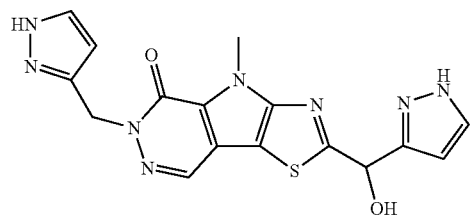 [SMILES: Cn1c2nc(C(O)c3cc[nH]n3)sc2c2cnn(Cc3cc[nH]n3)c(=O)c21]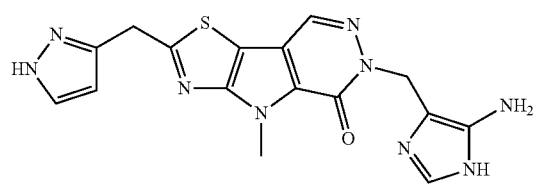 [SMILES: Cn1c2nc(Cc3cc[nH]n3)sc2c2cnn(Cc3nc[nH]c3N)c(=O)c21]

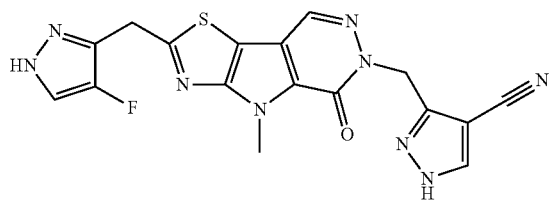 [SMILES: Cn1c2nc(Cc3n[nH]cc3F)sc2c2cnn(Cc3n[nH]cc3C#N)c(=O)c21]
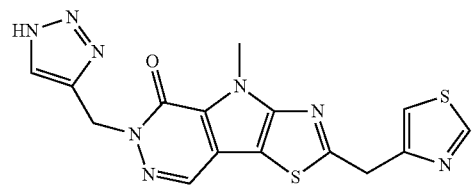 [SMILES: Cn1c2nc(Cc3cscn3)sc2c2cnn(Cc3c[nH]nn3)c(=O)c21]
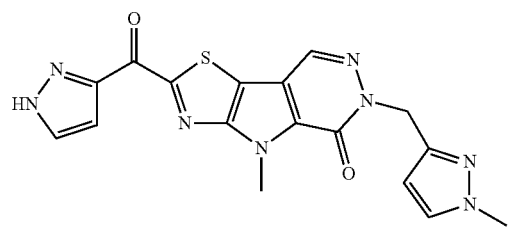 [SMILES: Cn1ccc(Cn2ncc3c4sc(C(=O)c5cc[nH]n5)nc4n(C)c3c2=O)n1]
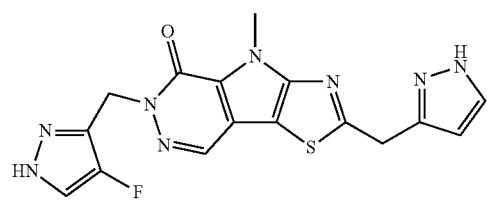 [SMILES: Cn1c2nc(Cc3cc[nH]n3)sc2c2cnn(Cc3n[nH]cc3F)c(=O)c21]
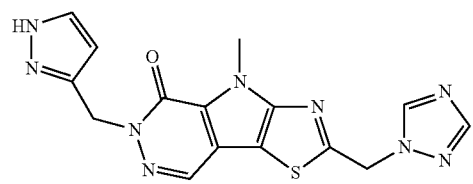 [SMILES: Cn1c2nc(Cn3cncn3)sc2c2cnn(Cc3cc[nH]n3)c(=O)c21]
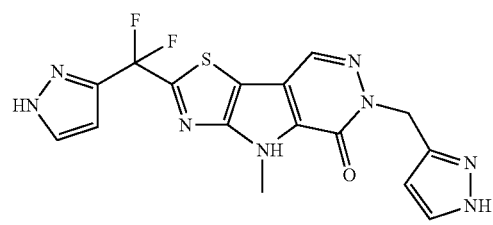 [SMILES: Cn1c2nc(C(F)(F)c3cc[nH]n3)sc2c2cnn(Cc3cc[nH]n3)c(=O)c21]
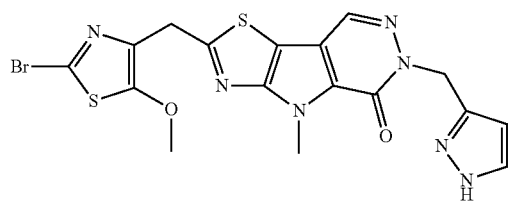 [SMILES: COc1sc(Br)nc1Cc1nc2c(s1)c1cnn(Cc3cc[nH]n3)c(=O)c1n2C]

-continued
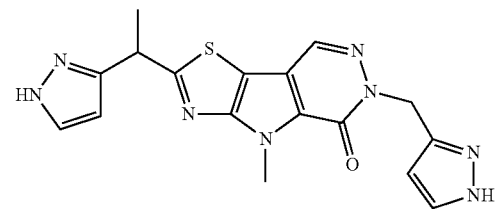 [SMILES: CC(c1cc[nH]n1)c1nc2c(s1)c1cnn(Cc3cc[nH]n3)c(=O)c1n2C]
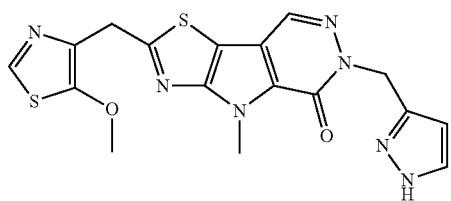 [SMILES: COc1scnc1Cc1nc2c(s1)c1cnn(Cc3cc[nH]n3)c(=O)c1n2C]
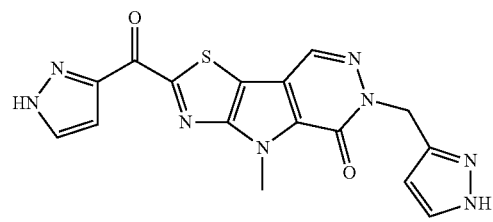 [SMILES: Cn1c2nc(C(=O)c3cc[nH]n3)sc2c2cnn(Cc3cc[nH]n3)c(=O)c21]
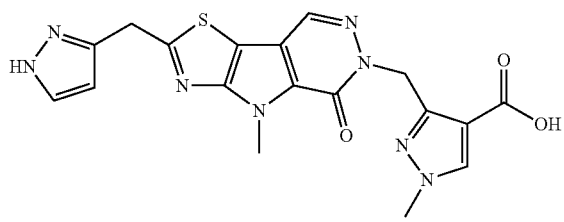 [SMILES: Cn1cc(C(=O)O)c(Cn2ncc3c4sc(Cc5cc[nH]n5)nc4n(C)c3c2=O)n1]
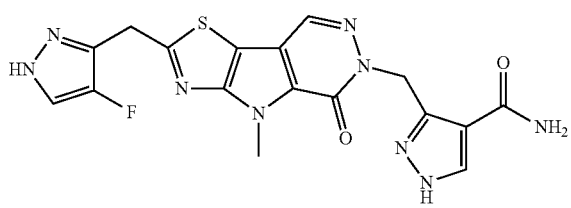
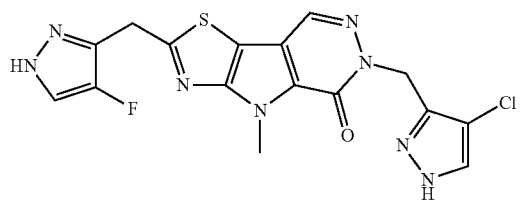 [SMILES: Cn1c2nc(Cc3n[nH]cc3F)sc2c2cnn(Cc3n[nH]cc3Cl)c(=O)c21]
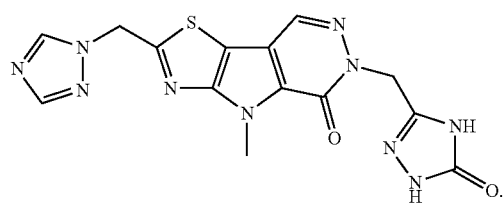 [SMILES: Cn1c2nc(Cn3cncn3)sc2c2cnn(Cc3n[nH]c(=O)[nH]3)c(=O)c21]

8. The compound according to claim 7 pharmaceutically acceptable salt thereof, wherein the compound is represented by the following structural formula:

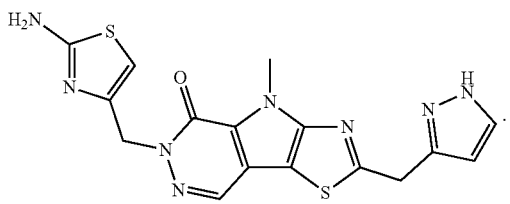 [SMILES: Cn1c2nc(Cc3cc[nH]n3)sc2c2cnn(Cc3csc(N)n3)c(=O)c21]

9. The compound according to claim 7 pharmaceutically acceptable salt thereof, wherein the compound is represented by the following structural formula:

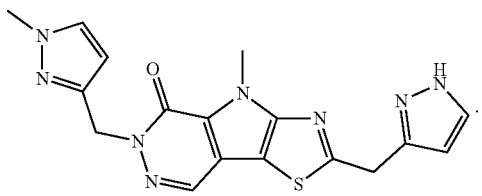 [SMILES: Cn1ccc(Cn2ncc3c4sc(Cc5cc[nH]n5)nc4n(C)c3c2=O)n1]

10. The compound according to claim 7 or pharmaceutically acceptable salt thereof, wherein the compound is represented by the following structural formula:

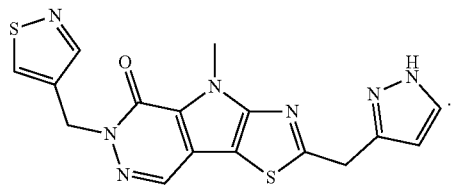 [SMILES: Cn1c2nc(Cc3cc[nH]n3)sc2c2cnn(Cc3cnsc3)c(=O)c21]

11. The compound according to claim 7 pharmaceutically acceptable salt thereof, wherein the compound is represented by the following structural formula:

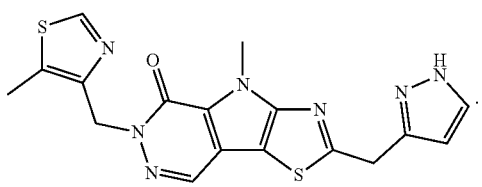 [SMILES: Cc1scnc1Cn1ncc2c3sc(Cc4cc[nH]n4)nc3n(C)c2c1=O]

12. The compound according to claim 7 or pharmaceutically acceptable salt thereof, wherein the compound is represented by the following structural formula:

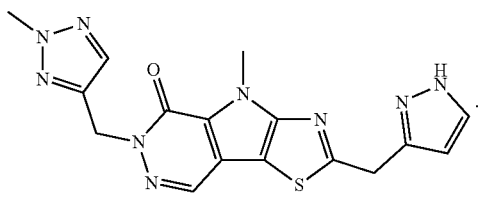 [SMILES: Cn1ncc(Cn2ncc3c4sc(Cc5cc[nH]n5)nc4n(C)c3c2=O)n1]

13. The compound according to claim 7 or pharmaceutically acceptable salt thereof, wherein the compound is represented by the following structural formula:

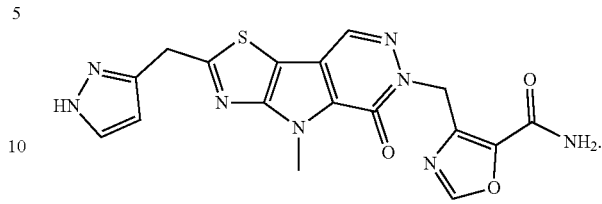

14. The compound according to claim 7 pharmaceutically acceptable salt thereof, wherein the compound is represented by the following structural formula:

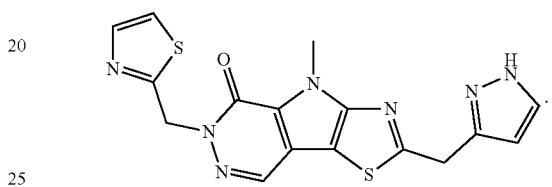

15. The compound according to claim 7 pharmaceutically acceptable salt thereof, wherein the compound is represented by the following structural formula:

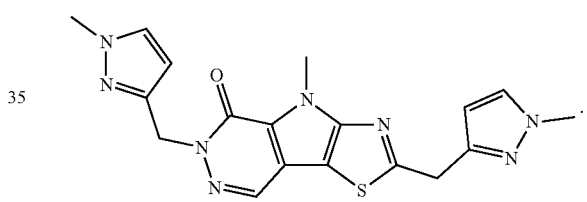

16. The compound according to claim 7 pharmaceutically acceptable salt thereof, wherein the compound is represented by the following structural formula:

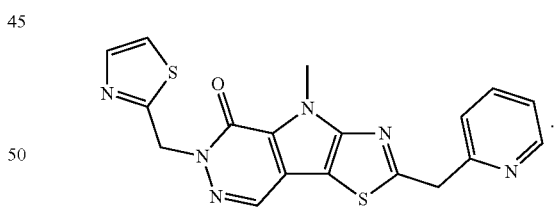

17. The compound according to claim 7 pharmaceutically acceptable salt thereof, wherein the compound is represented by the following structural formula:

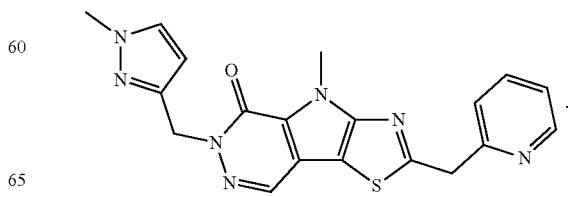

18. The compound according to claim 7 or pharmaceutically acceptable salt thereof, wherein the compound is represented by the following structural formula:

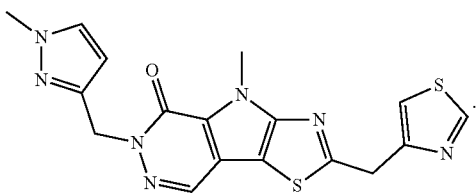 [SMILES: Cn1ccc(Cn2ncc3c4sc(Cc5cscn5)nc4n(C)c3c2=O)n1]

19. The compound according to claim 7 pharmaceutically acceptable salt thereof, wherein the compound is represented by the following structural formula:

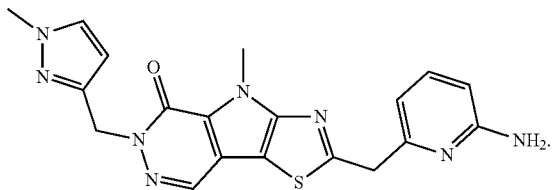 [SMILES: Cn1ccc(Cn2ncc3c4sc(Cc5cccc(N)n5)nc4n(C)c3c2=O)n1]

20. A pharmaceutical composition comprising an effective amount of the compound according to claim 1 or a pharmaceutically acceptable salt thereof, and a pharmaceutically acceptable carrier.

21. A method for treating hemolytic anemia in a subject comprising administering to the subject an effective amount of the compound according to claim 1 or a pharmaceutically acceptable salt thereof.

22. A method for treating sickle cell disease in a subject comprising administering to the subject an effective amount of the compound according to claim 1 or a pharmaceutically acceptable salt thereof.

23. A method of treating pyruvate kinase deficiency (PKD) in a subject comprising administering to the subject an effective amount of the compound according to claim 1 or a pharmaceutically acceptable salt thereof.

24. A method of treating thalassemia in a subject comprising administering to the subject an effective amount of the compound according to claim 1 or a pharmaceutically acceptable salt thereof.

25. The method of claim 24, wherein the thalassemia is beta-thalassemia or alpha-thalassemia.

* * * * *

UNITED STATES PATENT AND TRADEMARK OFFICE
CERTIFICATE OF CORRECTION

PATENT NO. : 12,133,853 B2  
APPLICATION NO. : 18/099311  
DATED : November 5, 2024  
INVENTOR(S) : Giovanni Cianchetta et al.

Page 1 of 3

It is certified that error appears in the above-identified patent and that said Letters Patent is hereby corrected as shown below:

In the Claims

In Claim 1, Column 229, Line number 13, please replace the variable "–N($R^{n5}$)C(=O) $R^{c5}$" with -- –N($R^{n5}$)C(=O)$R^{c5}$--.

In Claim 1, Column 229, Line numbers 15-16, please replace the phrase
"–S(=O)$_2$$R^{js}$,
–S(=O)$R^{js}$, or an optionally substituted –C$_1$-C$_6$ alkyl;" with the phrase -- –S(=O)$_2$$R^{js}$, –S(=O)$R^{js}$, or an optionally substituted –C$_1$-C$_6$ alkyl;--.

In Claim 1, Column 229, Line numbers 33-37, please replace the phrase "each instance of $R^{js}$ is independently an optionally substituted
–C$_1$-C$_6$ alkyl, an optionally substituted C$_{6-12}$ aryl, an optionally substituted heteroaryl, or a sulfur protecting group" with the phrase --each instance of $R^{js}$ is independently an optionally substituted –C$_1$-C$_6$ alkyl, an optionally substituted C$_{6-12}$ aryl, an optionally substituted heteroaryl, or a sulfur protecting group--.

In Claim 2, Column 229, Line number 54, please replace the variable "–OS(=O)$_2$$R^{o4}$" with the variable -- –OS(=O)$_2$$R^{c4}$--.

In Claim 4, Column 231, Line number 5, please replace the structure

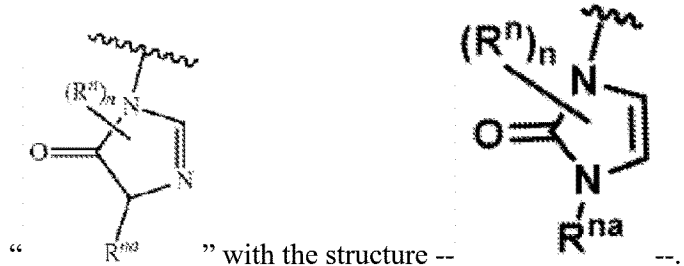

" with the structure -- --.

Signed and Sealed this  
Twenty-fifth Day of March, 2025

Coke Morgan Stewart  
*Acting Director of the United States Patent and Trademark Office*

In Claim 4, Column 231, Line 10, please replace the structures

" 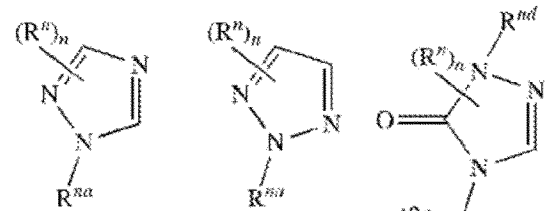 " with the structures

-- 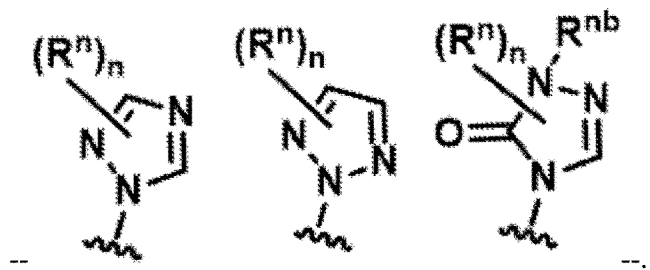 --.

In Claim 4, Column 231, Line numbers 15-20, please add the structure

-- 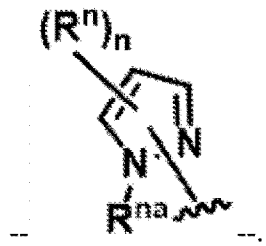 --.

In Claim 4, Column 232, Line number 8, please replace the variable "–OR$^4$" with the variable -- –OR$^{o4}$ --.

In Claim 8, Column 271, Line number 1, please replace the phrase "claim 7 pharmaceutically" with the phrase --claim 7 or pharmaceutically--.

In Claim 9, Column 271, Line number 15, please replace the phrase "claim 7 pharmaceutically" with the phrase --claim 7 or pharmaceutically--.

In Claim 11, Column 271, Line number 41, please replace the phrase "claim 7 pharmaceutically" with the phrase --claim 7 or pharmaceutically--.

In Claim 14, Column 272, Line number 14, please replace the phrase "claim 7 pharmaceutically" with the phrase --claim 7 or pharmaceutically--.

In Claim 15, Column 272, Line number 28, please replace the phrase "claim 7 pharmaceutically" with the phrase --claim 7 or pharmaceutically--.

In Claim 16, Column 272, Line number 41, please replace the phrase "claim 7 pharmaceutically" with the phrase --claim 7 or pharmaceutically--.

CERTIFICATE OF CORRECTION (continued)
U.S. Pat. No. 12,133,853 B2

In Claim 17, Column 272, Line number 54, please replace the phrase "claim 7 pharmaceutically" with the phrase --claim 7 or pharmaceutically--.

In Claim 19, Column 273, Line number 14, please replace the phrase "claim 7 pharmaceutically" with the phrase --claim 7 or pharmaceutically--.